(12) United States Patent
Tilson et al.

(10) Patent No.: US 11,219,351 B2
(45) Date of Patent: Jan. 11, 2022

(54) DEVICE FOR ENDOSCOPIC ADVANCEMENT THROUGH THE SMALL INTESTINE

(71) Applicant: NEPTUNE MEDICAL Inc., Burlingame, CA (US)

(72) Inventors: Alexander Q. Tilson, Burlingame, CA (US); Eugene F. Duval, Menlo Park, CA (US); Garrett J. Gomes, San Mateo, CA (US)

(73) Assignee: Neptune Medical Inc., Burlingame, CA (US)

( * ) Notice: Subject to any disclaimer, the term of this patent is extended or adjusted under 35 U.S.C. 154(b) by 483 days.

(21) Appl. No.: 15/757,230

(22) PCT Filed: Sep. 2, 2016

(86) PCT No.: PCT/US2016/050290
§ 371 (c)(1),
(2) Date: Mar. 2, 2018

(87) PCT Pub. No.: WO2017/041052
PCT Pub. Date: Mar. 9, 2017

(65) Prior Publication Data
US 2018/0271354 A1   Sep. 27, 2018

Related U.S. Application Data

(60) Provisional application No. 62/213,908, filed on Sep. 3, 2015, provisional application No. 62/339,593, filed on May 20, 2016.

(51) Int. Cl.
*A61B 1/00* (2006.01)
*A61M 25/01* (2006.01)
*A61B 1/12* (2006.01)

(52) U.S. Cl.
CPC ...... *A61B 1/00094* (2013.01); *A61B 1/00082* (2013.01); *A61B 1/00135* (2013.01);
(Continued)

(58) Field of Classification Search
CPC ............ A61B 1/00082; A61B 1/00135; A61B 1/00142; A61B 1/00151; A61B 1/00154;
(Continued)

(56) References Cited

U.S. PATENT DOCUMENTS 2,268,321 A    12/1941  Flynn
2,767,705 A *  10/1956  Moore ..................... A61B 1/31
                                                    600/184
(Continued)

FOREIGN PATENT DOCUMENTS

AU       2013207571 B1    8/2013
CN          2613655 Y     4/2004
(Continued)

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (year of pub sufficiently earlier than effective US filing date and any foreign priority date) 2009.
(Continued)

*Primary Examiner* — Aaron B Fairchild
*Assistant Examiner* — Shankar Raj Ghimire
(74) *Attorney, Agent, or Firm* — Shay Glenn LLP

(57) ABSTRACT

An apparatus for advancing a device through a gastrointestinal tract. In some embodiments, the apparatus includes first and second grabbing mechanisms adapted to grab and release tissue of the gastrointestinal tract, the first grabbing mechanism being releasably attachable to the device, the second grabbing mechanism being attached to an outer
(Continued)

element configured to at least partially surround the device, the first and second grabbing mechanisms being axially movable with respect to each other along the gastrointestinal tract; and a radially expandable blocking element disposed proximal to the first grabbing mechanism and movable with the first grabbing mechanism with respect to the second grabbing mechanism, the blocking element being adapted to move tissue of the intestinal tract with respect to the second grabbing mechanism when the blocking element is moved toward the second grabbing mechanism. The invention also includes corresponding methods.

15 Claims, 120 Drawing Sheets

(52) U.S. Cl.
CPC ...... *A61B 1/00142* (2013.01); *A61B 1/00151* (2013.01); *A61B 1/00154* (2013.01); *A61B 1/126* (2013.01); *A61M 25/0105* (2013.01); *A61M 25/0113* (2013.01)

(58) Field of Classification Search
CPC .. A61B 1/26; A61B 1/00094; A61M 25/0105; A61M 25/0113
See application file for complete search history.

(56) References Cited

U.S. PATENT DOCUMENTS

| | | | |
|---|---|---|---|
| 3,859,986 A | 1/1975 | Okada et al. | |
| 3,998,216 A | 12/1976 | Hosono | |
| 4,066,071 A | 1/1978 | Nagel | |
| 4,141,364 A | 2/1979 | Schultze | |
| 4,176,662 A | 12/1979 | Frazer | |
| 4,425,919 A | 1/1984 | Alston, Jr. | |
| 4,551,140 A | 11/1985 | Shinohara | |
| 4,690,131 A | 9/1987 | Lyddy, Jr. et al. | |
| 4,696,544 A | 9/1987 | Costella | |
| 4,717,379 A | 1/1988 | Ekholmer | |
| 4,794,412 A | 12/1988 | Casey et al. | |
| 4,794,912 A | 1/1989 | Lia | |
| 4,815,450 A | 3/1989 | Patel | |
| 4,817,613 A | 4/1989 | Jaraczewski et al. | |
| 4,893,613 A | 1/1990 | Hake | |
| 4,959,058 A * | 9/1990 | Michelson | A61B 1/00094 |
| | | | 600/114 |
| 4,961,738 A | 10/1990 | Mackin | |
| 5,018,436 A | 5/1991 | Evangelista et al. | |
| 5,019,121 A | 5/1991 | Krauter | |
| 5,037,386 A | 8/1991 | Marcus et al. | |
| 5,105,819 A | 4/1992 | Wollschlager et al. | |
| 5,123,421 A | 6/1992 | Sinofsky | |
| 5,174,276 A | 12/1992 | Crockard | |
| 5,188,595 A | 2/1993 | Jacobi | |
| 5,251,611 A | 10/1993 | Zehel et al. | |
| 5,337,733 A | 8/1994 | Bauerfeind et al. | |
| 5,496,292 A | 3/1996 | Burnham | |
| 5,531,685 A | 7/1996 | Hemmer et al. | |
| 5,531,719 A | 7/1996 | Takahashi | |
| 5,577,992 A | 11/1996 | Chiba et al. | |
| 5,601,588 A | 2/1997 | Tonomura et al. | |
| 5,607,435 A | 3/1997 | Sachdeva et al. | |
| 5,624,381 A | 4/1997 | Kieturakis | |
| 5,632,734 A | 5/1997 | Galel et al. | |
| 5,662,587 A | 9/1997 | Grundfest et al. | |
| 5,662,621 A | 9/1997 | Lafontaine | |
| 5,746,692 A | 5/1998 | Bacich et al. | |
| 5,759,151 A | 6/1998 | Sturges | |
| 5,779,624 A | 7/1998 | Chang | |
| 5,782,811 A * | 7/1998 | Samson | A61M 25/005 |
| | | | 604/527 |
| 5,882,347 A | 3/1999 | Mouris Laan et al. | |
| 5,891,112 A | 4/1999 | Samson | |
| 5,906,591 A | 5/1999 | Dario et al. | |
| 5,916,145 A | 6/1999 | Chu et al. | |
| 5,916,147 A | 6/1999 | Boury | |
| 5,951,539 A | 9/1999 | Nita et al. | |
| 5,976,074 A | 11/1999 | Moriyama | |
| 6,159,187 A | 12/2000 | Park et al. | |
| 6,162,171 A | 12/2000 | Ng et al. | |
| 6,179,776 B1 | 1/2001 | Adams et al. | |
| 6,190,357 B1 | 2/2001 | Ferrari et al. | |
| 6,217,565 B1 | 4/2001 | Cohen | |
| 6,309,346 B1 | 10/2001 | Farhadi | |
| 6,364,878 B1 | 4/2002 | Hall | |
| 6,468,203 B2 | 10/2002 | Belson | |
| 6,485,409 B1 * | 11/2002 | Voloshin | A61B 1/00147 |
| | | | 600/115 |
| 6,503,225 B1 * | 1/2003 | Kirsch | A61M 1/3627 |
| | | | 422/48 |
| 6,517,477 B1 * | 2/2003 | Wendlandt | A61B 1/00156 |
| | | | 600/114 |
| 6,547,724 B1 | 4/2003 | Soble et al. | |
| 6,572,538 B2 | 6/2003 | Takase | |
| 6,579,277 B1 | 6/2003 | Rabiner et al. | |
| 6,610,007 B2 | 8/2003 | Belson et al. | |
| 6,612,982 B1 | 9/2003 | Ouchi | |
| 6,616,628 B2 | 9/2003 | Hayzelden | |
| 6,620,126 B2 | 9/2003 | Unsworth et al. | |
| 6,623,424 B2 | 9/2003 | Hayakawa et al. | |
| 6,712,832 B2 | 3/2004 | Shah | |
| 6,726,677 B1 | 4/2004 | Flaherty et al. | |
| 6,730,020 B2 | 5/2004 | Peng et al. | |
| 6,780,151 B2 | 8/2004 | Grabover et al. | |
| 6,783,491 B2 | 8/2004 | Saadat et al. | |
| 6,790,173 B2 | 9/2004 | Saadat et al. | |
| 6,793,621 B2 | 9/2004 | Butler et al. | |
| 6,793,661 B2 | 9/2004 | Hamilton et al. | |
| 6,800,056 B2 | 10/2004 | Tartaglia et al. | |
| 6,869,393 B2 | 3/2005 | Butler | |
| 6,899,673 B2 | 5/2005 | Ogura et al. | |
| 6,911,004 B2 | 6/2005 | Kim et al. | |
| 6,923,754 B2 | 8/2005 | Lubock | |
| 6,960,162 B2 | 11/2005 | Saadat et al. | |
| 6,974,411 B2 | 12/2005 | Belson | |
| 6,984,203 B2 * | 1/2006 | Tartaglia | A61B 1/00147 |
| | | | 600/114 |
| 7,060,199 B2 | 6/2006 | Woydt et al. | |
| 7,141,055 B2 * | 11/2006 | Abrams | A61B 17/0686 |
| | | | 606/115 |
| 7,172,552 B2 * | 2/2007 | Wendlandt | A61B 1/00156 |
| | | | 600/114 |
| 7,214,230 B2 | 5/2007 | Brock et al. | |
| 7,288,101 B2 * | 10/2007 | Deem | A61B 17/064 |
| | | | 128/898 |
| 7,291,127 B2 | 11/2007 | Eidenschink | |
| 7,365,509 B2 | 4/2008 | Park et al. | |
| 7,438,712 B2 | 10/2008 | Chouinard | |
| 7,511,733 B2 | 3/2009 | Takizawa et al. | |
| 7,537,562 B2 | 5/2009 | Takano | |
| 7,559,916 B2 | 7/2009 | Smith et al. | |
| 7,591,782 B2 | 9/2009 | Fujikura | |
| 7,598,652 B2 | 10/2009 | Kornbluh et al. | |
| 7,695,428 B2 | 4/2010 | Machida | |
| 7,736,323 B2 | 6/2010 | Von Weymarn-Scharli | |
| 7,837,615 B2 | 11/2010 | Le et al. | |
| 7,850,725 B2 | 12/2010 | Vardi et al. | |
| 7,901,347 B2 | 3/2011 | Sekiguchi et al. | |
| 7,909,755 B2 | 3/2011 | Itoi | |
| 7,918,819 B2 | 4/2011 | Karmarkar et al. | |
| 7,918,845 B2 | 4/2011 | Saadat et al. | |
| 7,931,661 B2 | 4/2011 | Saadat et al. | |
| 7,935,047 B2 | 5/2011 | Yoshida et al. | |
| 7,947,000 B2 | 5/2011 | Vargas et al. | |
| 7,957,790 B2 | 6/2011 | Kleen | |
| 7,970,455 B2 | 6/2011 | Zilberstein et al. | |
| 7,988,621 B2 | 8/2011 | Smith et al. | |
| 8,047,236 B2 | 11/2011 | Perry | |
| 8,075,476 B2 | 12/2011 | Vargas | |
| 8,092,374 B2 | 1/2012 | Smith et al. | |
| 8,109,953 B1 | 2/2012 | King, III et al. | |

(56) References Cited

U.S. PATENT DOCUMENTS

| | | | |
|---|---|---|---|
| 8,125,755 B2 | 2/2012 | Garcia et al. | |
| 8,192,422 B2 | 6/2012 | Zubiate et al. | |
| 8,206,287 B2 | 6/2012 | Matsuo | |
| 8,226,548 B2 | 7/2012 | Kucklick | |
| 8,241,299 B2 | 8/2012 | Hibner | |
| 8,246,575 B2 | 8/2012 | Viola | |
| 8,257,257 B2 | 9/2012 | Takizawa et al. | |
| 8,298,161 B2 | 10/2012 | Vargas | |
| 8,361,090 B2 * | 1/2013 | Belson | A61B 1/31 606/150 |
| 8,366,606 B2 | 2/2013 | Watanabe et al. | |
| 8,388,519 B2 | 3/2013 | Garcia et al. | |
| 8,439,825 B2 | 5/2013 | Sekiguchi | |
| 8,460,179 B2 | 6/2013 | Ikeda et al. | |
| 8,485,968 B2 | 7/2013 | Weimer et al. | |
| 8,496,648 B2 | 7/2013 | Rogers | |
| 8,506,479 B2 | 8/2013 | Piskun et al. | |
| 8,517,923 B2 * | 8/2013 | Belson | A61B 1/0053 600/146 |
| 8,545,491 B2 | 10/2013 | Abboud et al. | |
| 8,550,989 B2 | 10/2013 | Dohi et al. | |
| 8,556,804 B2 | 10/2013 | Smith et al. | |
| 8,663,096 B2 | 3/2014 | Viola | |
| 8,663,196 B2 * | 3/2014 | Kassab | A61M 25/0053 604/523 |
| 8,708,894 B2 | 4/2014 | Smith et al. | |
| 8,721,530 B2 | 5/2014 | Ohline et al. | |
| 8,753,312 B2 | 6/2014 | Bowe et al. | |
| 8,920,369 B2 | 12/2014 | Salahieh et al. | |
| 8,969,639 B2 | 3/2015 | Xu et al. | |
| 9,011,318 B2 | 4/2015 | Choset et al. | |
| 9,066,655 B2 | 6/2015 | Stefanchik et al. | |
| 9,125,653 B2 | 9/2015 | Kovach | |
| 9,155,451 B2 | 10/2015 | Smith et al. | |
| 9,192,284 B2 | 11/2015 | Hirsch et al. | |
| 9,192,288 B2 | 11/2015 | Okaniwa | |
| 9,211,140 B2 | 12/2015 | Lauryssen et al. | |
| 9,220,398 B2 | 12/2015 | Woodley et al. | |
| 9,226,825 B2 | 1/2016 | Starksen et al. | |
| 9,241,611 B2 | 1/2016 | Konno | |
| 9,254,123 B2 | 2/2016 | Alvarez et al. | |
| 9,295,511 B2 | 3/2016 | Smith et al. | |
| 9,358,073 B2 | 6/2016 | Piligian et al. | |
| 9,364,955 B2 | 6/2016 | Oyola et al. | |
| 9,386,910 B2 | 7/2016 | West | |
| 9,498,108 B1 | 11/2016 | Lombardi | |
| 9,498,198 B2 | 11/2016 | Hu et al. | |
| 9,505,125 B2 | 11/2016 | Zubiate et al. | |
| 9,585,546 B2 | 3/2017 | Surti et al. | |
| 9,610,068 B2 | 4/2017 | Kappel et al. | |
| 9,763,562 B2 | 9/2017 | Avitsian et al. | |
| 9,814,372 B2 * | 11/2017 | Smith | A61B 1/00154 |
| 9,913,570 B2 | 3/2018 | Kucharski et al. | |
| 9,937,324 B2 | 4/2018 | Kim et al. | |
| 10,092,291 B2 | 10/2018 | Voegele et al. | |
| 10,307,042 B2 | 6/2019 | Lombardi | |
| 10,463,495 B2 | 11/2019 | Rogers et al. | |
| 2002/0107478 A1 * | 8/2002 | Wendlandt | A61B 1/018 604/95.01 |
| 2003/0023259 A1 | 1/2003 | Dubrul et al. | |
| 2003/0083546 A1 * | 5/2003 | Butler | A61B 1/00082 600/114 |
| 2003/0153866 A1 | 8/2003 | Long et al. | |
| 2003/0208220 A1 | 11/2003 | Worley et al. | |
| 2003/0216691 A1 | 11/2003 | Jacobson | |
| 2004/0019252 A1 | 1/2004 | Hirata | |
| 2004/0044350 A1 | 3/2004 | Martin et al. | |
| 2004/0092960 A1 | 5/2004 | Abrams et al. | |
| 2004/0186349 A1 | 9/2004 | Ewers et al. | |
| 2004/0186350 A1 | 9/2004 | Brenneman et al. | |
| 2004/0243227 A1 | 12/2004 | Starksen et al. | |
| 2004/0260236 A1 | 12/2004 | Manning et al. | |
| 2005/0085829 A1 * | 4/2005 | Kraemer | A61B 17/07207 606/142 |
| 2005/0165275 A1 | 7/2005 | Von Felten et al. | |
| 2005/0203340 A1 | 9/2005 | Butler et al. | |
| 2005/0272974 A1 | 12/2005 | Iddan | |
| 2005/0277966 A1 | 12/2005 | Ewers et al. | |
| 2006/0041188 A1 | 2/2006 | Dirusso et al. | |
| 2006/0047183 A1 | 3/2006 | Park | |
| 2006/0058582 A1 | 3/2006 | Maahs et al. | |
| 2006/0129130 A1 | 6/2006 | Tal et al. | |
| 2006/0192465 A1 | 8/2006 | Kornbluh et al. | |
| 2006/0258906 A1 | 11/2006 | Binmoeller | |
| 2006/0264707 A1 * | 11/2006 | Kinney | A61B 1/00151 600/115 |
| 2006/0287666 A1 | 12/2006 | Saadat et al. | |
| 2007/0015965 A1 * | 1/2007 | Cox | A61B 1/0052 600/114 |
| 2007/0038025 A1 | 2/2007 | Yoshida | |
| 2007/0088367 A1 | 4/2007 | Von Weymarn-Scharli | |
| 2007/0100414 A1 | 5/2007 | Licata et al. | |
| 2007/0106302 A1 | 5/2007 | Ortiz | |
| 2007/0118015 A1 | 5/2007 | Wendlandt | |
| 2007/0219411 A1 | 9/2007 | Dejima et al. | |
| 2067/0260121 A1 | 11/2007 | Bakos et al. | |
| 2008/0051635 A1 | 2/2008 | Tanaka et al. | |
| 2008/0058722 A1 | 3/2008 | Oepen et al. | |
| 2008/0091073 A1 | 4/2008 | Park | |
| 2008/0103440 A1 | 5/2008 | Ferren et al. | |
| 2008/0139887 A1 | 6/2008 | Fitzpatrick | |
| 2008/0172037 A1 | 7/2008 | Huang et al. | |
| 2008/0188928 A1 | 8/2008 | Salahieh et al. | |
| 2008/0200762 A1 | 8/2008 | Stokes et al. | |
| 2008/0214893 A1 | 9/2008 | Tartaglia et al. | |
| 2008/0234546 A1 | 9/2008 | Kawano et al. | |
| 2008/0242928 A1 | 10/2008 | Kawano et al. | |
| 2008/0262300 A1 | 10/2008 | Ewers et al. | |
| 2008/0275299 A1 | 11/2008 | Park | |
| 2009/0048483 A1 | 2/2009 | Yamamoto | |
| 2009/0062611 A1 | 3/2009 | Toyama | |
| 2009/0062837 A1 | 3/2009 | Gasche et al. | |
| 2009/0112063 A1 | 4/2009 | Bakos et al. | |
| 2009/0131752 A1 | 5/2009 | Park | |
| 2009/0157068 A1 * | 6/2009 | Kallel | A61B 18/1492 606/33 |
| 2009/0187163 A1 | 7/2009 | Uihlein | |
| 2009/0240202 A1 | 9/2009 | Drasler et al. | |
| 2009/0264704 A1 | 10/2009 | Shtul | |
| 2010/0010308 A1 * | 1/2010 | Braun | A61B 1/00142 600/121 |
| 2010/0016663 A1 | 1/2010 | Maisch et al. | |
| 2010/0069712 A1 | 3/2010 | Yamaya | |
| 2010/0076451 A1 | 3/2010 | Zwolinski et al. | |
| 2010/0087711 A1 | 4/2010 | Edwards | |
| 2010/0137686 A1 | 6/2010 | Meron et al. | |
| 2010/0145151 A1 | 6/2010 | Fukunaga et al. | |
| 2010/0160735 A1 | 6/2010 | Bakos | |
| 2010/0204546 A1 * | 8/2010 | Hassidov | A61B 1/053 600/114 |
| 2010/0268025 A1 | 10/2010 | Belson | |
| 2010/0331625 A1 | 12/2010 | Rosemurgy et al. | |
| 2010/0331820 A1 | 12/2010 | Prisco et al. | |
| 2011/0015729 A1 | 1/2011 | Jimenez et al. | |
| 2011/0040282 A1 | 2/2011 | Uihlein | |
| 2011/0046442 A1 | 2/2011 | Matsushita | |
| 2011/0049282 A1 | 3/2011 | Danielsson | |
| 2011/0054253 A1 | 3/2011 | Jordá Albiñana et al. | |
| 2011/0237888 A1 | 9/2011 | Matsushita | |
| 2011/0245611 A1 | 10/2011 | Yeh et al. | |
| 2011/0282149 A1 | 11/2011 | Vargas et al. | |
| 2011/0306950 A1 | 12/2011 | Cucin | |
| 2012/0022329 A1 | 1/2012 | Wagh et al. | |
| 2012/0041291 A1 | 2/2012 | Ferren et al. | |
| 2012/0108992 A1 | 5/2012 | Frassica et al. | |
| 2012/0130173 A1 | 5/2012 | Lutze et al. | |
| 2012/0143005 A1 | 6/2012 | Yeh et al. | |
| 2012/0165607 A1 | 6/2012 | Ashida et al. | |
| 2012/0165792 A1 | 6/2012 | Ortiz et al. | |
| 2012/0172651 A1 | 7/2012 | Cutrer | |
| 2012/0209062 A1 | 8/2012 | Qiao | |
| 2012/0277528 A1 | 11/2012 | Qiao | |
| 2013/0131641 A1 | 5/2013 | Jimenez et al. | |

(56) References Cited

U.S. PATENT DOCUMENTS

| | | |
|---|---|---|
| 2013/0190565 A1 | 7/2013 | Gora et al. |
| 2013/0338440 A1 | 12/2013 | Sinai et al. |
| 2014/0005683 A1 | 1/2014 | Stand et al. |
| 2014/0081169 A1 | 3/2014 | Gerding et al. |
| 2014/0088459 A1* | 3/2014 | Roush ............... A61M 25/0069 600/569 |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0243873 A1 | 8/2014 | Franklin |
| 2014/0275860 A1 | 9/2014 | Rottenberg et al. |
| 2014/0276642 A1 | 9/2014 | Cully et al. |
| 2014/0371764 A1 | 12/2014 | Oyola et al. |
| 2015/0073409 A1 | 3/2015 | Watson et al. |
| 2015/0094656 A1 | 4/2015 | Salahieh et al. |
| 2015/0133729 A1 | 5/2015 | Reydel |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1 | 8/2015 | Wittenberger et al. |
| 2015/0342608 A1 | 12/2015 | Hernandez |
| 2016/0007832 A1 | 1/2016 | Shimada |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1* | 7/2016 | Choi ..................... A61B 1/2736 600/115 |
| 2016/0270870 A1 | 9/2016 | Kowshik |
| 2016/0287059 A1* | 10/2016 | Ha ........................ A61M 29/02 |
| 2016/0324412 A1* | 11/2016 | Hassidov ............ A61B 1/00112 |
| 2017/0156567 A1 | 6/2017 | Kaneko |
| 2017/0157363 A1 | 6/2017 | Barrish et al. |
| 2018/0015257 A1 | 1/2018 | Krolik et al. |
| 2018/0184885 A1 | 7/2018 | St. George |
| 2018/0249893 A1* | 9/2018 | Yeung ................ A61B 1/00135 |
| 2018/0263469 A1 | 9/2018 | Okaniwa et al. |
| 2018/0361116 A1 | 12/2018 | Quick et al. |
| 2021/0137366 A1 | 5/2021 | Tilson et al. |
| 2021/0138187 A1 | 5/2021 | Tilson et al. |

FOREIGN PATENT DOCUMENTS

| | | | |
|---|---|---|---|
| CN | 101129255 A | | 2/2008 |
| CN | 201899767 U | | 7/2011 |
| CN | 104287684 B | | 3/2016 |
| DE | 102005039601 A1 | | 2/2007 |
| EP | 401129 A1 | | 12/1990 |
| EP | 1662972 A2 | | 6/2006 |
| EP | 1695657 A1 | | 8/2006 |
| EP | 1487318 B1 | | 3/2008 |
| EP | 2016914 A2 | | 1/2009 |
| EP | 1499227 B1 | | 10/2010 |
| EP | 2364637 A1 * | 9/2011 | ......... A61B 1/00082 |
| EP | 2368481 A1 | | 9/2011 |
| EP | 2368483 A1 | | 9/2011 |
| EP | 3256052 A1 | | 12/2017 |
| JP | H05293077 A | | 11/1993 |
| JP | 2002125921 A | | 5/2002 |
| JP | 2905152300 A | | 6/2005 |
| JP | 03965108 B2 | | 8/2007 |
| KR | 10-2015-0131502 A | | 11/2015 |
| WO | WO97/43941 A1 | | 11/1997 |
| WO | WO99/053827 A1 | | 10/1999 |
| WO | WO03/013348 A1 | | 2/2003 |
| WO | WO2007/035931 A2 | | 3/2007 |
| WO | WO2008/041809 A1 | | 4/2008 |
| WO | WO2008/122997 A1 | | 10/2008 |
| WO | WO2011/018147 A1 | | 2/2011 |
| WO | WO2011/018157 A1 | | 2/2011 |
| WO | WO2011/148172 A2 | | 12/2011 |
| WO | WO-2012054480 A2 * | 4/2012 | ......... A61M 25/0069 |
| WO | WO2012/080947 A1 | | 6/2012 |
| WO | WO2017/041052 A1 | | 3/2017 |
| WO | WO2018/035452 | | 8/2017 |

OTHER PUBLICATIONS

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; 2011.

Loeve et al.; Endoscope Shaft-Rigidity Control Mechanism: "FORGUIDE"; IEEE Trans. on Biomed. Eng.; 59(2); pp. 542-551; Feb. 2012.

Valdastri et al.; Advanced Technologies for Gastrointestinal Endoscopy; Annu. Rev. Biomed. Eng.; 14; pp. 397-429; May 2012.

Tilson et al.; U.S. Appl. No. 16/325,497 entitled "Device and method for enhanced visualization of the small intestine," filed Feb. 14, 2019.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Zhao et al.; Development of a variable stiffness over tube based on low-melting-point-alloy for endoscopic surgery; J. Med. Devices; 10(2); 8 pages; May 12, 2016.

Tilson et al.; U.S. Appl. No. 16/631,473 entitled "Dynamically rigidizing overtube," filed Jan. 16, 2020.

Loeve et al.; Vacuum packed particles as flexible endoscope guides with controllable rigidity; Granular Matter; 12(6); pp. 543-554; Jun. 24, 2010.

* cited by examiner

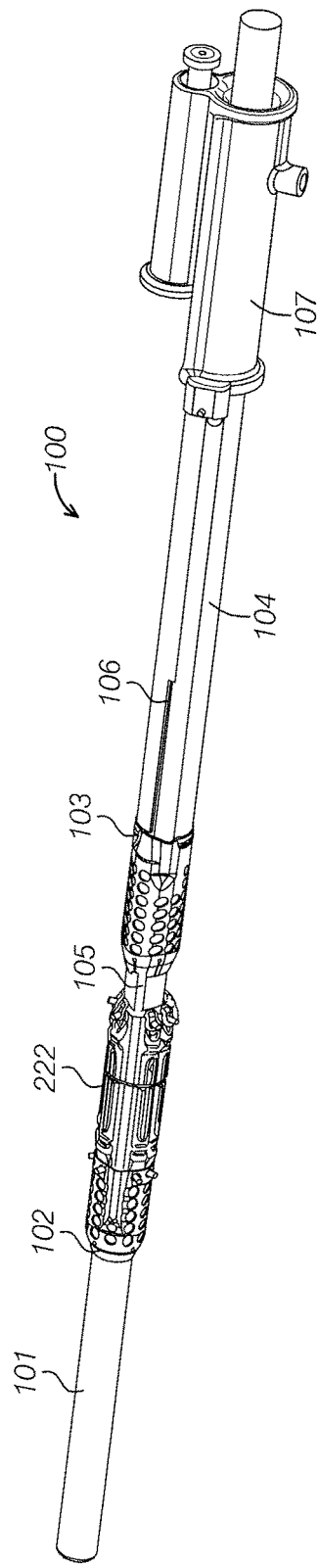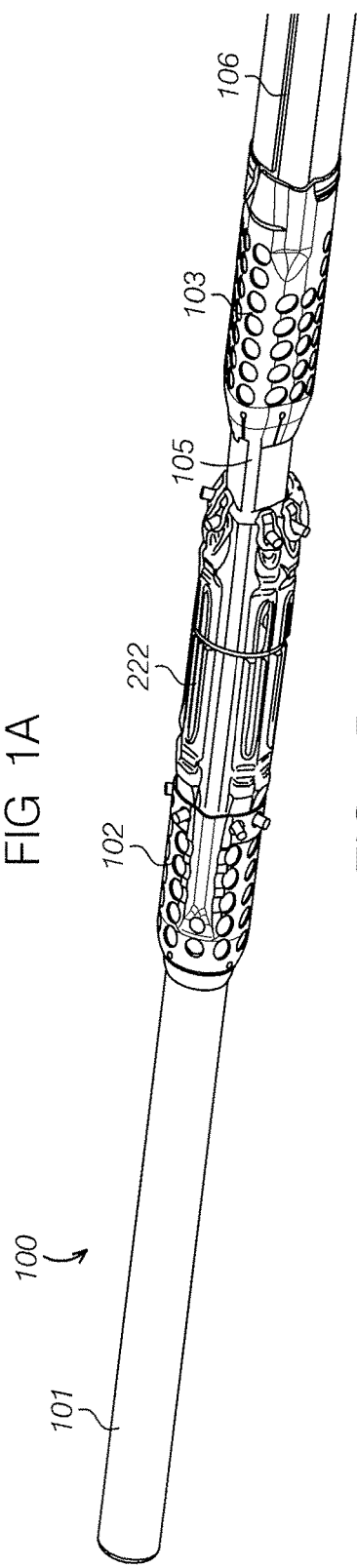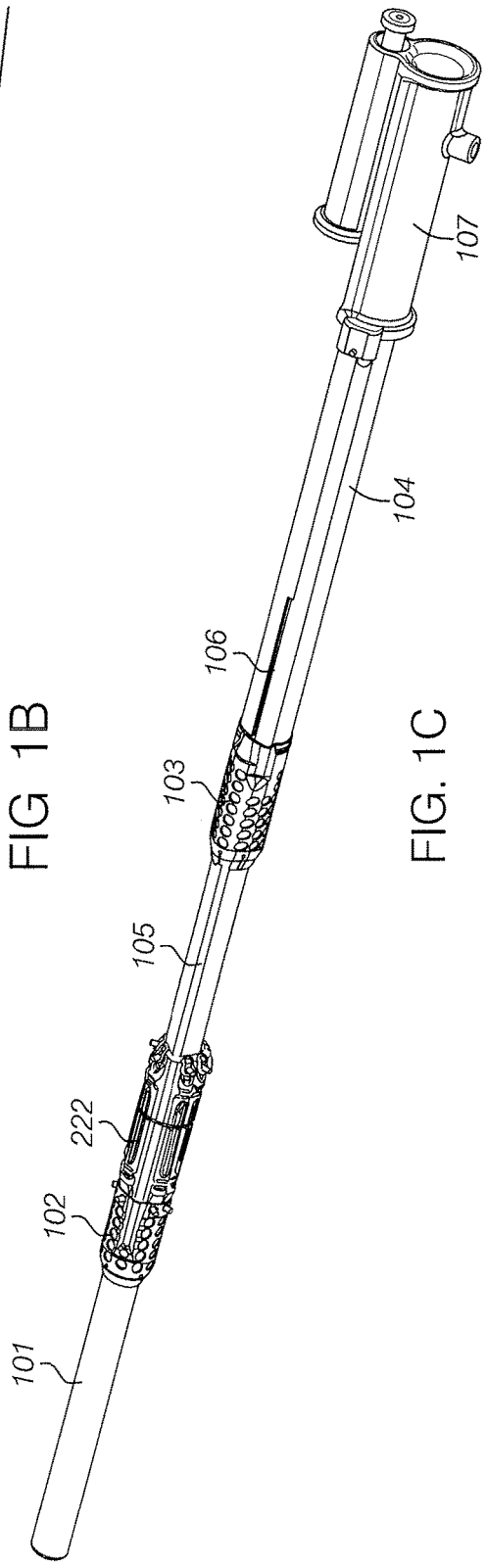

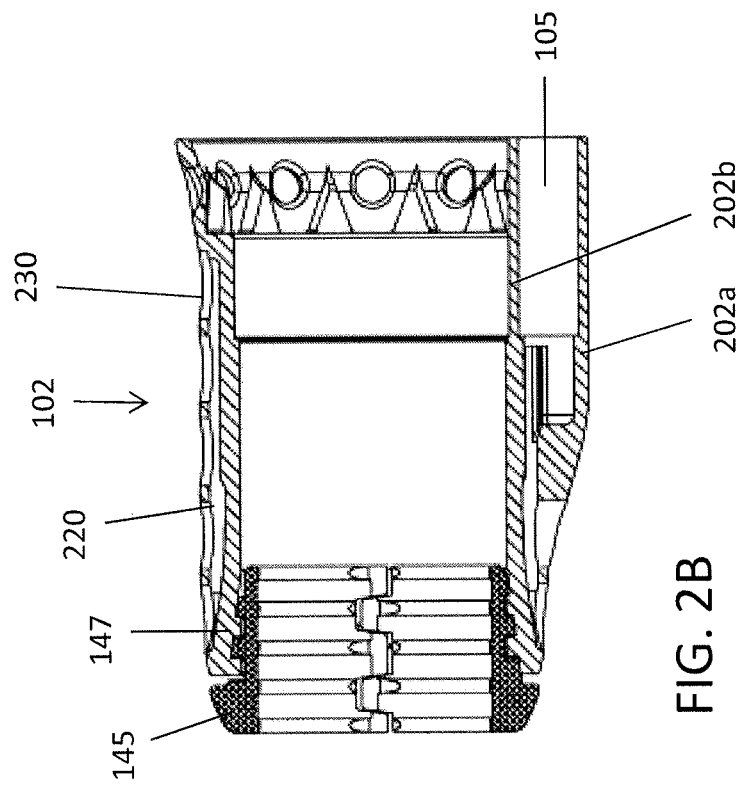
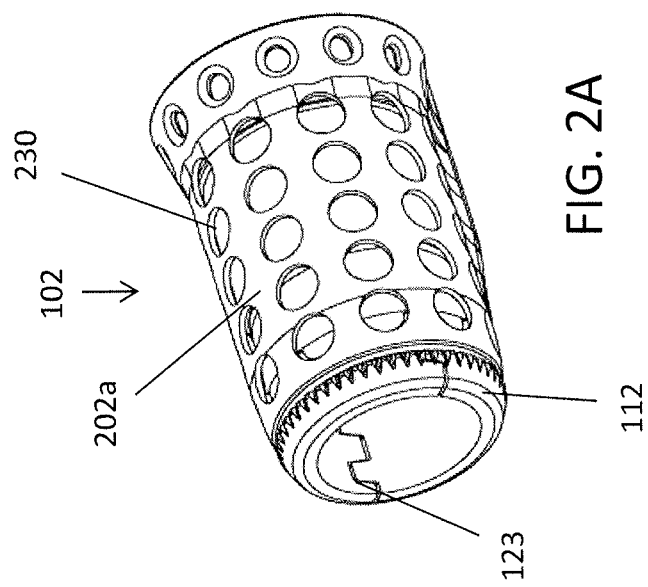
FIG. 2B
FIG. 2A

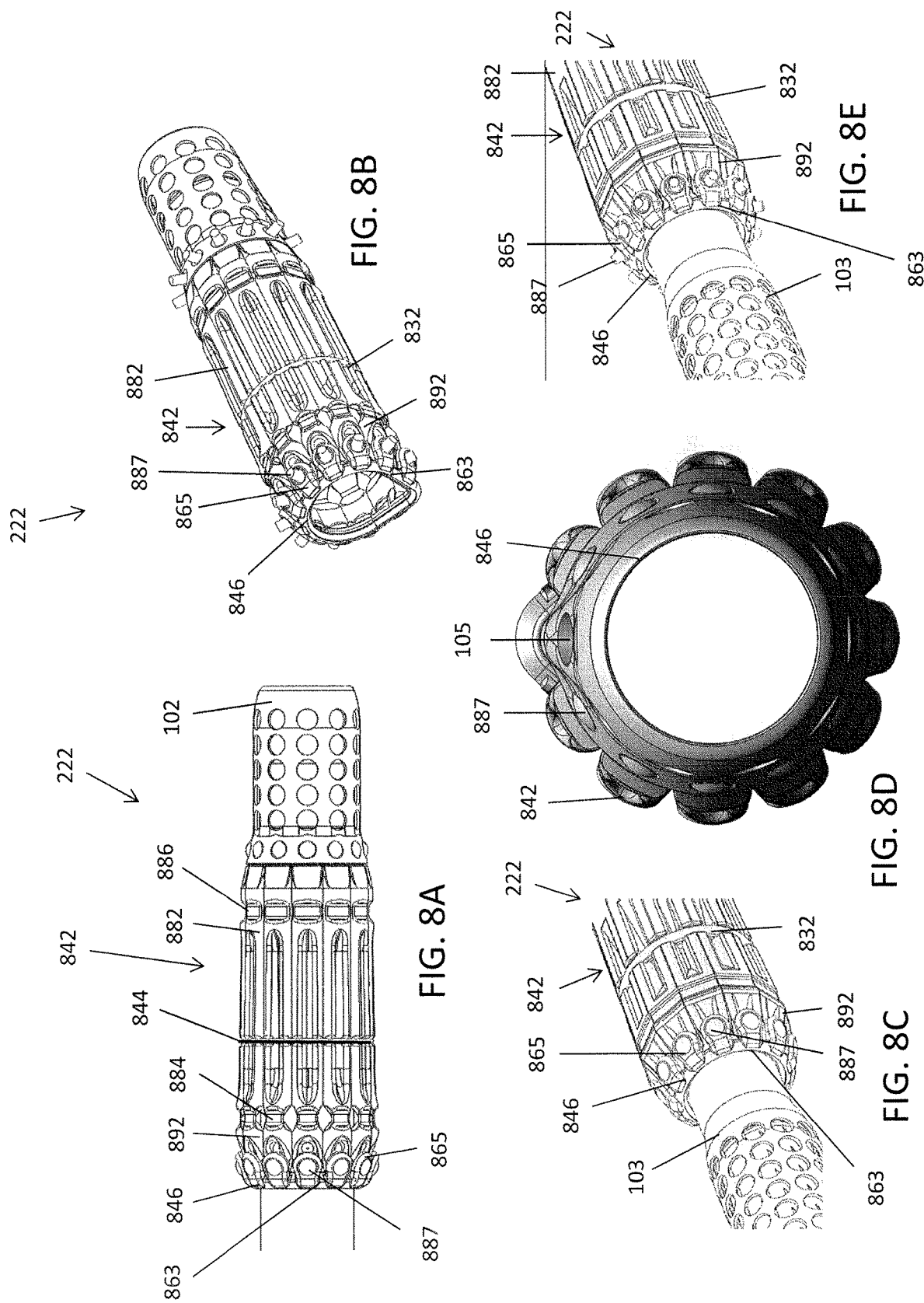

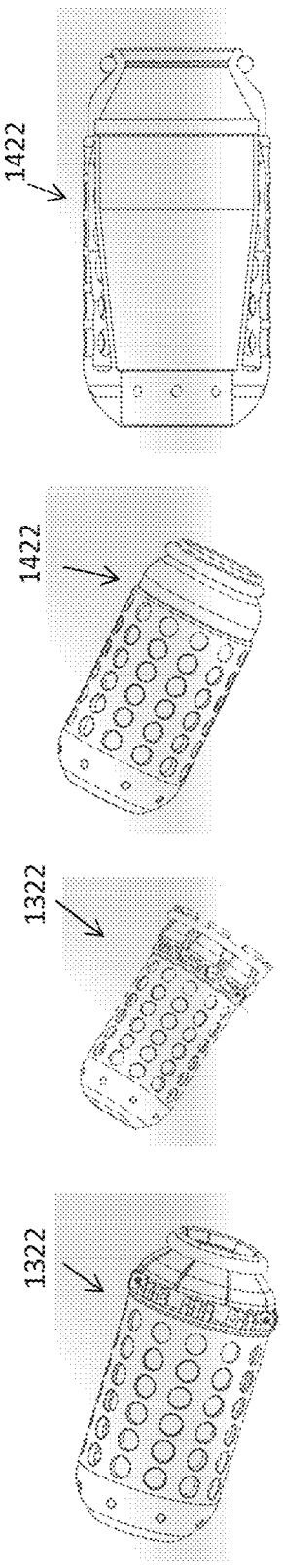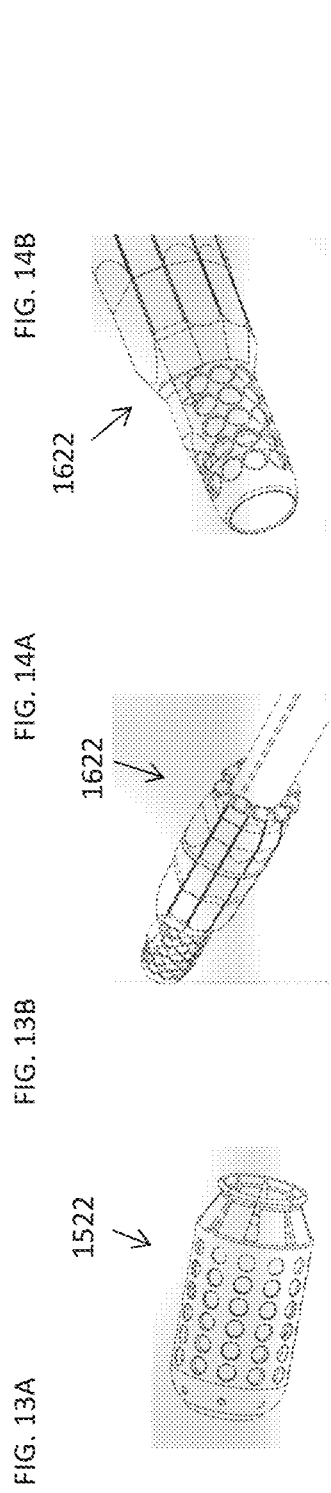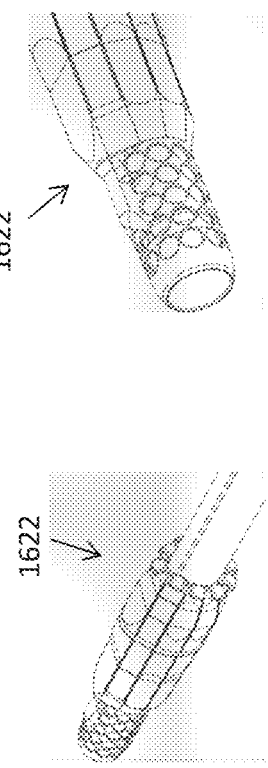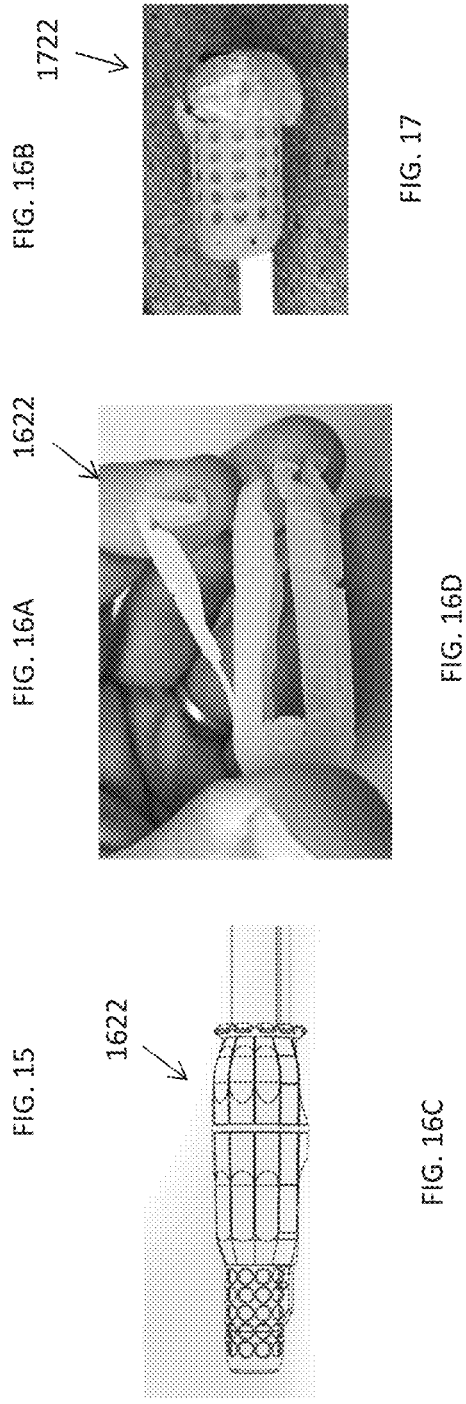

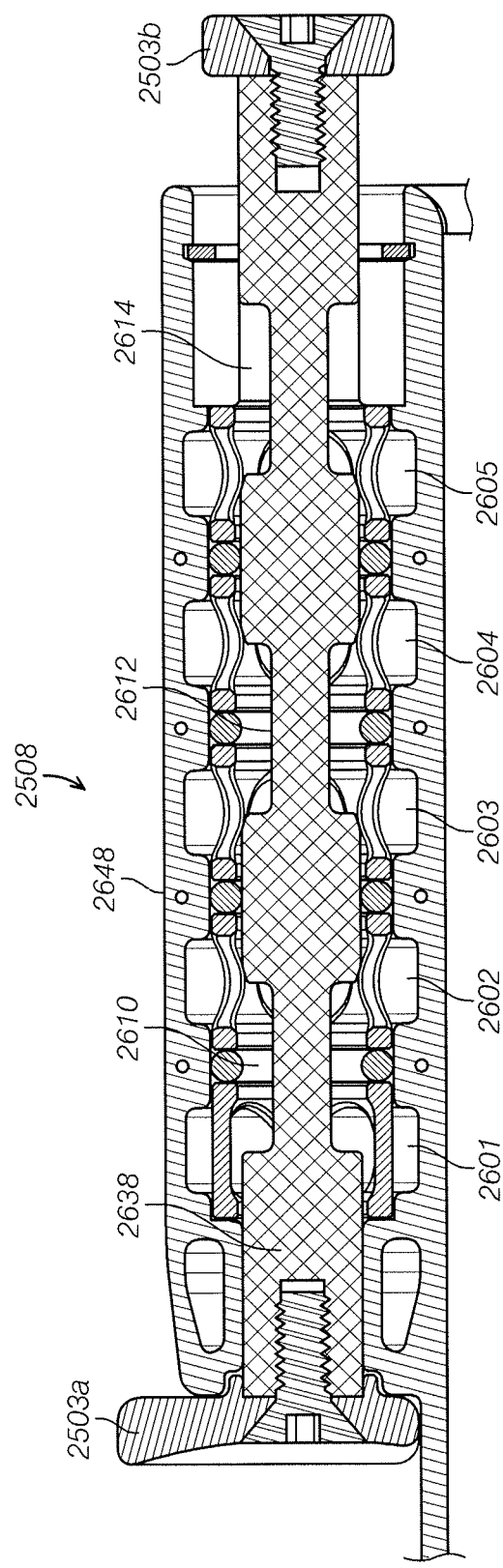
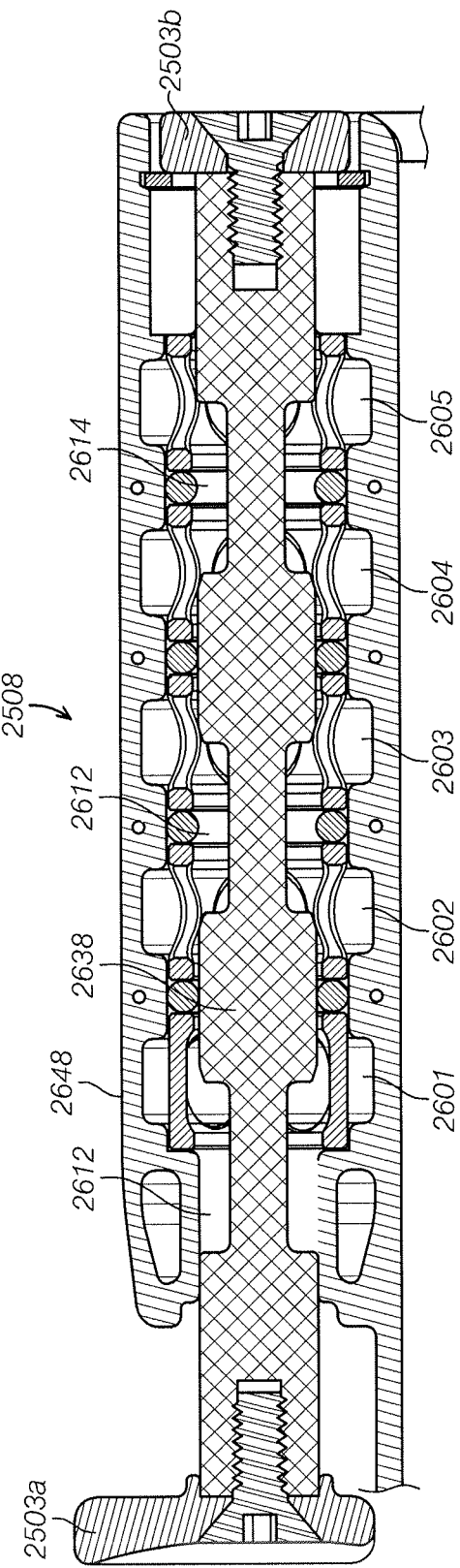

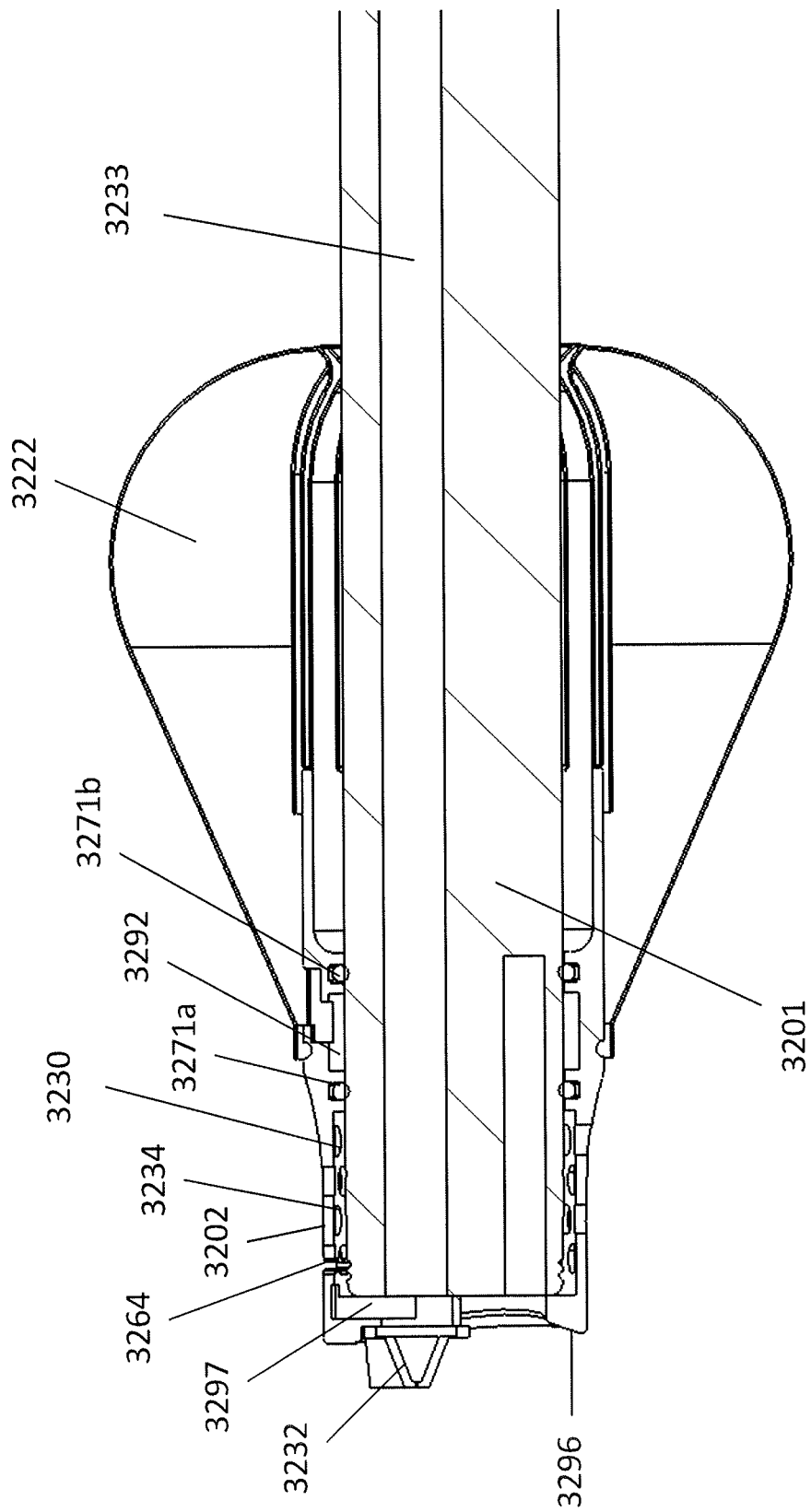

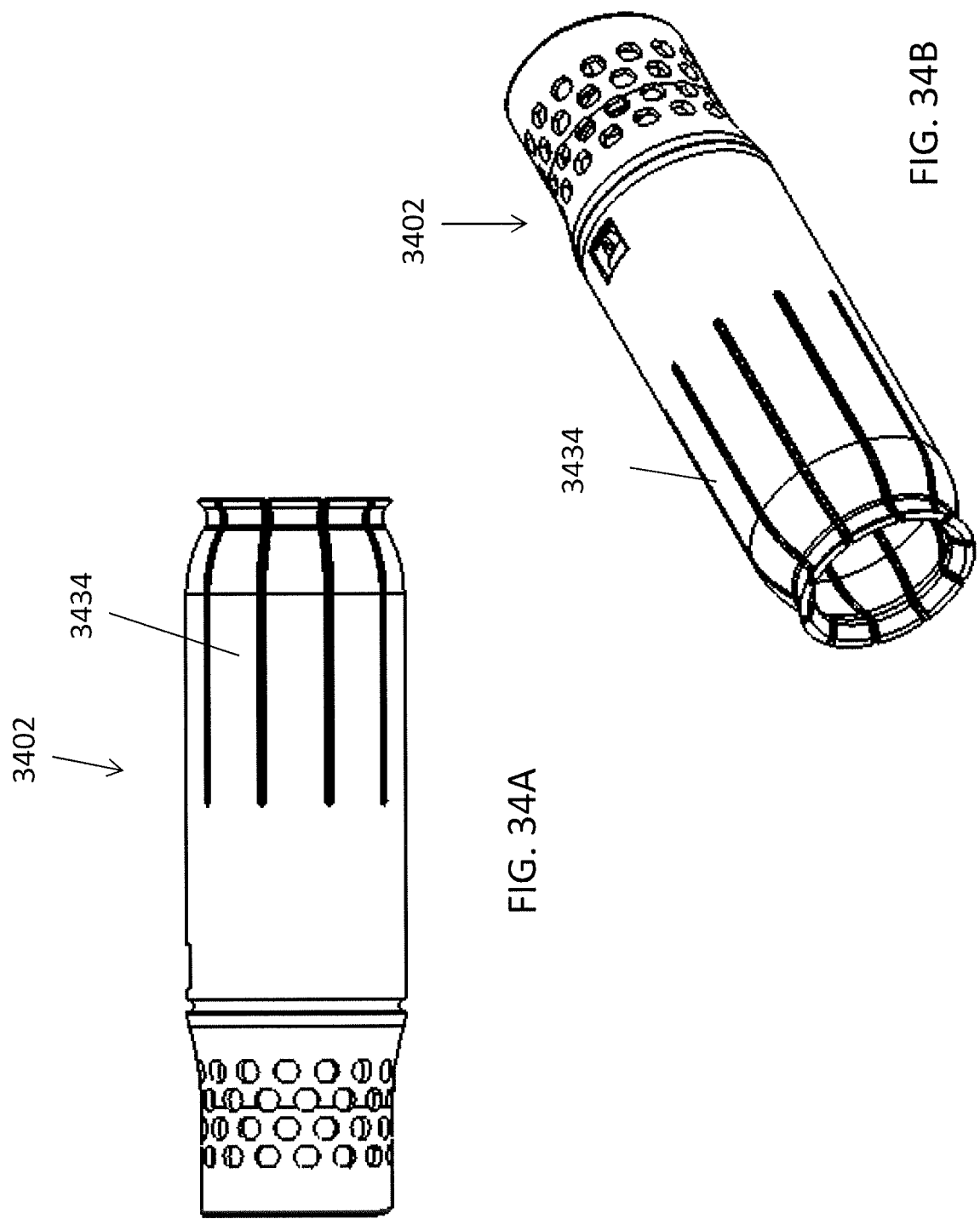

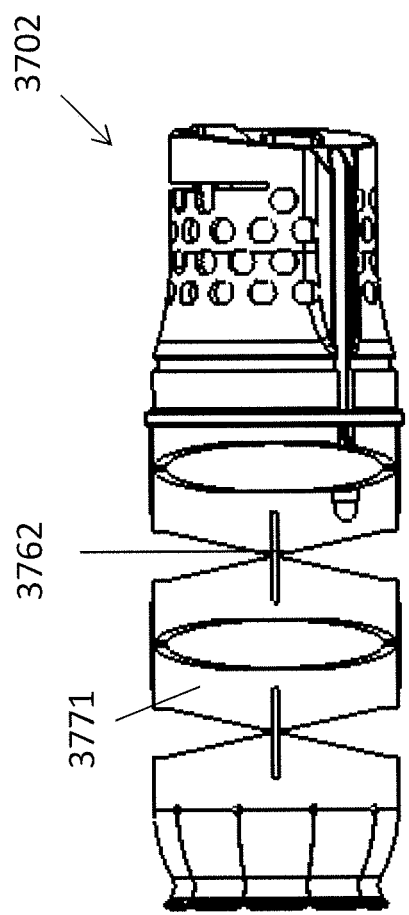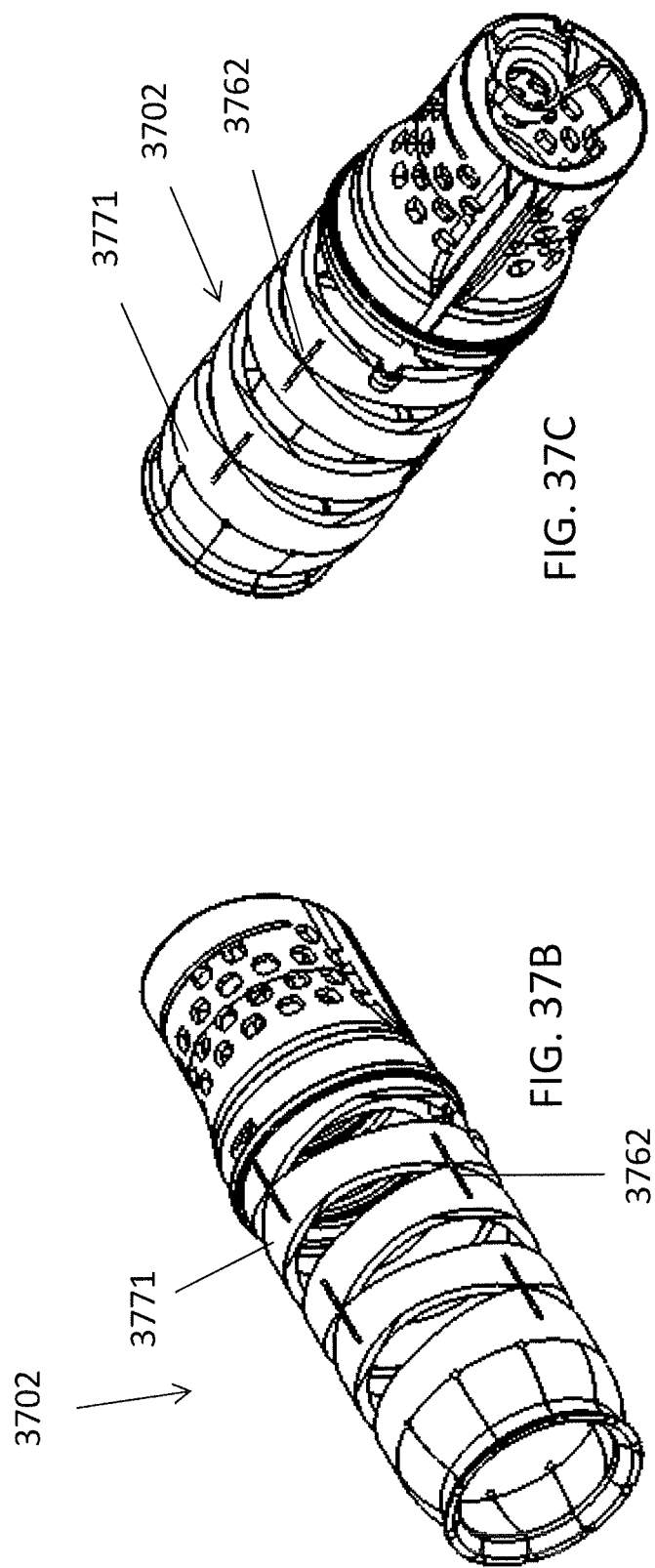
FIG. 37A
FIG. 37B
FIG. 37C

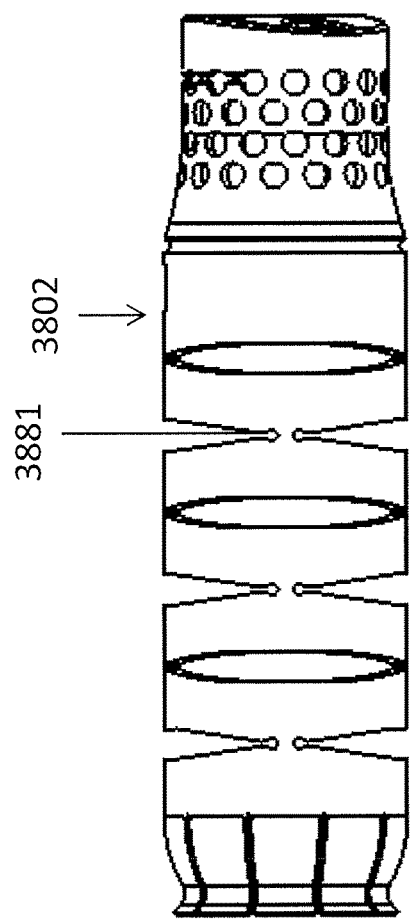
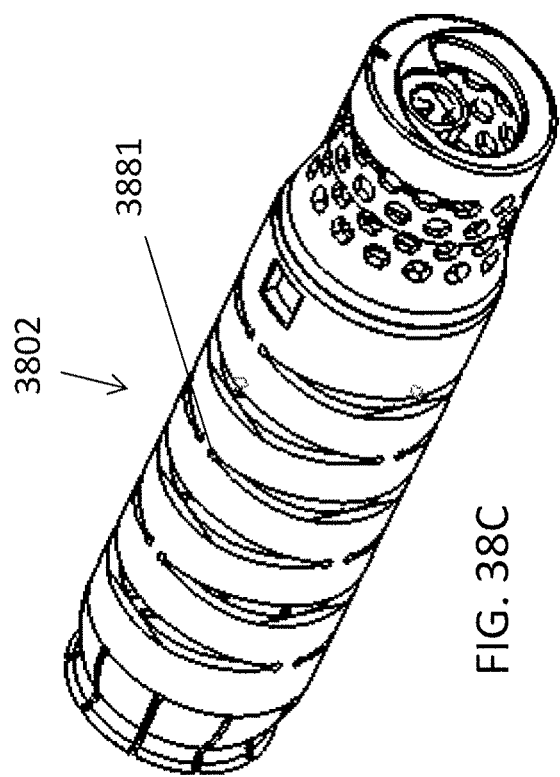
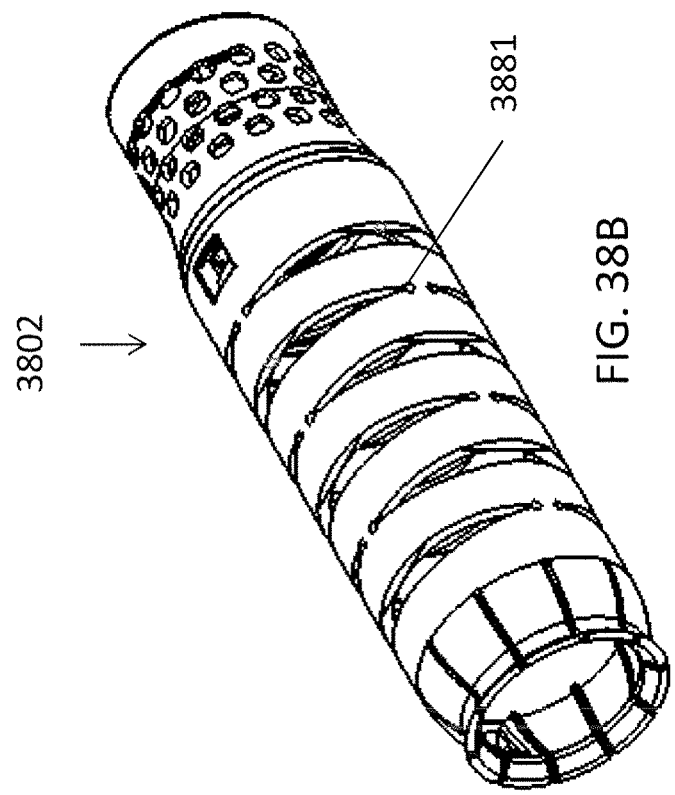
FIG. 38A
FIG. 38C
FIG. 38B

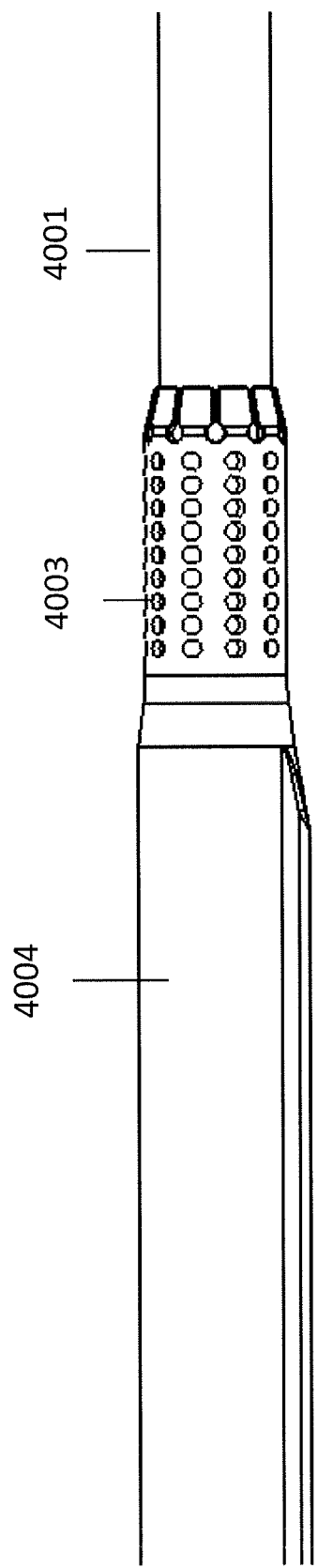

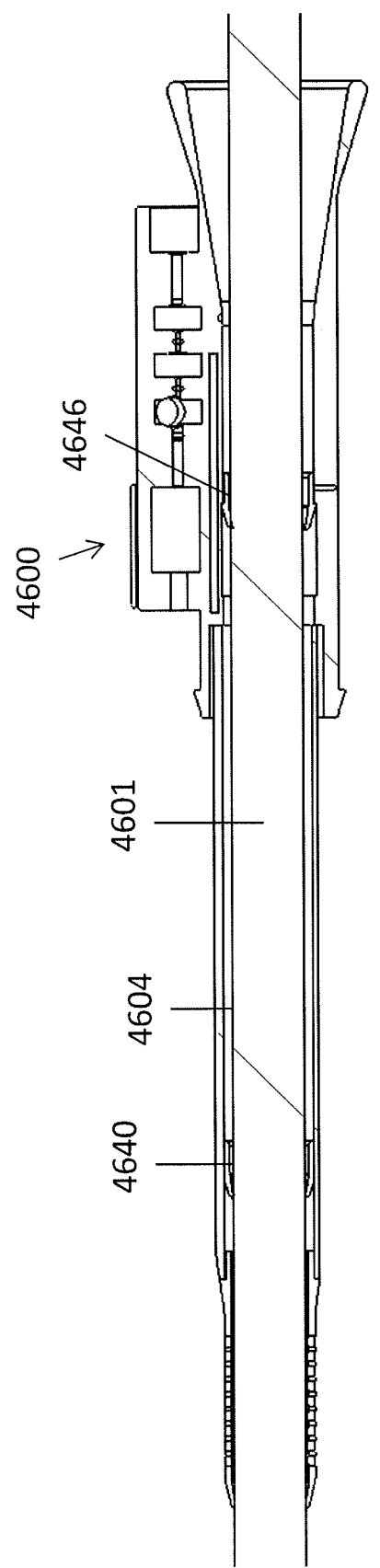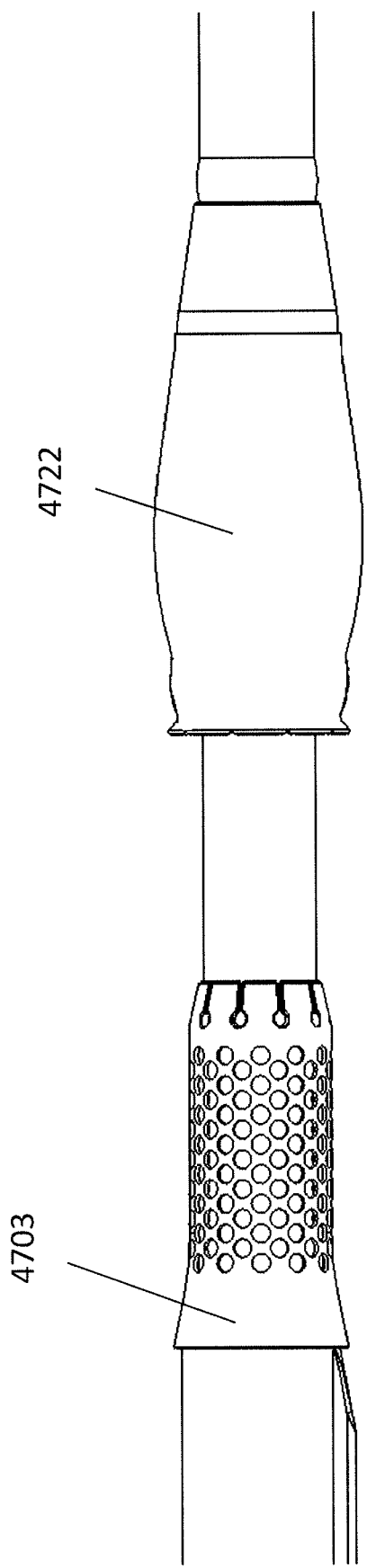

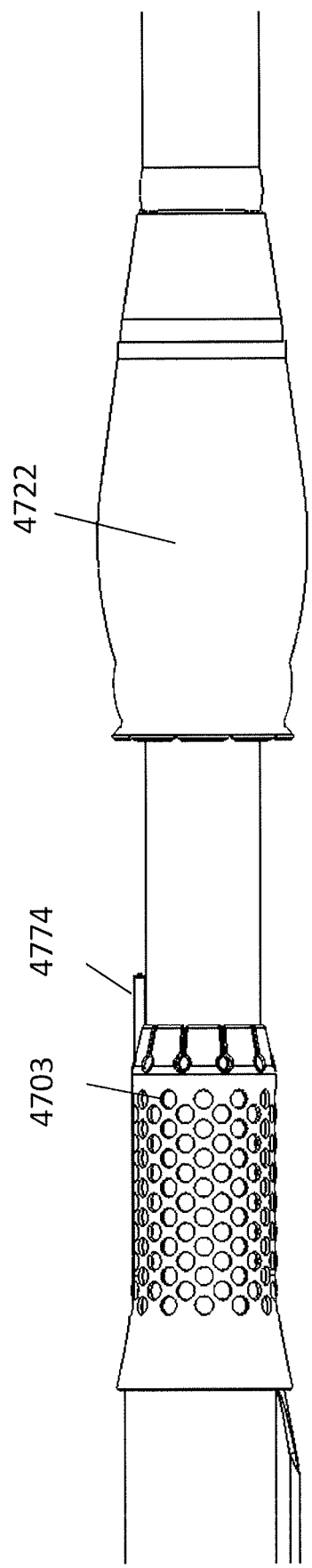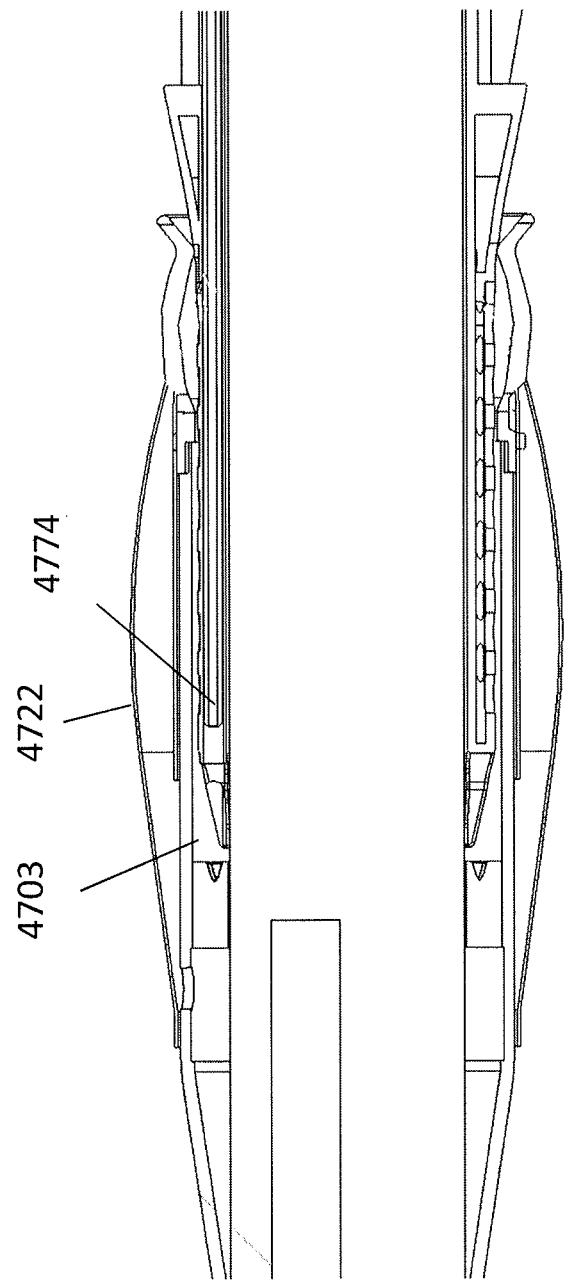

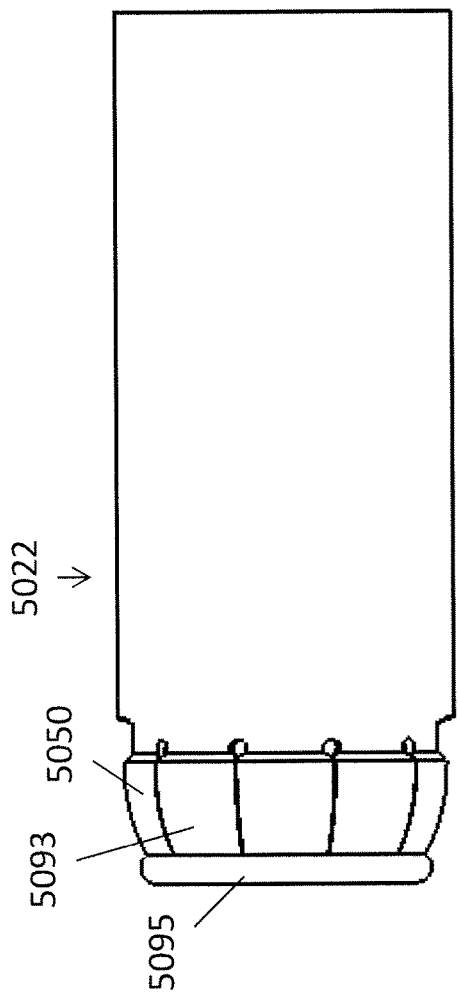
FIG. 50A
FIG. 50B
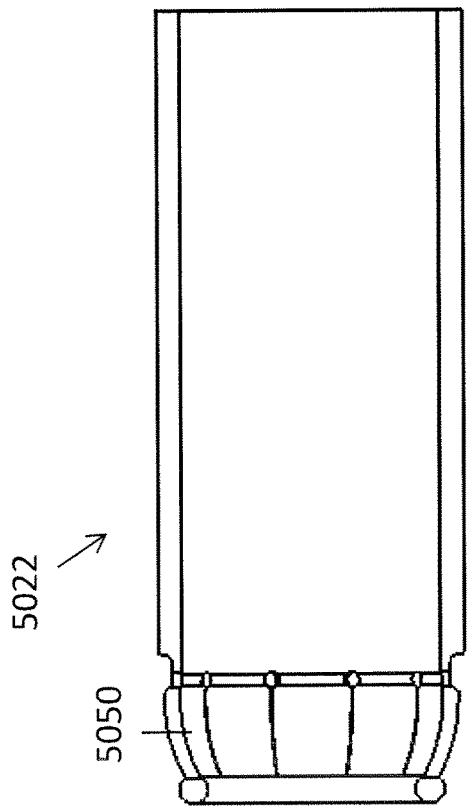
FIG. 50C
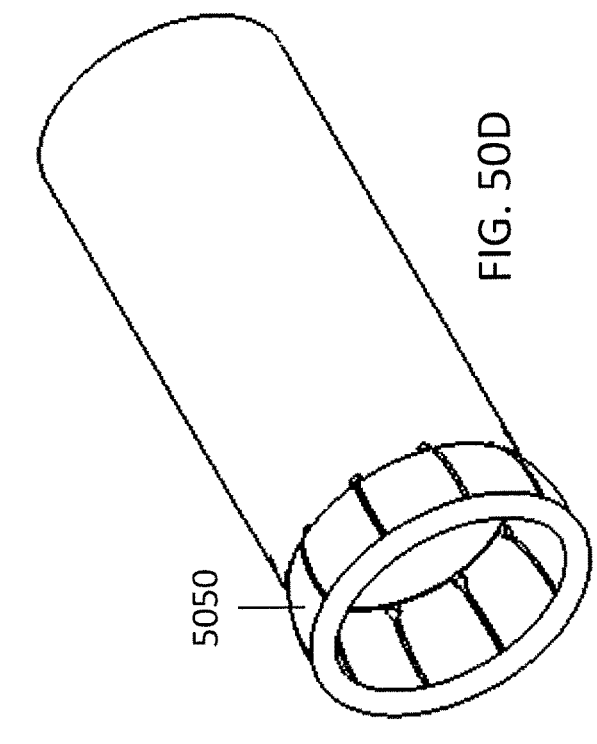
FIG. 50D

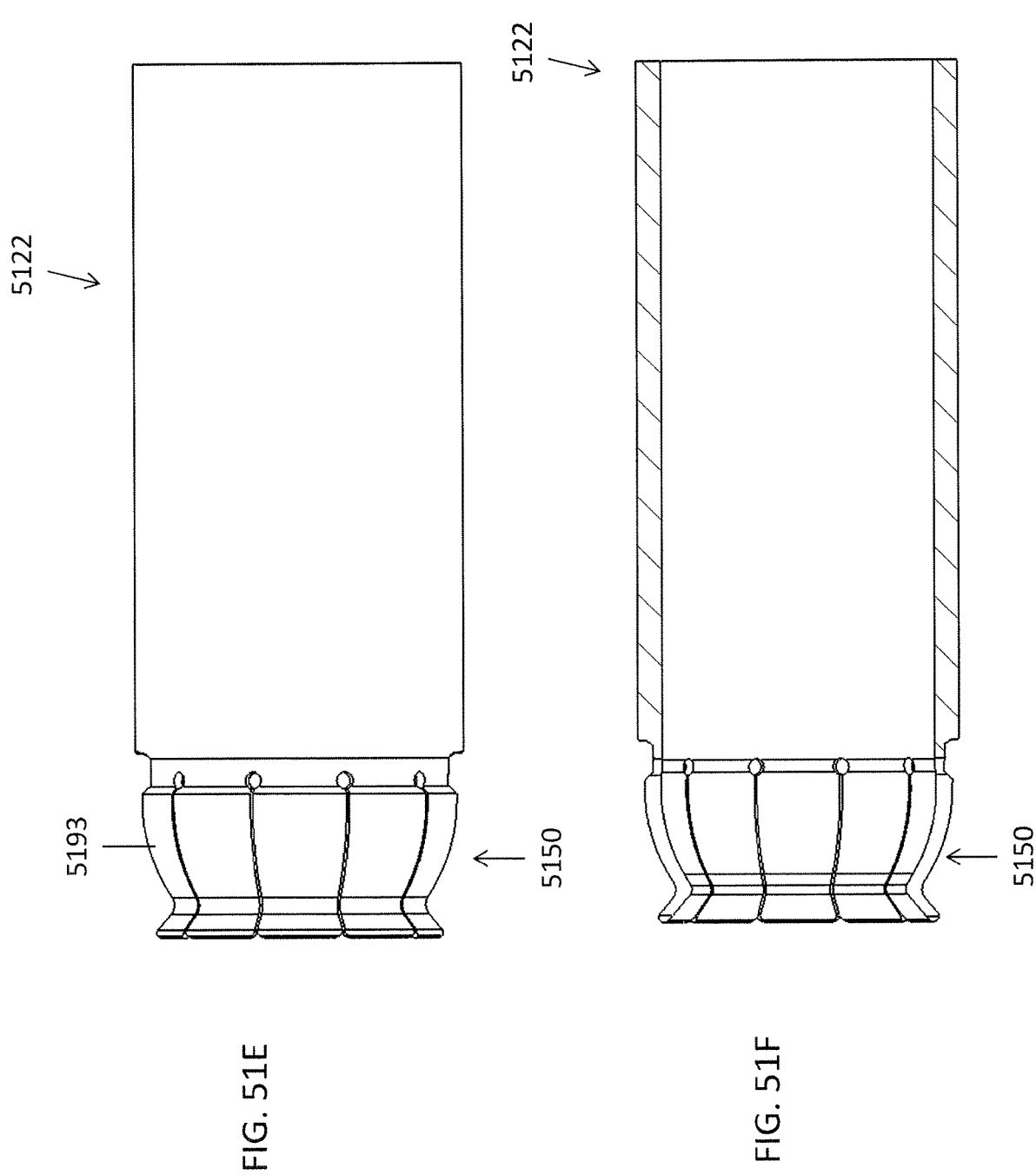

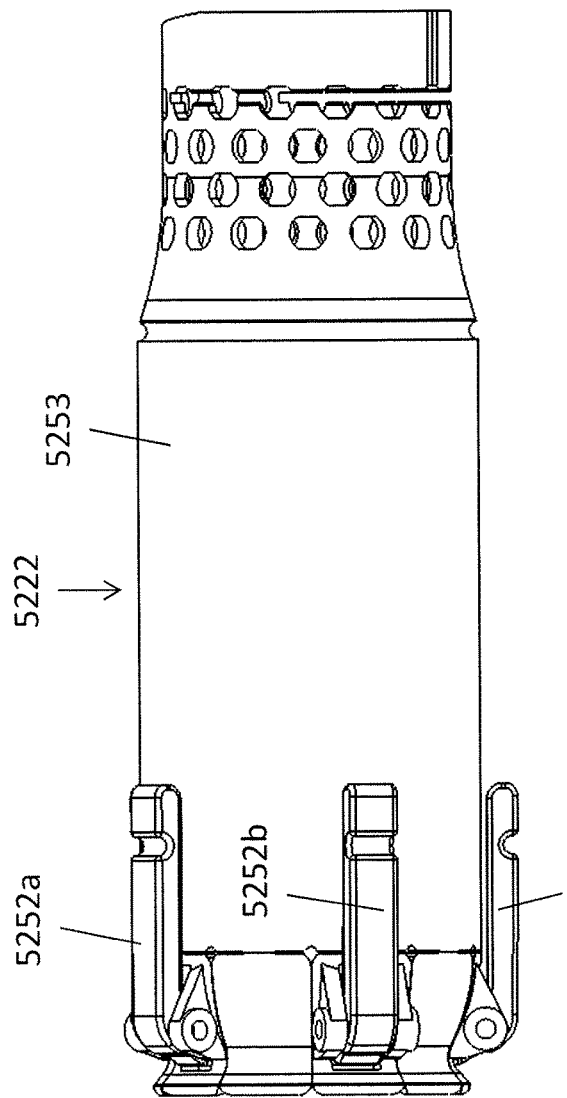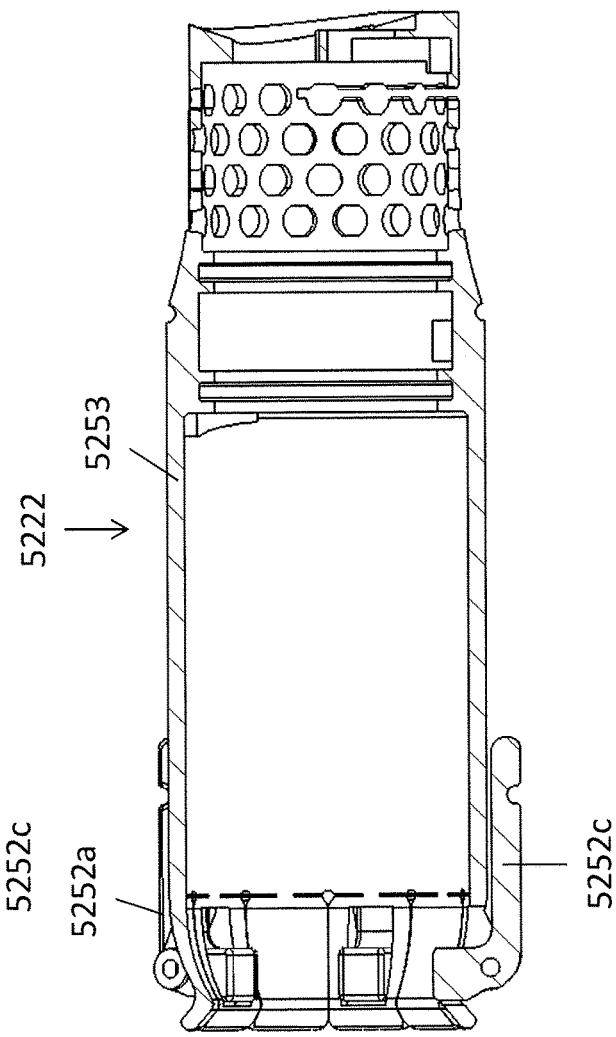
FIG. 52B
FIG 52C

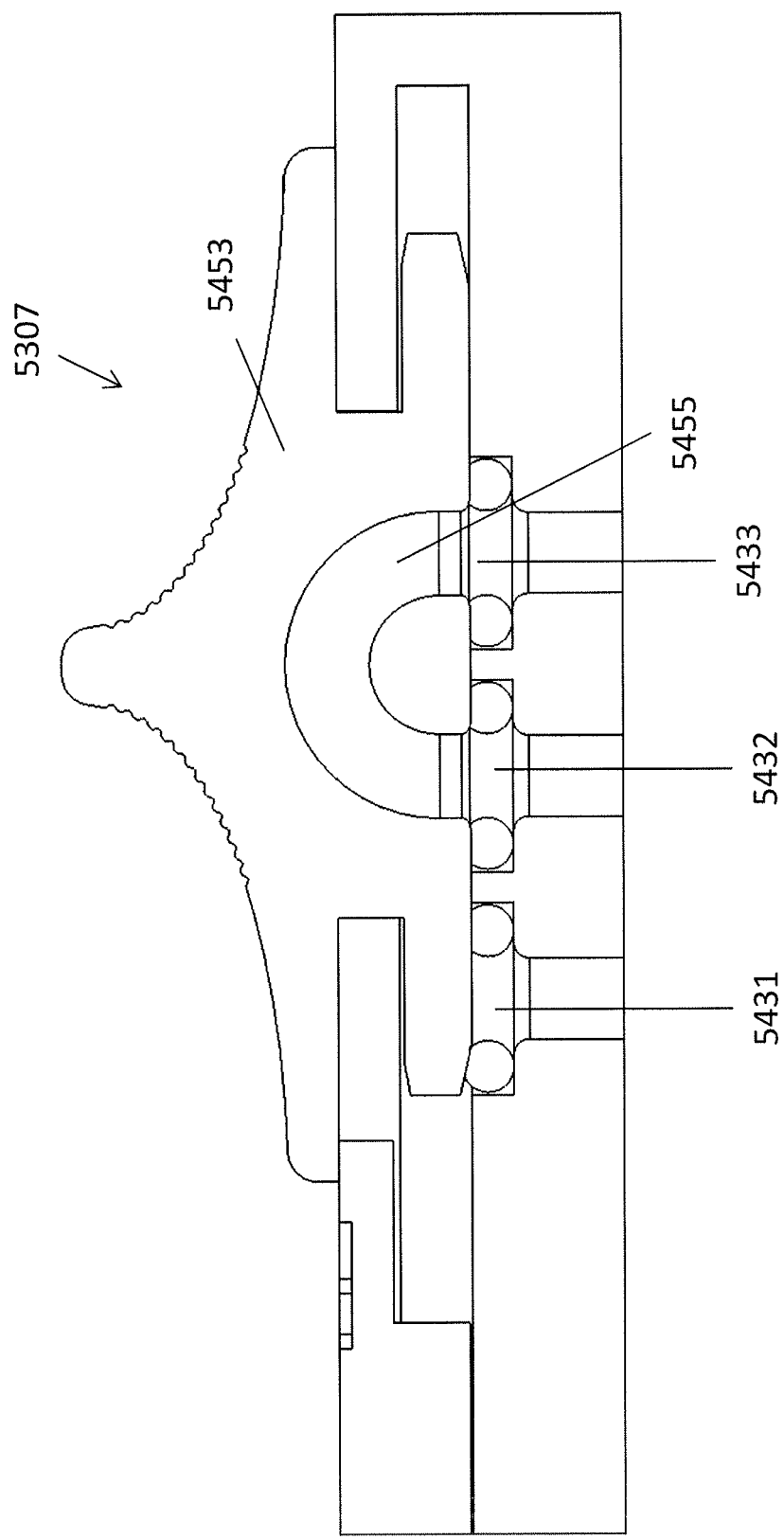

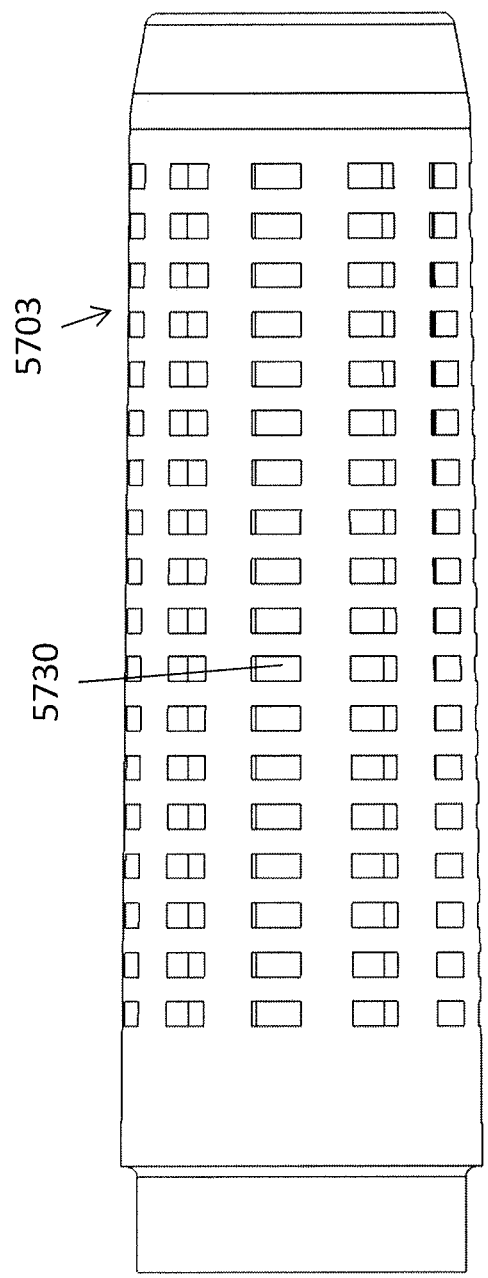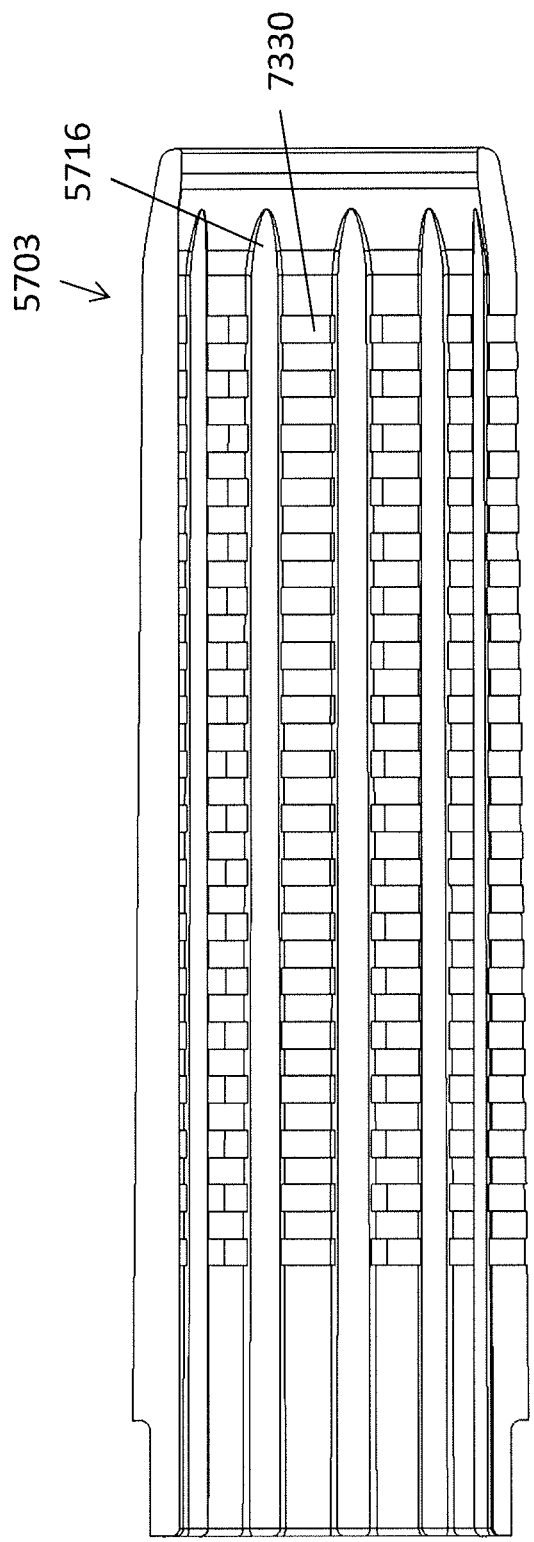
FIG. 57B
FIG. 57C

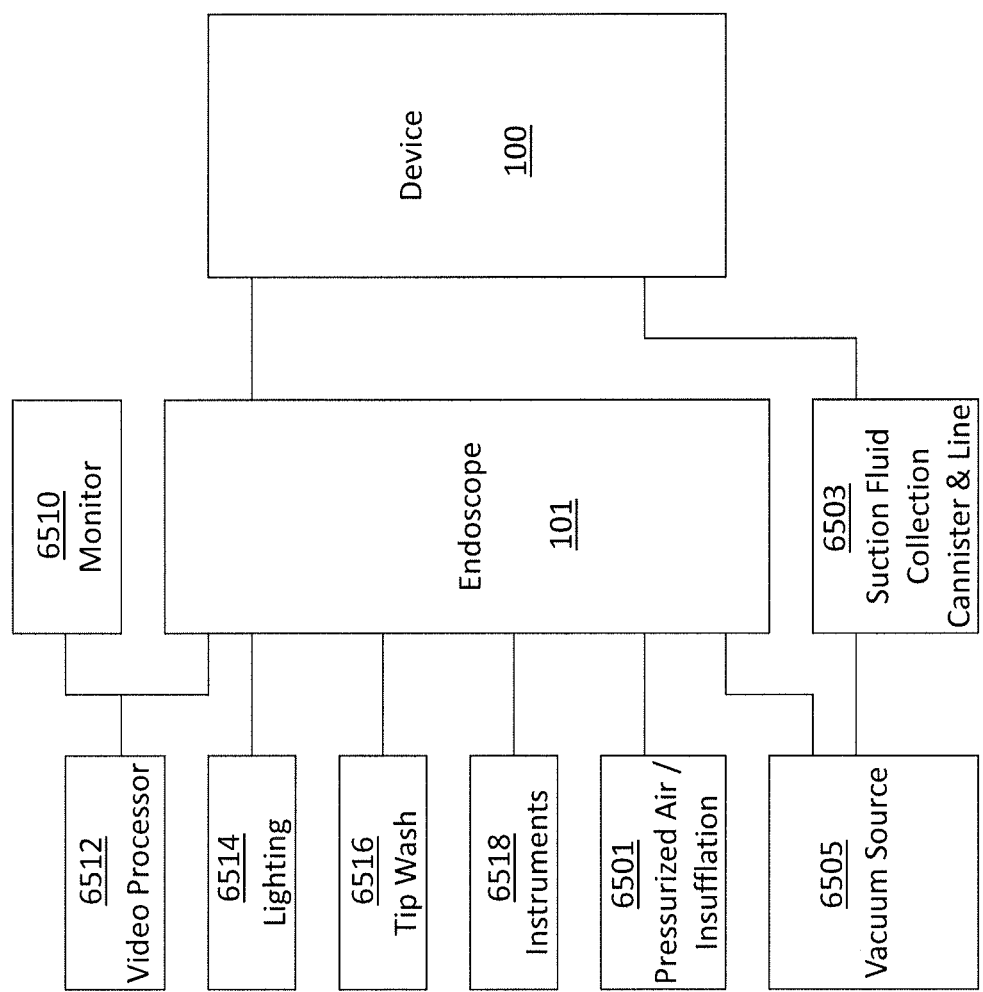

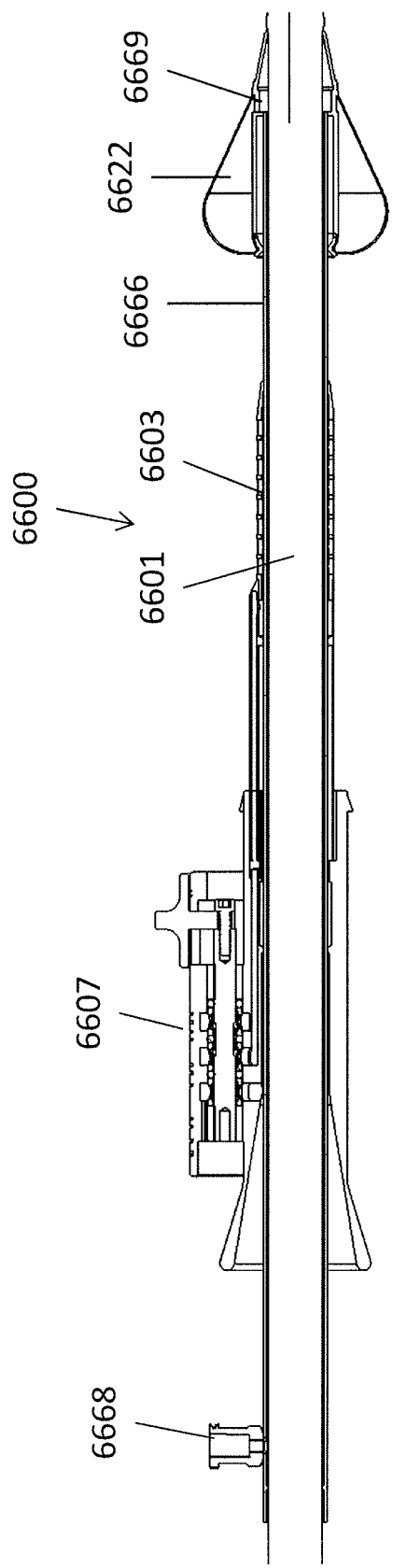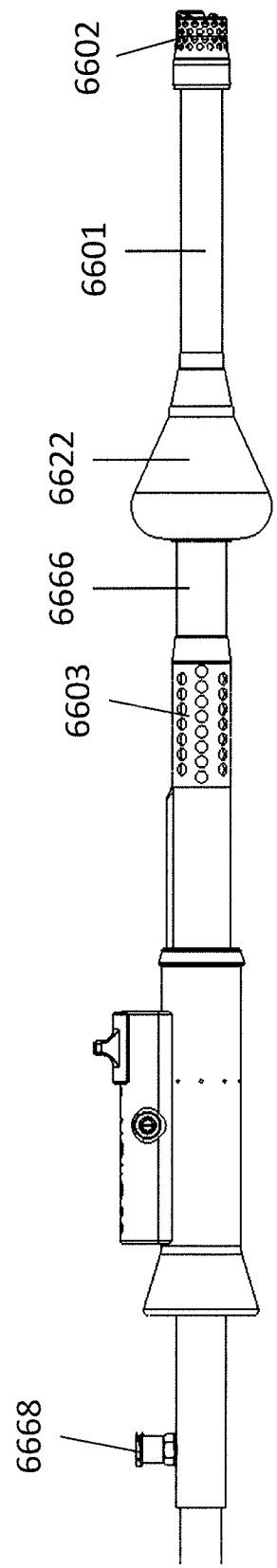
FIG. 66A
FIG. 66B

DEVICE FOR ENDOSCOPIC ADVANCEMENT THROUGH THE SMALL INTESTINE

CROSS REFERENCE TO RELATED APPLICATIONS

This application claims priority to U.S. Provisional Application No. 62/213,908, titled "DEVICE FOR ENDOSCOPIC ADVANCEMENT THROUGH THE SMALL INTESTINE," and filed Sep. 3, 2015, and to U.S. Provisional No. 62/339,593, titled "DEVICE FOR ENDOSCOPIC ADVANCEMENT THROUGH THE SMALL INTESTINE," and filed May 20, 2016, both of which are incorporated by reference herein in their entireties.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Endoscopic insertion into the small intestine is important, for example, for retrieving foreign bodies, obtaining biopsies, removing small intestinal tumors or polyps, diagnosing Chrohn's Disease, performing hemostatis of ulcers, adenomas, arteriovenous malformations, or other GI bleeding, marking for surgeries of the small intestine. However, current endoscopic procedures cannot quickly and reliably advance through the small intestine.

One system for advancing through the small intestine is the FujiFilm Double Balloon ('DB') system, which is used as an adjunct to an endoscope. The DB system consists of a first latex balloon that is attached to a scope tip and a second latex balloon that is attached to an overtube. By sequentially inflating the tip balloon to grab the inside of the small intestine, advancing the deflated overtube balloon, inflating the overtube balloon once it has been full advanced, pulling back on both the overtube and the scope to pleat the intestine, deflating the tip balloon, re-advancing the scope tip, and repeating the cycle, the small intestine can be moved over the endoscope, allowing the small intestine to be explored with the scope. However, the DB system has numerous drawbacks, resulting in long procedure times, sub-optimal procedural clinical efficacy, and low professional adoption.

Accordingly, there is an unmet clinical need for a device that permits easier and faster navigation through the entire length of the small intestine.

SUMMARY OF THE DISCLOSURE

One aspect of the invention provides an apparatus for advancing a device (such as, e.g., an endoscope) through a gastrointestinal tract, with the apparatus including first and second grabbing mechanisms adapted to grab and release tissue of the gastrointestinal tract, the first grabbing mechanism being releasably attachable to the device, the second grabbing mechanism being attached to an outer element configured to at least partially surround the device, the first and second grabbing mechanisms being axially movable with respect to each other along the gastrointestinal tract; and a radially expandable blocking element disposed proximal to the first grabbing mechanism and movable with the first grabbing mechanism with respect to the second grabbing mechanism, the blocking element being adapted to move tissue of the intestinal tract with respect to the second grabbing mechanism when the blocking element is moved toward the second grabbing mechanism.

In some embodiments, the apparatus also includes actuators adapted to actuate the first and second grabbing mechanisms to grab and release tissue. The apparatus may also include a connecting mechanism configured to releasably attach the first grabbing mechanism to the device. The outer element may be an overtube, and the overtube may support actuator lines extending to the first and second grabbing mechanisms.

In some embodiments, at least one of the first grabbing mechanism and the second grabbing mechanism comprises a vacuum port. In some embodiments in which the second grabbing mechanism comprises a vacuum port and the device is an endoscope, the apparatus also includes a distal cap adapted to cover a distal end of the endoscope and a seal adapted to seal against an outer surface of the endoscope proximal to the cap to form a vacuum chamber in fluid communication with a working channel of the endoscope and with the vacuum port. The cap may also have an opening adapted to align with the working channel of the endoscope and a valve disposed in the opening.

In some embodiments, the blocking element comprises a balloon. The apparatus may also include an overtube attached to the balloon and defining a balloon inflation channel communicating with an interior of the balloon.

In some embodiments, the blocking element comprises a plurality of radially movable elements. In some embodiments, the blocking element has a wiping element. In any of the preceding embodiments, the blocking element is configured to slide over at least a portion of the second grabbing mechanism.

Another aspect of the invention provides a method of advancing a device through the gastrointestinal tract including the following steps: inserting a device comprising first and second vacuum ports into the gastrointestinal tract; advancing the first vacuum port distally through the gastrointestinal tract; activating vacuum through the first vacuum port to suction tissue of the gastrointestinal tract to the first vacuum port; sliding the second vacuum port towards the first vacuum port while the vacuum through the first vacuum port is activated; moving tissue proximally past at least a portion of the second vacuum port using a blocking element that is positioned proximal to the first vacuum port; activating vacuum through the second vacuum port to suction tissue of the gastrointestinal tract to the second vacuum port; and releasing vacuum on the first vacuum port to allow the first vacuum port to move further distally through the gastrointestinal tract.

In some embodiments, the moving step comprises sliding the blocking element over the second vacuum port before activating vacuum through the second vacuum port. In some embodiments, the blocking element comprises a balloon.

Some embodiments of the method include the step of expanding the blocking element. Some such embodiments also include the step of keeping the blocking element expanded during all of the advancing, activating vacuum through the first vacuum port, sliding, preventing, activing vacuum through the second vacuum port, and releasing steps.

Some embodiments of the invention repeat the steps of advancing, activating vacuum through the first vacuum port, sliding, preventing, and activating vacuum through the second port steps, e.g., until the device has moved through a desired distance, such as until the device is entirely through a small intestine of the gastrointestinal tract. Some embodiments of the method include the step of inserting a scope (such as an endoscope) into the device to advance the scope through the gastrointestinal tract as the device advances through the gastrointestinal tract.

Yet another aspect of the invention provides an apparatus for advancing through a gastrointestinal tract, with the apparatus including first and second grabbing mechanisms adapted to grab and release tissue of the gastrointestinal tract, the first and second grabbing mechanisms being axially movable with respect to each other along the gastrointestinal tract; and a radially expandable blocking element disposed proximal to the first grabbing mechanism and movable with the first grabbing mechanism, the blocking element being adapted to enable tissue of the intestinal tract to move with respect to second grabbing mechanism. In some embodiments, the apparatus also includes actuators adapted to actuate the first and second grabbing mechanisms to grab and release tissue.

In some embodiments, the first grabbing mechanism is attachable to an inner element and the second grabbing mechanism is attached to an outer element configured to at least partially surround the inner element. Some such embodiments also include a connecting mechanism configured to releasably attach the first grabbing mechanism to the inner element. The inner element may be, e.g., an endoscope, and the outer element may be, e.g., an overtube. In embodiments with an overtube, the overtube may support actuator lines extending to the first and second grabbing mechanisms.

In some embodiments, at least one of first grabbing mechanism and second grabbing mechanism comprises a vacuum port. In some embodiments, the second grabbing mechanism comprises a vacuum port and the device is an endoscope, with the apparatus further comprising a distal cap adapted to cover a distal end of the endoscope and a seal adapted to seal against an outer surface of the endoscope proximal to the cap to form a vacuum chamber in fluid communication with a working channel of the endoscope and with the vacuum port. In some such embodiments, the apparatus also may include an opening in the cap adapted to align with the working channel of the endoscope and a valve disposed in the opening.

In some embodiments, the blocking element comprises a balloon. Some such embodiments also include an overtube attached to the balloon and defining a balloon inflation channel communicating with an interior of the balloon.

In some embodiments, the blocking element comprises a plurality of radially movable elements. In some embodiments, the blocking mechanism comprises a wiping element. In any of the preceding embodiments, the blocking element may be configured to slide over at least a portion of the second grabbing mechanism.

Yet another aspect of the invention provides a method of advancing a device through the gastrointestinal tract, with the method including the following steps: inserting a device comprising first and second ports into the gastrointestinal tract; advancing the first port distally through the gastrointestinal tract away from the second port; sliding the second port towards the first port; moving tissue proximally past the second port using a blocking element that is positioned proximal to the first port; activating vacuum through the second port to suction tissue of the gastrointestinal tract to the second port; and advancing the first port distally through the gastrointestinal tract while the vacuum is activated through the second port.

Some embodiments of the method include the step of sliding the blocking element over the second port before activating vacuum through the second port. In some embodiments, the blocking element comprises a balloon.

Some embodiments of the method include the step of expanding the blocking element. Some such embodiments also include the step of keeping the blocking element expanded during all of the advancing, sliding, preventing, and activating, steps.

Some embodiments of the method repeat the steps of sliding, preventing, activating, and advancing the first port distally through the gastrointestinal tract while the vacuum is activated through the second port, e.g., until the device has moved through a desired distance, such as entirely through a small intestine of the gastrointestinal tract.

Some embodiments of the method include the step of inserting a scope into the device to advance the scope through the gastrointestinal tract as the device advances through the gastrointestinal tract.

Still another aspect of the invention provides a method of advancing a device through the gastrointestinal tract, the method including the following steps: inserting a device having a first grabbing mechanism and a second grabbing mechanism into the gastrointestinal tract; activating the first grabbing mechanism to grab tissue of the gastrointestinal tract; moving the first and second grabbing mechanisms towards each other; using a blocking element to urge tissue of the gastrointestinal tract proximal to the second grabbing mechanism during the moving step; activating the second grabbing mechanism to grab tissue of the gastrointestinal tract; deactivating the first grabbing mechanism; and advancing the first grabbing mechanism distally while the second grabbing mechanism is activated. In some embodiments, at least one of the first and second grabbing mechanisms is a vacuum port.

Some embodiments of the method include the step of sliding the blocking element over the second grabbing mechanism before activating the second grabbing mechanism. In some such embodiments, sliding the blocking element over the second grabbing mechanism urges pleated tissue of the gastrointestinal tract proximally over the second grabbing mechanism.

In some embodiments, the blocking element comprises a balloon. Some embodiments include the step of expanding the blocking element. In some such embodiments, the blocking element is kept expanded during all of the steps of activating the first grabbing mechanism, moving, preventing, activating the second grabbing mechanism, deactivating, and advancing steps.

Some embodiments of the method include the step of deactivating the second grabbing mechanism after advancing the first grabbing mechanism distally. Some embodiments of the method repeat the steps of activating the first grabbing mechanism, moving, preventing, activating the second grabbing mechanism, deactivating the first grabbing mechanism, advancing the first grabbing mechanism, and deactivating the second grabbing mechanism until the device has been advanced a desired distance, e.g., until the device is entirely through a small intestine of the gastrointestinal tract.

Some embodiments of the method include the step of inserting a scope into the device to advance the scope through the gastrointestinal tract as the device advances through the gastrointestinal tract.

Yet another aspect of the invention provides a method of advancing a device through the gastrointestinal tract, with the method including the following steps: inserting a device having a first grabbing mechanism and a second grabbing mechanism into the gastrointestinal tract; activating the first grabbing mechanism to grab tissue of the gastrointestinal tract; moving the first and second grabbing mechanisms towards each other to create pleats of tissue therebetween; moving the pleats of tissue proximal to a portion of the second grabbing mechanism; activating the second grabbing mechanism to grab tissue of the gastrointestinal tract that is distal to substantially all of the pleats of tissue; and advancing the first grabbing mechanism distally while the second grabbing mechanism is activated. In some embodiments, at least one of the grabbing mechanisms is a vacuum port.

Some embodiments of the method include the step of moving tissue proximally past the second grabbing mechanism using a blocking element that is positioned proximal to the first grabbing mechanism. Some such methods also include the step of sliding the blocking element over the second grabbing mechanism before activating the second grabbing mechanism. Sliding the blocking element over the second grabbing mechanism may urge pleated tissue of the gastrointestinal tract proximally over the second grabbing mechanism. In some embodiments, the blocking element comprises a balloon. In some embodiments, the method may include the step of expanding the blocking element. The blocking element may be kept expanded throughout all of the steps of activating the first grabbing mechanism, moving the first and second grabbing mechanisms, moving the pleats of tissue, activating the second grabbing mechanism, and advancing the first grabbing mechanism.

Some embodiments of the method repeat the steps of activating the first grabbing mechanism, moving the first and second grabbing mechanisms, moving the pleats of tissue, activating the second grabbing mechanism, and advancing the first grabbing mechanism, e.g., until the device has moved through a desired distance, such as entirely through a small intestine of the gastrointestinal tract.

Some embodiments of the method include the step of inserting a scope into the device to advance the scope through the gastrointestinal tract as the device advances through the gastrointestinal tract. In some embodiments, the step of moving the pleats of tissue proximal to a portion of the second grabbing mechanism comprises sliding an element of the device over the second grabbing mechanism.

In general, in one embodiment, a method of advancing a device through the gastrointestinal tract, includes: (1) inserting a device comprising first and second vacuum ports into the gastrointestinal tract; (2) advancing the first vacuum port distally through the gastrointestinal tract; (3) activating vacuum through the first vacuum port to suction tissue of the gastrointestinal tract to the first vacuum port; (4) sliding the second vacuum port towards the first vacuum port while the first vacuum port is activated; (5) preventing tissue from moving distally past a blocking element that is positioned proximal to the first vacuum port; (6) activating vacuum through the second vacuum port to suction tissue of the gastrointestinal tract to the second port; (7) releasing vacuum on the first vacuum port; and (8) advancing the first vacuum port distally through the gastrointestinal tract.

This and other embodiments can include one or more of the following features. The method can further include sliding the blocking element over the second vacuum port before activating vacuum through the second vacuum port. Sliding the blocking element over the second vacuum port can urge pleated tissue of the gastrointestinal tract proximally over the second vacuum port. The blocking element can include a balloon. The method can further include expanding the blocking element. The method can further include keeping the blocking element expanded throughout an entire advancement procedure.

In general, in one embodiment, a method of advancing a device through the gastrointestinal tract, includes: (1) inserting a device comprising first and second ports into the gastrointestinal tract; (2) advancing the first port distally through the gastrointestinal tract away from the second port; (3) sliding the second port towards the first port; (4) preventing tissue from moving distally past the a blocking element that is positioned proximal to the first port; (5) activating vacuum through the second port to suction tissue of the gastrointestinal tract to the second port; and (6) advancing the first port distally through the gastrointestinal tract.

This and other embodiments can include one or more of the following features. The method can further include sliding the blocking element over the second port before activating vacuum through the second vacuum port. Sliding the blocking element over the second port can urge pleated tissue of the gastrointestinal tract proximally over the vacuum port. The blocking element can include a balloon. The method can further include expanding the blocking element. The method can further include keeping the blocking element expanded throughout an entire advancement procedure.

In general, in one embodiment, a device for advancing a scope through the gastrointestinal tract includes a first vacuum, a second vacuum and a blocking element proximal to the first vacuum port. A first vacuum port is configured to maintain a fixed position relative to the scope. A second vacuum port is configured to slide relative to the first vacuum port. The blocking element proximal to the first vacuum port includes a radially expandable portion.

This and other embodiments can include one or more of the following features. The first vacuum port or the second vacuum port can further include a plurality of vacuum holes extending therearound. The blocking element can be a balloon. The blocking element can be configured to slide over at least a portion of the second vacuum port.

In general, in one embodiment, a method of advancing a device through the gastrointestinal tract includes: (1) inserting a device having a first grabbing mechanism and a second grabbing mechanism into the gastrointestinal tract; (2) activating the first grabbing mechanism to grab tissue of the gastrointestinal tract; (3) moving the first and second grabbing mechanisms towards each other; (4) preventing tissue of the gastrointestinal tract from moving distally past the first grabbing mechanism with a blocking element; (5) activating the second grabbing mechanism to grab tissue of the gastrointestinal tract; (6) deactivating the first grabbing mechanism; and (7) advancing the first grabbing mechanism distally while the second grabbing mechanism is activated.

This and other embodiments can include one or more of the following features. At least one of the grabbing mechanisms can be a vacuum port. The method can further include sliding the blocking element over the second grabbing mechanism before activating the second grabbing mechanism. Sliding the blocking element over the second vacuum port can urge pleated tissue of the gastrointestinal tract proximally over the second grabbing mechanism. The blocking element can include a balloon. The method can further include expanding the blocking element. The method can further include keeping the blocking element expanded throughout an entire advancement procedure.

In general, in one embodiment, a device for advancing a scope through the gastrointestinal tract includes a first tissue grabbing mechanism, a second tissue grabbing mechanism and a blocking element proximal to the first grabbing mechanism. A first tissue grabbing mechanism is configured to maintain a fixed position relative to the scope. A second tissue grabbing mechanism is configured to slide relative to the first tissue grabbing mechanism. A blocking element proximal to the first grabbing mechanism includes a radially expandable portion.

This and other embodiments can include one or more of the following features. The blocking element can be configured to slide over at least a portion of the second tissue grabbing mechanism. The blocking element can be a balloon. The first grabbing mechanism or the second grabbing mechanism can be a vacuum port.

In general, in one embodiment, a method of advancing a device through the gastrointestinal tract includes: (1) inserting a device having a first grabbing mechanism and a second grabbing mechanism into the gastrointestinal tract; (2) activating the first grabbing mechanism to grab tissue of the gastrointestinal tract; (3) moving the first and second grabbing mechanisms towards each other to create pleats of tissue therebetween; (4) moving the pleats of tissue proximal to a portion of the second grabbing mechanism; (5) activating the second grabbing mechanism to grab tissue of the gastrointestinal tract that is distal to substantially all of the pleats of tissue; and (6) advancing the first grabbing mechanism distally while the second grabbing mechanism is activated.

This and other embodiments can include one or more of the following features. At least one of the grabbing mechanisms can be a vacuum port. The method can further include preventing tissue of the gastrointestinal tract from moving distally past the first grabbing mechanism with a blocking element. The method can further include sliding the blocking element over the second grabbing mechanism before activating the second grabbing mechanism. Sliding the blocking element over the second vacuum port can urge pleated tissue of the gastrointestinal tract proximally over the second grabbing mechanism. The blocking element can include a balloon. The method can further include expanding the blocking element. The method can further include keeping the blocking element expanded throughout an entire advancement procedure. Moving the pleats of tissue proximal to a portion of the second grabbing mechanism can include sliding an element of the device over the second grabbing mechanism.

In general, in one embodiment, a device for advancing a scope through the gastrointestinal tract includes a first vacuum port, a second vacuum port, and a blocking element configured to slide over a portion of the second vacuum port. A first vacuum port is configured to maintain a fixed position relative to the scope. A second vacuum port is configured to slide relative to the first vacuum port.

This and other embodiments can include one or more of the following features. The first vacuum port or the second vacuum port can further include a plurality of vacuum holes extending therearound. The blocking element can be a balloon. The blocking element can be configured to slide over at least a portion of the second vacuum port.

In general, in one embodiment, a device for advancing a scope through the gastrointestinal tract includes a blocking element and a vacuum port. A blocking element is configured to be in a fixed position relative to the scope. The blocking element includes a radially expandable portion. A vacuum port is configured to slide relative to the first blocking element.

This and other embodiments can include one or more of the following features. The first vacuum port can include a plurality of vacuum holes extending therearound. The blocking element can be a balloon. The blocking element can be configured to slide over at least a portion of the vacuum port.

In general, in one embodiment, a device for advancing a scope through the gastrointestinal tract includes a blocking element and a grabbing mechanism proximal to the blocking element. A blocking element is configured to be in a fixed position relative to the scope. The blocking element includes a radially expandable portion. A grabbing mechanism proximal to the blocking element is configured to slide over at least a portion of the grabbing mechanism.

This and other embodiments can include one or more of the following features. The grabbing mechanism can be a vacuum port. The blocking element can be a balloon. The blocking element can be configured to slide over at least a portion of the second vacuum port.

In general, in one embodiment, a device for advancing an endoscope through the gastrointestinal tract includes a vacuum port attached to an overtube. The overtube is configured to be positioned around a scope. The overtube is configured to create a reciprocating closed volume and vacuum seal between an inner circumference of the overtube and the outer circumference of the endoscope.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1C show various views of a device for endoscopic advancement through the small intestine.

FIGS. 2A-2B show various views of a distal vacuum port of a device for endoscopic advancement through the small intestine.

FIGS. 8A-8E show various views of a blocking element of a device for endoscopic advancement through the small intestine.

FIGS. 13A-13B show various views of another embodiment of a blocking element.

FIGS. 14A-14B show various views of another embodiment of a blocking element.

FIG. 15 shows another embodiment of a blocking element.

FIGS. 16A-16D show various views of another embodiment of a blocking element.

FIG. 17 shows another embodiment of a blocking element.

FIGS. 27A-27B show a cross-section of a spool valve for a handle for a device for endoscopic advancement through the small intestine.

FIGS. 32A-G show an embodiment of a device for endoscopic advancement having an inflatable blocking element.

FIGS. 34A-34C show another embodiment of a distal vacuum port including axially extending arms for increased flexibility.

FIGS. 37A-37C show another embodiment of a distal vacuum port including annular links connected with wire joints for increased flexibility.

FIGS. 38A-38C show a distal vacuum port including living hinges for increased flexibility.

FIGS. 40A-40C show a proximal vacuum port including a single wall.

FIG. 46 shows a sealed space between the endoscope and the overtube.

FIGS. 47A-I show a device having an extendable needle for inflation of a balloon blocking element.

FIGS. 50A-F show an exemplary wiping element.

FIGS. 51A-F show another exemplary wiping element.

FIGS. 52A-F show an exemplary blocking element.

FIGS. 54A-D show a portion of an exemplary handle for controlling inflation of the proximal vacuum port.

FIGS. 57A-D show an exemplary proximal vacuum port with ribs extending on the inner circumference and rectangular holes.

FIG. 65 shows an exemplary system lay-out.

FIGS. 66A-H show another embodiment of a device for endoscopic advancement through the small intestine that includes an overtube connected to a balloon blocking element for inflation thereof.

DETAILED DESCRIPTION

Figure 3A:
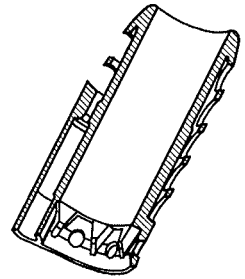
FIGS. 3A-3D show various views of another embodiment of a distal vacuum port.
Figure 3B:
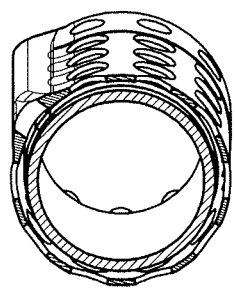
Figure 3C:
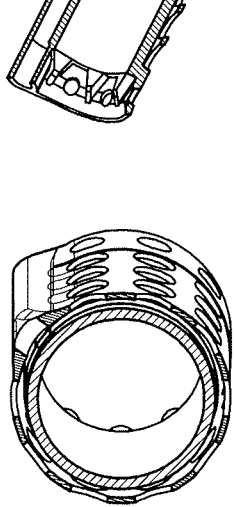
Figure 3D:
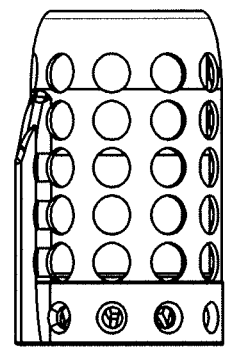

In general, the devices described herein are configured to allow an endoscope or other device to travel through the small intestine. The devices include first and second grabbing mechanisms, such as vacuum ports, that are slideable relative to one another and can be sequentially activated to grab and release tissue of the small intestine. The devices can further include a blocking element that pushes grabbed tissue proximally, plicating the tissue, and ensuring efficient movement of the device and endoscope through the small intestine.

Referring to FIGS. 1A-1C, an exemplary device 100 is configured to ride over an interior element, such as endoscope 101. Other interior elements may be used with the advancement apparatus of this invention, such as sheaths, tools, etc. The device 100 includes a distal vacuum port 102 and a proximal vacuum port 103. The distal vacuum port 102 is configured to attach to the endoscope 101 while the proximal vacuum port 103 is attached to an overtube 104 that extends over the endoscope 101. Further, the vacuum ports 102/103 are configured to be axially slideable relative to one another (see, e.g., the transition from FIG. 1A to FIG. 1C). A telescoping vacuum line 105 extends from the distal vacuum port 102 and through the overtube 104. Further, another vacuum line 106 extends to the proximal vacuum port 103. The device 100 further includes a blocking element 222 axially movable with, and proximal to, the distal vacuum port 102 that is configured to expand upon activation by axial movement of the proximal vacuum port 103. A handle 107 controls the relative movement of the ports 102, 103, the blocking element 222, as well as the vacuum applied thereto through the vacuum lines 105, 106.

Referring to FIG. 31A-31F, another exemplary device 3100 is configured to ride over an endoscope 3100 for advancement of the scope through a lumen 3131, such as the small intestine. The device 3100 is similar to device 100 and includes a distal vacuum port 3102 and a proximal vacuum port 3103. The distal vacuum port 3102 in this configuration, however, is attached to the very tip of the endoscope 3101 while the proximal vacuum port 3103 is attached to an overtube 3104 that extends over the endoscope 3101. The vacuum ports 3102/3103 are configured to be axially slideable relative to one another, as described with respect to device 100. The device 3100 further includes a support 3110 extending connected to, and proximally from, the distal vacuum port 3102 and a blocking element 3122 connected to support 3110 proximal to the distal vacuum port 3102 so that blocking element 3122 and distal vacuum port 3102 move together with the endoscope 3101. The blocking element 3222 in this embodiment is an inflatable balloon, and the proximal vacuum port 3103 is configured to slide thereunder when the endoscope 3101 is drawn proximally with respect to the overtube 3104.

Grabbing Mechanisms/Vacuum Ports

The devices described herein can include a distal grabbing mechanism configured to grab tissue, such as a distal vacuum port, and a proximal grabbing mechanism configured to grab tissue, such as a proximal vacuum port. The proximal and distal grabbing mechanisms can be movable relative to one another. Many of the embodiments described herein include vacuum grabbing mechanisms. However, for any of these embodiments, the proximal and/or distal vacuum grabbing mechanism can be replaced with an inflatable element, such as a balloon. Further, although many of the embodiments described herein include two grabbing mechanisms, the devices can be used with only one grabbing mechanism, such as only the proximal grabbing mechanism.

Distal Vacuum Port

The distal vacuum port can be configured to connect to the scope and/or remain fixed axially relative to the scope. In some embodiments, as shown in FIG. 1A-1C, the distal vacuum port 102 can be configured to attach to the endoscope 101 just proximal to the steerable section of the scope, such as just proximal to the bump created at the connection between the steerable and flexible sections. In this embodiment, the port 102 leaves the steerable section substantially uncovered. In other embodiments, referring to FIGS. 32A-32C, the distal vacuum port 3202 can be configured to attach over the distal-most tip of the endoscope 3201 (see also device 3100 in FIG. 31).

Referring to FIGS. 2A-2B, in some embodiments, a connecting mechanism 123, such as a split collet, can allow the distal vacuum port 102 to clamp around the endoscope. The connecting mechanism 123 can further include mating threads 145, 147 that, when rotated relative to one another, tighten the distal vacuum port 102 around the endoscope. Alternative attachment mechanisms include set screws or interference fit parts. Referring to FIGS. 32A-G, in some embodiments, the distal vacuum port 3202 can be attached with a shear clip 3245 (see FIG. 32E), which can be placed within a feature 3246 (see FIGS. 32D-E) that prevents the clip from coming dislodged. Other mechanisms of attachment are possible, such as a split clamp or set screws (see FIGS. 33A-33C) or an elastomeric band.

In some embodiments, the distal vacuum port can include a double walled port, where vacuum is created between the walls. For example, referring to FIGS. 2A-2B, the distal vacuum port 102 includes an inner cylindrical portion 202b and an outer cylindrical portion 202a and a sealed space 220 therebetween. A plurality of holes 230 extend through the outer cylindrical portion 202a into the sealed space 220. Further, the vacuum line 105 extends into the sealed space 220 to provide vacuum thereto. The holes 230 can be arranged along the outer circumference of the outer cylindrical portion 202a. The holes 230, which can be circular, can further be arranged as an array around the circumference of the outer cylindrical portion 202a. In one embodiment, there can be five circumferential rows of holes 230.

Figure 32B:
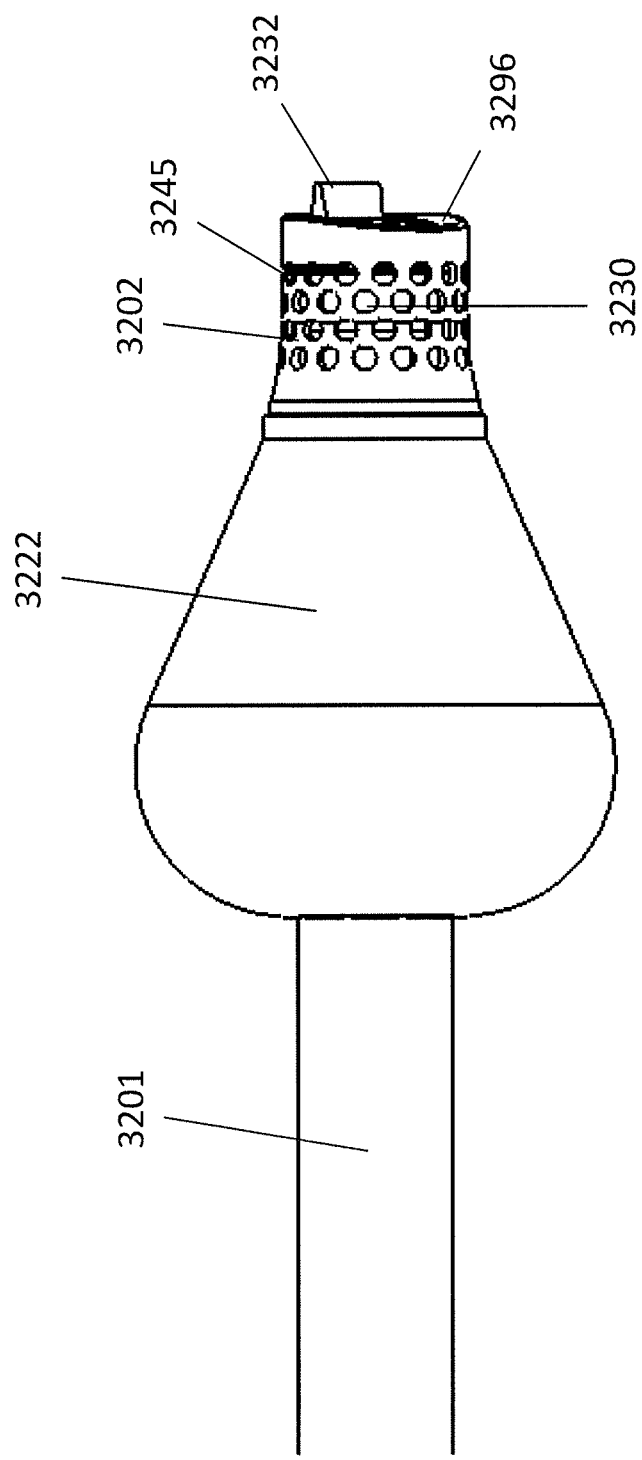
Figure 32C:
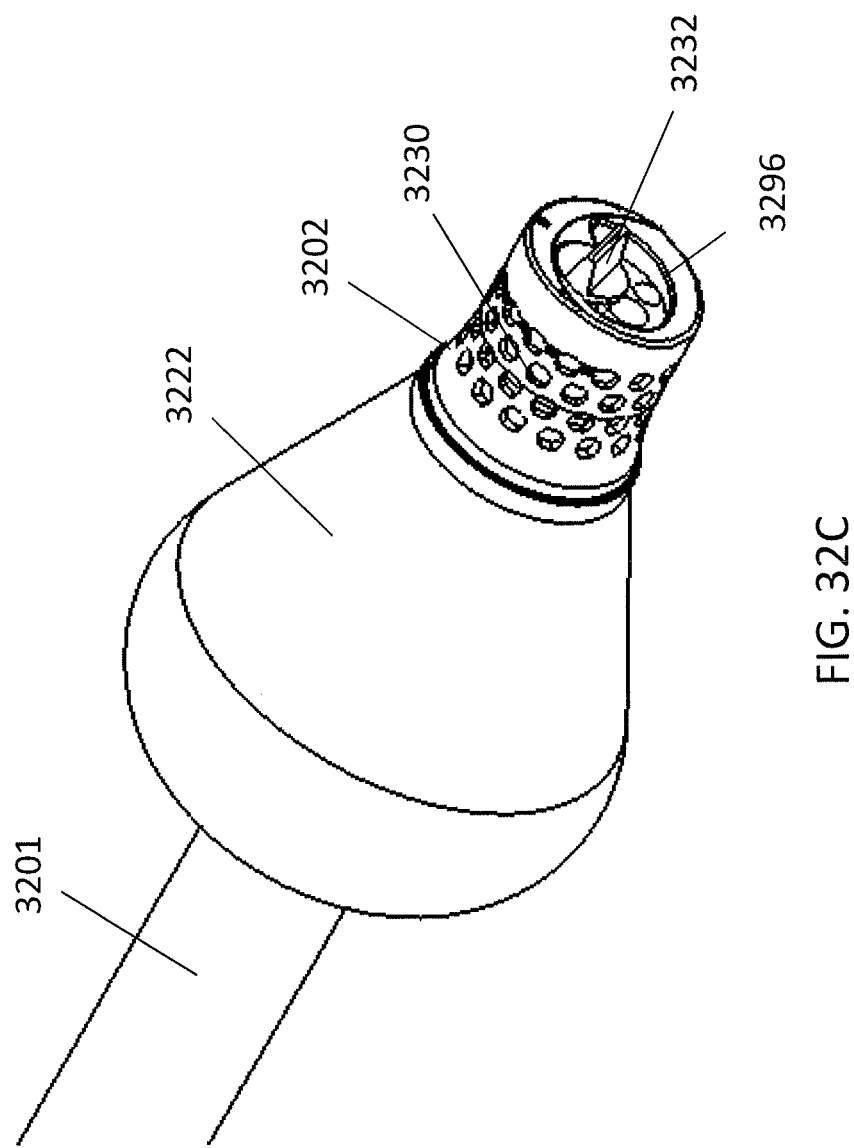
Figure 32D:
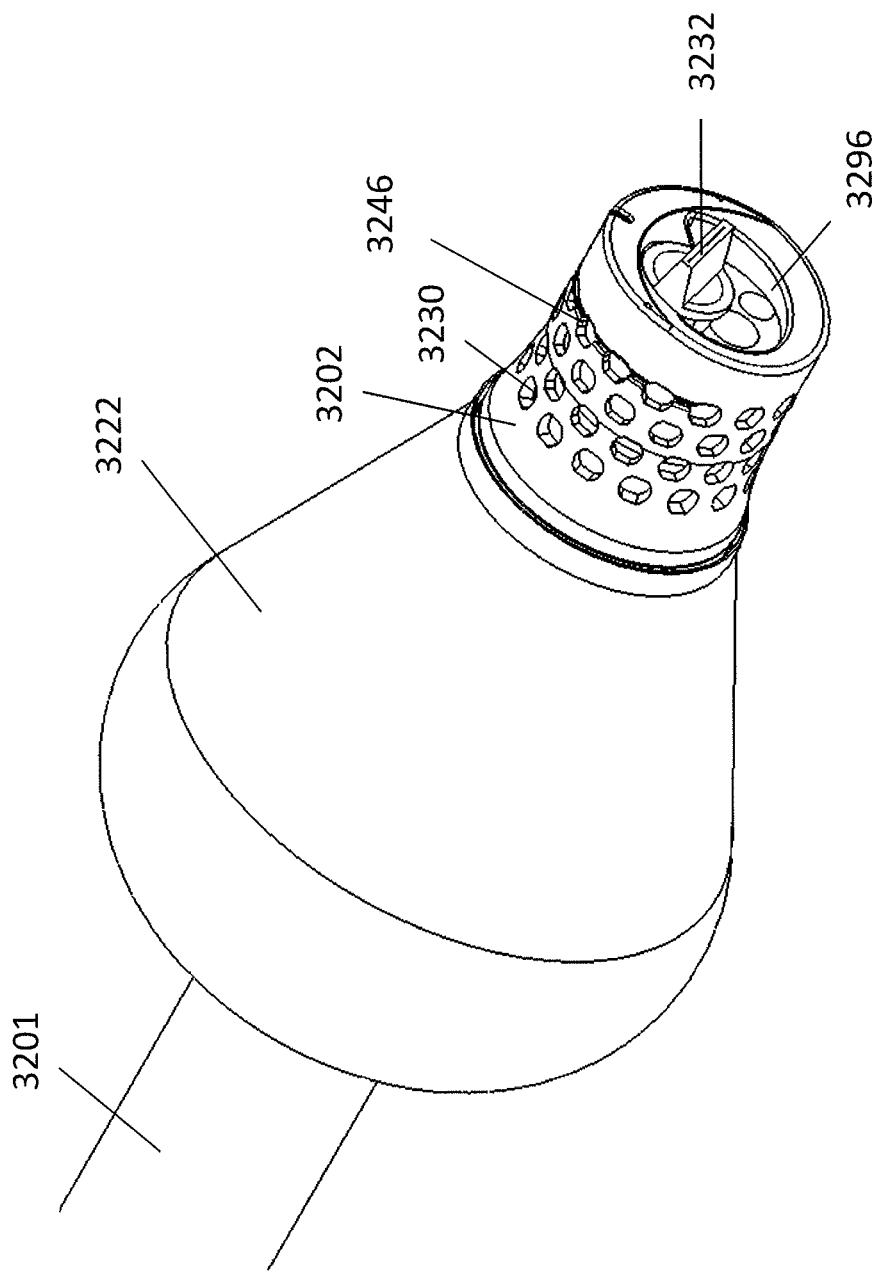
Figure 32E:
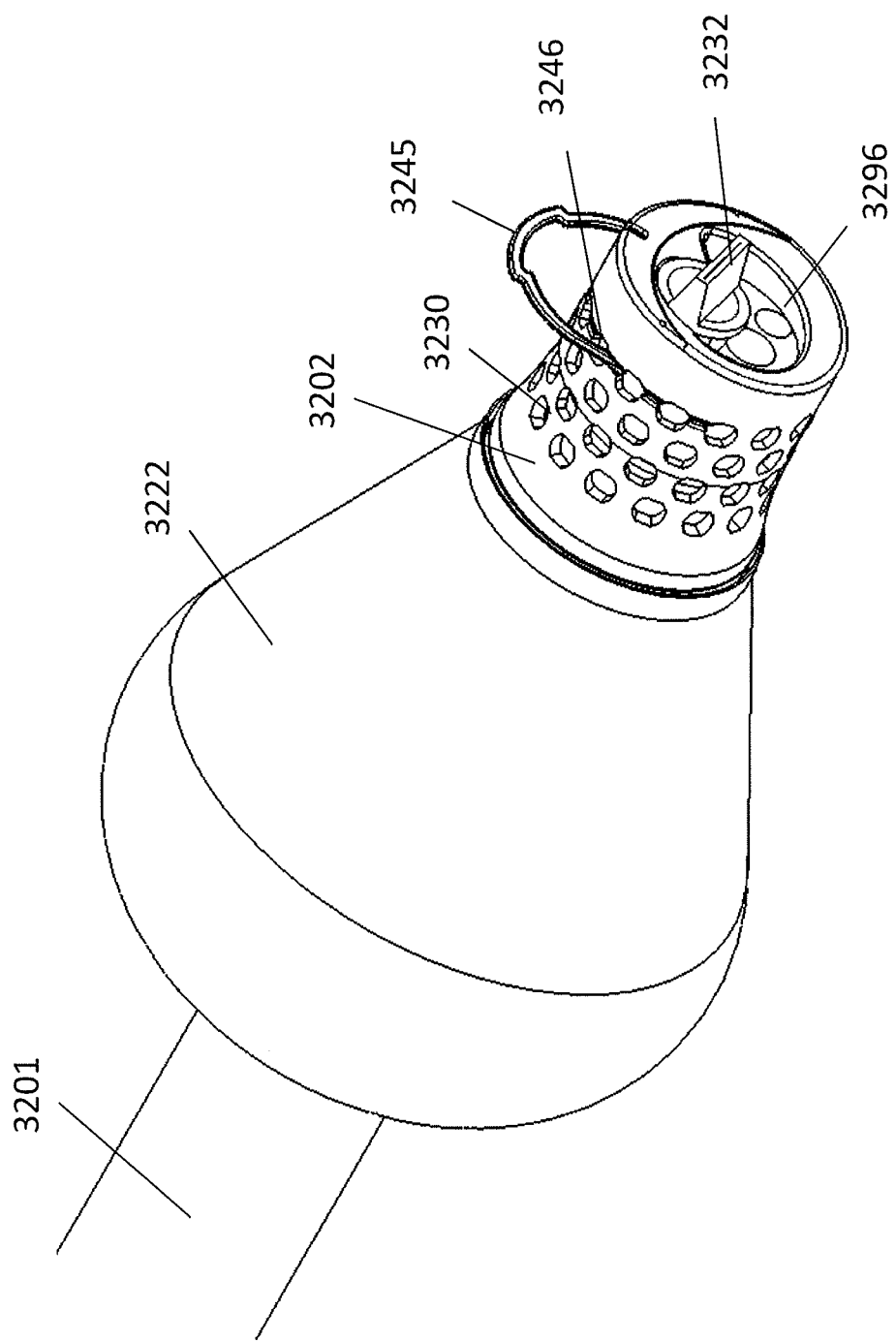
Figure 32F:
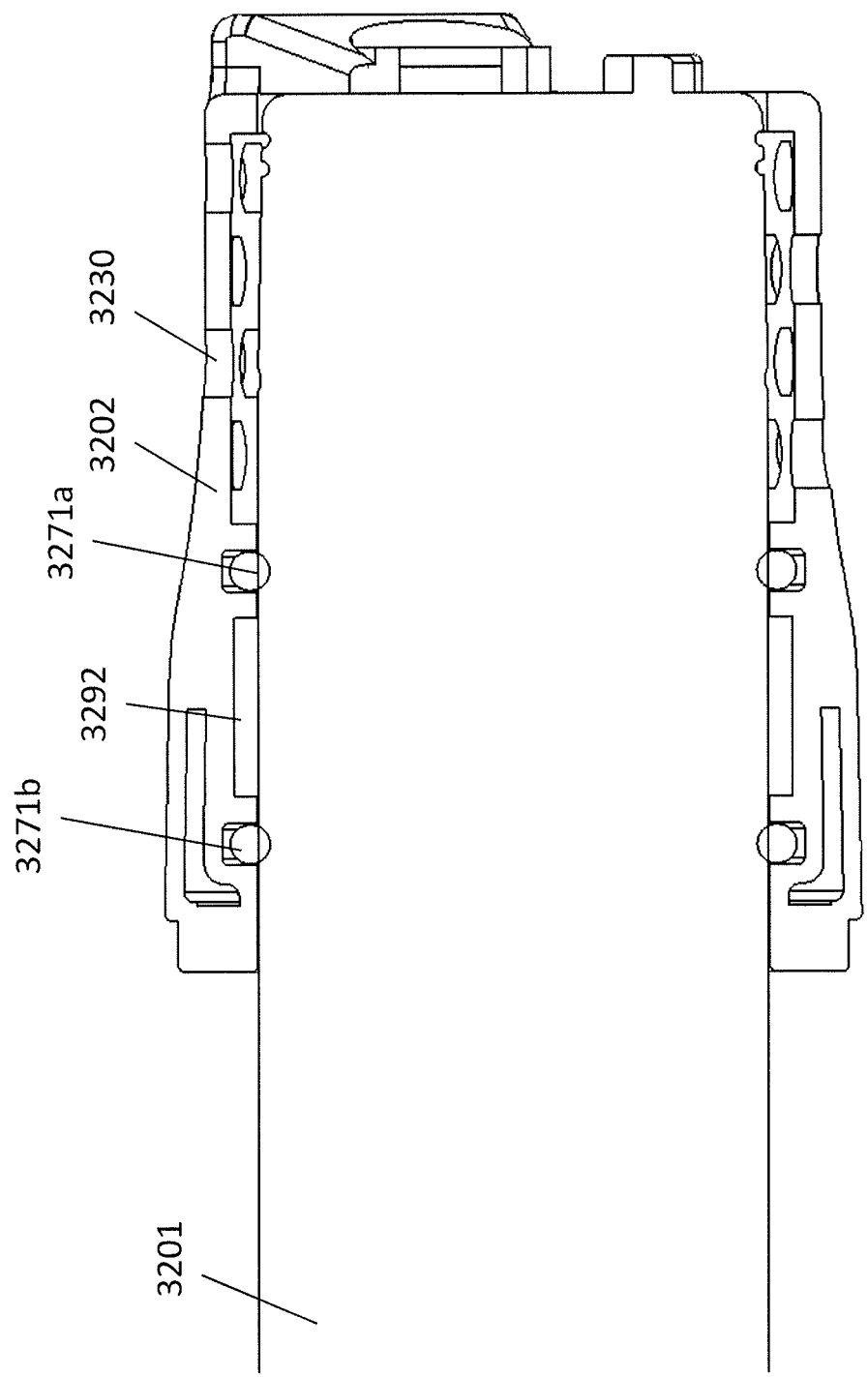
Figure 32G:
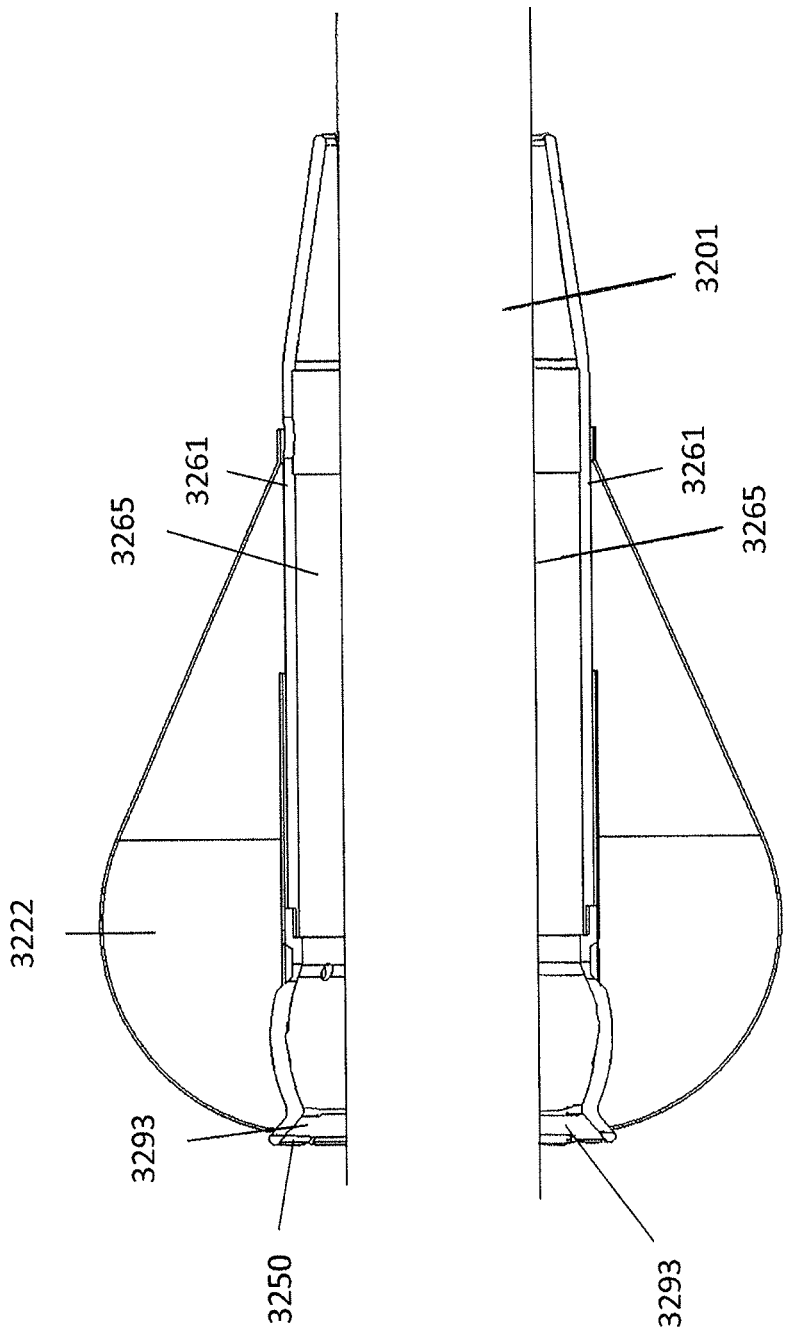

In other embodiments, the distal vacuum port can include a singled walled port, where vacuum is created between the single wall and the scope. Thus, for example, as shown in FIGS. 32A-32C, the distal vacuum port 3202 can be sealed to the scope 3201 with an end cap 3296 and an o-ring 3271a or sealing cartridge so as to provide a sealed vacuum chamber between the single wall of the distal vacuum port 3202 and the scope 3201. Holes 3230 extending through the wall of the port 3202 allow for suction of the tissue thereto.

In some embodiments, the distal vacuum port can include linkages therein to ensure that the distal tip of the endoscope can still flex or move without hindrance from the distal vacuum port. The linkages can thus go over the steering section of the endoscope without impeding its native ability to articulate, thereby allowing the distal vacuum port to be placed at the end of the scope (as shown in FIGS. 32A-32C). The linkages can also be useful if the distal vacuum port is placed at a more proximal location by allowing the scope to more easily flex as, for example, it bends within a tight radius inside of the patient. The articulating sections can withstand and/or accommodate torsion, tension, and compression and can have low bending force.

Figure 33A:
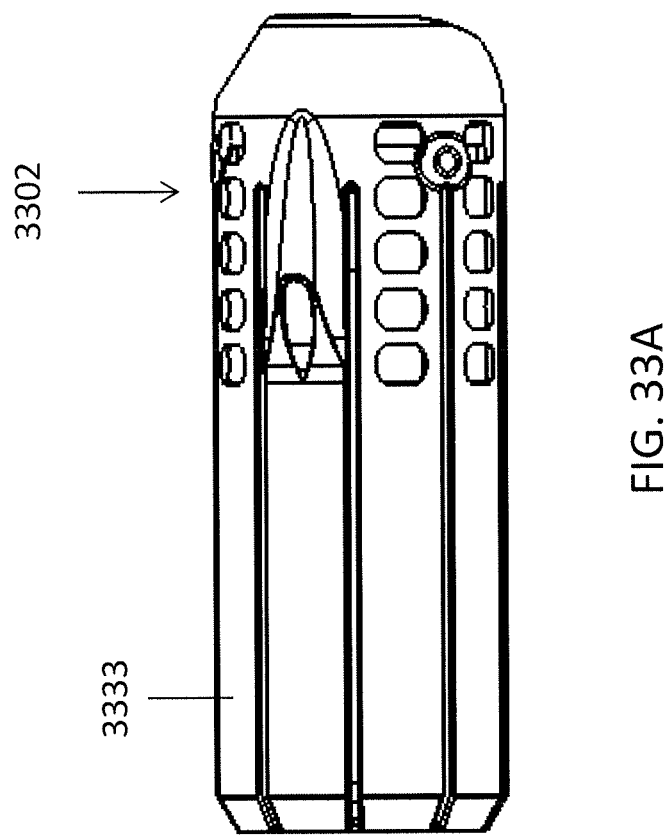
FIGS. 33A-33C show a distal vacuum port including axially extending arms for increased flexibility.
Figure 33C:
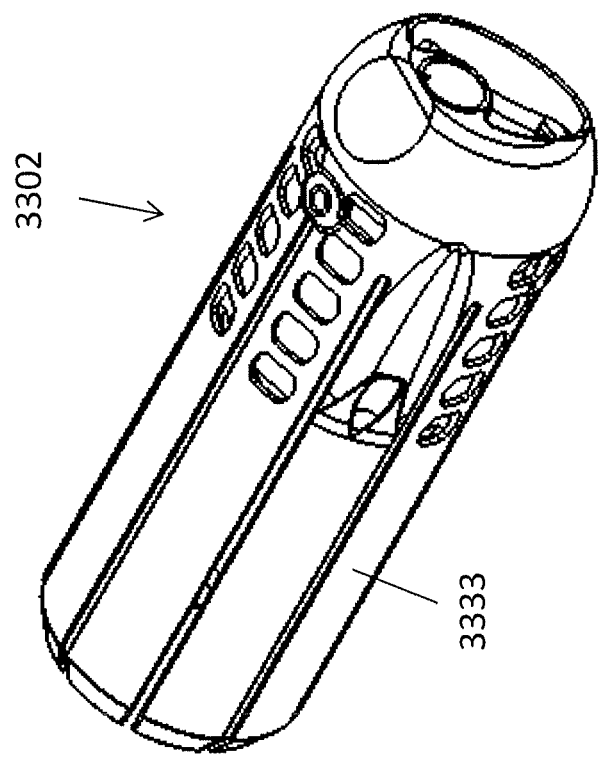
Figure 33B:
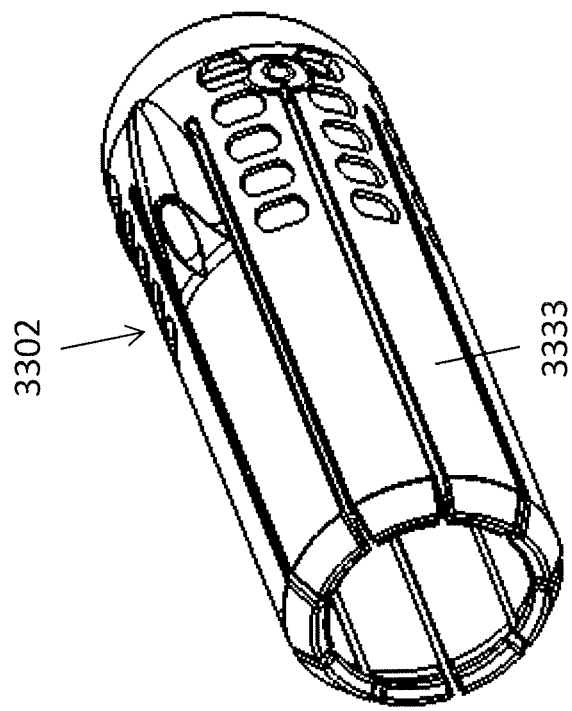
Figure 35A:
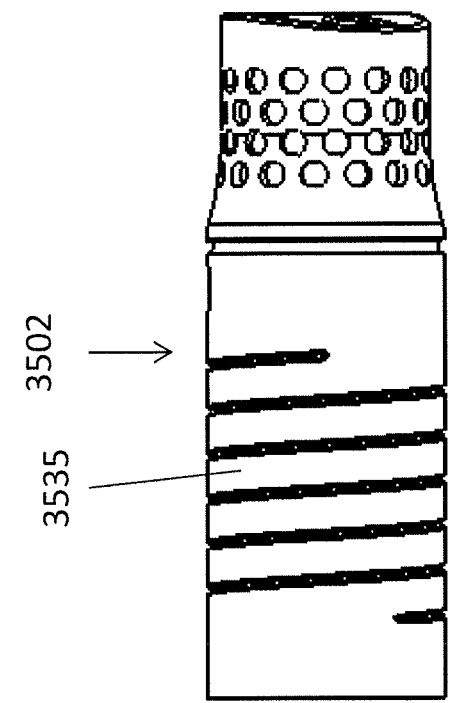
FIGS. 35A-C show a distal vacuum port including laser-cut coils for increased flexibility.
Figure 34C:
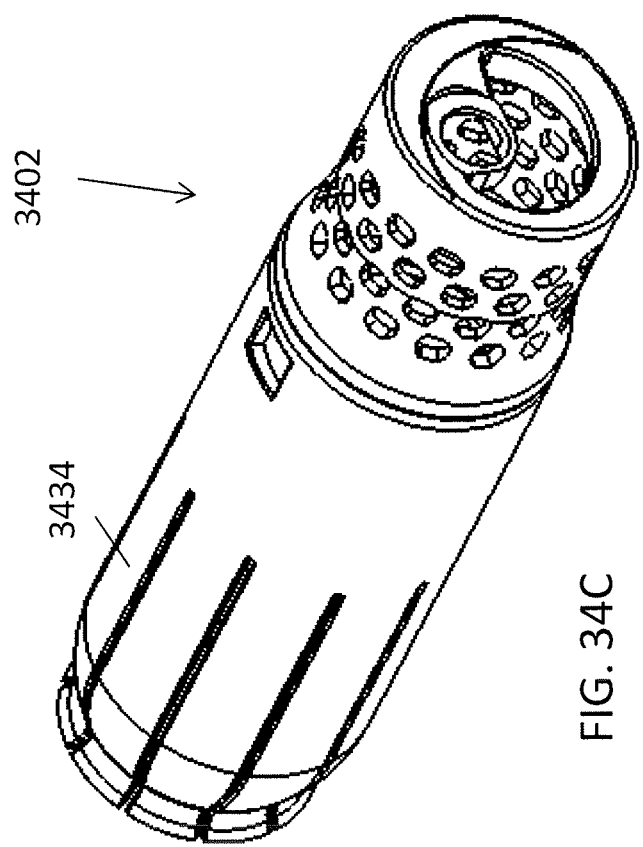
Figure 35C:
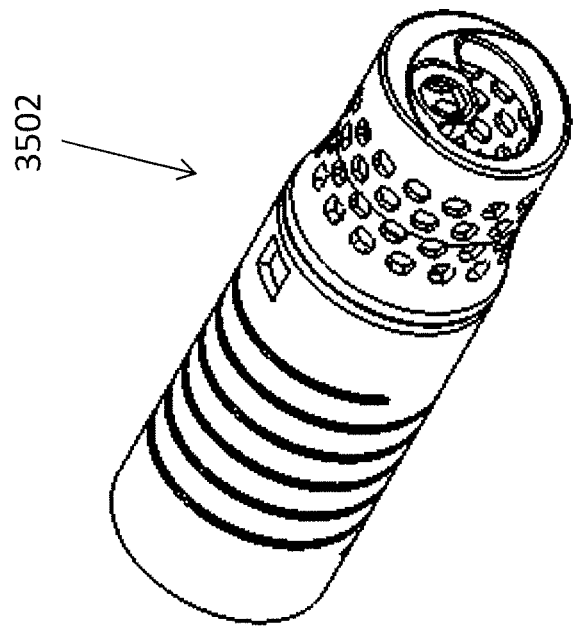
Figure 35B:
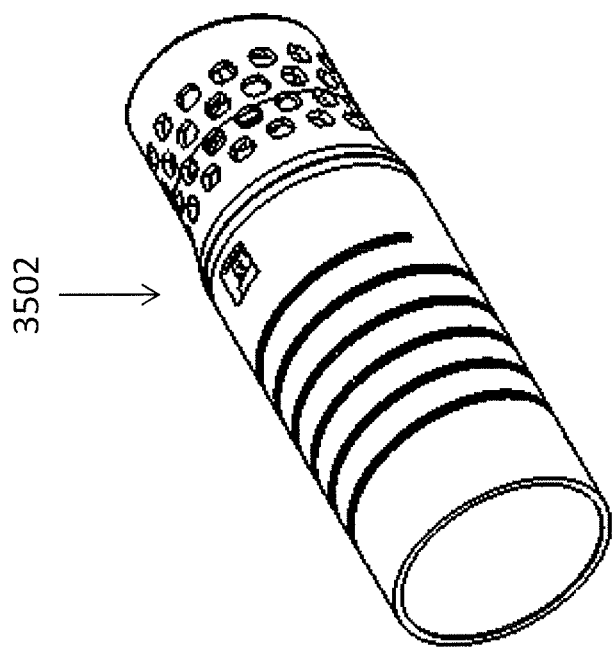
Figure 36A:
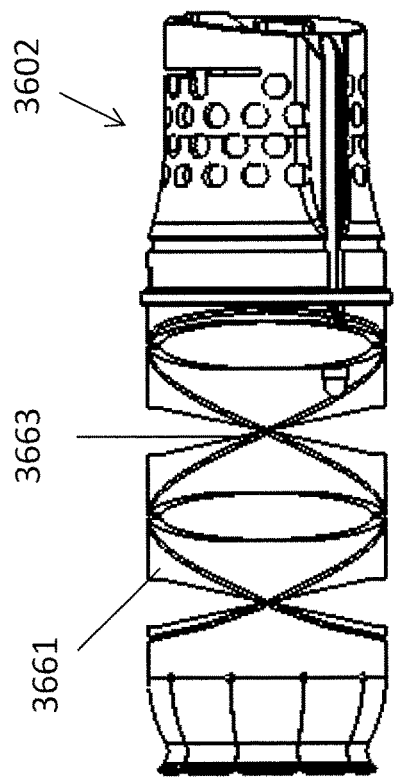
FIGS. 36A-36C show a distal vacuum port including annular links connected with wire joints for increased flexibility.
Figure 36C:
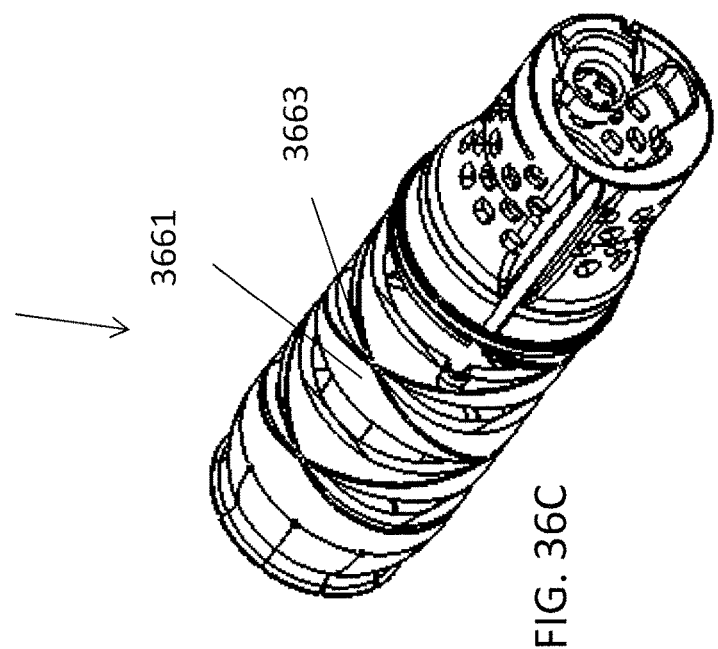
Figure 36B:
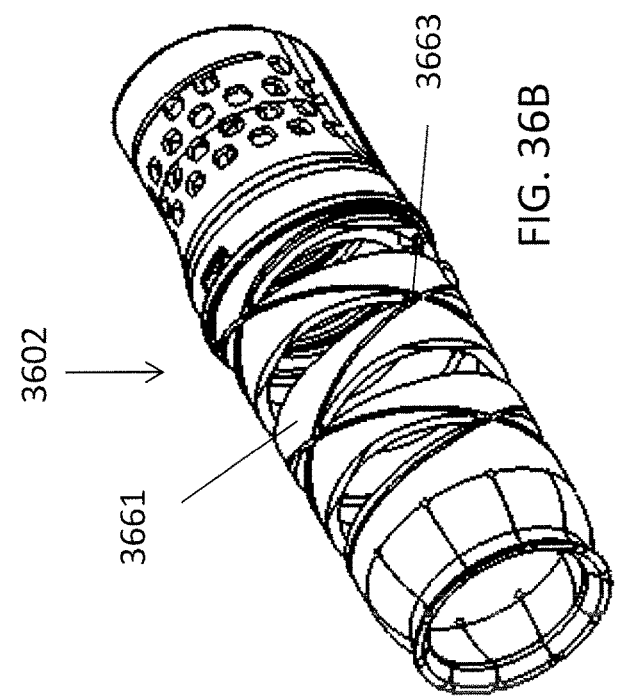

For example, referring to FIGS. 33A-33C, the distal vacuum port 3302 can include axially extending arms 333 having a vacuum passage therethrough, which can enhance the flexibility of the distal tip 3302. FIGS. 34A-34C show another distal vacuum port 3402 includes long axially extending arms 3434. In contrast to the port 3302 of FIGS. 33A-33C, the port 3402 includes a single wall vacuum design, allows for sealing around the inflation port of the scope for inflation of a blocking element, and attaches with a shear clip rather than set screws. Referring to FIGS. 35A-35C, as another example, the distal vacuum port 3502 includes laser-cut coils 3535 extending therearound to enhance flexibility. Referring to FIGS. 36A-36C, as another example, the distal tip 3602 can include annular plastic links 3661 connected together with wire joints 3663. The wire joints 3663 can be part of a single wire (or two) that is wrapped and bonded around all of the links 3661. The links 3661 can be made, for example, of a high stiffness plastic, such as acrylonitrile butadiene styrene (ABS), polycarbonate, thermoplastic polyurethane, high density polyethylene, PEEK, Ultem, or a mineral filled plastic. The wire can be made, for example, of stainless steel or nitinol and can be a solid wire, a spring wire, or a multi-filament cable. Referring to FIGS. 37A-C, as another example, the distal tip 3702, similar to distal tip 3602, can include annular plastic links 3771 connected together with wire joints 3762. In this embodiment, however, the wire joints 3762 are short studded segments present at each junction (i.e., not part of a continuous wire). Referring to FIGS. 38A-38C, as another example, the distal tip 3802 includes living hinges 3881 cut therein to allow bending or flexing. The tip 3802 can thus be made, for example, of a cylindrical material that is laser cut or by depositing different materials with rapid prototyping. In some embodiments, the tip 2802 can be made of injection molded polypropylene or from nitinol.

All of the distal tip embodiments shown in FIGS. 33A-38C advantageously help increase flexibility of the distal vacuum port so as to avoid hindering movement of the scope (e.g., for the section that generally includes steerability and/or for bending of the more proximal regions of the scope). Other mechanisms for increasing the flexibility of the distal vacuum port are also possible. For example, the distal tip can include a coil reinforced elastomer, a braid over an angled coil cut, links made such that they can angle relative to one another while being captured, or steel metal that is cut, bent, and welded with joints. In one example, the device distal vacuum port can include a braid overlay with a thin elastomeric or plastic sealing tube thereof. The sealing tube can be coated or plated to deliver enhanced features, such as stiffness.

Figure 4:
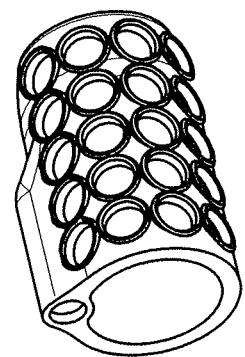
FIG. 4 shows another embodiment of a distal vacuum port.
Figure 5:
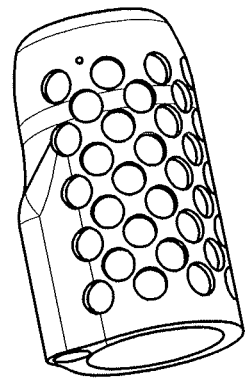
FIG. 5 shows another embodiment of a distal vacuum port.
Figure 6:
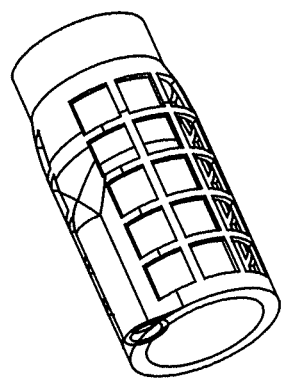
FIG. 6 shows another embodiment of a distal vacuum port.

Additional embodiments of the distal vacuum port are shown in FIGS. 3A-6. The holes of the distal vacuum port can be circular, as shown in FIGS. 3A-3D and 5-6 or non-circular (e.g., square, oval, rectangular, hexagonal, or hexagonal with radiused corners), as shown in FIG. 4. Further, the distal vacuum port can have raised ridges around the edges of the holes, as shown in FIG. 6, to help increase the suction force. The ridges can be made of a single material or of multiple materials and can include flexible elastomeric and/or highly conformable flanges. Further, in some embodiments, the distal vacuum port can be slideable relative to the endoscope rather than attached to the endoscope. In some embodiments, studs can connect the inner cylindrical portion and the outer cylindrical portion of the distal vacuum port to provide structural support therebetween.

The holes of the proximal and/or distal vacuum ports can be between 0.02 inches and 0.16 inches. The hole size can be chosen to optimize redundancy, manufacturability, vacuum strength, and ability to resist clogging from debris both externally and internally.

The distal vacuum port can include a distal tip. For Example, as shown in FIG. 2A-2B, the distal vacuum port 102 can include a rounded, atraumatic distal end 112.

Proximal Vacuum Port

The proximal vacuum port can be attached to an overtube and can be configured to slide relative to the endoscope.

In some embodiments, the proximal vacuum port can include a double wall and vacuum chamber therebetween. Thus, Referring to FIGS. 7A-7C, the proximal vacuum port 103 can include an inner cylindrical portion 302b and an outer cylindrical portion 302a and a sealed space 320 therebetween. A plurality of holes 330 extend through the outer cylindrical portion 302a and into the sealed space 320. Further, the vacuum line 106 extends into the sealed space 320 to provide vacuum thereto. Moreover, a channel 335 can extend axially therethrough for passage of the vacuum line for the distal port.

Figure 40A:
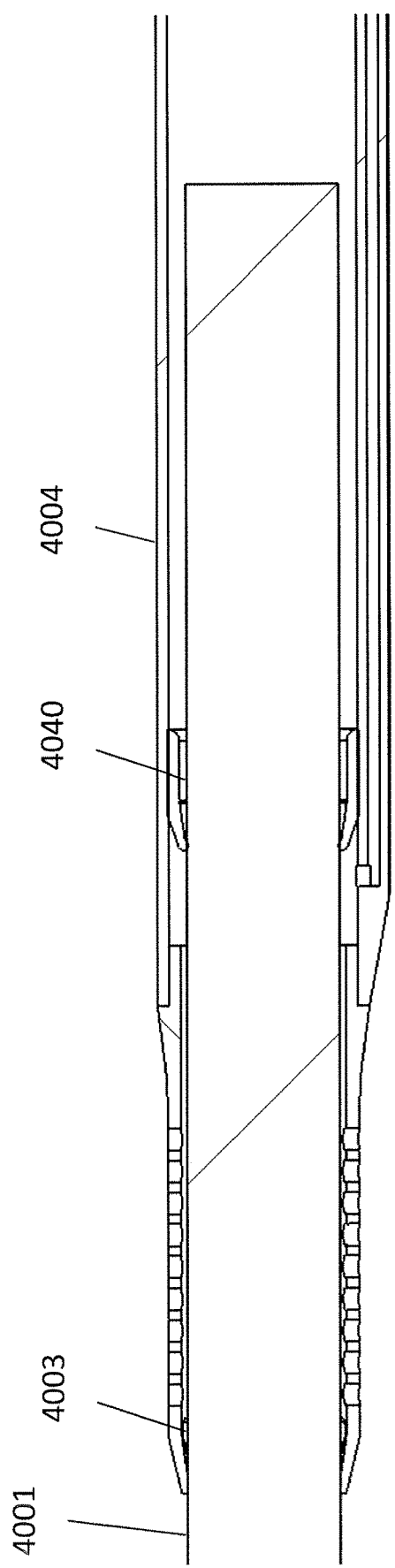
Figure 40C:
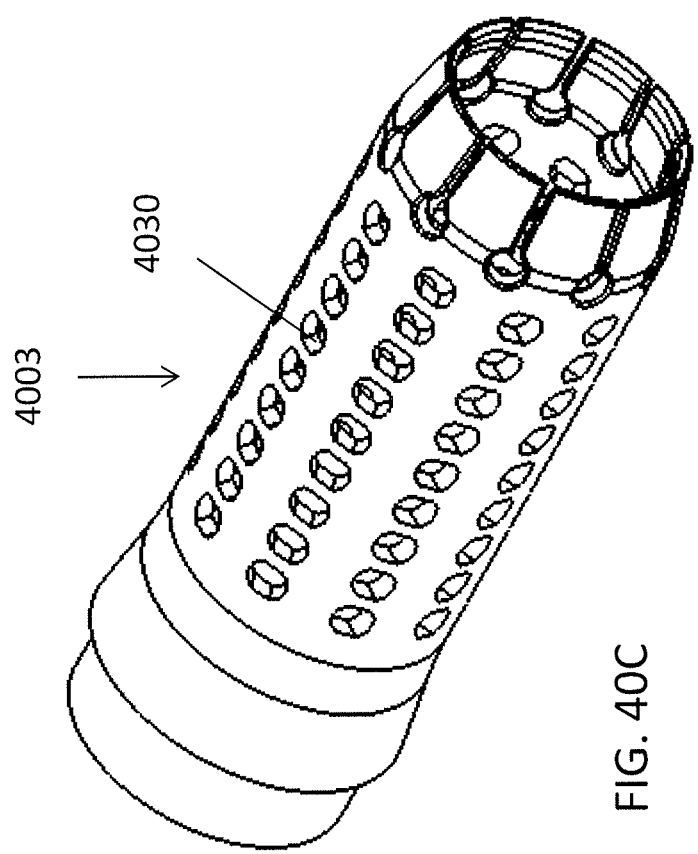
Figure 41:
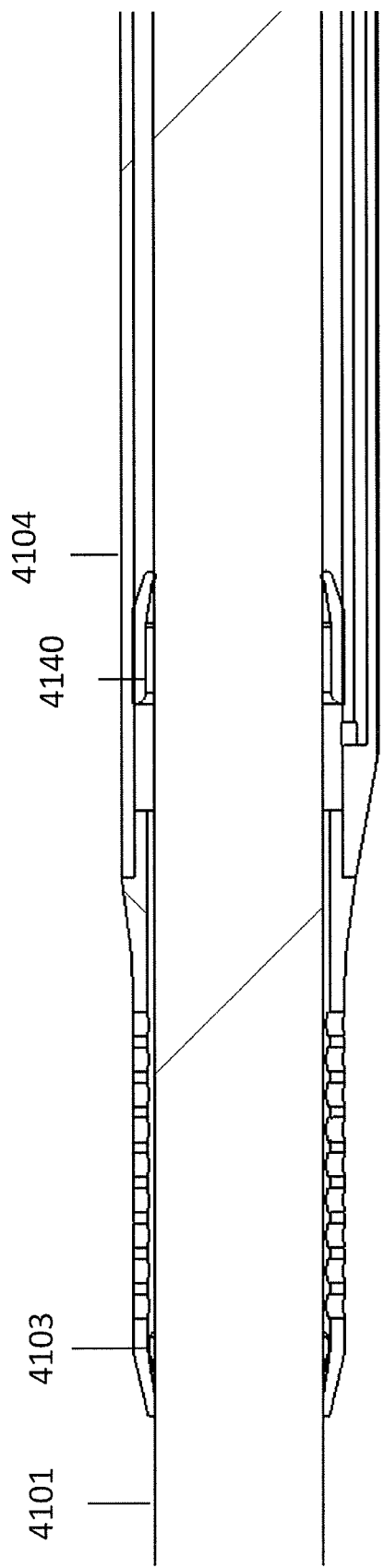
FIG. 41 shows another embodiment of a proximal vacuum port including a single wall.

In other embodiments, the proximal vacuum port can include a single wall, and creation of vacuum can occur between the wall and the scope. For example, FIGS. 40A-40C show a single walled port 4003 configured to form a vacuum chamber with the outer wall of the scope 4001. Further, the proximal vacuum port 4003 can include a seal 4040. As shown in the FIGS. 40A-40C, the seal 4040 can be a cone-shaped seal, which can advantageously be fault tolerant to an irregular surface. As shown in FIGS. 40A-40C, in some embodiments, the seal 4040 can have the taper facing in the distal direction. As shown in FIG. 41, in some embodiments, the seal 4140 can have a taper that faces in the proximal direction. The seal can be made of a material, such as silicone, or thermoplastic polyurethane, that provides low drag when moved along the scope. In some embodiments, the seal can be installed in a rigid cartridge to maintain dimensional integrity. Further, the seal can help maintain the vacuum (i.e. avoid vacuum leaks) while allowing areas of tissue distal to the seal to be insufflated, as described further below.

Referring to FIG. 46, in some embodiments, a device 4600 can include a distal seal 4640 and a proximal seal 4646. The two seals can create a captured volume therebetween and between the inner surface of the overtube 4604 and the outer surface of the endoscope 4601. This volume can be filled with water and/or other fluid to provide a lubricious layer between the overtube 6404 and the scope 4601. The two seals 4604, 4646 can keep the lubricant from leaking out during the procedure.

Figure 42A:
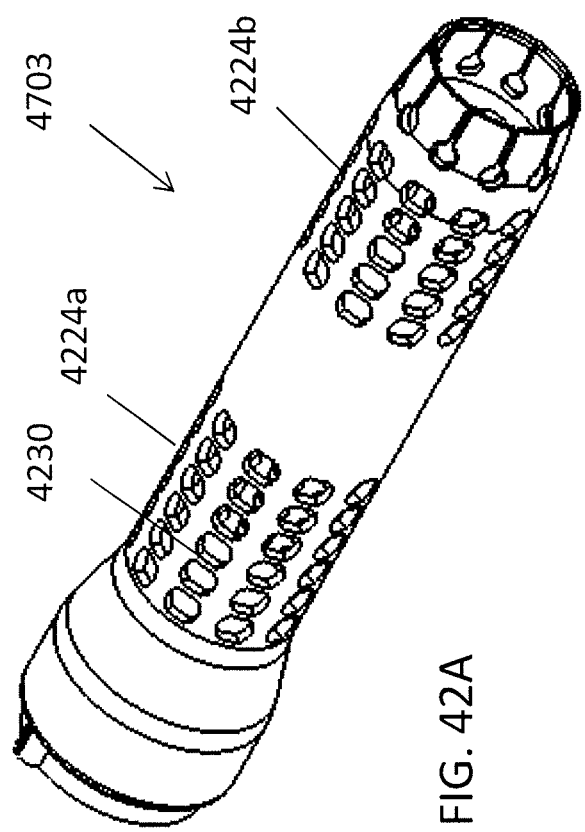
FIGS. 42A-42B show a proximal vacuum port including two arrays of holes.
Figure 42B:
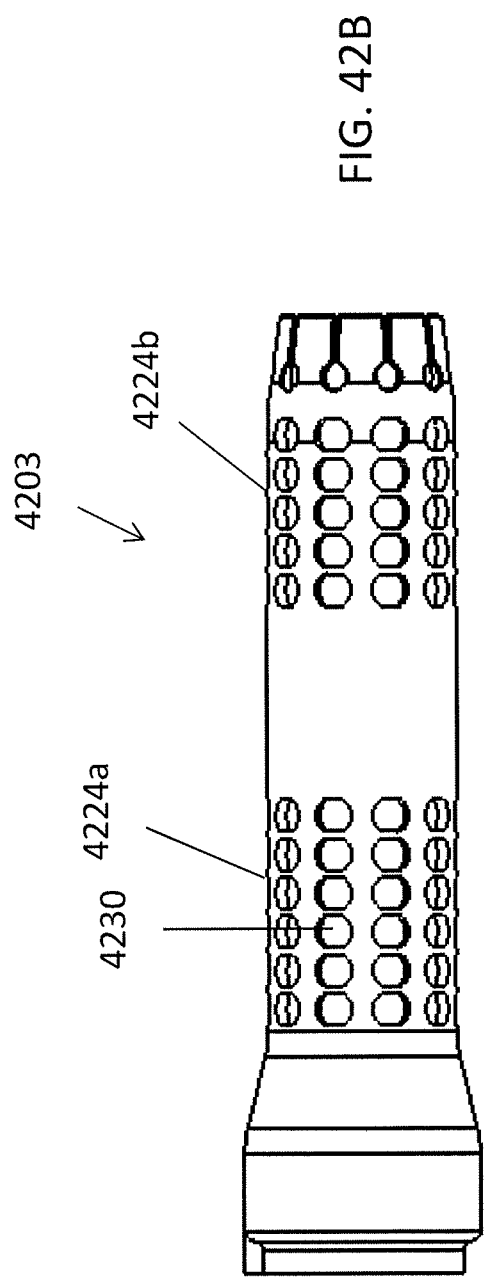

The holes of the proximal vacuum port can be between 0.02 inches and 0.16 inches. The hole size can be chosen to optimize redundancy, manufacturability, vacuum strength, and ability to resist clogging from debris both externally and internally. The holes can be of a variety of shapes, such as circular, square, oval, rectangular, hexagonal, or hexagonal with radiused corners. Further, the holes of the vacuum port can be arranged in a variety of different patterns. For example, referring to FIGS. 7A-7C, the holes 330 can be arranged along the outer circumference of the outer cylindrical portion 302a. The holes 330, which can be circular, can further be arranged as an array around the circumference of the outer cylindrical portion 302a. The axial length across which the holes 330 extend can be longer for the proximal vacuum port 103 than the distal vacuum port 102. For example, in one embodiment, there can be seven circumferential rows of holes 330 (as opposed to five for the distal vacuum port 102). The increased length of the area covered by holes 330 can advantageously increase the grabbing force of the proximal vacuum port 103. Referring to FIGS. 40A-40C, the holes 4030 can be part of a single array or, as shown in FIGS. 42A-42B, the holes 4230 can be arranged a plurality of different arrays 4224a,b separated axially from one another. In some embodiments, the different arrays 4224a,b can be activated independently of one another. For example, the distal-most array 4224b can be released when pushed underneath the blocking element to prevent suctioning portion of the blocking element thereto and/or getting tissue stuck between the blocking element and the distal part of the port 4203.

Figure 7A:
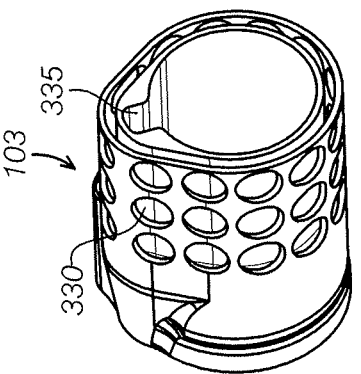
FIGS. 7A-7C show various views of another embodiment of a distal vacuum port.
Figure 7B:
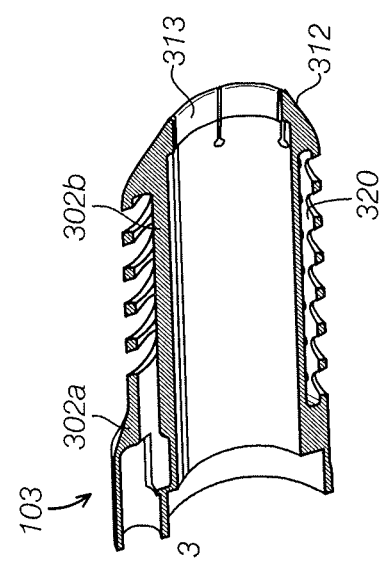
Figure 7C:
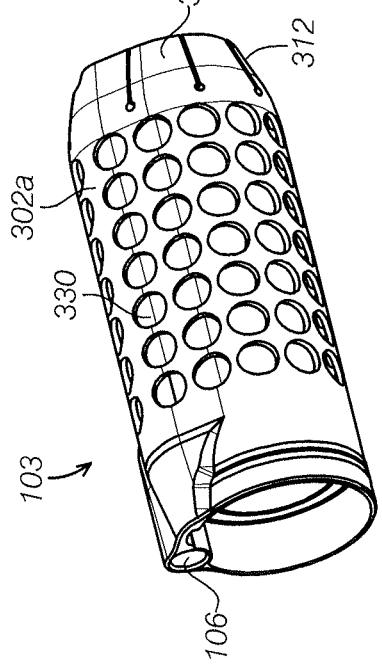
Figure 9A:
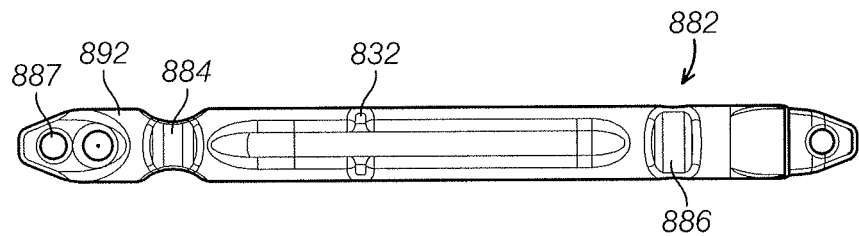
FIGS. 9A-9C show various views of a strut of a blocking element.
Figure 9B:
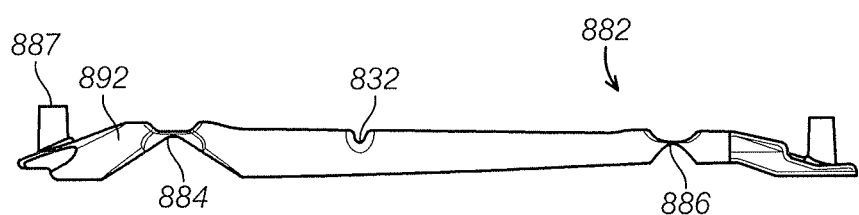
Figure 9C:
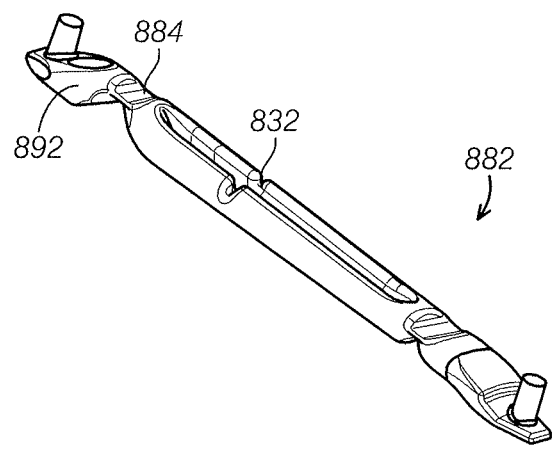
Figure 10A:
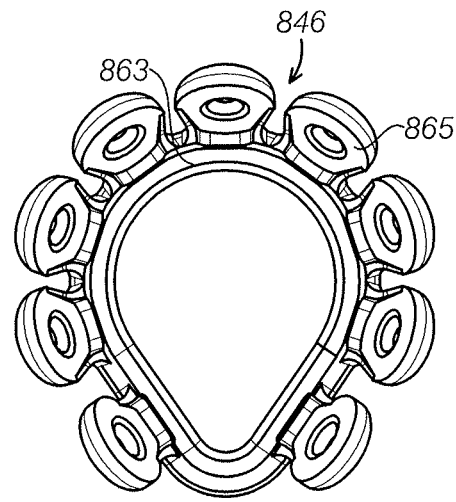
FIGS. 10A-10B show various views of a seal of a blocking element.
Figure 10B:
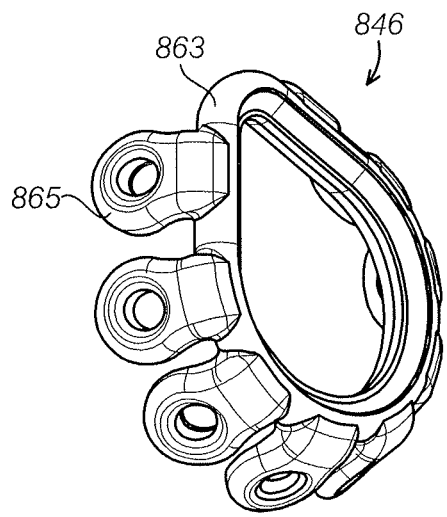
Figure 43A:
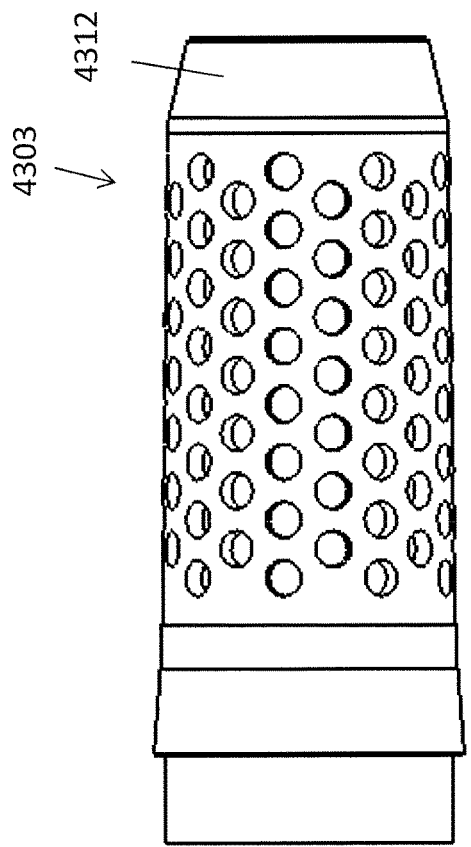
FIGS. 43A-43B show another embodiment of a proximal vacuum port.
Figure 43B:
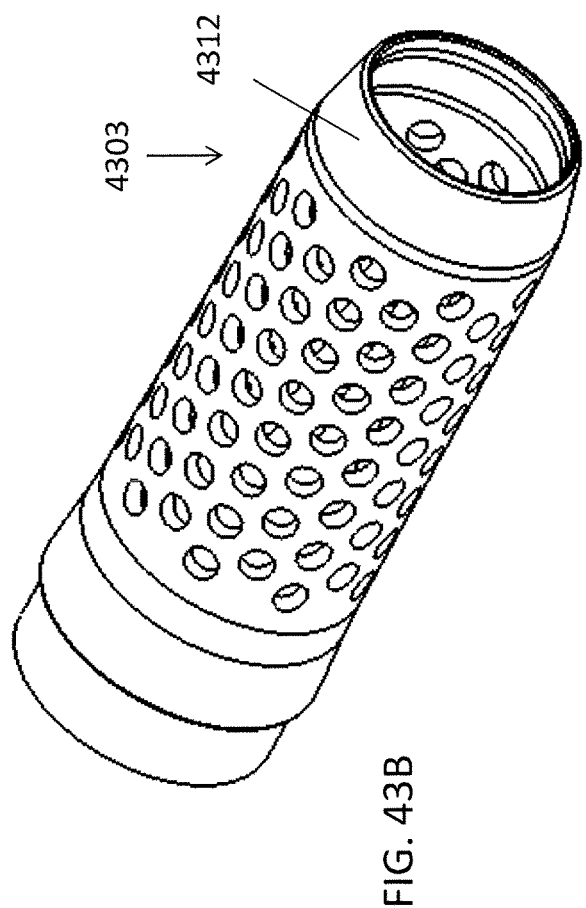

The proximal vacuum port can further include a tapered distal end. The tapered distal end of the proximal vacuum port can be longer than the tapered distal end of the distal port. Referring to FIGS. 7A-7C, in some embodiments, the tapered distal end 312 can include a plurality of flexures 313 therein configured to allow the end 312 to ride closely over the outer diameter of the endoscope (e.g., to prevent tissue from getting caught between the scope and the port 103) while providing flexion at points where the outer diameter of the endoscope increases (such as at the ridge between the steerable end and the flexible portion). Alternatively, referring to FIGS. 43A-43B, the tapered end 4312 can be made of an elastomeric material so that it stays against the scope, limits pinching, goes under the blocking element, does not bend up, and does not have any cracks or crevasses that things can get caught in.

Figure 44A:
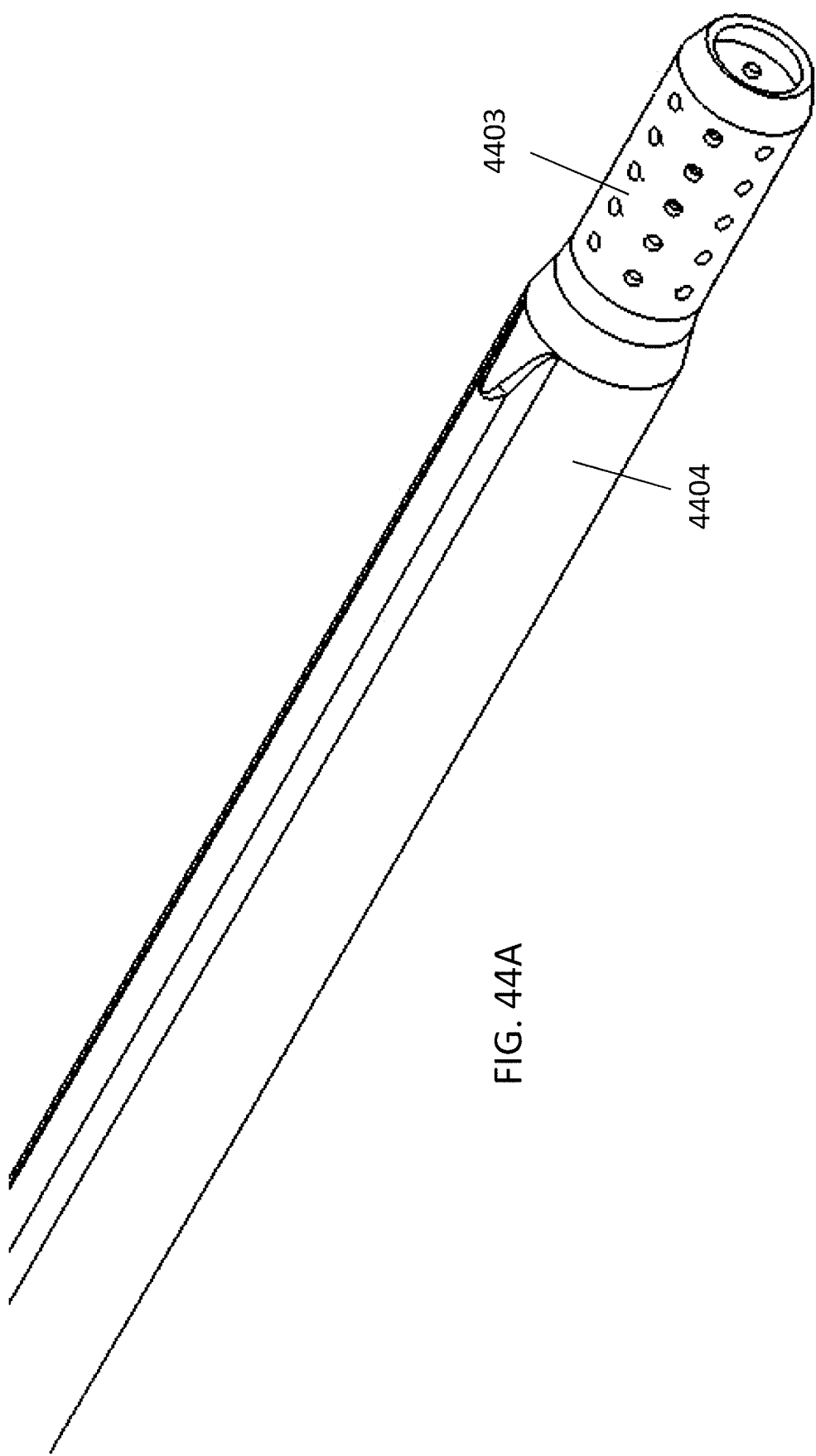
FIGS. 44A-44D show a proximal vacuum port formed as an extension of the overtube.
Figure 44B:
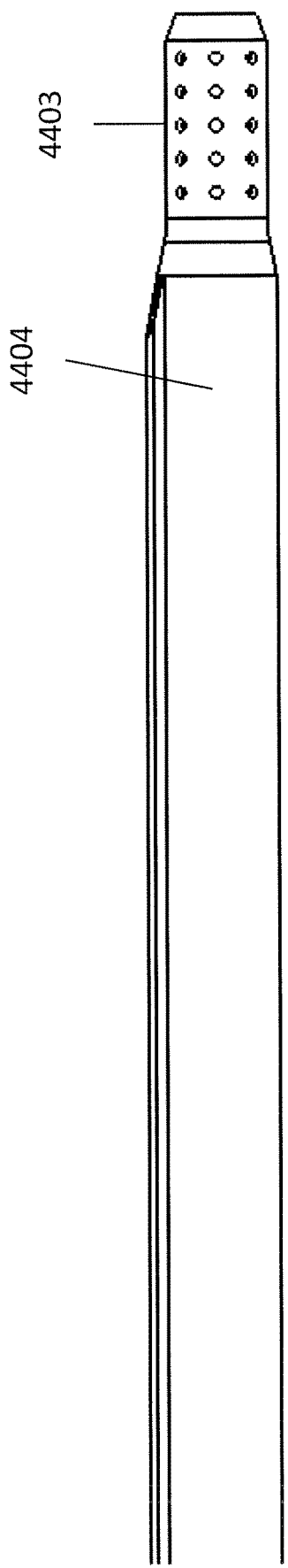
Figure 44C:
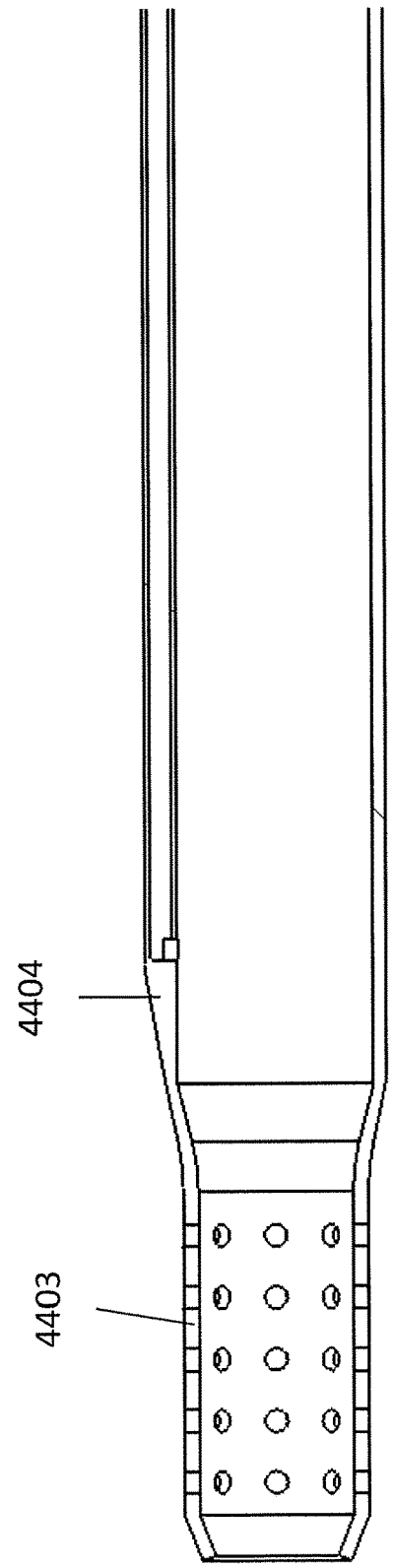
Figure 44D:
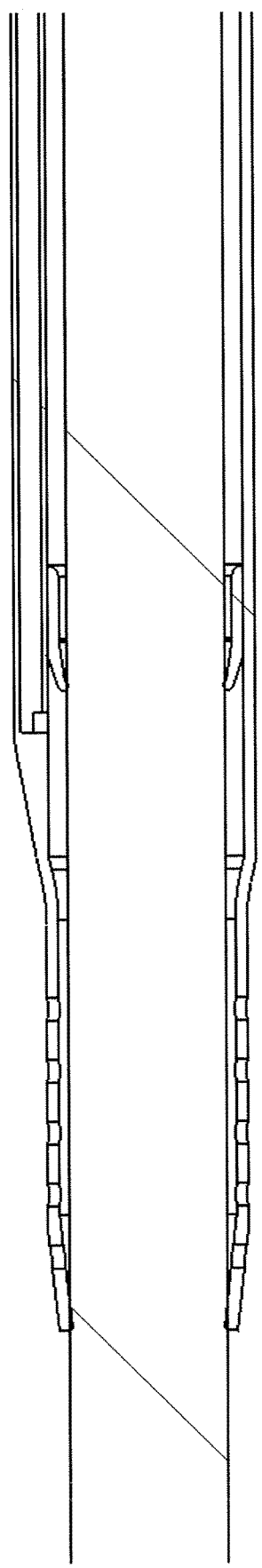
Figure 45:
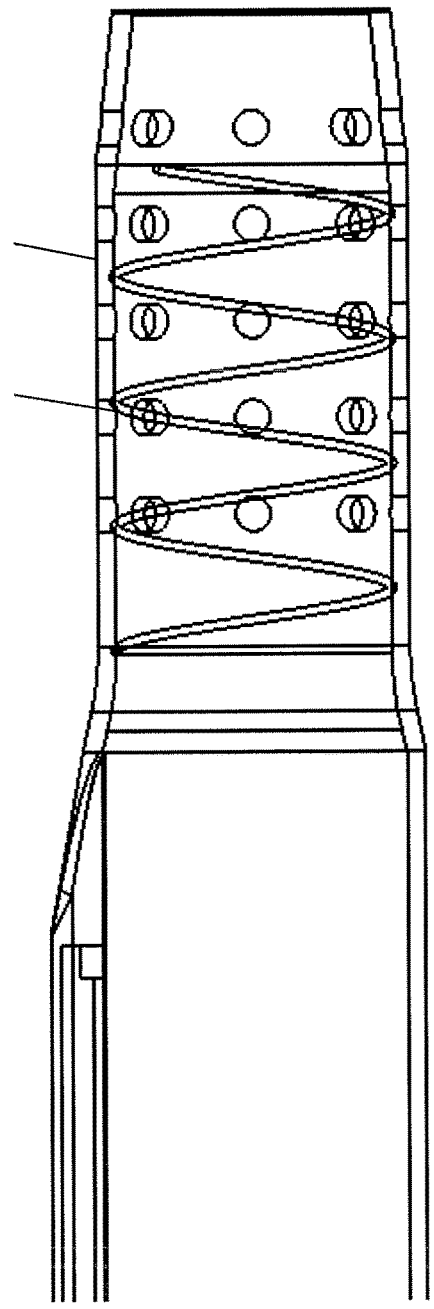
FIG. 45 shows a proximal vacuum port with a reinforcement coil.

In some embodiments, referring to FIGS. 44A-44C, the proximal vacuum port 4403 can be formed as an extension of the overtube itself (i.e., rather than being bonded or otherwise attached thereto). Further, as shown in FIG. 45, in embodiments where the proximal vacuum port is formed as an extension of the overtube and/or in embodiments where the proximal vacuum port is a separate piece, a reinforcement coil 4554 or spring can be placed around the distal vacuum port 4503 to prevent the port 4503 from collapsing under vacuum.

In some embodiments, the proximal vacuum port can include ribs along the inner circumference thereof to help keep the port from collapsing under vacuum. For example, FIGS. 56A-D show a proximal vacuum port 5603 including longitudinal ribs 5616 extending therein. The ribs 5616 are rounded so as to allow the proximal vacuum port 5603 to slide freely along the scope 5601. FIGS. 57A-D show a similar proximal vacuum port 5703 with ribs 5716, but the holes 5730 in this embodiment are square rather than round.

Figure 70A:
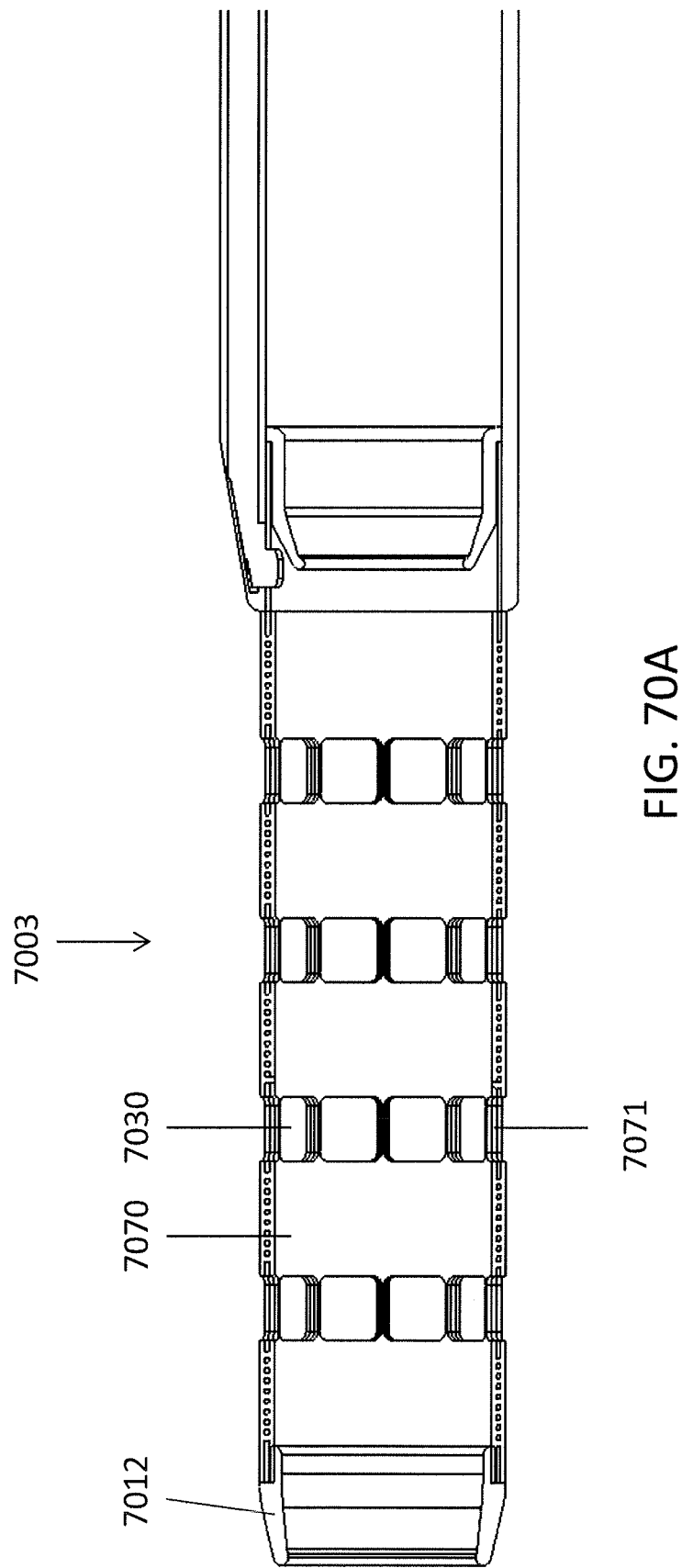
FIGS. 70A-70B show another embodiment of a proximal vacuum port.
Figure 70B:
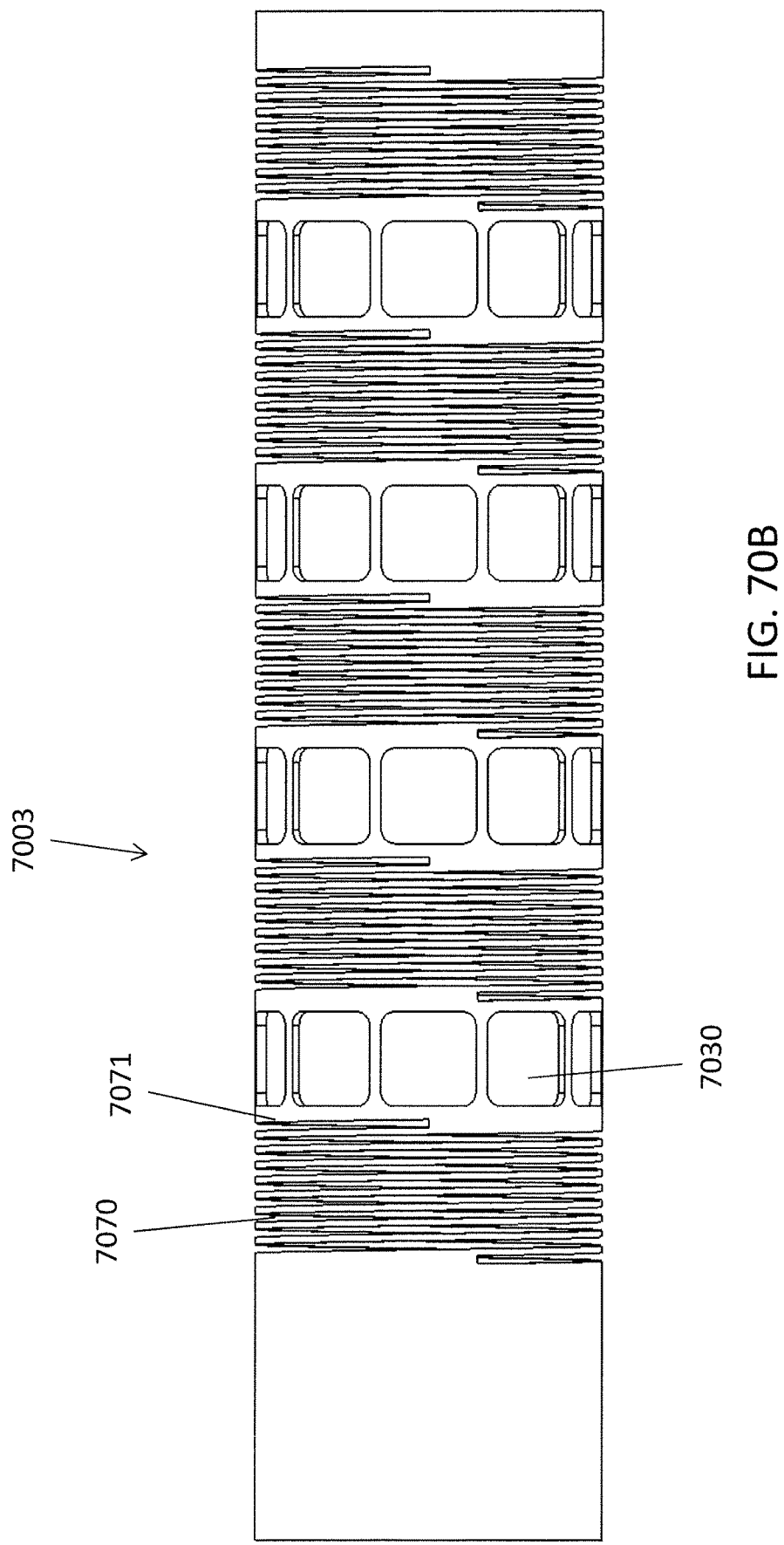

In some embodiments, referring to FIGS. 70A-70B, the proximal vacuum port 7003 can include flexible sections 7070 and rigid sections 7071 along the length thereof. For example, the flexible sections 7070 and rigid sections 7071 can be in an alternative pattern along the length. The rigid sections 7071 can include the vacuum holes 7030 therein. In some embodiments, the flexible sections 7071 can include spiraled material (as shown in FIG. 70B). The vacuum port 7003 can be made, for example, by laser cutting the vacuum holes 7030 and the spiral design into a tube. As shown in FIG. 70A, the vacuum port 7003 can further include a tapered distal tip 7012. In some embodiments, the distal tip 7012 can include a separate piece of material that is attached to the rest of the port 7003. Further, the tip 7012 and/or the entire port 7003 can be encased and/or coated with a material, such as urethane and/or a hydrophilic material, to help make the tip smooth and atraumatic. The flexible sections 7070 can advantageously ensure that the proximal vacuum port 7003 flexes with the endoscope during advancement through the small intestine.

Blocking Element

The blocking elements described herein can be configured to expand radially (i.e., such that the overall radial dimension of the blocking element increases from the collapsed to the expanded configuration). The increased radial dimension of the blocking element can prevent pleated tissue from moving distally past the blocking element, thereby ensuring that the tissue is properly transferred to the proximal vacuum port. In some embodiments, the proximal vacuum port extends between 0.5 inches and 2 inches, such as approximately 1 inch, underneath the blocking element. The blocking element moves with the distal grabbing mechanism and in various embodiments is attached to the distal grabbing mechanism or is attached to the endoscope (or other device) to the which the distal grabbing mechanism is attached.

Referring to FIGS. 8A-8E, in one embodiment, the blocking element 222 of the device 100 can include a flexure 842, a return spring 844, and a rolling seal 846. The flexure 842 can be configured to attach to the distal vacuum port 102. Further, as shown in FIGS. 8A-8E and 9A-9C, the flexure 842 can include a plurality of rigid struts 882, each with two hinges 884, 886 therein. There can be a circumferential array of struts 882, such as between 6 and 12 struts, such as 9 struts. The flexure 842 can be configured to bend at the hinges 884, 886 to allow the struts to extend radially outwards such that the blocking element 222 can expand to a larger overall diameter. The proximal hinge 884 can be configured to bend inward while the distal hinge 886 can be configured to bend outward such that a proximal wall is formed by the proximal ends 892 of the struts 882 when the hinges 884, 886 are bent. Further, the flexure 842 can be configured to expand when axially compressed by the proximal vacuum port 103, as described further below. In some embodiments, the flexure 842 can be injection molded from polypropylene. In some embodiments, the hinges 884, 886 are living hinges.

Figure 11:
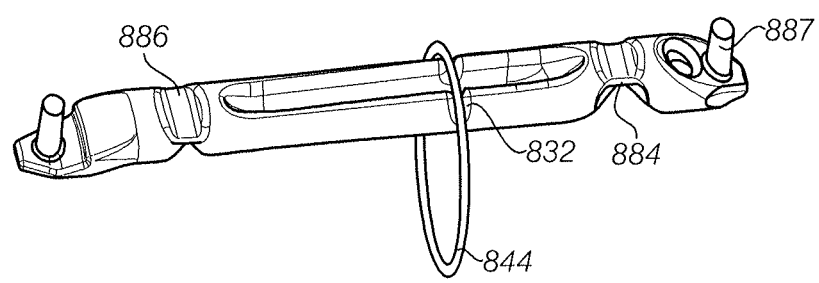
FIG. 11 shows a strut and a return spring of a blocking element.

Referring to FIGS. 8A and 11, the return spring 844 can be configured to return the flexure to its unexpanded neutral position. In one embodiment, the spring 844 can sit within a groove 832 (see FIGS. 8B and 8C) of the flexure 842. The spring 844 can be, for example, an elastic band or ring surrounding the struts 882. Alternatively, return spring functionality can be obtained by making flexure 886 of a high stiffness.

Referring to FIGS. 8A-8E, the rolling seal 846 can be attached to the proximal end of the flexure 842 and can be configured to slide snugly along the outer diameter of the proximal vacuum port 103 when moved relative thereto. Referring to FIG. 8A-8E and 10A-11B, the seal 846 can thus include an elastic annular member 863 and a plurality of attachment mechanisms 865 configured to attach to attachment mechanisms 887 on the flexure 842. For example, the attachment mechanisms 887 on the flexure 842 can be radially extending posts or pins while the attachment mechanisms 865 on the rolling seal 846 can be small annular elastic rings configured to fit over the posts or pins to attach the seal 846 to the flexure 842. The elastic annular member 863 can be configured to stretch radially as it slides along the tapered distal surface 312 of the proximal vacuum port 103. In one embodiment, the rolling seal 846 can be cast from urethane. Alternatively, the rolling seal 846 can be attached to the flexure 842 by insert molding them together.

Figure 12A:
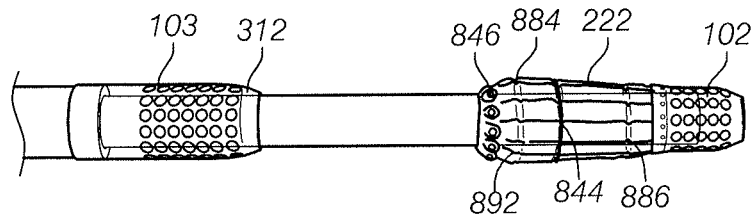
FIGS. 12A-G show an exemplary method of activating a blocking element.
Figure 12B:
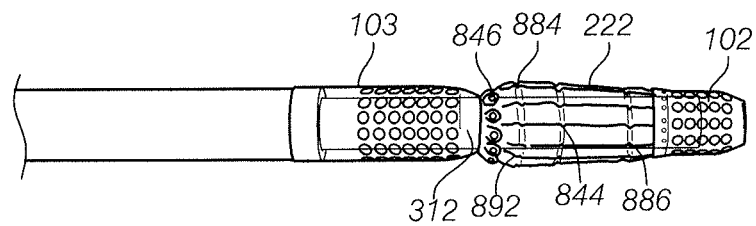
Figure 12C:
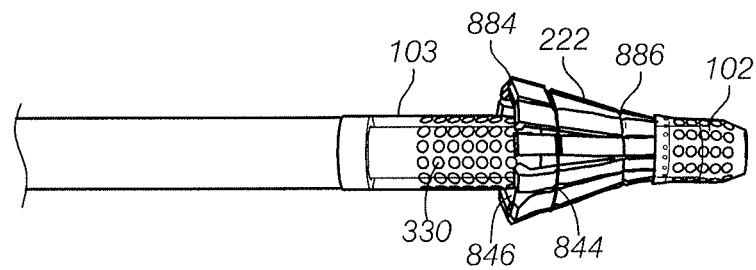
Figure 12D:
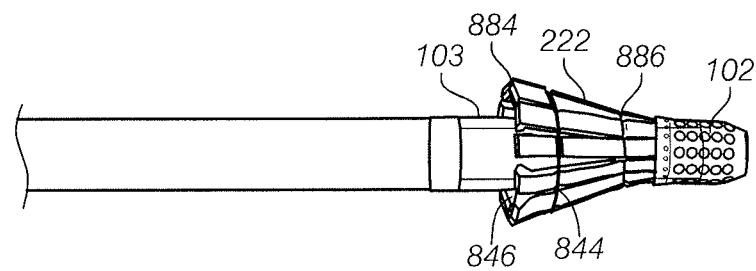
Figure 12E:
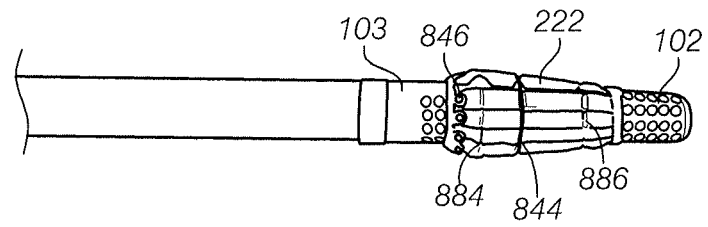
Figure 12F:
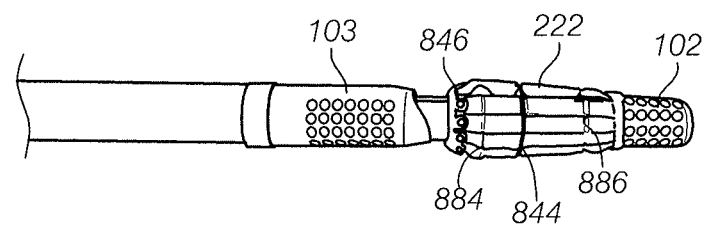
Figure 12G:
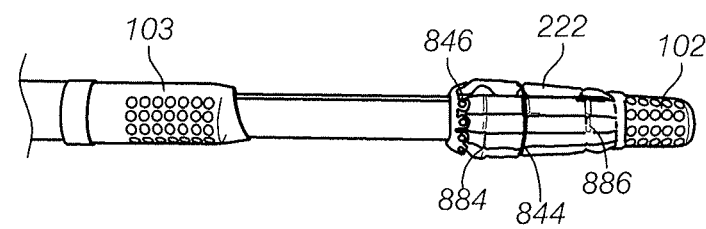
Figure 18A:
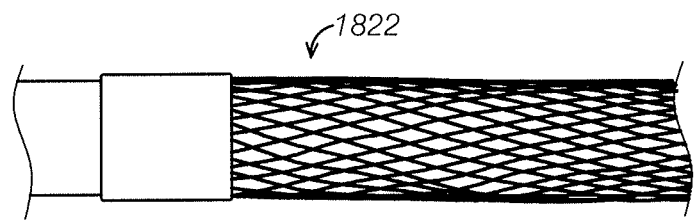
FIGS. 18A-18D show various views of another embodiment of a blocking element.
Figure 18B:
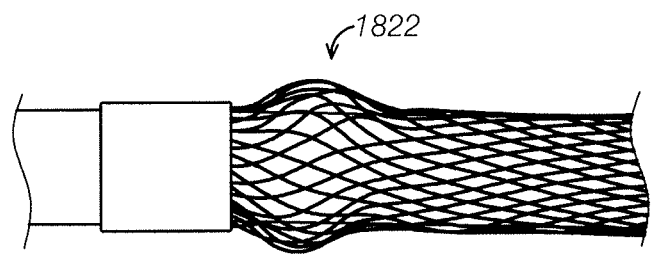
Figure 18C:
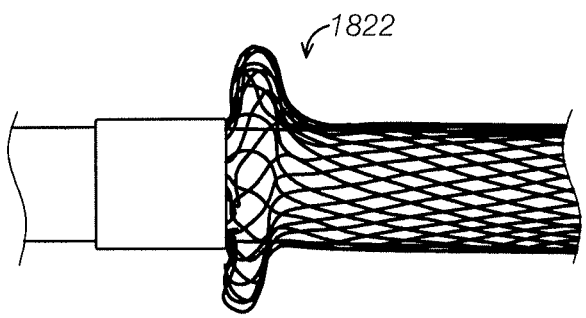
Figure 18D:
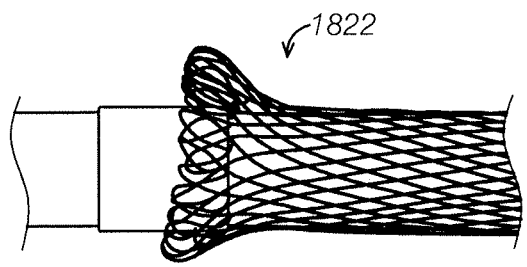

Referring to FIGS. 12A-12G, the position of blocking element 222 is fixed with respect to the position of distal vacuum port 102. The blocking element 222 can be activated (i.e., radially expanded) through axial relative movement between the proximal vacuum port 103 and distal vacuum port 102. In an initial configuration, shown in FIG. 12A, the proximal vacuum port 103 can be in a retracted position relative to the blocking element 222 and distal vacuum port 102. The proximal vacuum port 103 and distal vacuum port 102 can then be moved axially toward each other to place proximal vacuum port 103 into contact with the blocking element 222, as shown in FIG. 12B. Referring to FIG. 12C, as the proximal vacuum port 103 is pushed against the seal 846, it causes the flexure 222 to bend at hinges 884, 886 such that the distal portions 892 extend radially outwards. As shown in FIG. 12D, once the flexure 222 is fully expanded through movement of the hinges 884, 886, the proximal vacuum port 103 and distal vacuum port 102 can continue to be moved axially toward each other, forcing the tapered end 312 to slide underneath the seal 846. The flexure 222 can thus continue to expand as the seal 846 moves along the taper 312 and over the holes 330 of the proximal vacuum port 103. Relative axial movement of the proximal vacuum port 103 with respect to distal vacuum port 102 can continue until the proximal vacuum port 103 hits the proximal end of the distal vacuum port 102 and/or until the holes 330 of the proximal vacuum port 103 are fully covered by blocking element 222. Referring to FIG. 12E, as the vacuum port 103 and blocking element 222 move apart, the diameter of the blocking element 222 will decrease due to the radially inward force provided by the return spring 844. The proximal vacuum port 103 can then be fully retracted, as shown in FIGS. 12F-12G.

Figure 28:
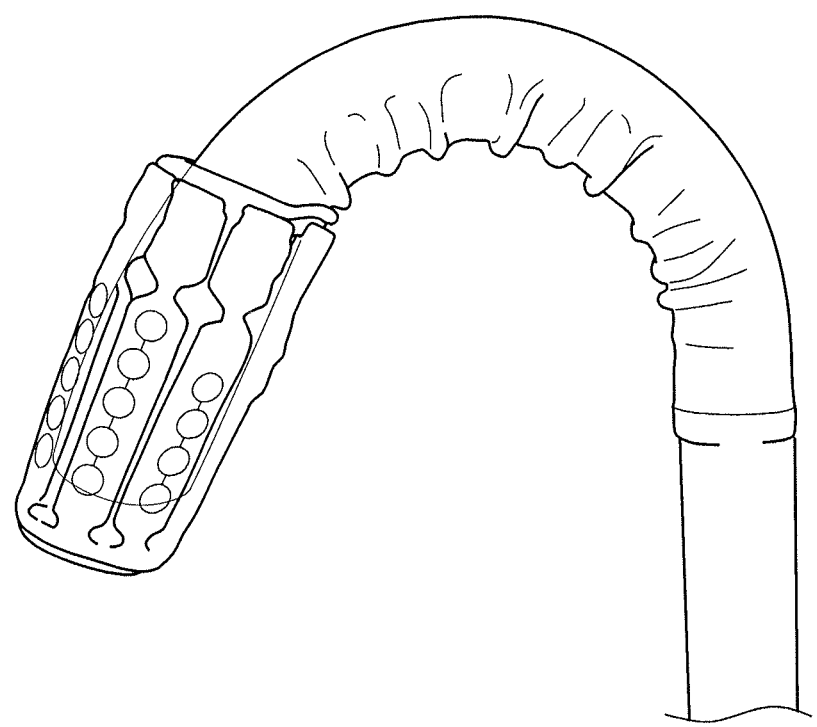
FIG. 28 shows another embodiment of a blocking element of a device for advancement through the small intestine.

Additional embodiments of blocking elements are shown in FIGS. 13A-18D and 28. In the embodiment of FIGS. 13A-13B, a blocking element 1322 includes rigid linkages 1313 configured to pivot. An o-ring 1314 keeps the blocking element 1322 in the constrained configuration. The linkages 1313 can be configured to pivot out and increase their diameter upon activation by axial movement of the proximal vacuum port. In the embodiment of FIGS. 14A-B, the blocking element 1422 can be similar to FIG. 1322, but can be entirely elastomeric. The blocking element 1422 can flex or stretch. In the embodiment of FIG. 15, the blocking element 1522 can include linkages 1513 that can be directly integrated into the distal vacuum port. In the embodiment of FIGS. 16A-16D, the blocking element 1622 can include both rigid regions and flexing regions. In the embodiment of FIG. 17, the blocking element 1722 can include an inflatable cuff 1717. In the embodiment of FIG. 18, the blocking element 1822 can include a sheath, such as a braided sheath, that is configured to compress to create radial expansion when activated by axial movement of the proximal vacuum port. The braids can be configured to move relative to one another and/or can be welded or attached at some or all cross-over points. The blocking element 1822 can advantageously be flexible, smooth, small, and simple. The braids and linkages can be created with continuous outer skin such that there are no pinch points. In the embodiment of FIG. 28, the blocking element and distal vacuum port are combined into a single integrated structure. As shown, in such an embodiment, the vacuum holes can be positioned along the struts of the blocking element.

Figure 52A:
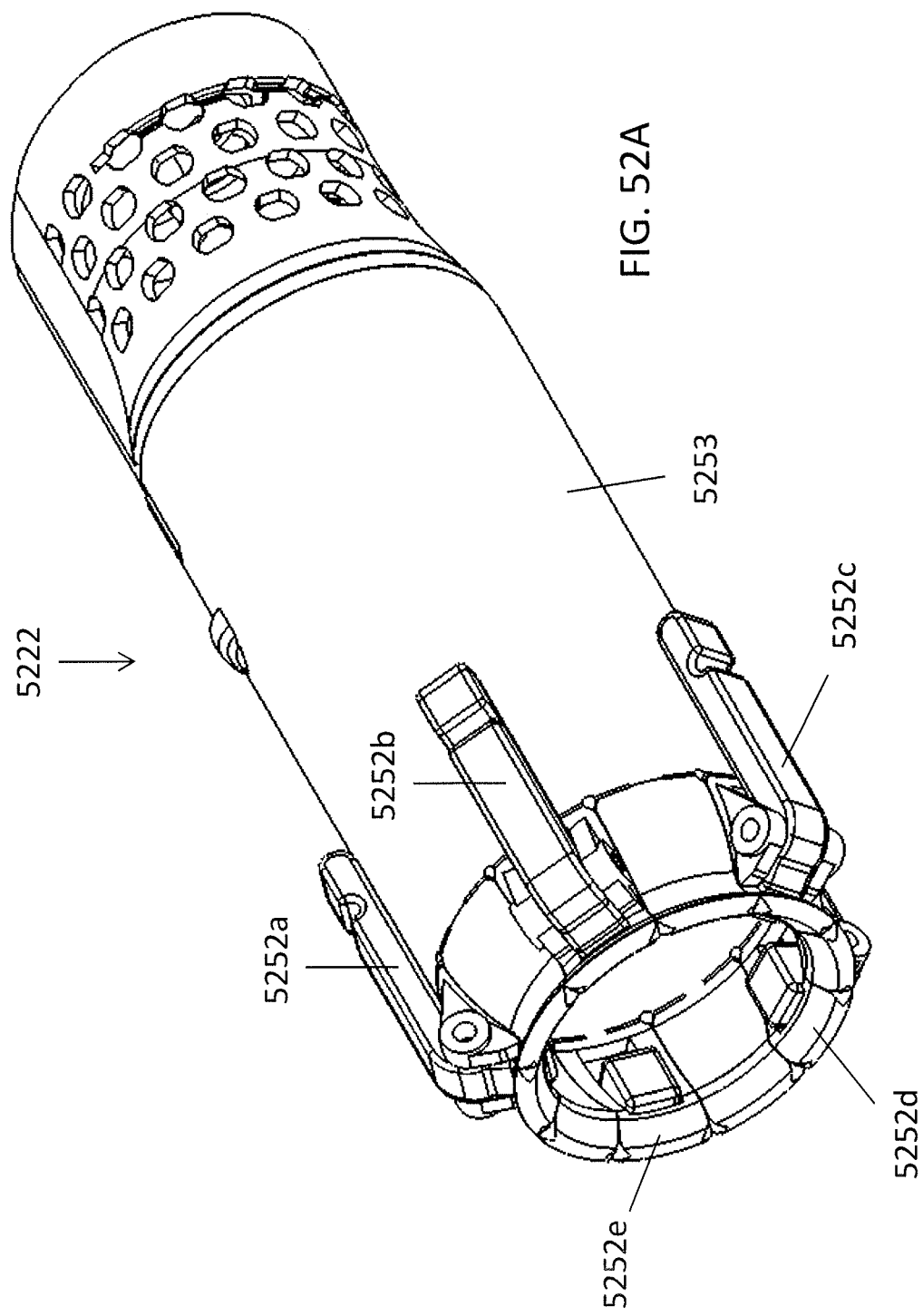
Figure 52D:
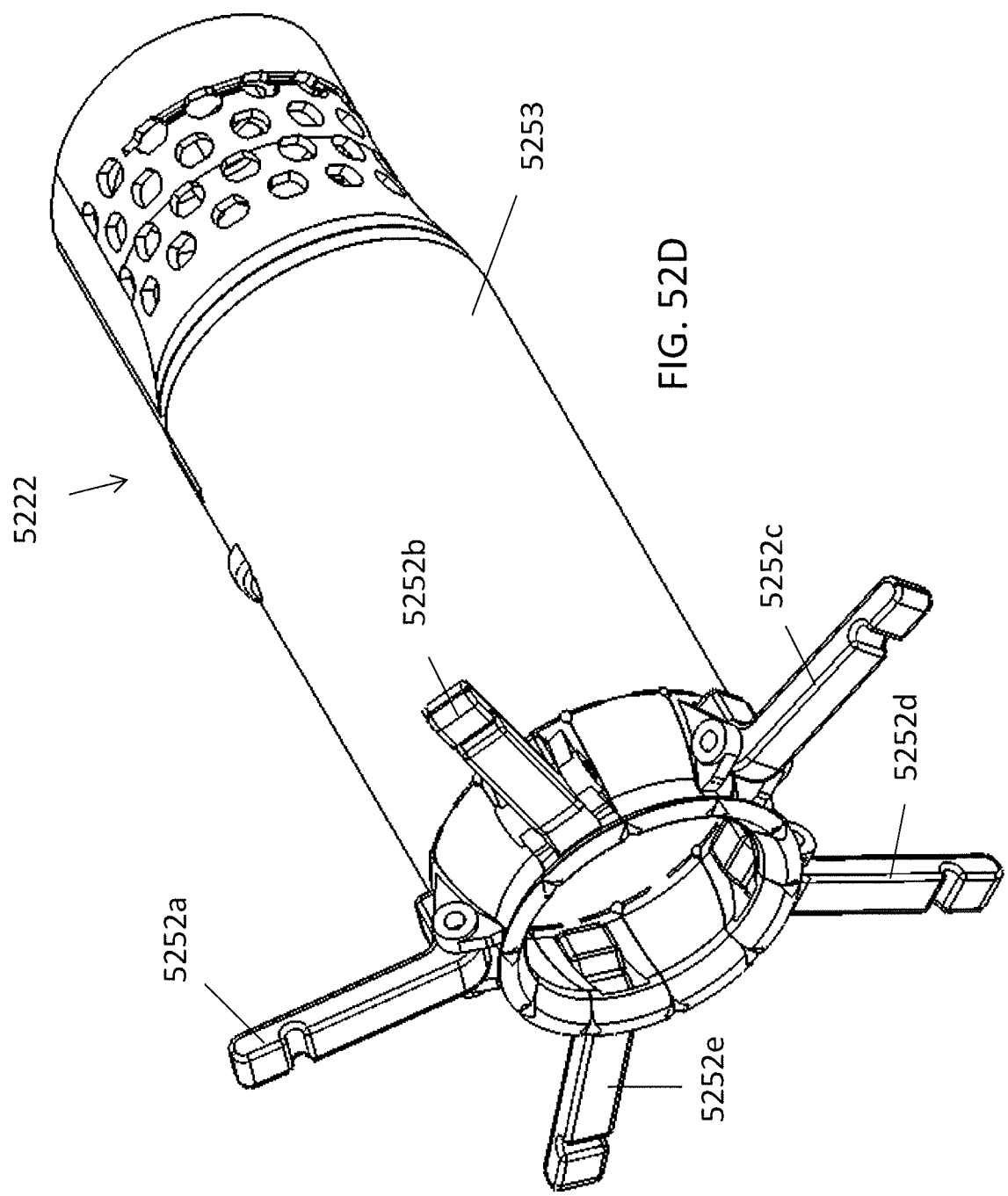
Figure 52E:
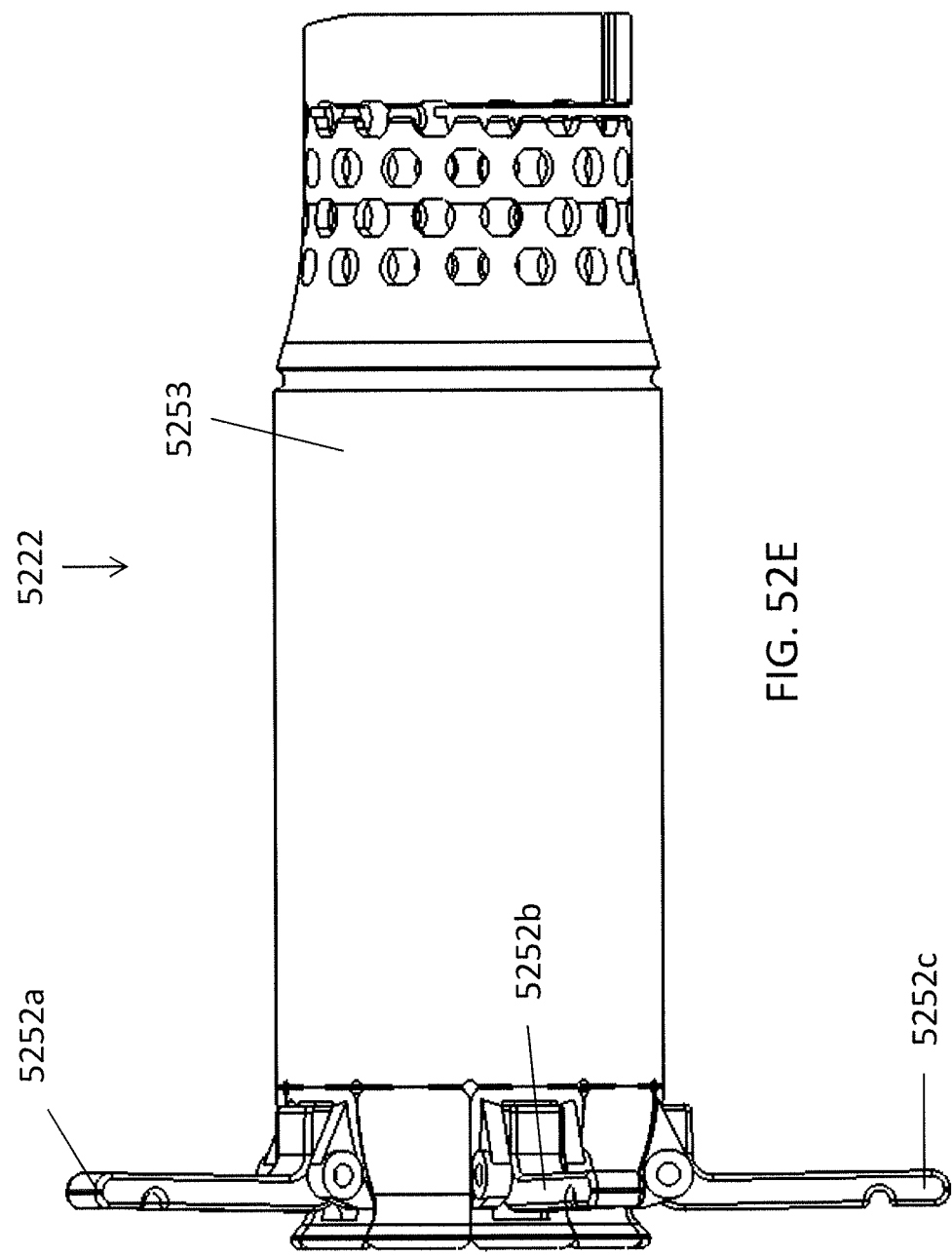
Figure 52F:
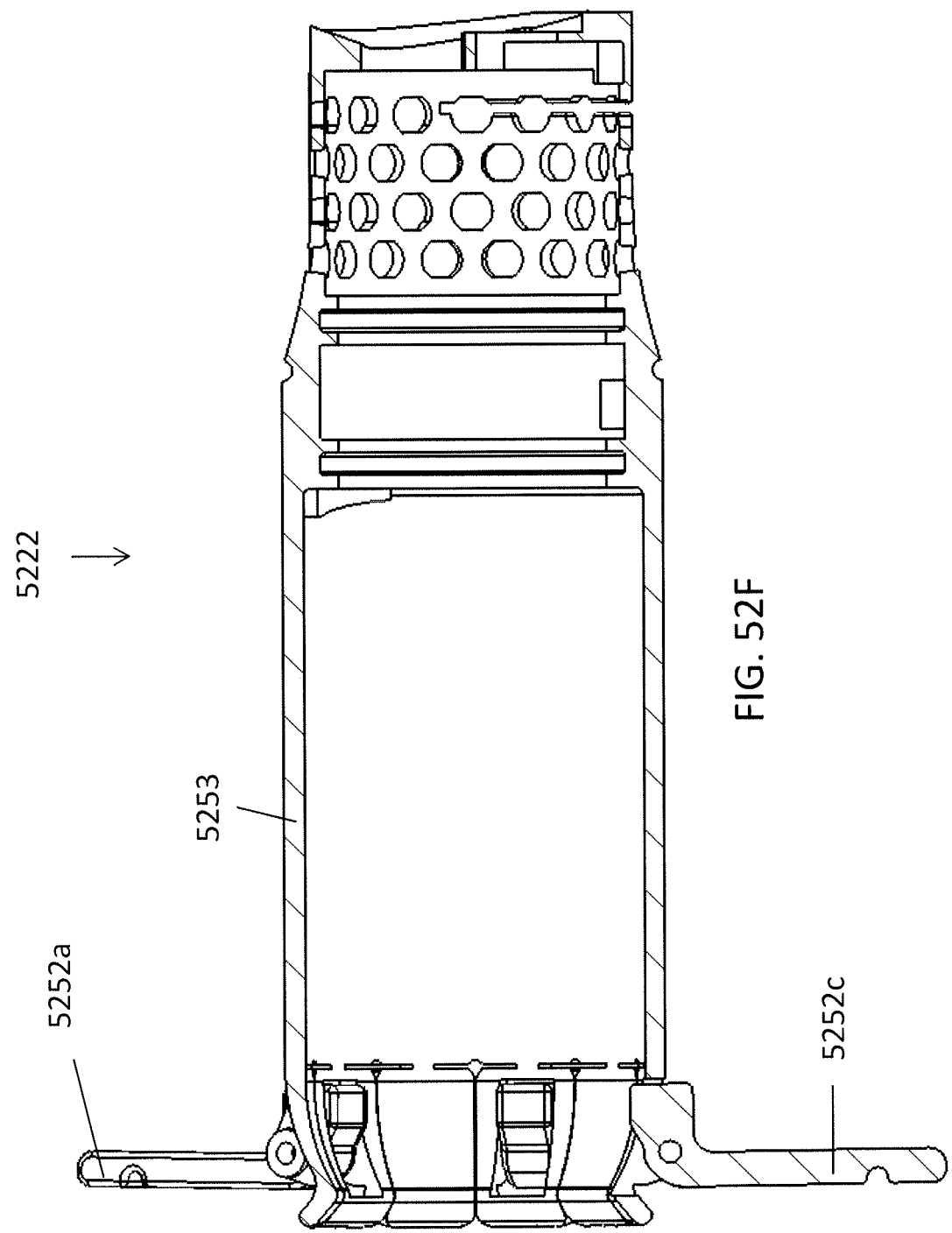

Another exemplary blocking element 5222 is shown in FIGS. 52A-52F. The blocking element 5222 is activated with contact from the proximal vacuum port, as described with reference to blocking element 222 and includes a plurality of links 5252a-e at a proximal end of a tube 5253. The linkages 5252a-e can be configured to pivot such that the tips of the linkages 5252a-e rotate from a distal position that is flush with the tube 5253 (FIGS. 52A-C) to a proximal position that extends radially outward from the tube 5253 (FIGS. 52D-F). In some embodiments, a spring mechanism can be configured to hold the links 5252a-c down when in the collapsed position.

Figure 39A:
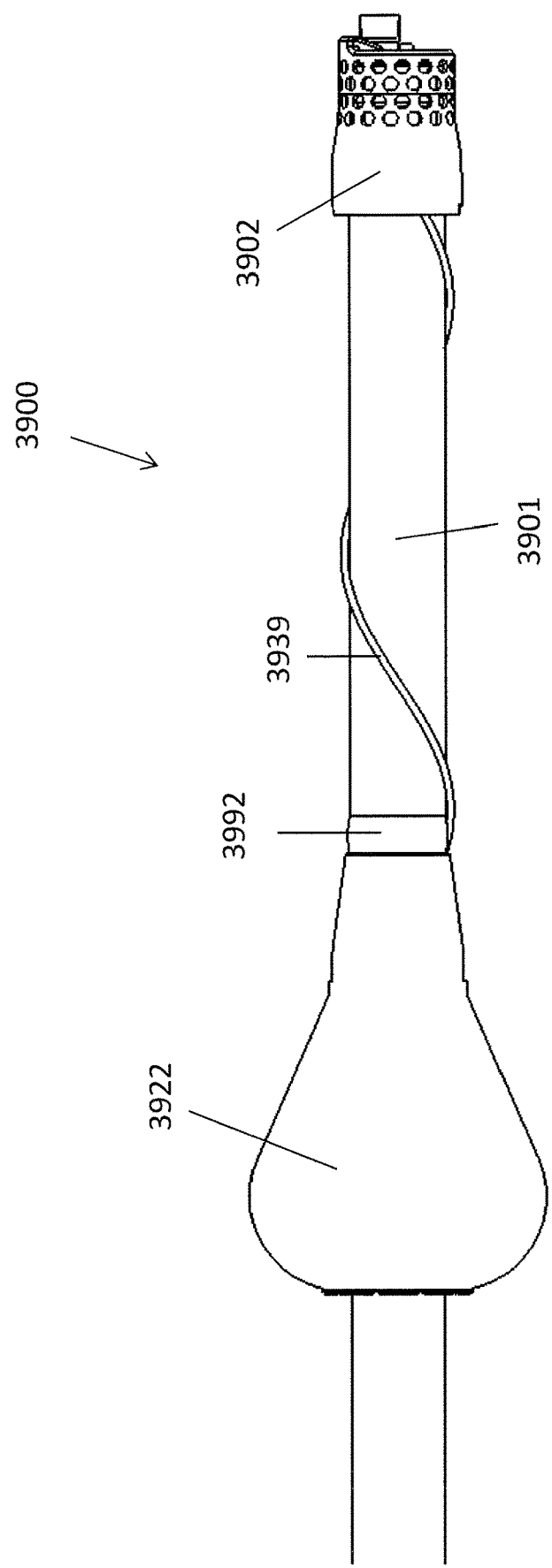
FIGS. 39A-39D shows a device for endoscopic advancement in the small intestine with the blocking element axially spaced away from the distal vacuum port.
Figure 39B:
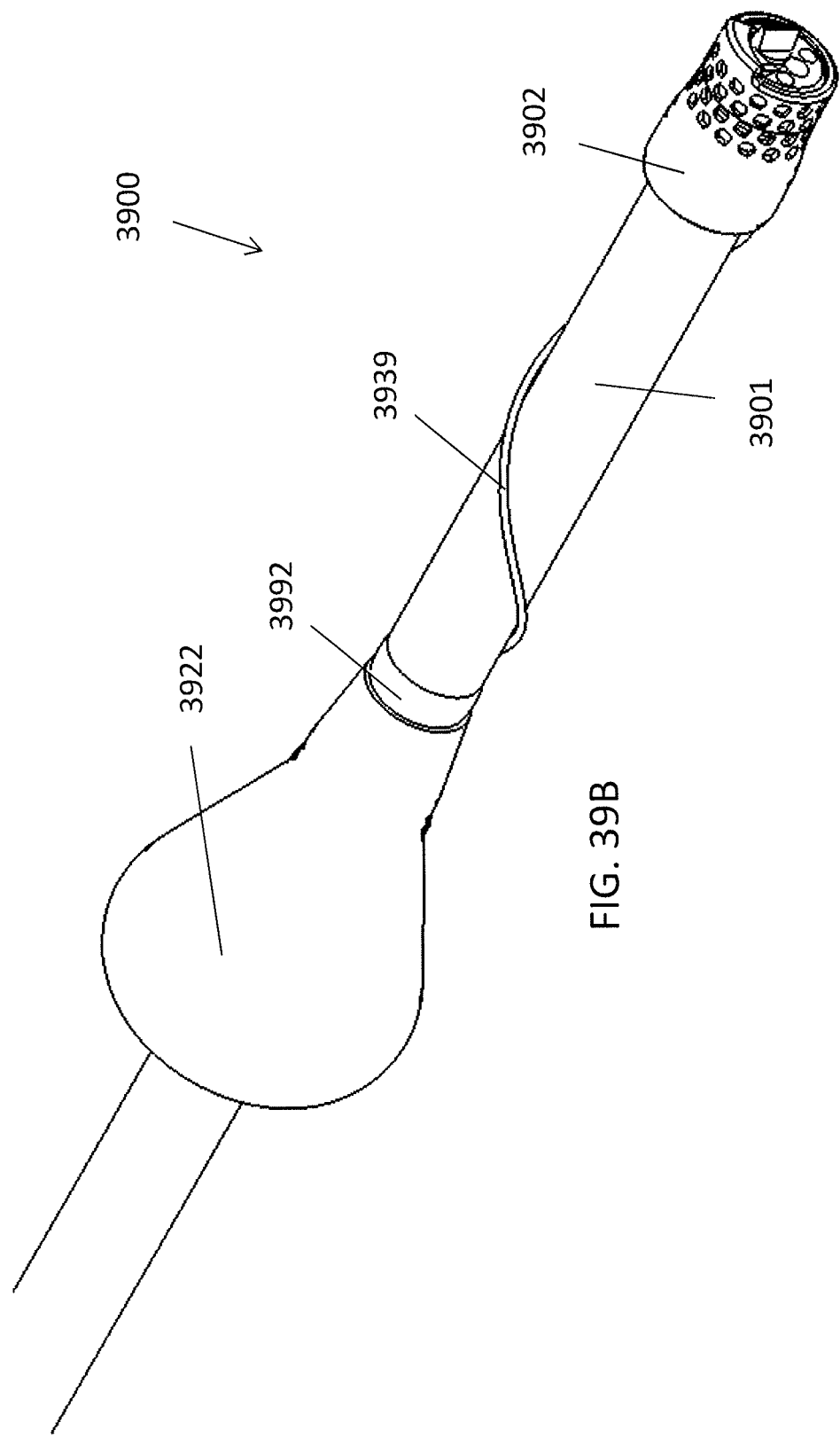
Figure 39C:
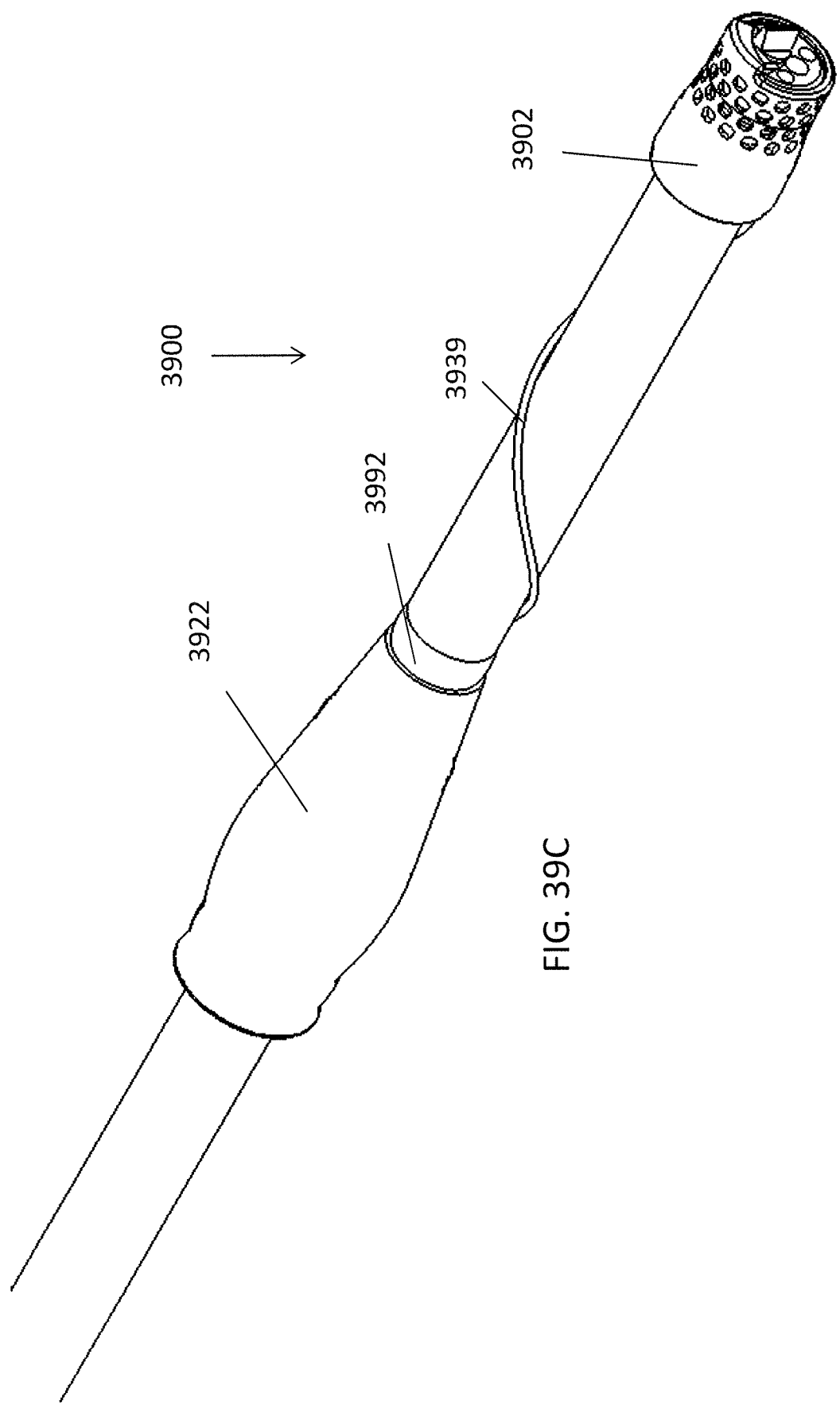
Figure 39D:
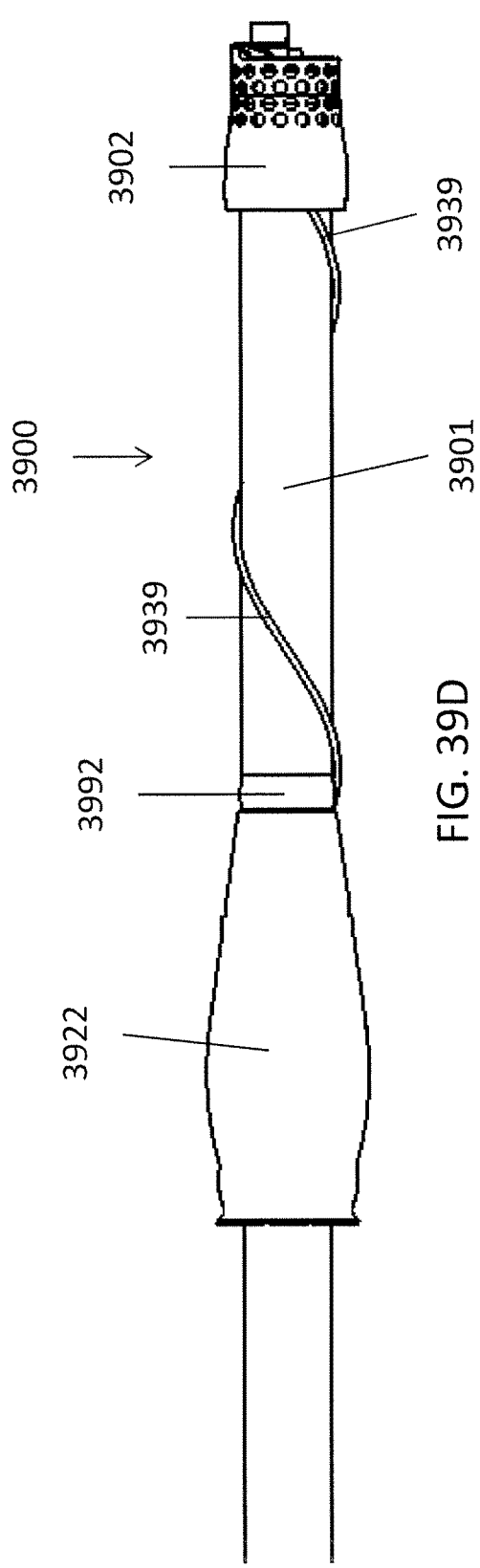

In some embodiments, the blocking element can be an inflatable element, such as a balloon. For example, FIGS. 39A-D show a balloon blocking element 3922 (FIGS. 39C-D show a balloon blocking element 3922 deflated while FIGS. 39A-B show the balloon blocking element 3922 inflated). The balloon 3922 is advantageously soft and atraumatic so as to avoid damaging tissue as the device travels therethrough. In some embodiments, the balloon 3922 can be a compliant balloon. In other embodiments, the balloon can be non-compliant. As shown in FIGS. 39A-39B, the balloon blocking element 3922, when inflated, can have a larger radius than the scope 3901. Further, in some embodiments, the radius of the proximal portion of the balloon can be greater than the radius of the distal portion of the balloon. For example, the balloon can have a conical shape. The balloon can be symmetrical about the scope 3901 so as to help center the scope during transfer through the lumen.

Further, in some embodiments, the blocking element is separate from the distal vacuum port (i.e., not integral therewith). For example, referring to FIGS. 39A-39D, the device 3900 can include a balloon blocking element 3922 that is separated from the distal port 3902. Separating the blocking element 3922 from the distal port 3902 advantageously allows the blocking element 3922 to be placed proximal to the steering section of the scope 3901, thereby improving docking of the proximal port within the blocking element 3922. Thus, as shown in FIG. 39A, the balloon blocking element 3922 can be configured to sit directly proximal to the bump 3992 on the scope 3901.

Any of the blocking elements described herein can include a wiping element on a proximal end thereof configured to facilitate movement of pleated tissue over the proximal vacuum port while ensuring that none of the tissue gets pinched thereunder during relative movement between the proximal vacuum port and the blocking element. For example, referring to FIG. 32G, the balloon blocking element 3222 is attached over a wiper element 3250 that includes a rigid sleeve 3261 and a plurality of flexures 3293 at a proximal end thereof. The flexures 3293 expand outward when the proximal port is moved thereagainst such that the proximal port can move within the space 3265 to dock within the blocking element 3222. The blocking element 3222 can be attached to the scope with a friction fit.

Figure 58A:
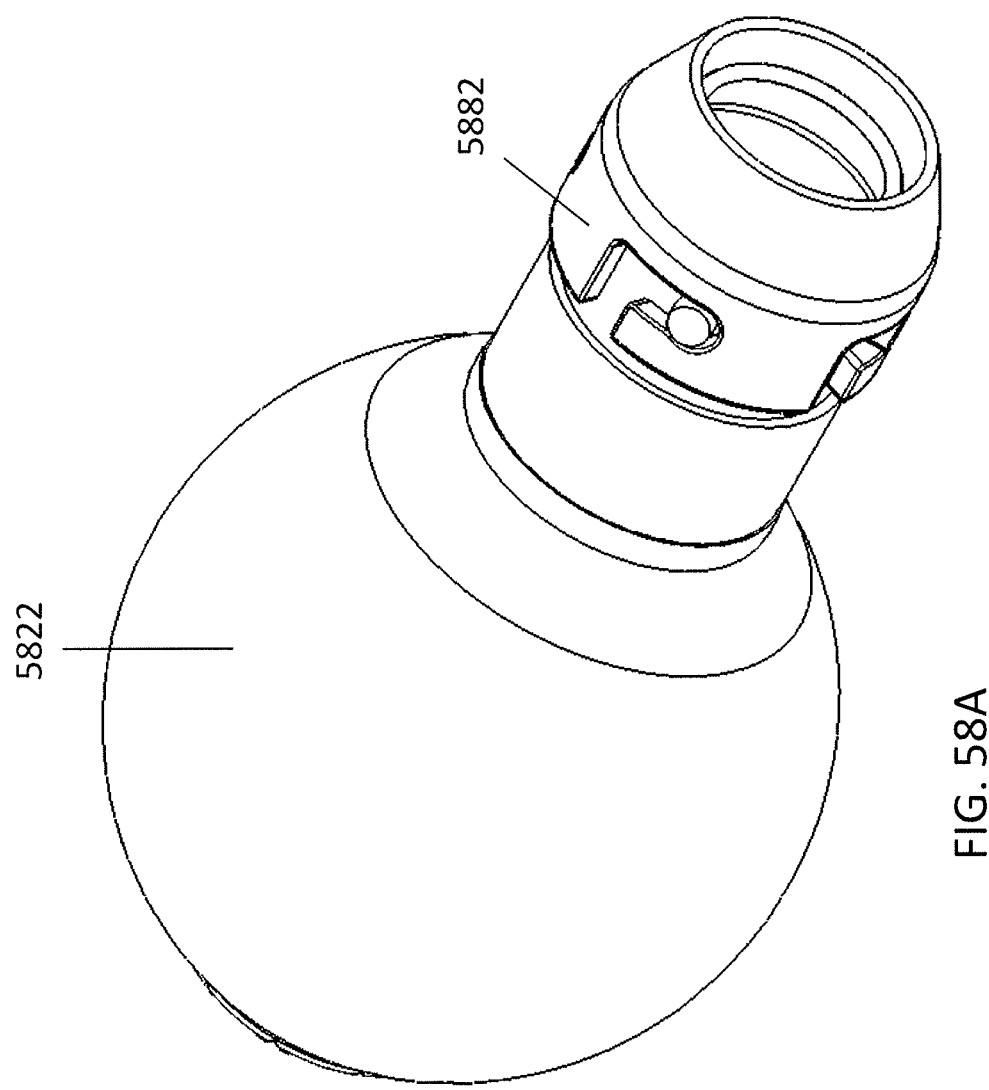
FIGS. 58A-C show another example of a balloon blocking element.
Figure 58B:
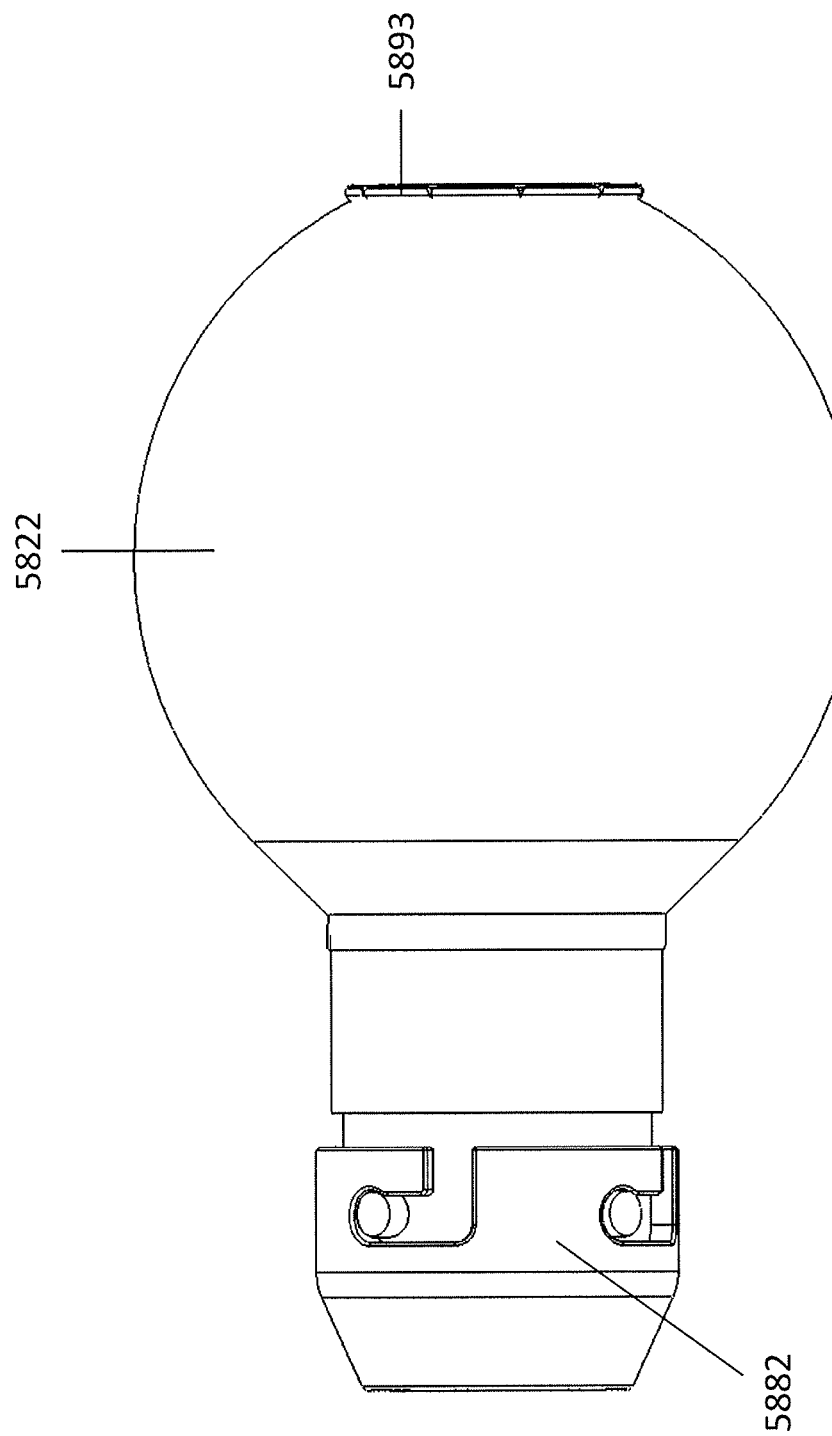
Figure 58C:
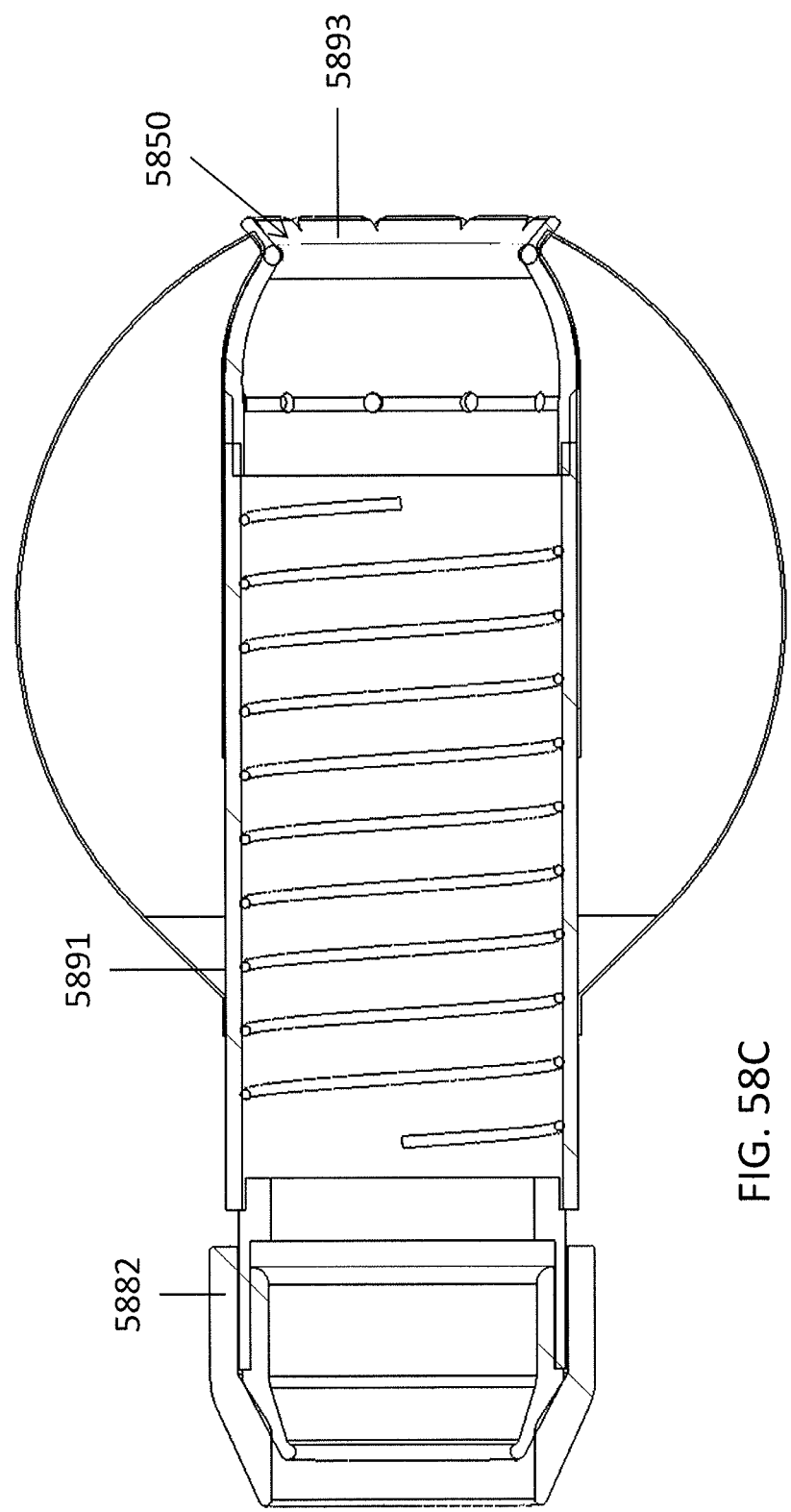

As yet another example, referring to FIGS. 58A-C, the balloon blocking element 5822 is attached over a wiper element 5850 (see FIG. 58C) that includes an elastomeric sleeve 5891 reinforced with coil. The coil reinforced sleeve 5891 advantageously prevents collapse under vacuum while allowing some flexibility without buckling when bent. The wiper element also includes flexures 5893 that extend outwards, similar to flexures 3293. A bayonet fitting 5882 on the distal end twists into the rest of the unit and compresses the conical piece thereunder to keep the unit in place proximal to the bump in the scope.

Figure 51A:
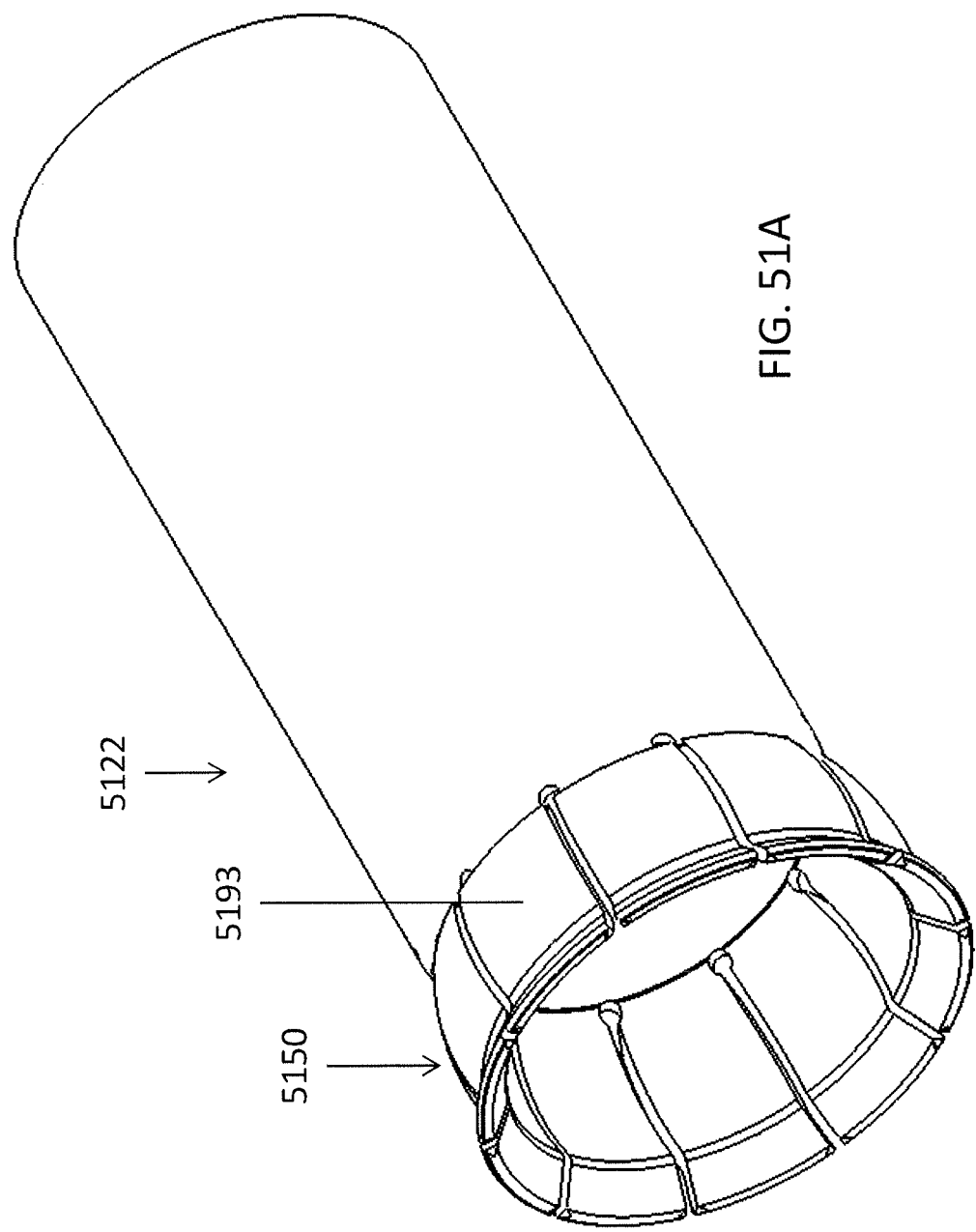
Figure 51B:
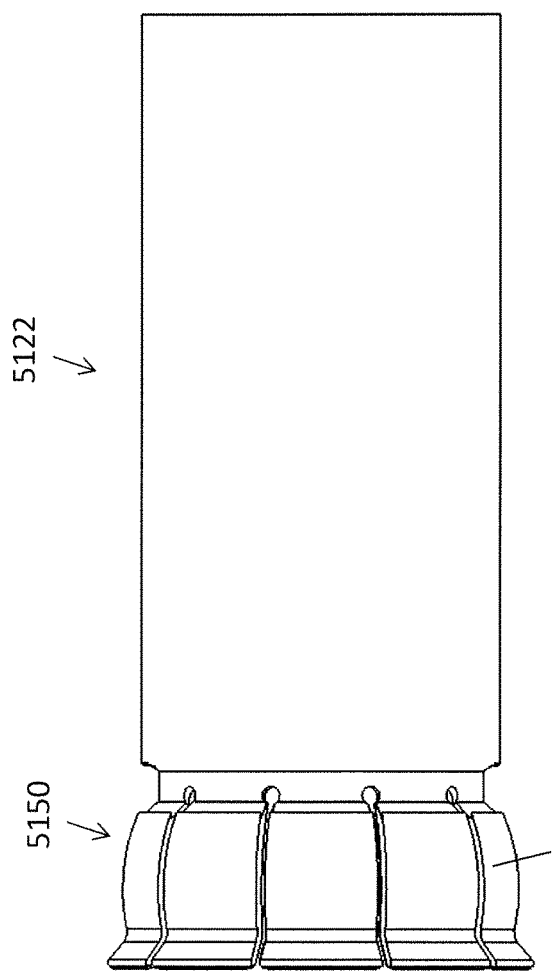
Figure 51C:
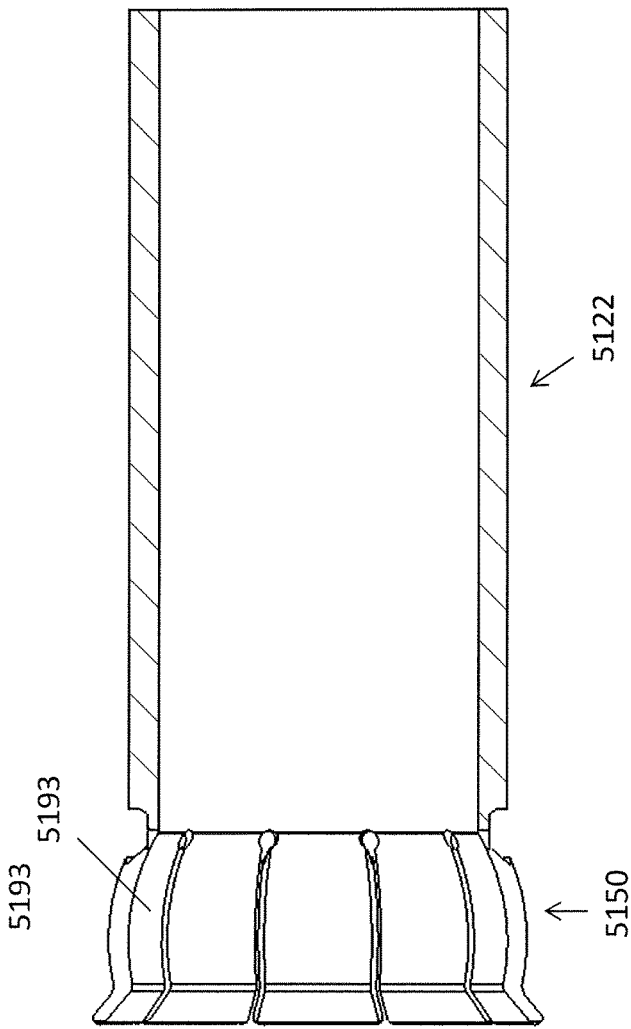
Figure 51D:
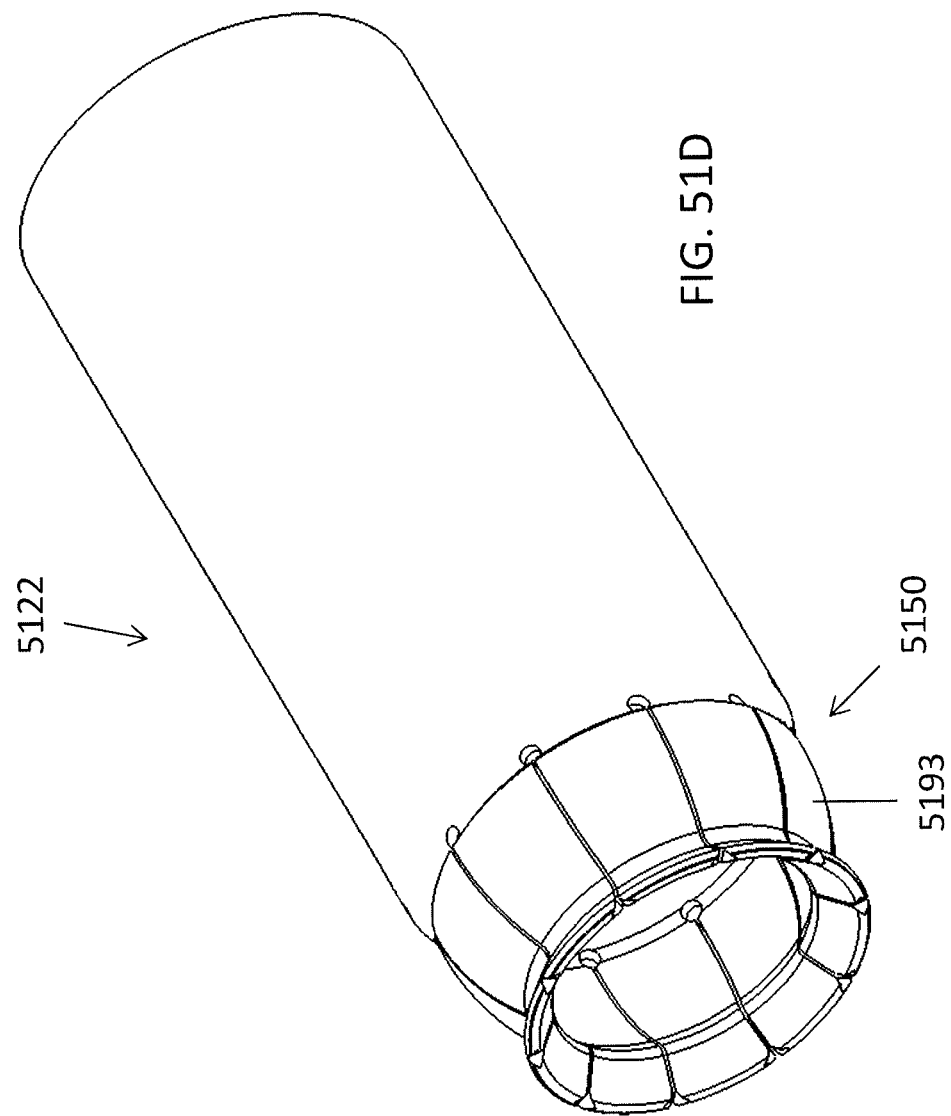

As yet another example, referring to FIGS. 50A-F, the blocking element 5022 (the radially expandable elements of the blocking element 5022, such as the balloon, are not shown for clarity) includes wiping element 5050. Wiping element 5050 includes a plurality of flexures 5093 configured to expand (FIGS. 50D-E) or contract (FIG. 50A-C) when extending over the proximal vacuum port when it extends thereunder. An elastomeric o-ring 5095 at the proximal end holds the proximal ends of the flexures 5093 together and expands and contracts with the flexures. FIGS. 51A-51F show another embodiment of a blocking element 5122 (again, radially expandable elements, such as the balloon, are not shown for clarity) with wiping element 5150. Wiping element 5150 includes flexures 5193 that are similarly configured to expand and contract. In this embodiment, flexures 5193 are hinged. FIGS. 51A-51C show the flexures 4193 expanded while FIGS. 51D-F show the flexures contracted.

Other embodiments of wiping elements are possible. For example, the wiping elements can include Teflon segments, coated o-rings, hinged up segments, coil springs, or iris style. In some embodiments, the wiping elements can further include a low friction coating or be made of a material that is inherently low friction (such as polypropylene, Teflon, or FEP). The wiping elements can be configured such that there is minimal contact with the proximal vacuum port so as to reduce friction. For example, only the o-ring and/or only the tips of the flexures can touch the proximal vacuum port as it passes thereunder.

In some embodiments, when the blocking element is a balloon, inflation of the balloon blocking element can occur by inflation through an already existing inflation port on the scope. For example, as shown in FIG. 32A, an inflation port 3292 from the endoscope 3201 can be sealed off using o-rings 3271*a,b* to provide inflation to the balloon blocking element 3222. A close-up of the inflation port 3292 with surrounding o-rings 3271*a,b* can be seen in FIG. 32F.

In embodiments where the balloon blocking element is moved distally, a line can be run from the inflation port to the blocking element for inflation. For example, FIGS. 39A-D show an inflation line 3939 extending from the distal end of the scope's inflation port back to the balloon blocking element 3922.

In other embodiments, the balloon blocking element can be inflated through an inflation line (e.g., a telescoping inflation line) that runs down the working channel of the scope or through an inflation line extending through an overtube or alongside the outer circumference of the scope.

Figure 47D:
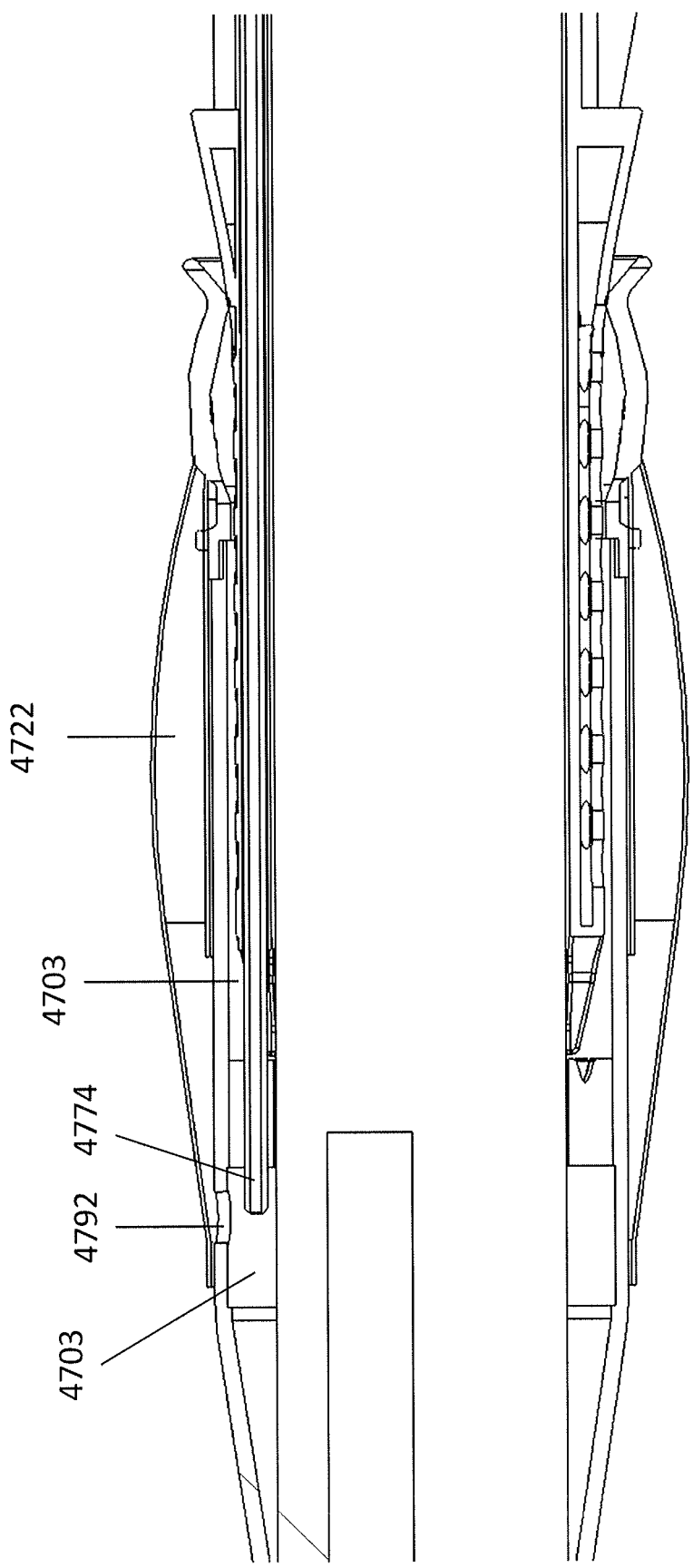
Figure 47E:
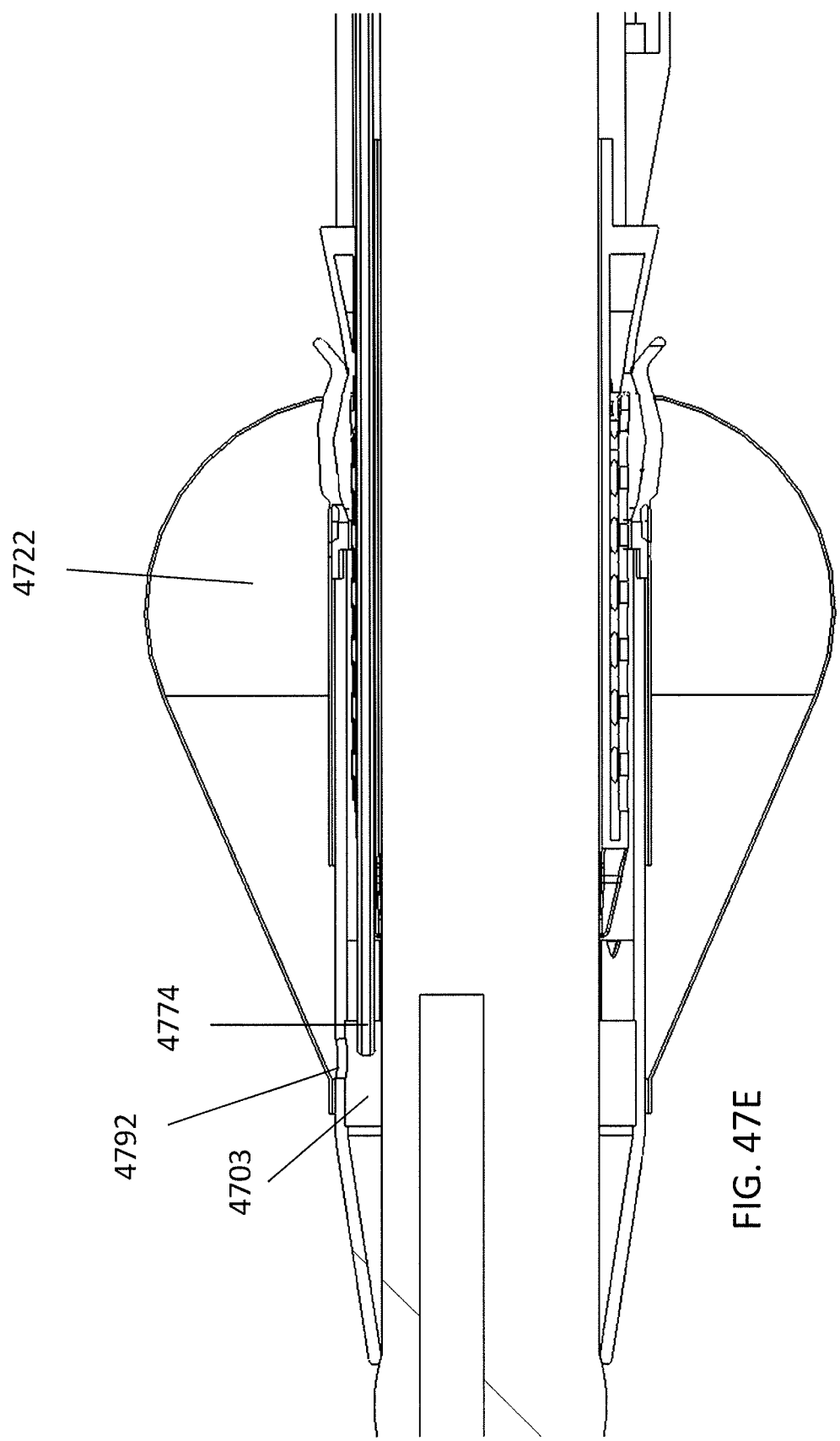
Figure 47F:
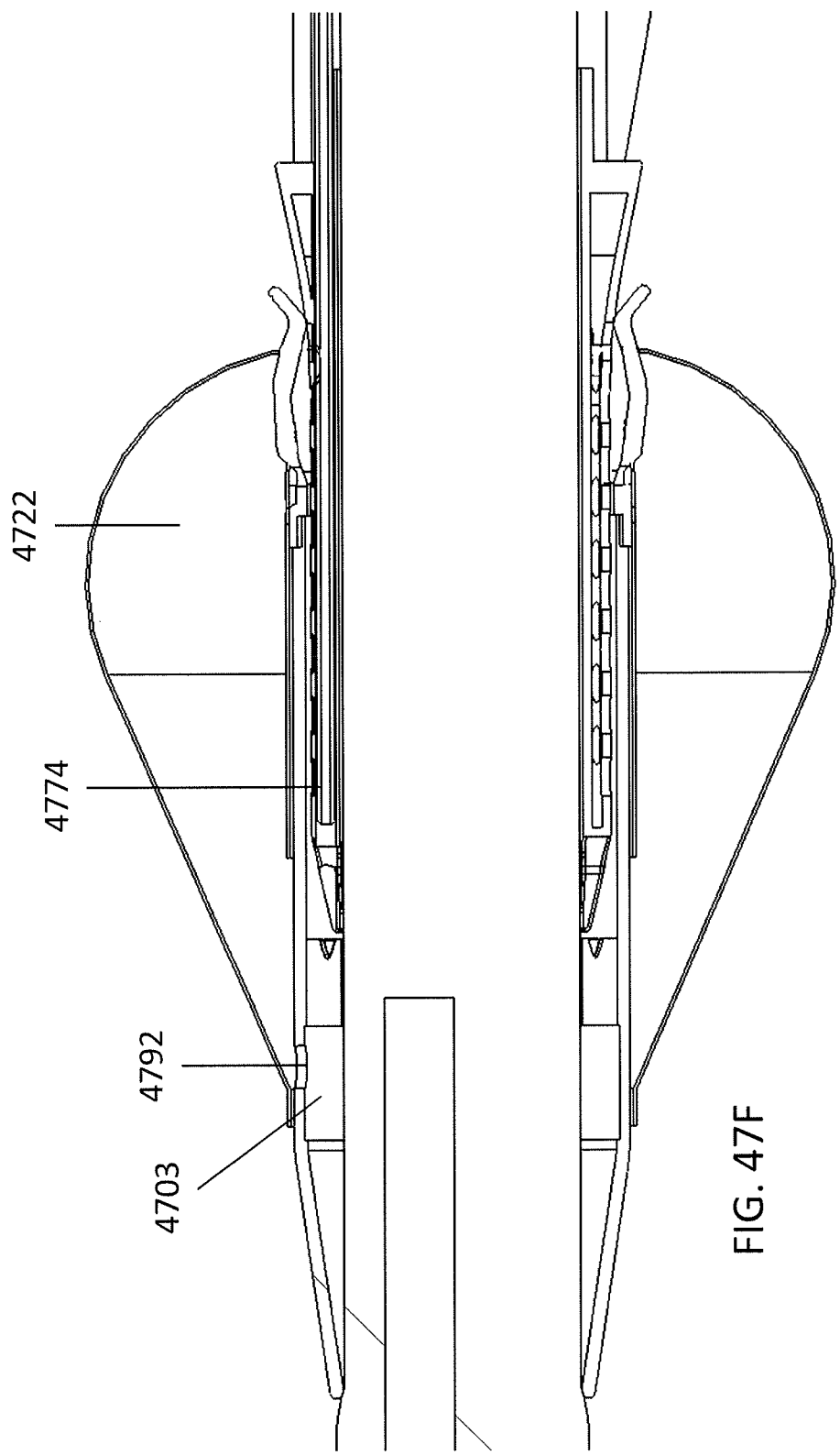
Figure 47G:
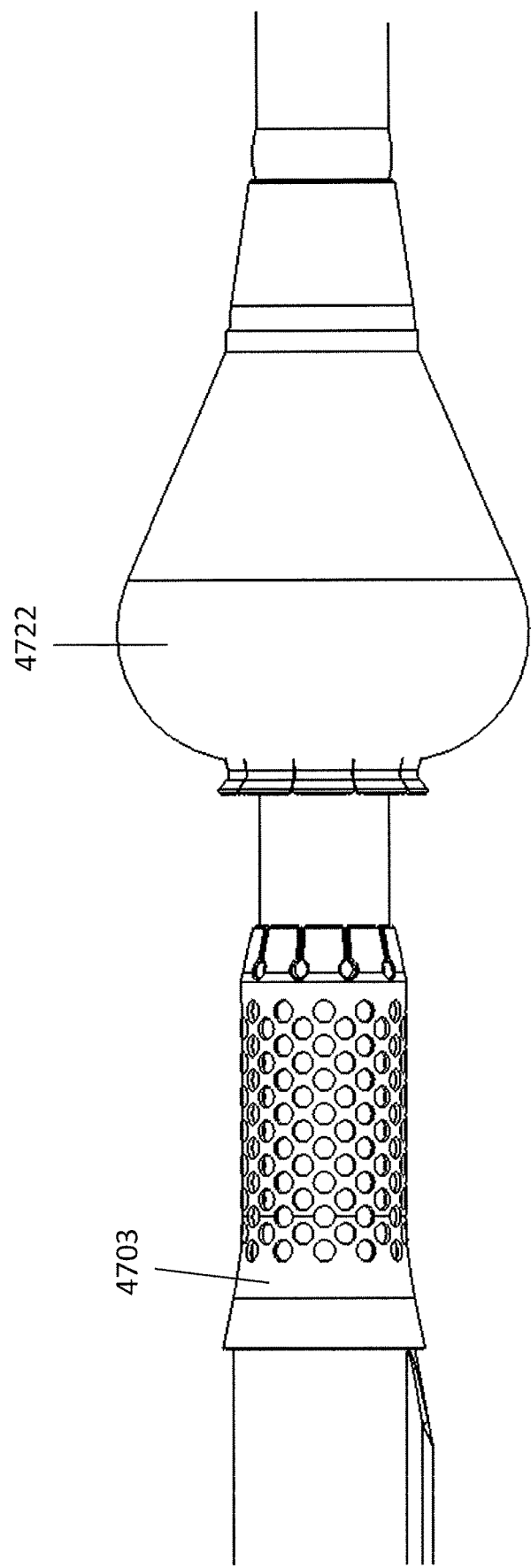
Figure 47I:
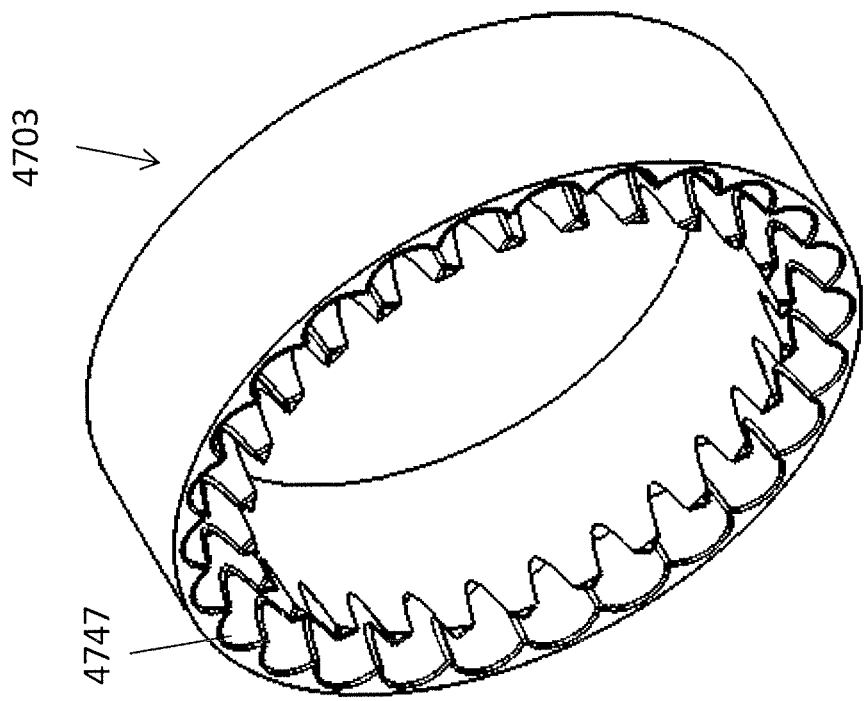
Figure 47H:
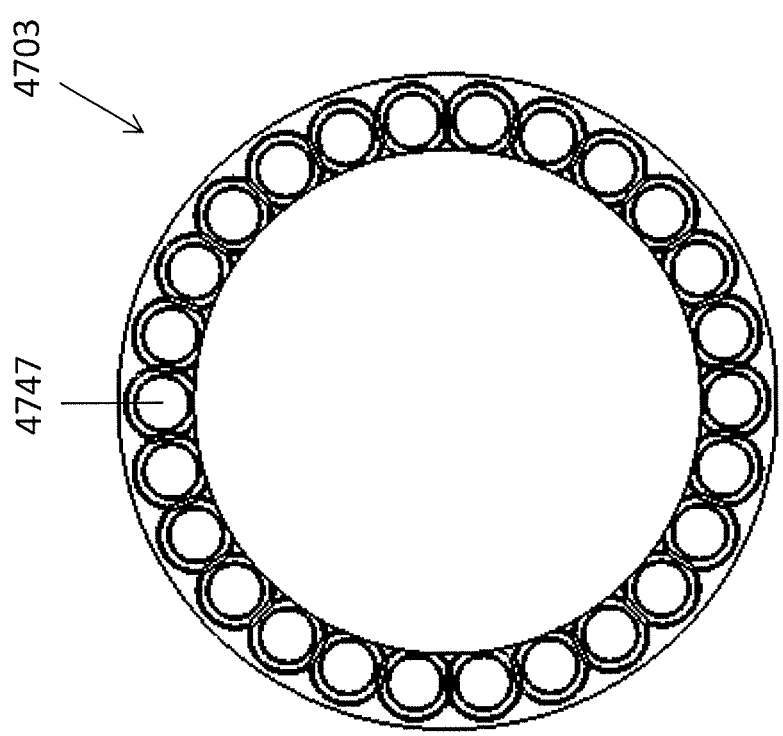
Figure 48A:
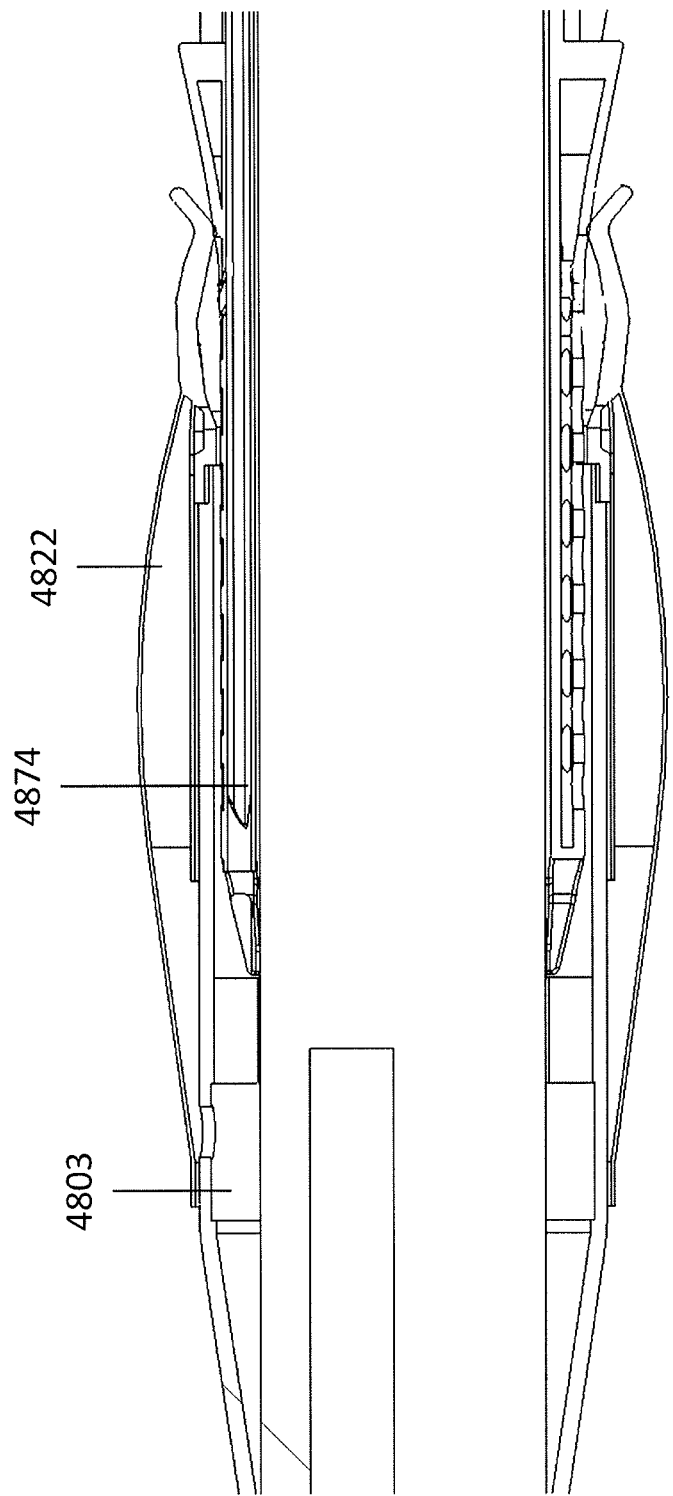
FIGS. 48A-D show another embodiment of a device having an extendable needle for inflation of a balloon blocking element.
Figure 48B:
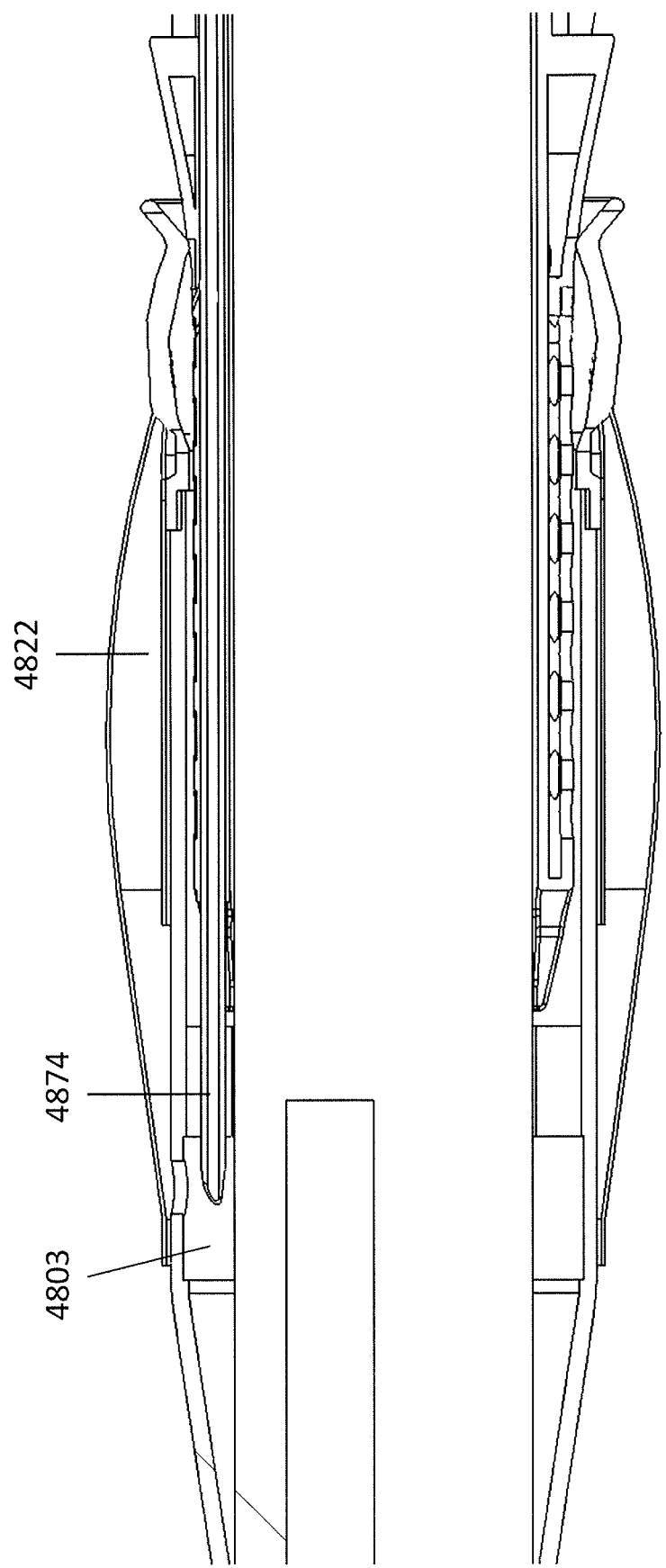
Figure 48C:
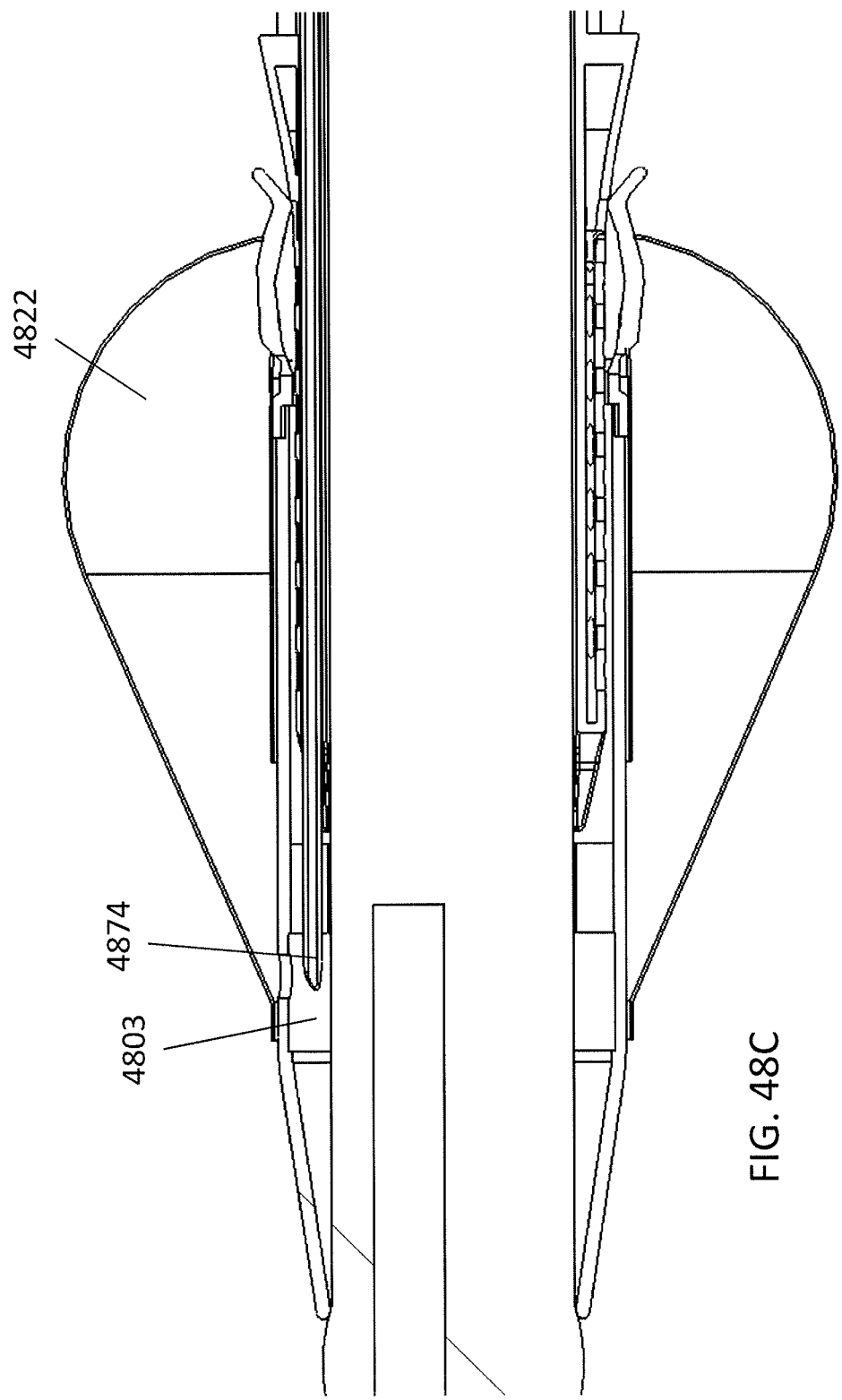
Figure 48D:
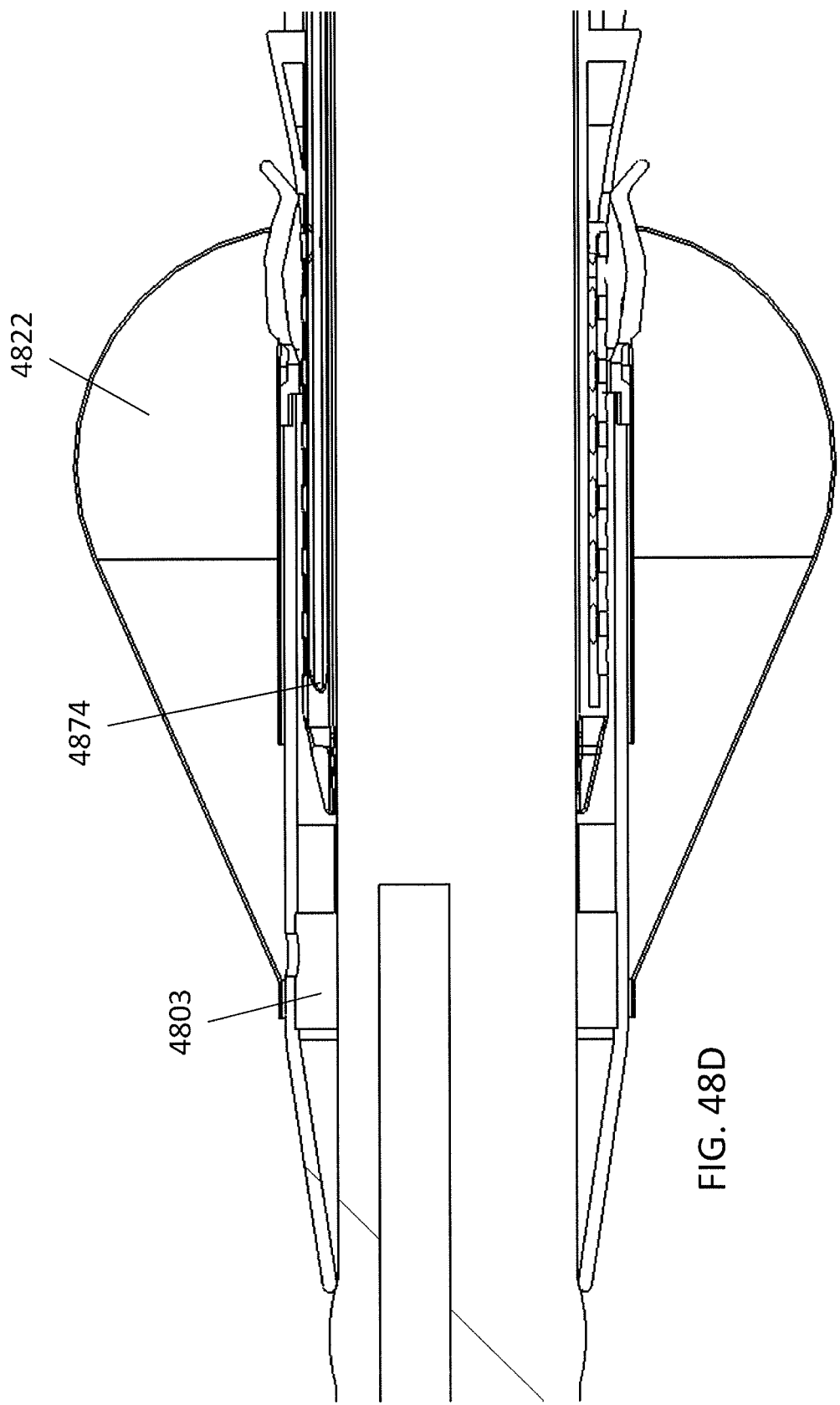

Referring to FIGS. 47A-I, in some embodiments, an extendable tube or needle 4774 (see FIG. 47B) can be attached to the proximal port 4703 to aid with inflation of the balloon blocking element 4722. Thus, the needle 4774 can be stored within the wall of the proximal port 4703 (FIG. 47C). When the proximal port 4703 is fully within the blocking element 4722, the needle 4774 can extend outwards to provide access to the inflation port 4792 (FIG. 47D), and fluid can be supplied through the needle 4774 and port 4792 to inflate the balloon blocking element 4722 (FIG. 47E). The needle can then be withdrawn back into the proximal port 4703 (FIG. 47F). FIGS. 47H-I show a cross-section of the distal end of the proximal port 4703, which can include a plurality of self-sealing holes 4747 for transfer of a plurality of needles therethrough.

A similar embodiment is shown in FIGS. 48A-D. The distal end of the proximal port 4803 can include a solid rubber element rather than an array of holes. The needle 4874 can be used to pierce through the rubber element to inflate the blocking element 4822.

In other embodiments, the balloon blocking element can be inflated through an annular channel formed between an additional overtube and the scope. That is, referring to FIG. 66A-H, a device 6600 can include a balloon blocking element 6622 attached to an additional overtube 6666 that extends through the handle 6607 to the balloon blocking element 6622. An annular space or lumen 6667 is created between the overtube 6666 and the scope 6601 through which a fluid or gas can be supplied to the balloon blocking element 6622 (e.g., through balloon inflation entry port 6669). An insufflation supply port 6668 communicating with annular space or lumen 6667 can be positioned on the overtube 6666 and/or be configured as part of the handle 6607. This embodiment also has tissue grabbing mechanisms (distal vacuum ports 6602 and proximal vacuum ports 6603) as discussed above with respect to other embodiments.

Figure 69A:
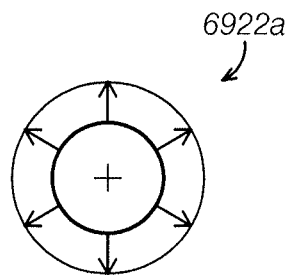
FIGS. 69A-69C show various radial expansion mechanisms for a blocking element.
Figure 69B:
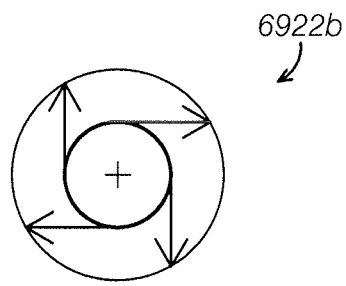
Figure 69C:
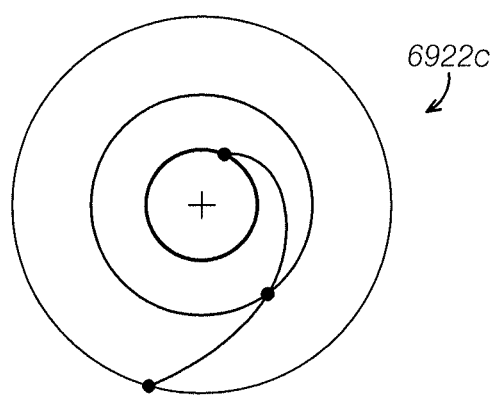

The blocking elements herein are described as expanding radially. Such radial expansion includes any increase in overall radius from the collapsed configuration to the expanded configuration, regardless of the process or direction of expansion. Thus, for example, referring to FIG. 69A, a blocking element 6922*a* might extend purely in the radial direction. Further, as shown in FIG. 69B, a blocking element 6922*b* might extend in a tangential direction while still resulting in an overall radially expansion. Likewise, as shown in FIG. 69C, a blocking element 6922*c* might extend in a rotational direction while resulting in an overall radial expansion.

Overtube Design

Referring back to FIGS. 1A-1C, the overtube 104 can be configured to ride over an endoscope 101 and can attach to the proximal vacuum port 103. Further, referring to FIGS. 19A-19D, the overtube can be designed to include a plurality of lumens configured to hold the endoscope and the vacuum lines 105, 106 therein.

Figures 19A, 19B:
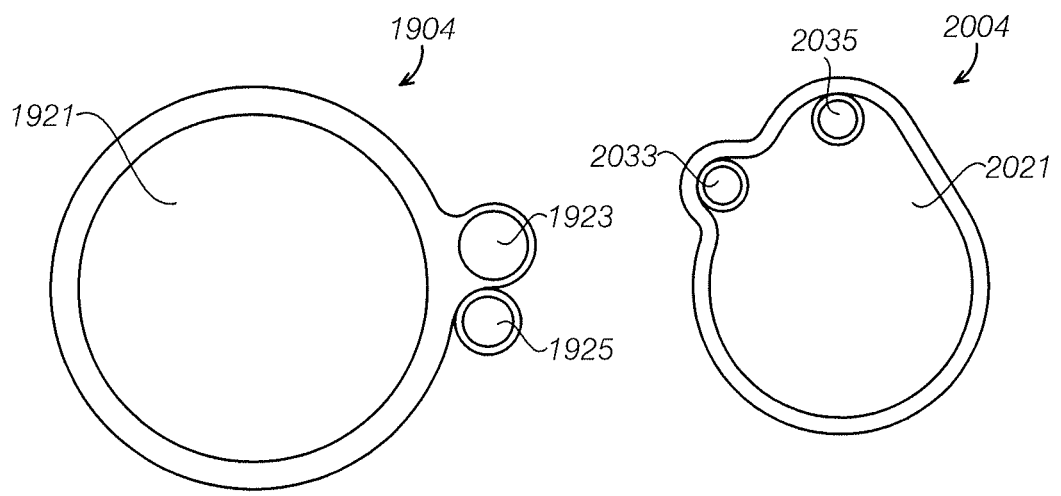
FIGS. 19A-19D show various embodiments of overtubes of a device for endoscopic advancement through the small intestine.

For example, as shown in FIG. 19A, an overtube 1904 can be a multi-lumen extrusion with a large central lumen 1921 for the endoscope, a side lumen 1923 for one of the vacuum lines 105, 106, and a separate tube 1925 attached thereto for the other vacuum line 105, 106. The overtube 1904 can advantageously allow for the union of different structures made of different materials, thereby potentially providing an effective composite structure (for example, one that has very high push stiffness, but very low bending stiffness).

Referring to FIG. 19B, an overtube 2004 can include a single lumen extrusion with a lumen 2021 for the endoscope and two separate tubes 2035, 2033 attached for the vacuum lines 105, 106. The two separate tubes 2035, 2033 can be inside of the lumen 2021, as shown, or outside. Further, the shape of the lumen 2021 or the outer diameter of the tube 2004 can be modified to include grooves or channels/indents for the separate tubes 2035, 2033.

Figures 19C, 19D:
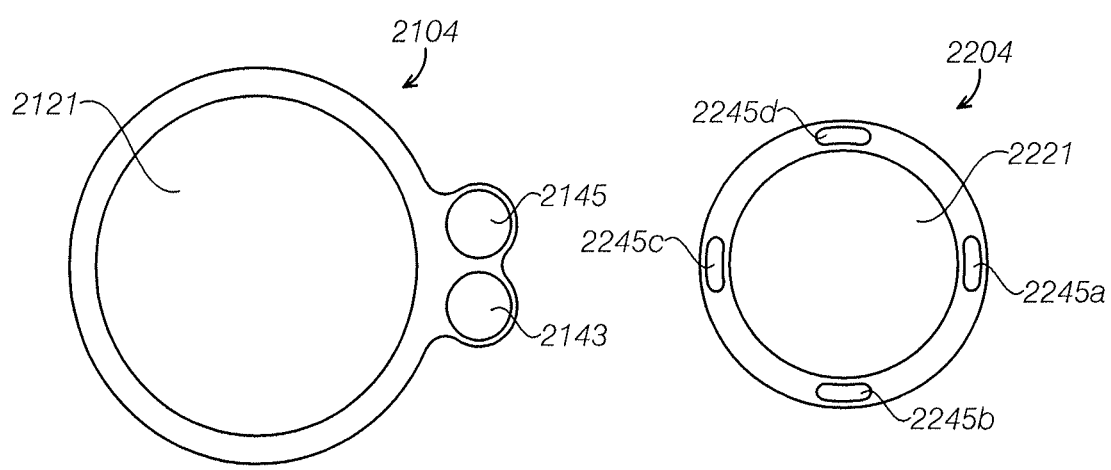

Referring to FIG. 19C, the overtube 2104 can be a multi-lumen extrusion with a large central lumen 2121 for the endoscope and two lumens 2145, 2145 for the vacuum lines 105, 106.

Finally referring to FIG. 19D, the overtube 2204 can include a large central lumen 2221 for the endoscope and redundant smaller lumens 2245*a-d* in the wall thereof for the vacuum lines. Redundant lumens can advantageously ensure a working vacuum even if one of the lumens becomes clogged.

Vacuum Connection to Distal Port

The distal vacuum port can be connected to vacuum through vacuum lines running down the side of the scope (such as a telescoping line), through a tube extending down the working channel, or through vacuum applied to the working channel itself.

Referring to FIGS. 1A and 1C, in some embodiments, the vacuum tube 105 connected to the distal vacuum port can be a telescoping tube that telescopes within the overtube 104 to allow for movement of the distal vacuum port 102 and endoscope 101 relative to the handle 107 and/or vacuum supply.

Figure 20A:
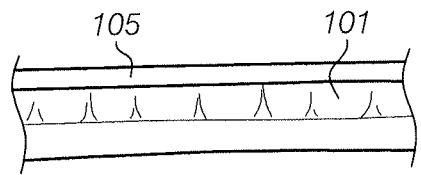
FIGS. 20A-20B show various views of one mechanism for attaching a telescoping vacuum tube to the outer tube of a device for endoscopic advancement through the small intestine.
Figure 20B:
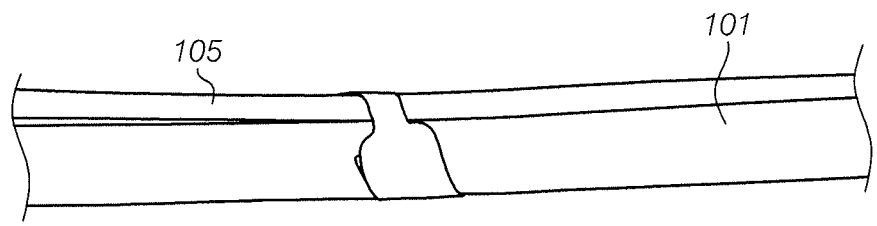
Figure 21A:
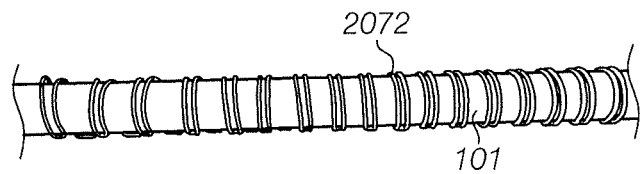
FIGS. 21A-21C show various views of another mechanism for attaching a telescoping vacuum tube to the outer tube of a device for endoscopic advancement through the small intestine.
Figure 21B:
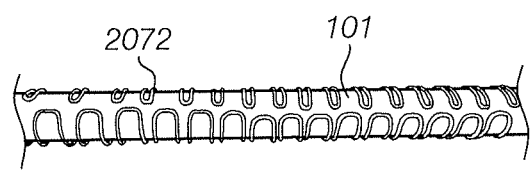
Figure 21C:
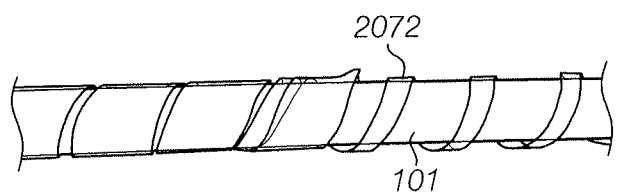
Figure 22:
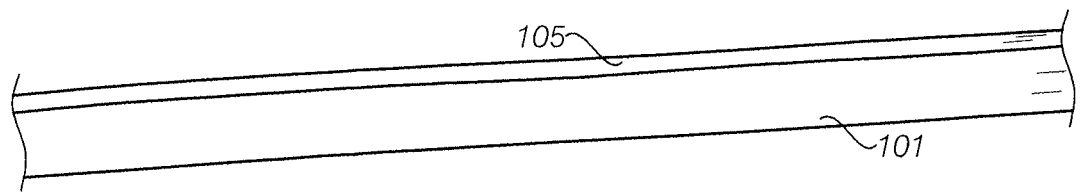
FIG. 22 shows an embodiment of a telescoping vacuum tube attached to the outer tube of a device for endoscopic advancement through the small intestine.
Figure 23:
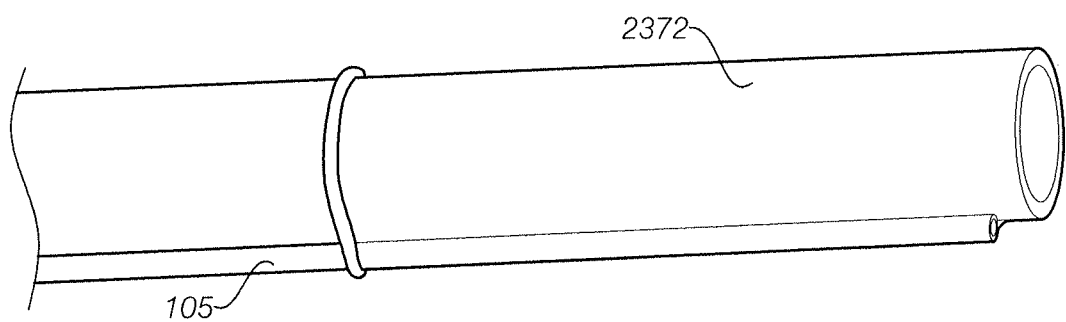
FIG. 23 shows another embodiment of a telescoping vacuum tube attached to the outer tube of a device for endoscopic advancement through the small intestine.

Referring to FIGS. 20A-23, the telescoping vacuum tube 105 can be attached to the endoscope 101 to ensure that the proximal vacuum port can move easily thereover. The attachment mechanism can be configured to: (1) hold the tube 105 against the endoscope 101; (2) slide freely relative to the proximal vacuum structure and small intestine; (3) prevent lateral movement of the vacuum tube 105; and/or (4) be easy to install. Exemplary methods of attachment are shown in FIGS. 20A-23. Referring to FIGS. 20A-20B, the vacuum tube 105 can be attached to the endoscope 101 with an adhesive, such as tape (e.g., bonded or heat-sealed). Referring to FIGS. 21A-21C, the tube 105 can be attached to the endoscope 101 with a coil 2072. The coil 2072 can extend all the way around the endoscope 101 or partially around the endoscope 101. The coil 2072 can be made, for example, of stainless steel (e.g., 0.007"), Nitinol or plastic. Referring to FIG. 22, the vacuum tube 105 can be shrunk onto the endoscope 101, such as activated by heat, chemistry, or UV light. Finally, referring to FIG. 23, the tube 105 can be sealed via a stretchable material 2372 that rolls over the endoscope 101 and tube 105, such as made of urethane or latex.

Figure 24A:
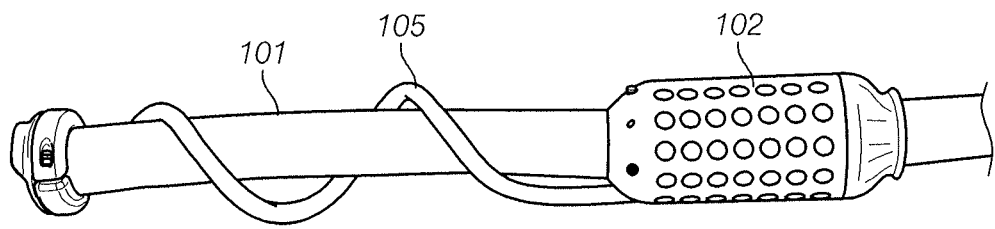
FIGS. 24A-24B show different modes of extending the distal vacuum line from the distal vacuum port.
Figure 24B:
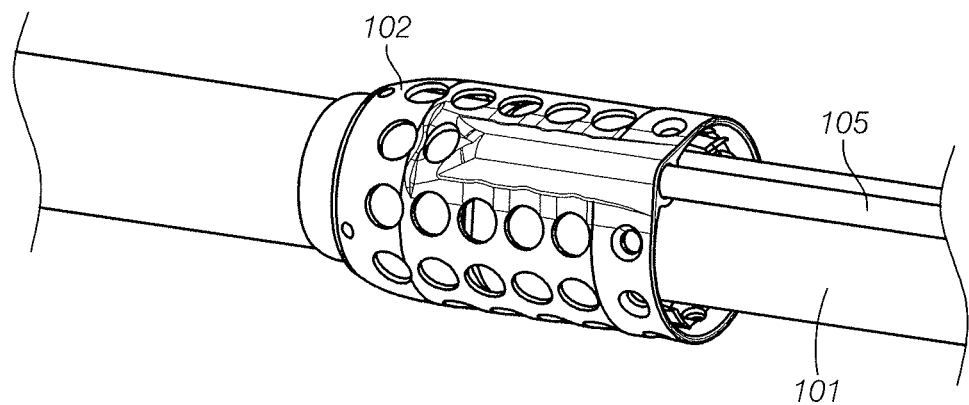

Referring to FIG. 24A, in some embodiments, the vacuum line 105 can extend from the distal vacuum port 102 for entry into the working channel of the endoscope 101. In this embodiment, the vacuum line 105 can coil around the tip of the endoscope 101 so as to not disturb the tip flexure. In embodiments where the distal vacuum port is mounted at the tip, the vacuum line can directly enter the working channel. Further, the working channel can be used to provide vacuum to the vacuum line 105. At the exit, there can be a flapper valve that is normally closed to maintain a vacuum path, but can be pushed open by an instrument so that the working channel can still function as an instrument working channel. In other embodiments, referring to FIG. 24B, the vacuum line 105 can extend from the distal vacuum port 102 proximally towards the handle.

Figure 55A:
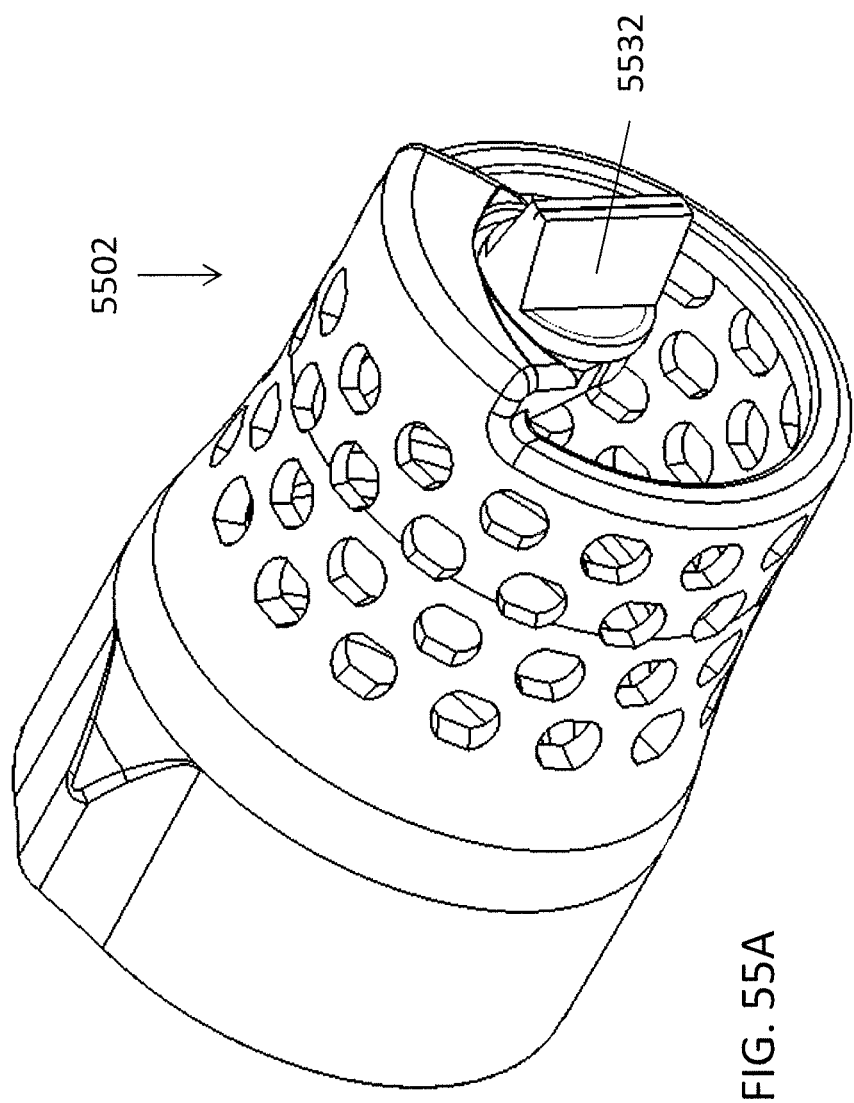
FIGS. 55A-C show an exemplary valve on the end of the working channel of a scope.
Figure 55B:
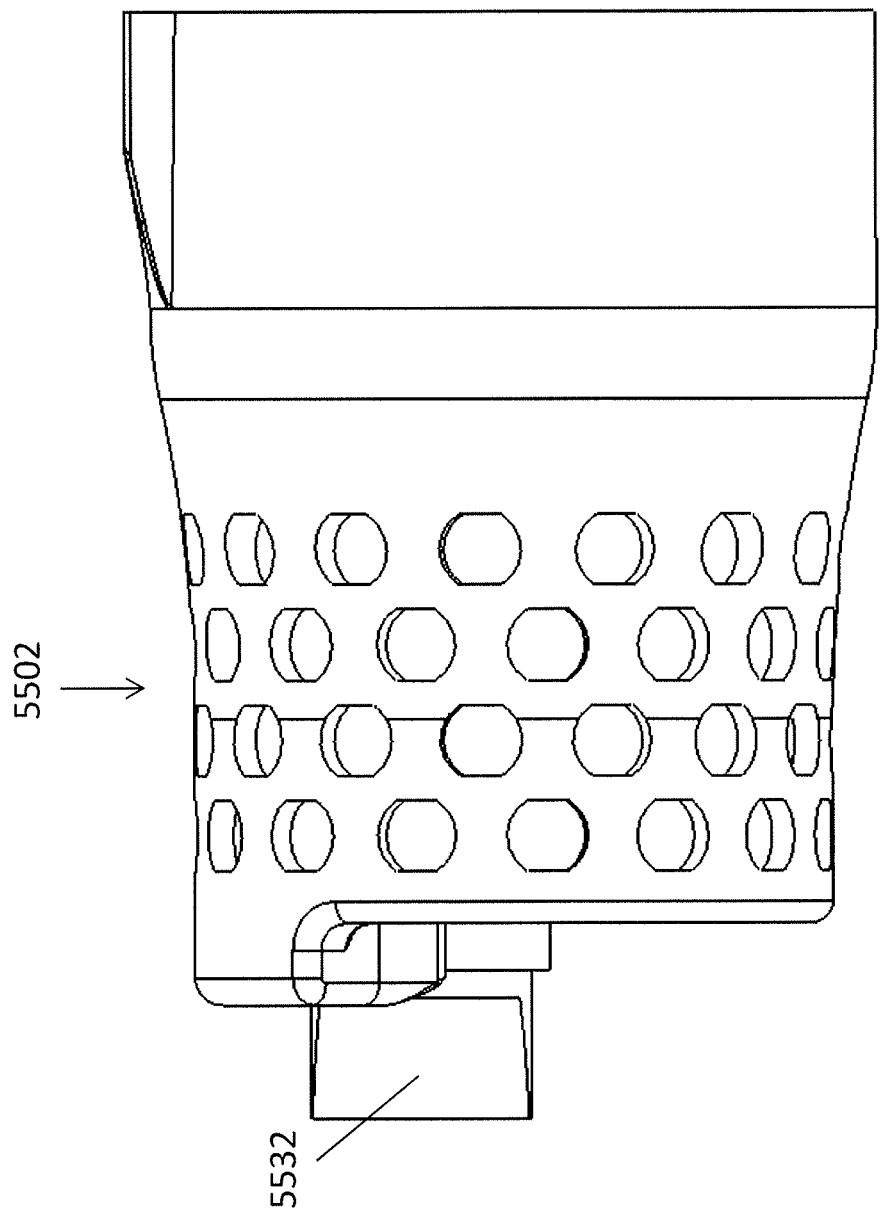
Figure 55C:
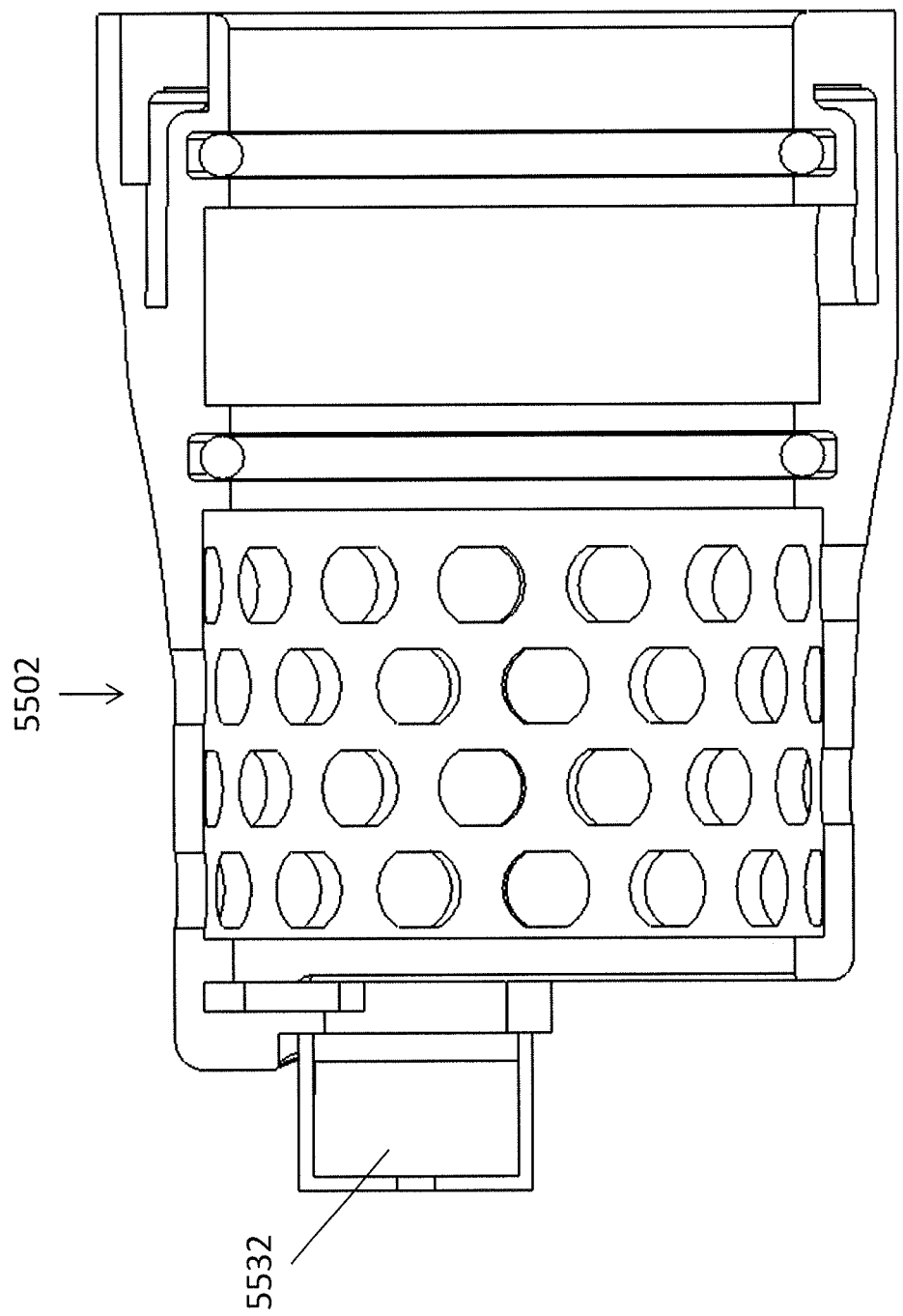
Figure 56A:
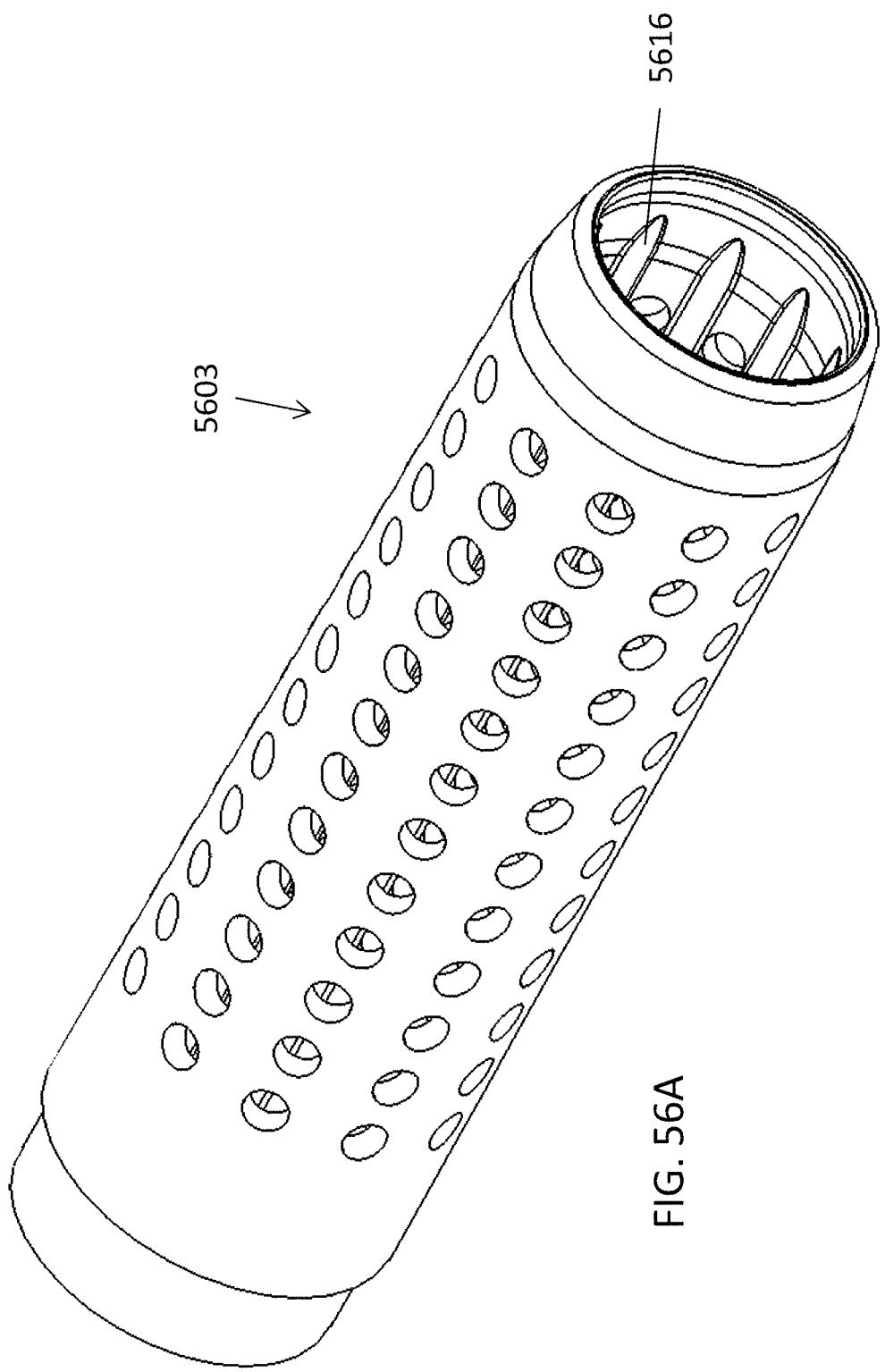
FIGS. 56A-D show an exemplary proximal vacuum port with ribs extending on the inner circumference and circular holes.
Figure 56B:
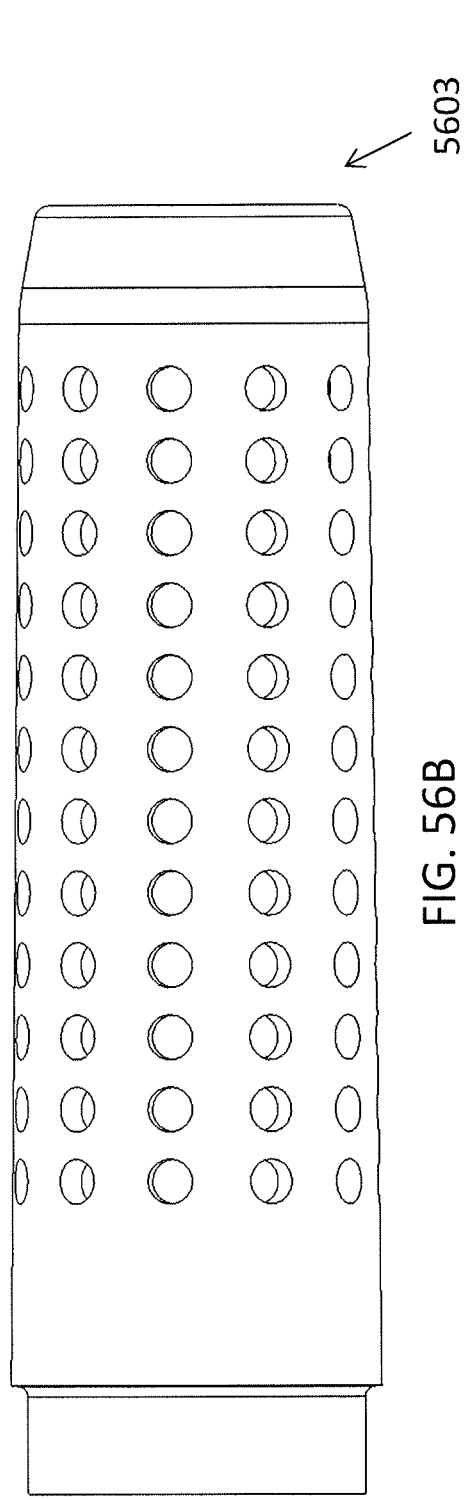
Figure 56C:
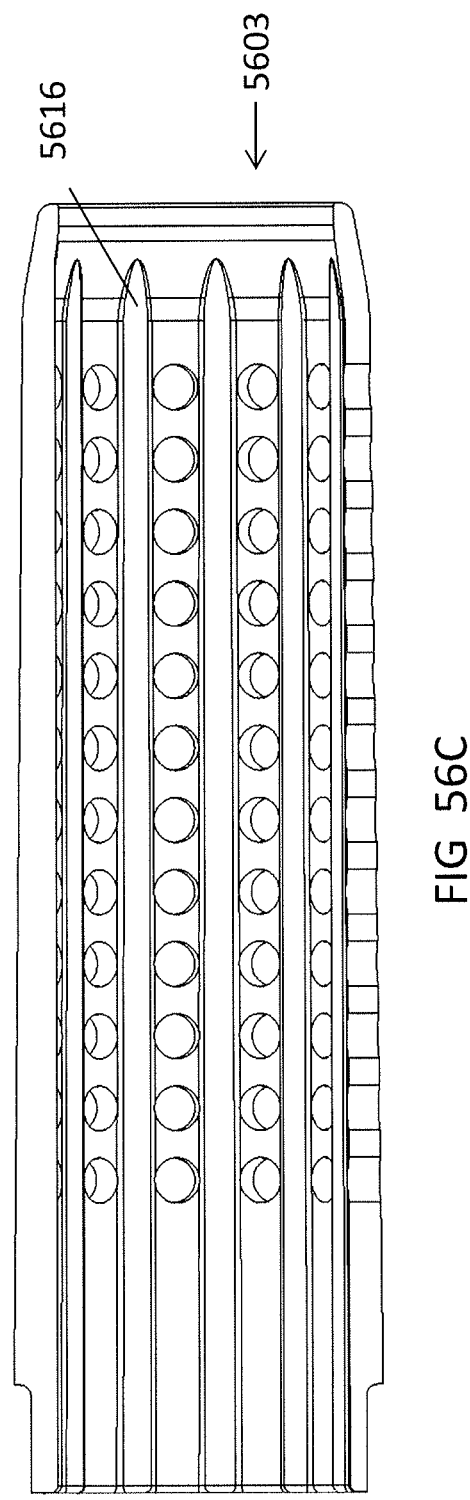
Figure 56D:
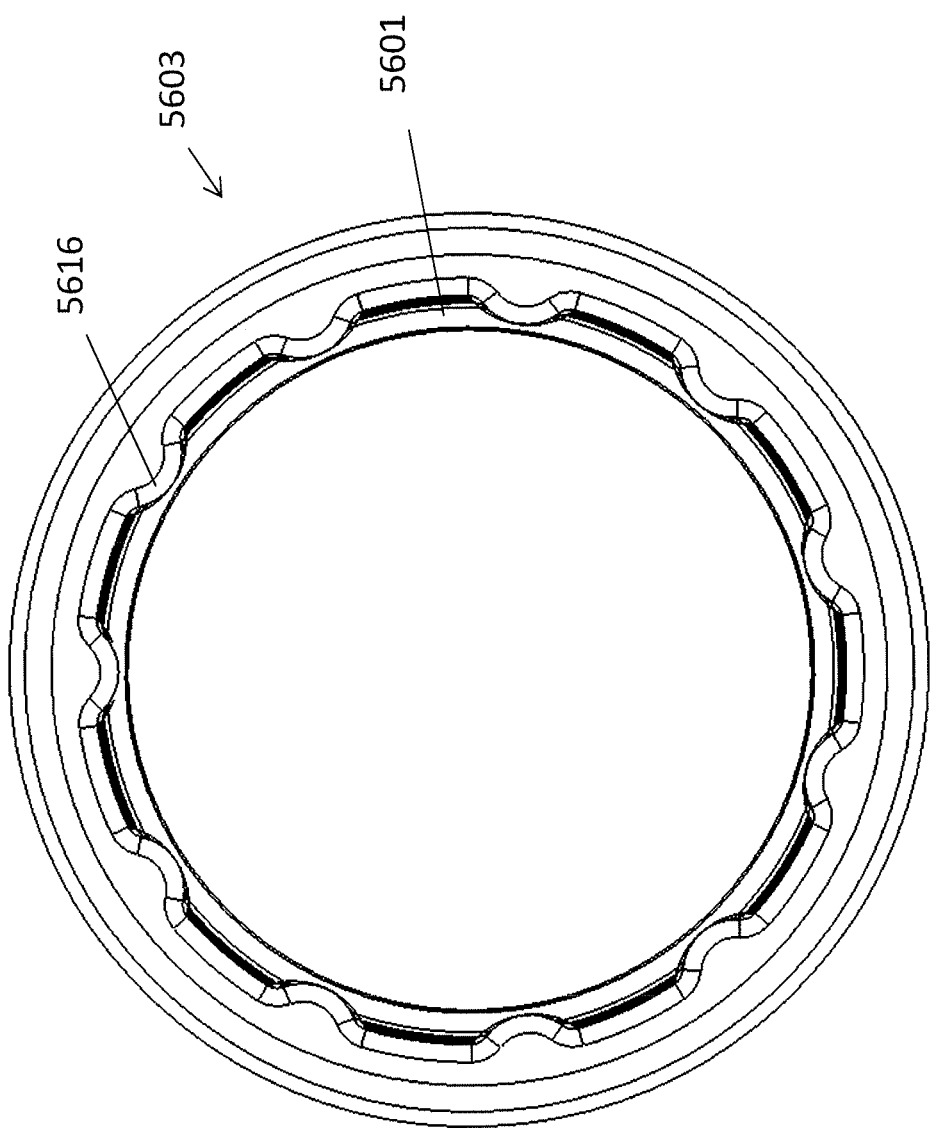
Figure 57A:
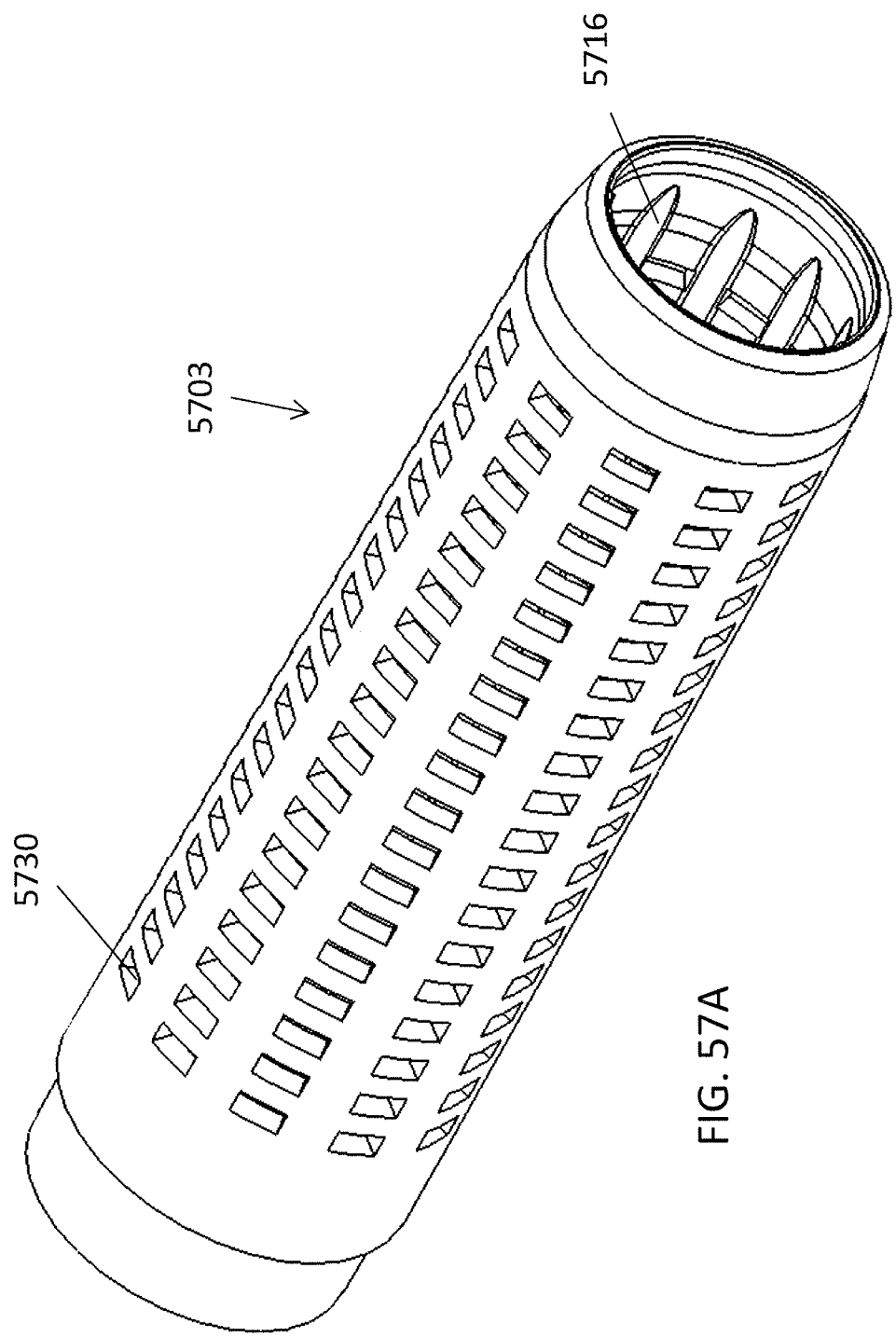
Figure 57D:
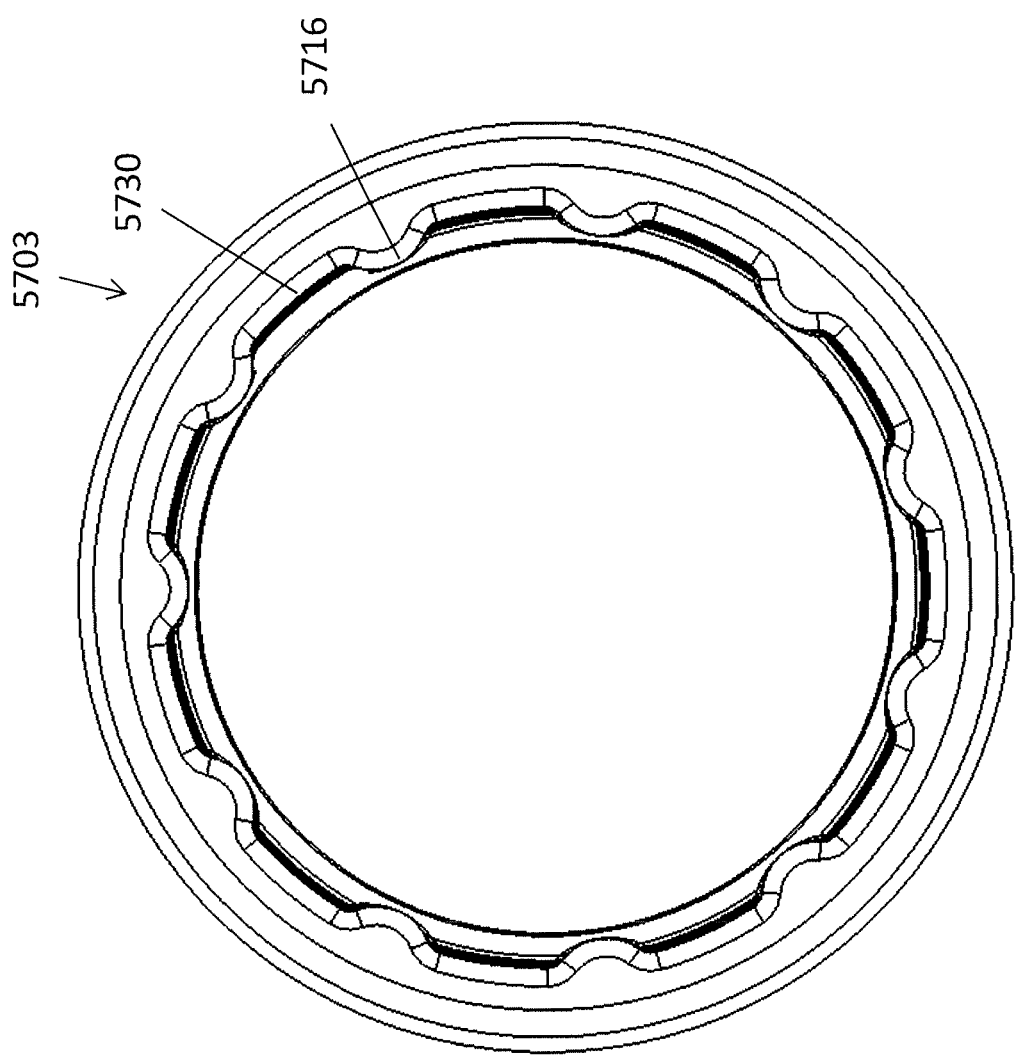

Referring to FIG. 32A, in some embodiments, the working channel 3233 itself can be used to provide vacuum through channel 3297. A valve 3232 in an opening in end cap 3296, such as a duckbill valve, prevents the vacuum from pulling out the distal end of the channel 3233, but still allows a working element to travel therethrough. Another embodiment of a distal tip 5502 with a duckbill valve 5532 is shown in FIGS. 55A-55C.

Handle

The devices described herein can have handles, actuators or controls for activating the grabbing mechanisms and/or blocking elements.

Figure 25A:
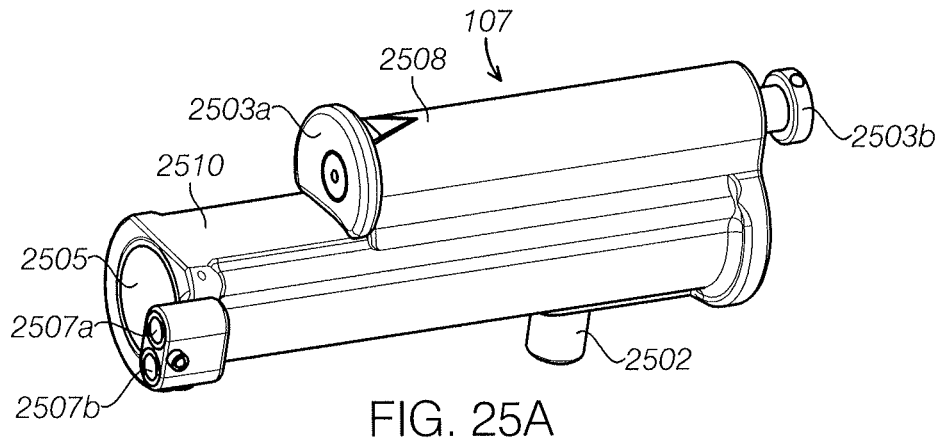
FIGS. 25A-C show various views of a handle for a device for endoscopic advancement through the small intestine.
Figure 25B:
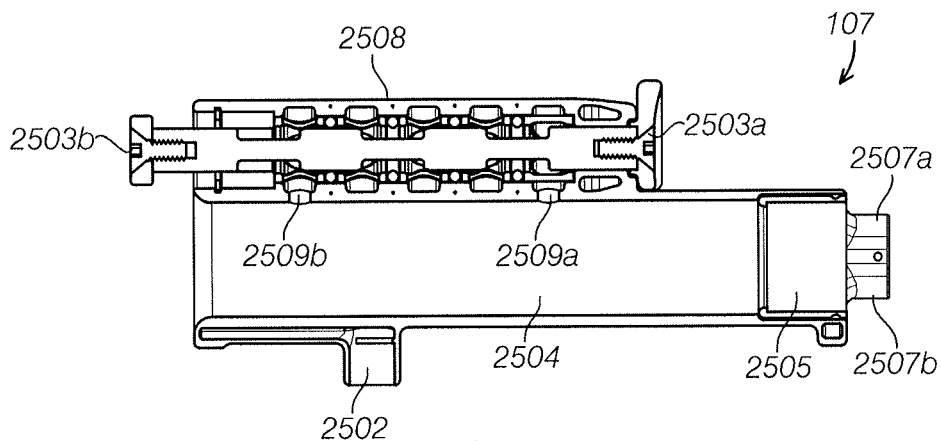
Figure 25C:
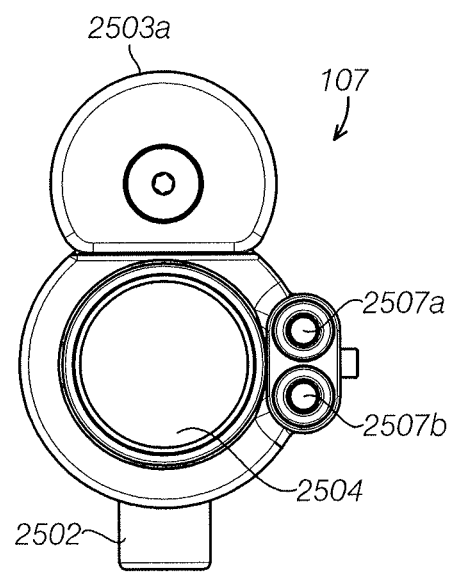

For example, referring to FIGS. 25A-25C, a handle 107 can include a handle body 2510 having a distal opening 2505 configured to mount to the overtube. The handle 107 can further include a large central lumen 2504 configured to ride over the endoscope and a vacuum attachment 2502. The handle 107 can further include a spool valve assembly 2508 configured to control the release of vacuum to either the proximal vacuum line or the distal vacuum line, respectively, through vacuum lumen connections 2507a,b. User-activated buttons 2503a,b can be configured to interface with the spool valve assembly 2508 to manually control the release of vacuum. Vents 2509a,b can also be positioned within the system to release vacuum pressure substantially instantly when the vacuum is released.

Figure 26A:
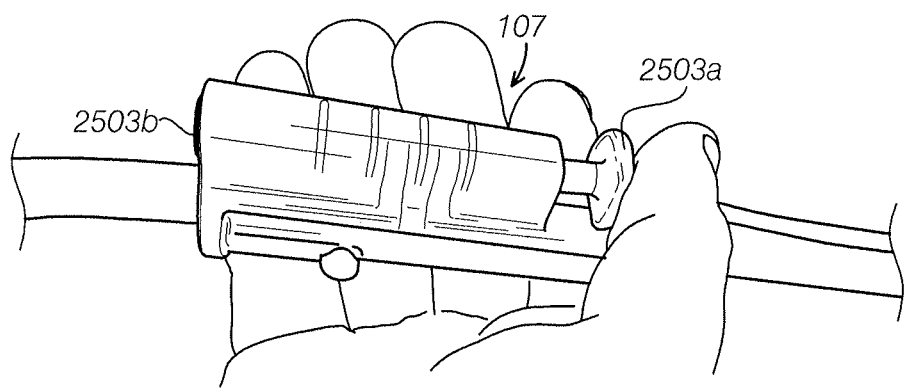
FIGS. 26A-26C show various views of a handle for a device for endoscopic advancement through the small intestine.
Figure 26B:
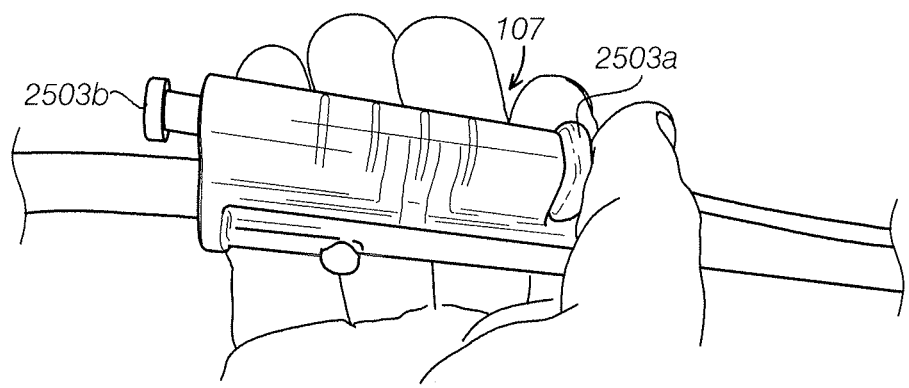
Figure 26C:
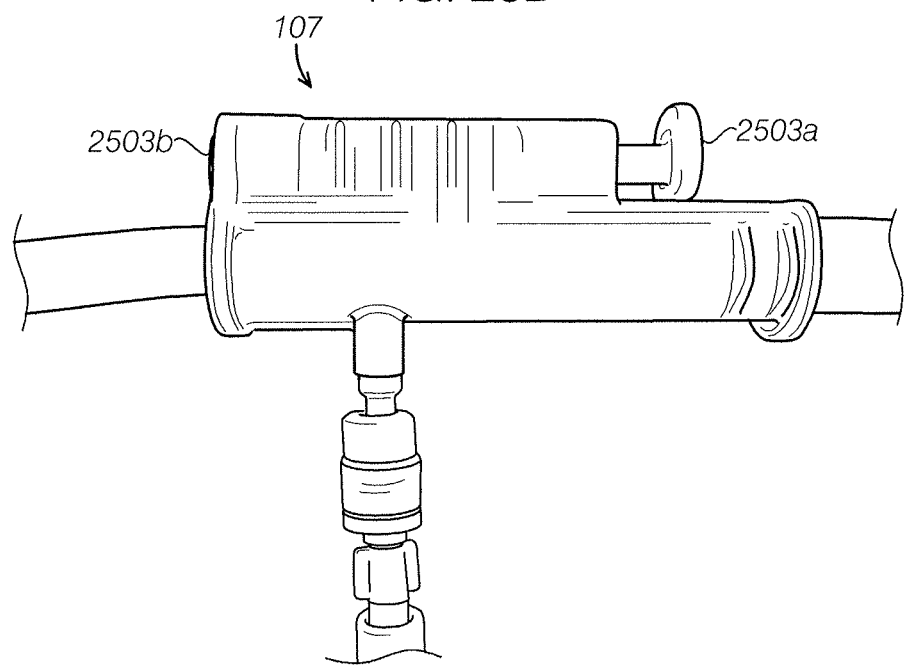

As shown in FIGS. 26A-26C, the handle 107 can be configured to fit easily in the user's hand. Further, the handle 107 can be designed to allow the user to both hold the handle and activate the buttons 2503a,b with a single hand.

In some embodiments, the vacuum input 2502 can be removed to provide flush-through. In other embodiments, the handle 107 can include a separate flush port with a valve for the vacuum line.

The spool valve assembly 2508 is shown in more detail in FIGS. 27A-27B. The spool valve housing 2648 includes annular or toroidal grooves or rings 2601, 2602, 2603, 2604, 2605. Further, annular grooves 2610, 2612, 2614 can extend along the spool 2638. Each ring can be connected to a different component of the system. For example, ring 2601 can be connected to a first vent 2509a, ring 2602 can be connected to the vacuum lumen 2507a for the distal vacuum port, ring 2603 can be connected to the vacuum input 2502, ring 2604 can be connected to the vacuum lumen 2507b for the proximal vacuum port, and ring 2605 can be connected to a second vent 2509b. Thus, referring to FIG. 27A, when the button 2503a is pushed all the way in, a first connection is made between the annular ring 2603 (connected to vacuum input 2502) and the annular ring 2604 (connected to the vacuum lumen 2508b for the proximal vacuum port) via groove 2612 and a second connection is made between annular ring 2601 (connected to first vent 2509a) and annular ring 2602 (connected to the vacuum lumen 2507a for the distal vacuum port) via groove 2610. As a result, vacuum can be applied to the proximal vacuum port and a vent can be applied to the distal vacuum port. In contrast, referring to FIG. 27B, when the button 2503b is pushed all the way in, a first connection can be made between ring 2602 (connected to the vacuum lumen 2507a for the distal vacuum port) and ring 2603 (connected to vacuum input 2502) and via groove 2612 a second connection can be made between 2604 (connected to the vacuum lumen 2508b for the proximal vacuum port) and 2605 (connected to second vent 2509b) via groove 2614. As a result, the vacuum can be applied to the distal vacuum port while the proximal vacuum port is vented.

Figure 53A:
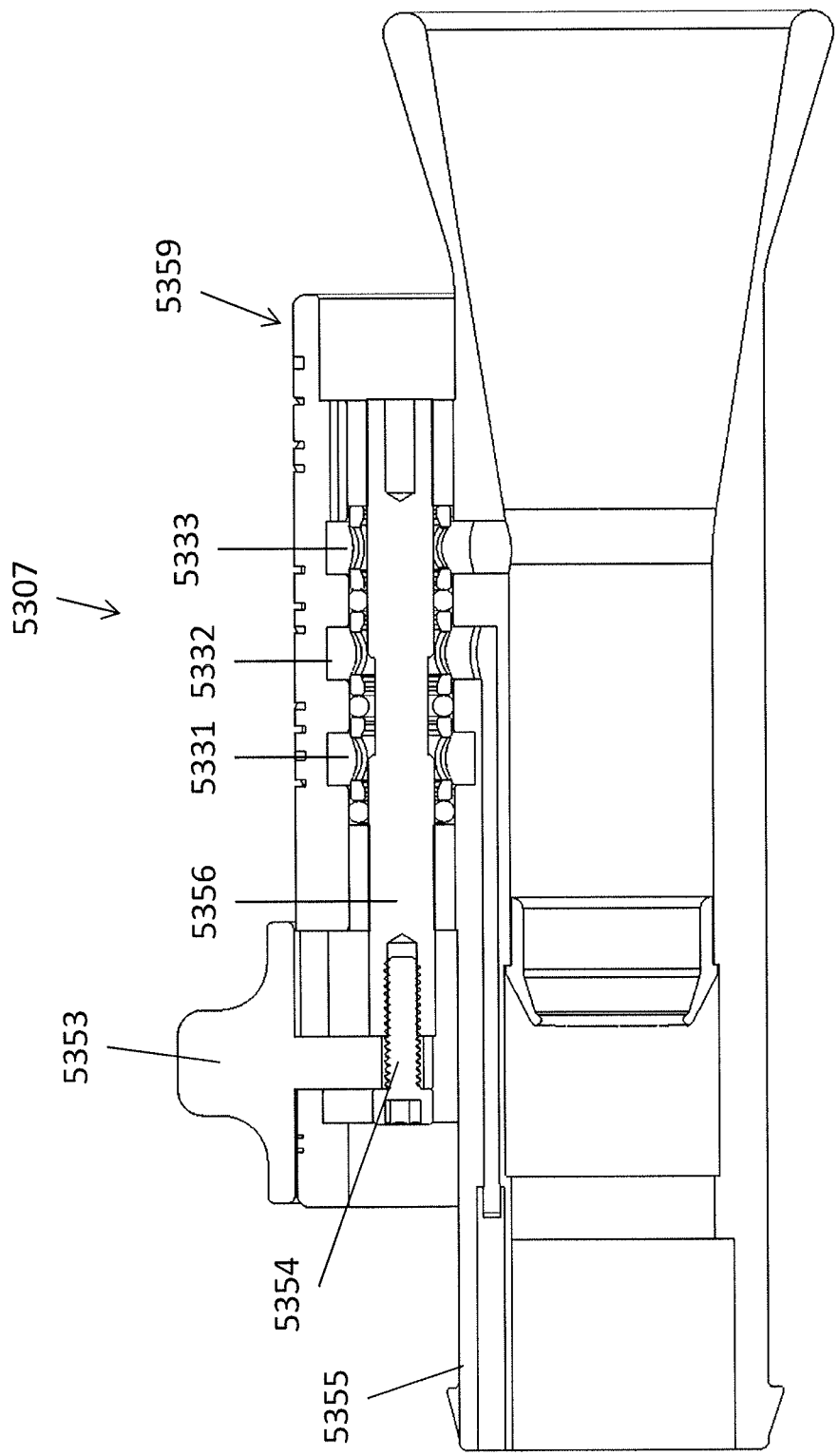
FIGS. 53A-53H show an exemplary handle for controlling inflation of the proximal vacuum port.
Figure 53B:
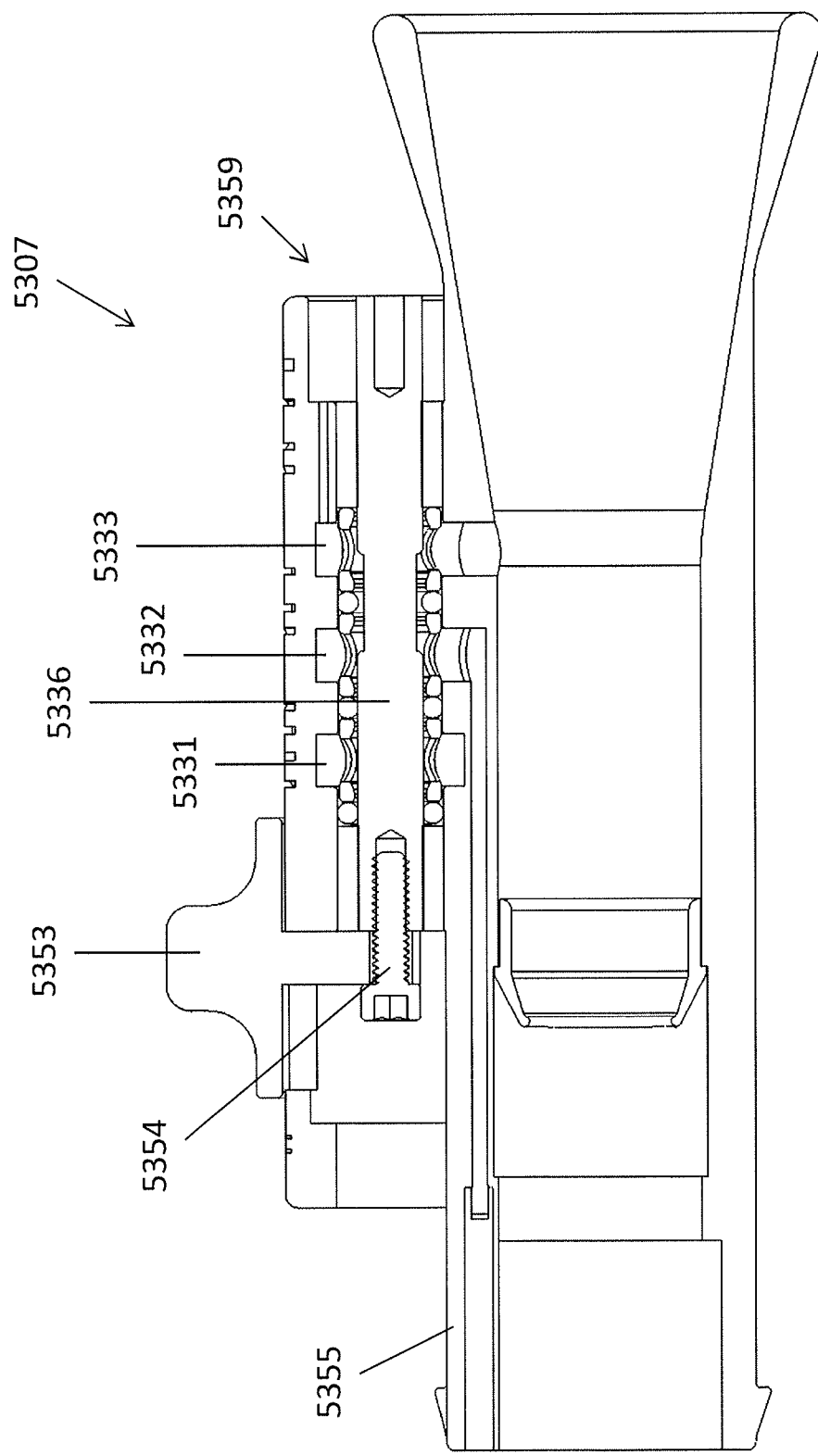
Figure 53C:
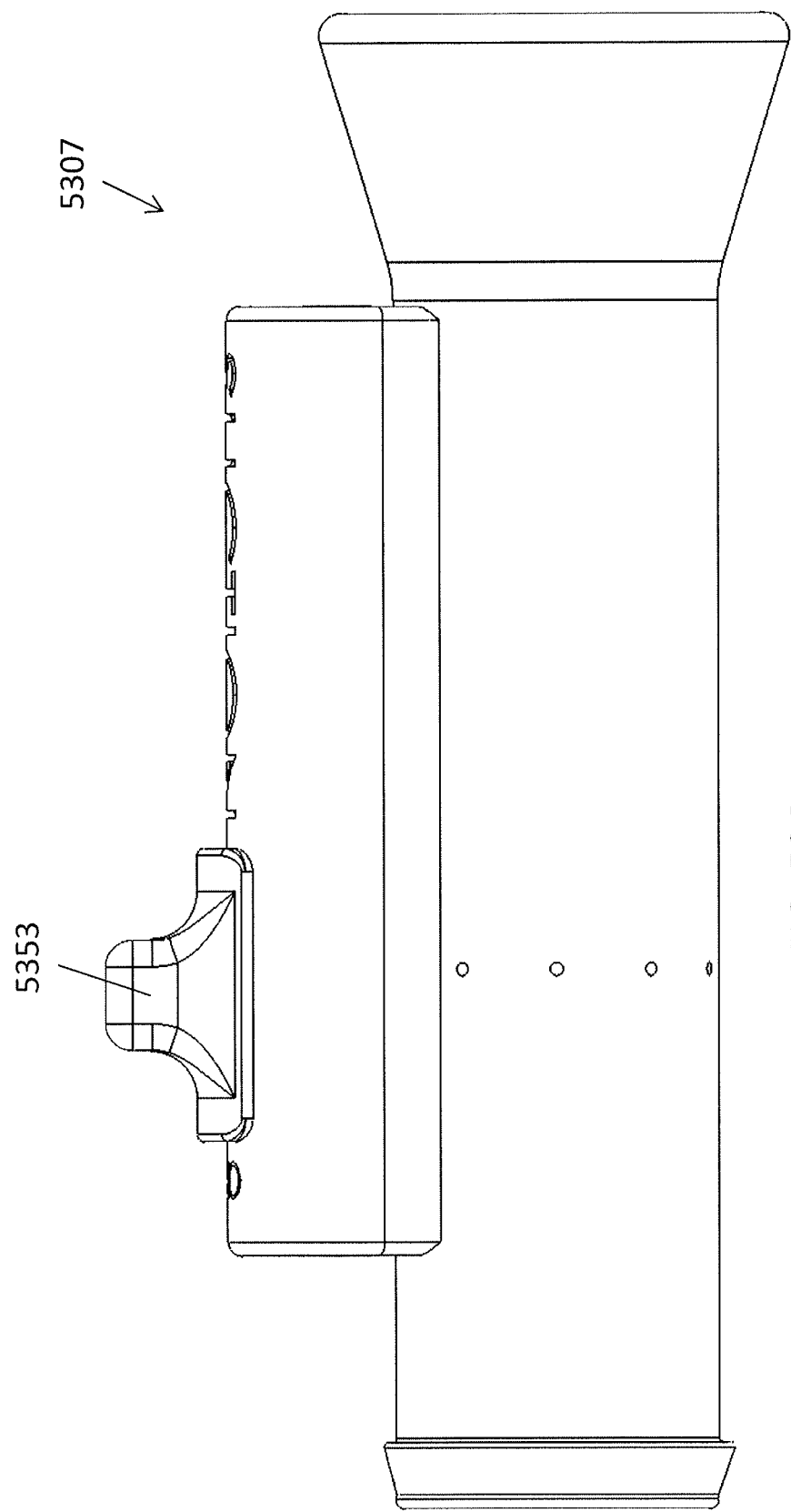
Figure 53D:
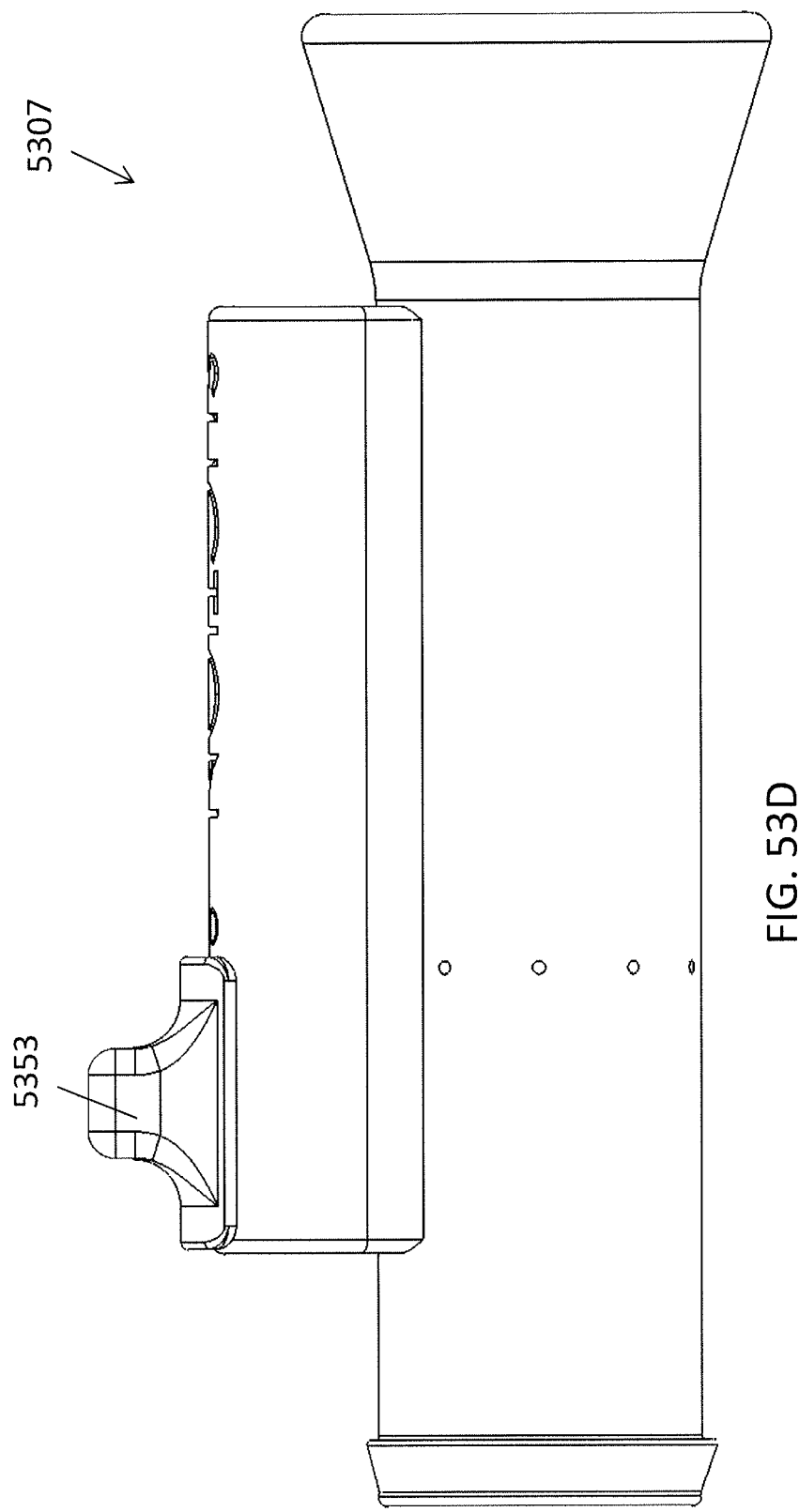
Figure 53E:
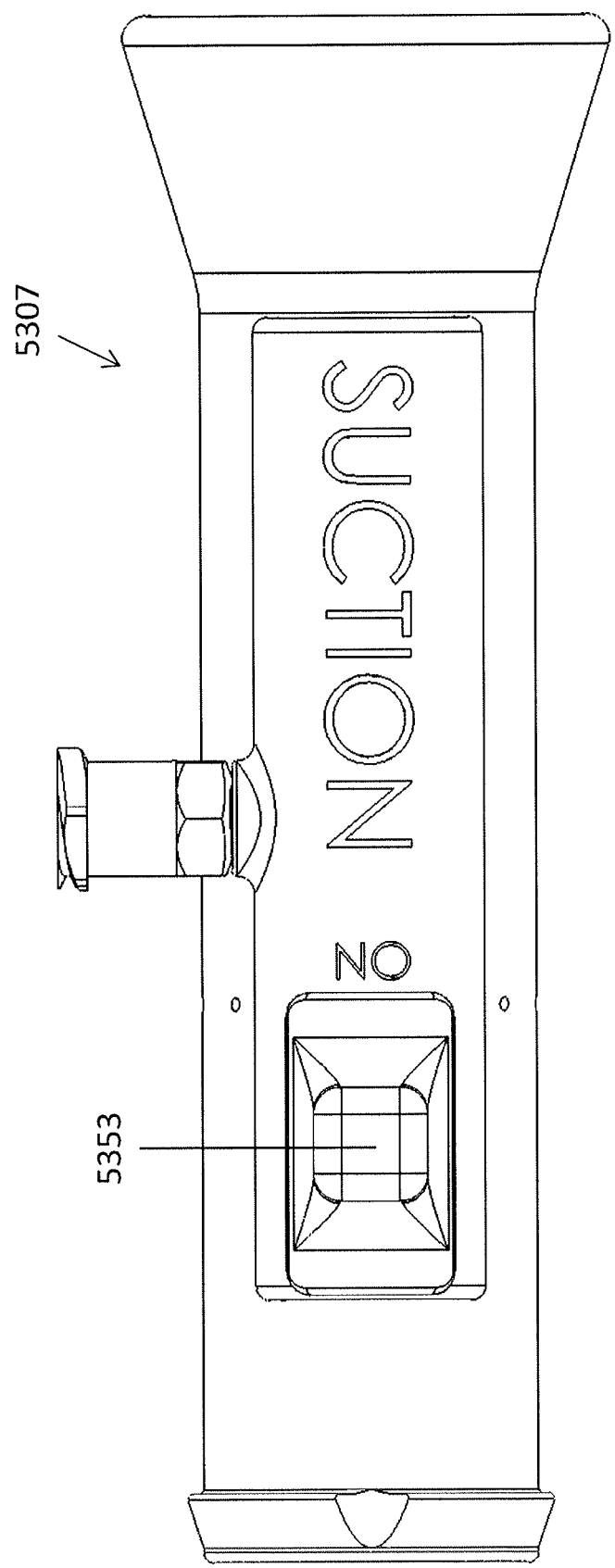
Figure 53F:
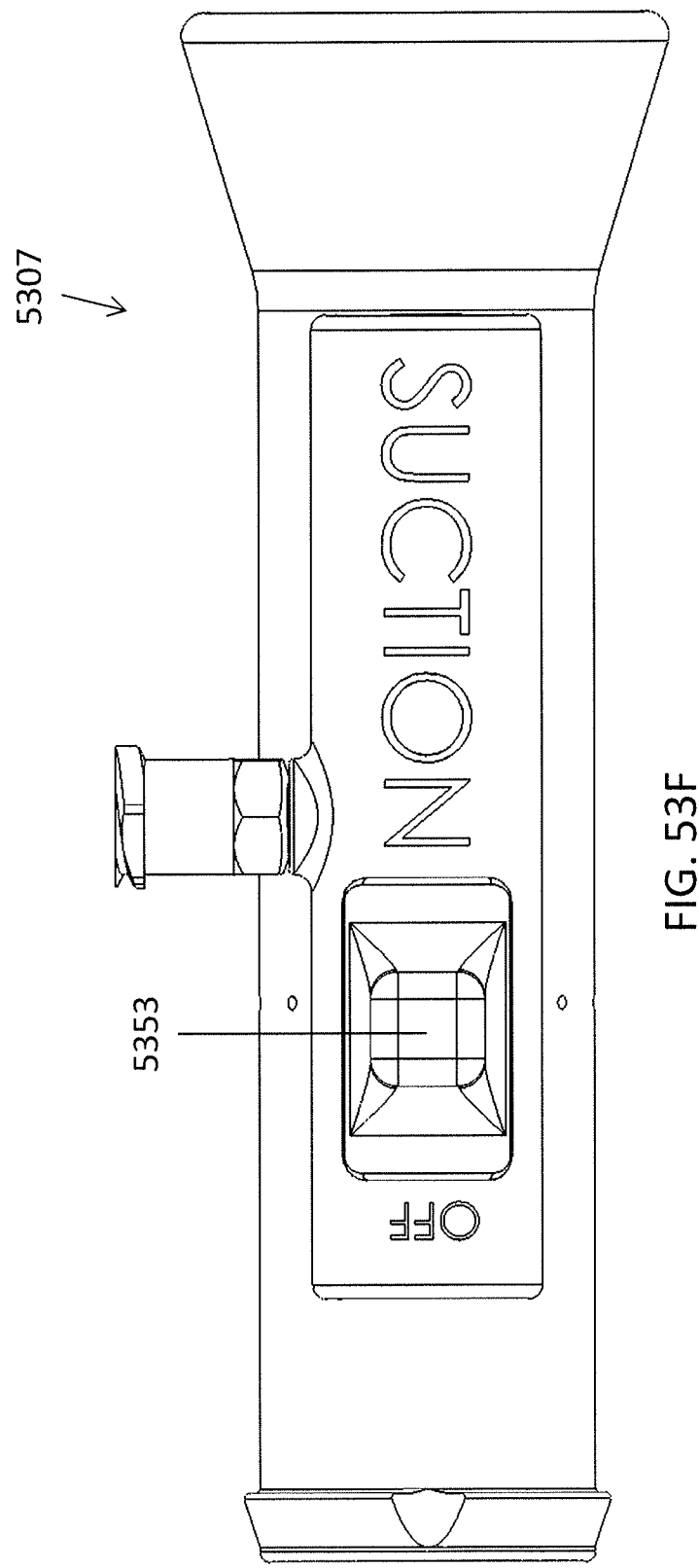
Figure 53G:
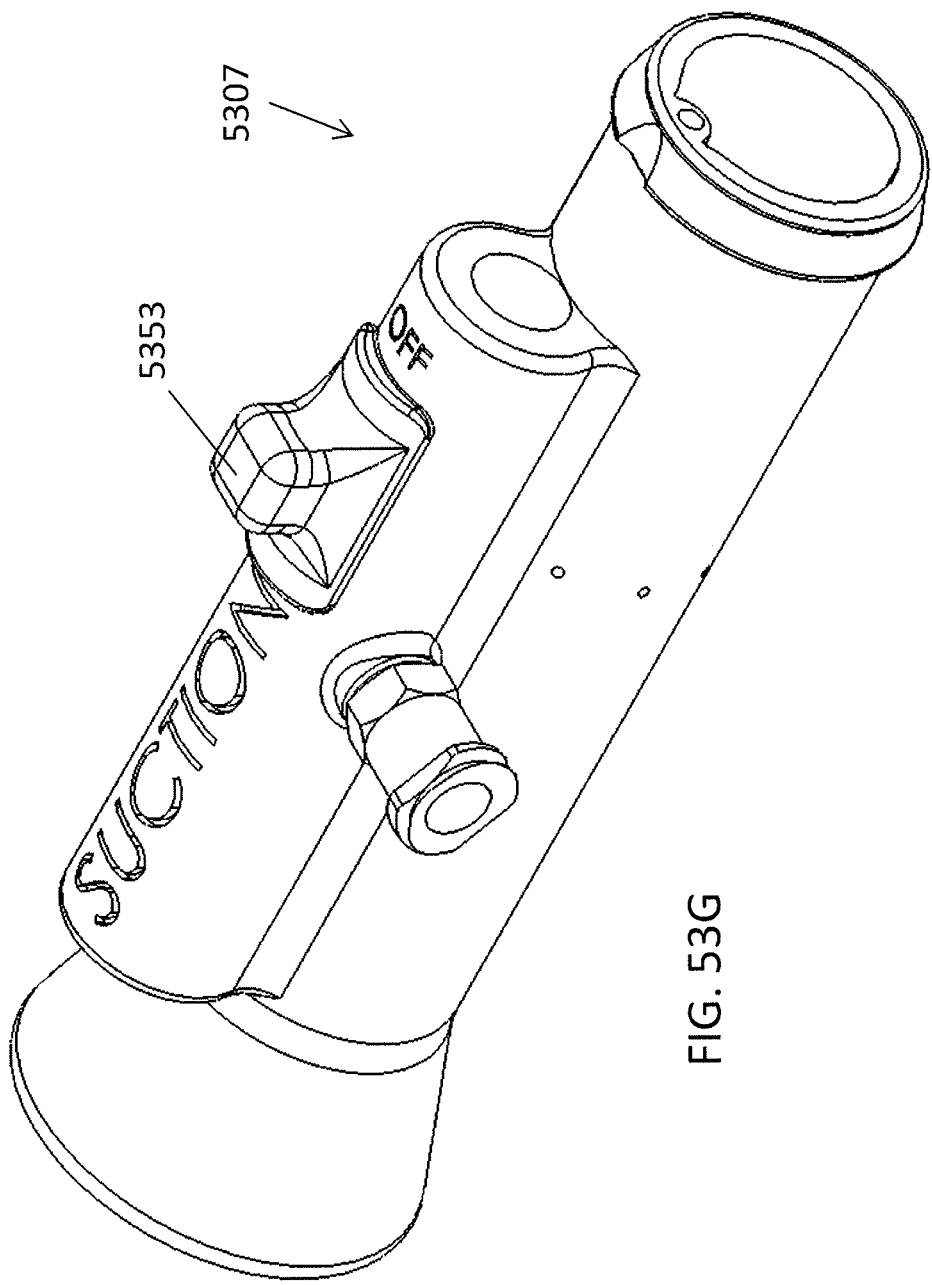
Figure 53H:
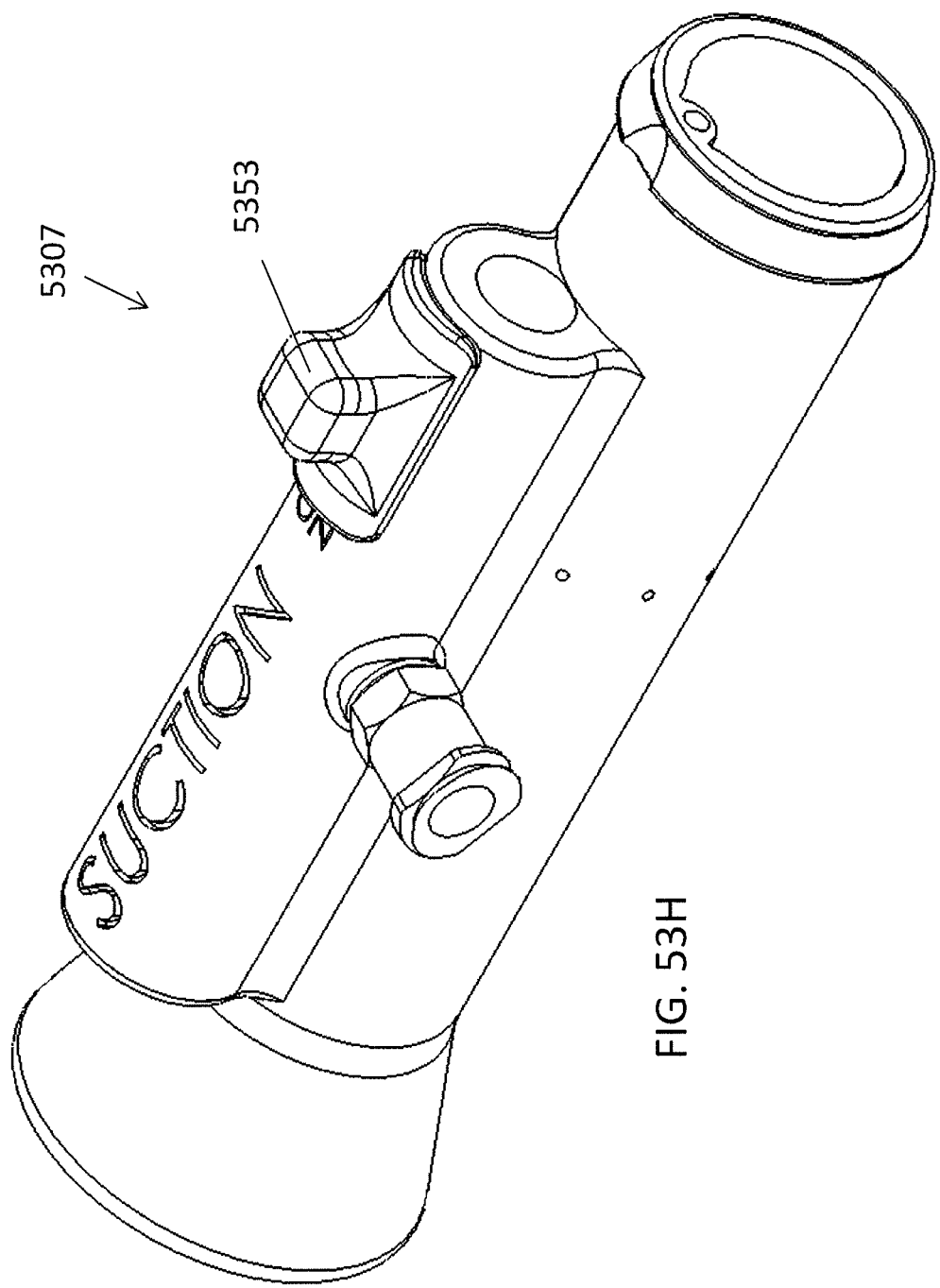

Another exemplary handle 5307 is shown in FIGS. 53A-53H. The handle 5307 can include a spool mechanism 5359 configured to connect the proximal vacuum port to the vacuum source. Thus, as shown in FIG. 53A, the spool mechanism 5359 can include a vacuum input chamber 5331, a proximal vacuum chamber 5332 connected to a second vacuum port, and a third chamber 5333 configured to vent to atmosphere. A spool 5336 can be moved proximally and distally using button 5353 (through connection 5354). FIG. 53A thus shows the spool 5356 configured such that chambers 5331 and 5332 are connected together, thereby allowing vacuum to be applied to the proximal vacuum port through line 5355. In contrast, FIG. 53B shows that chambers 5332 and 5333 are connected together, thereby placing deactivating the proximal vacuum port (and venting to atmosphere).

In this embodiment, vacuum to the distal port is supplied through the working channel of the endoscope. As such, control of vacuum through the distal vacuum port can be performed through a button or vacuum activation mechanism on the scope itself.

FIGS. 54A-D show an alternative embodiment of a handle 5407 that can be used to control vacuum to the proximal vacuum port. In this embodiment, the handle 5407 includes three chambers 5431 (for the vacuum input), 5432 (for the proximal vacuum port), and 5433 (for venting to atmosphere). A u-channel 5455 moves back and forth with the button 5453 to connect the chambers as desired. FIG.

Figure 54A:
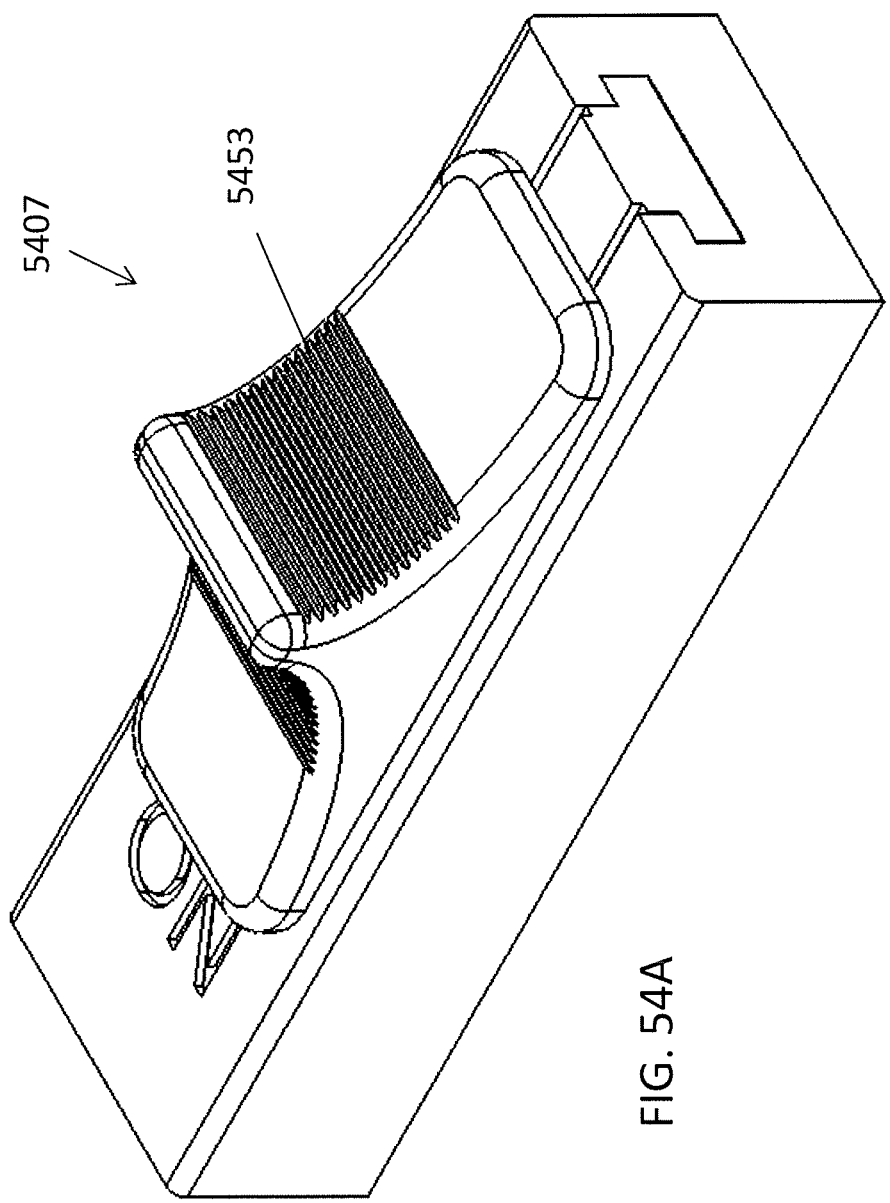
Figure 54B:
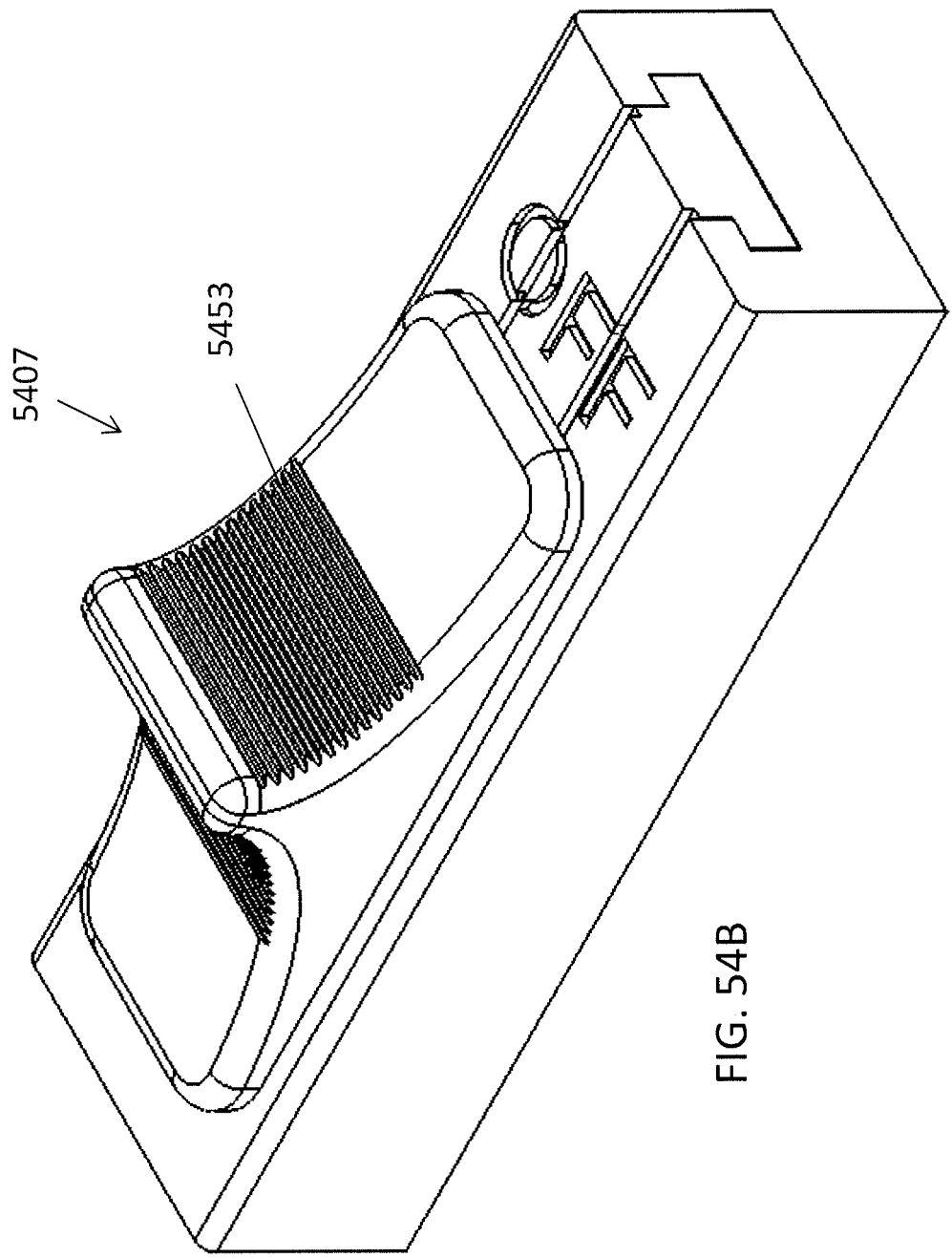
Figure 54D:
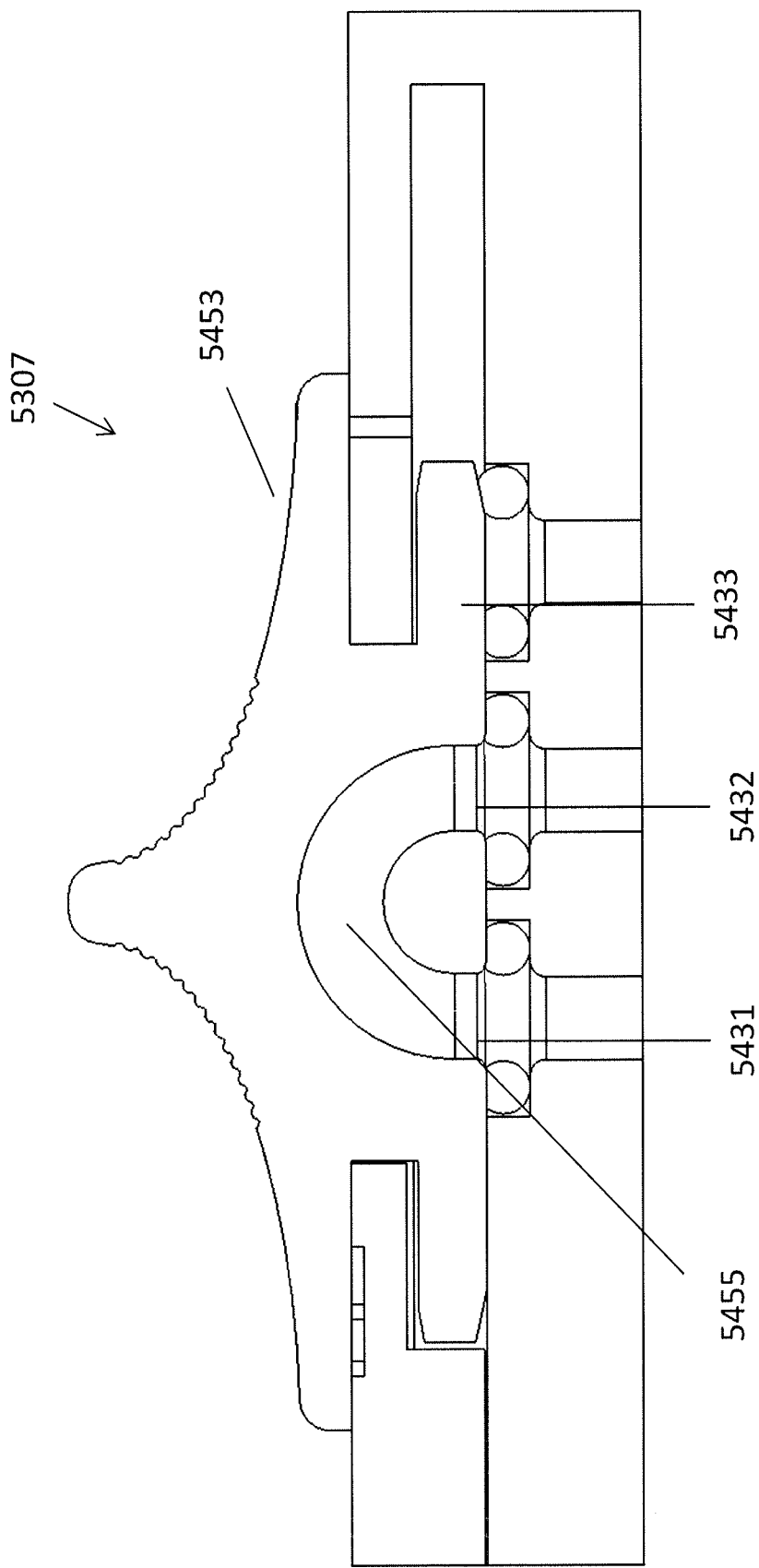

54C thus shows the suction off (chamber 5432 for vacuum port connected to chamber 4333 for venting to the atmosphere). In contrast, FIG. 54D shows suction/vacuum on (chamber 5431 for vacuum input connected to 5432 for proximal vacuum port).

In Use

The devices described herein can be used to quickly and efficiently move an endoscope through the small intestine.

Figure 29A:
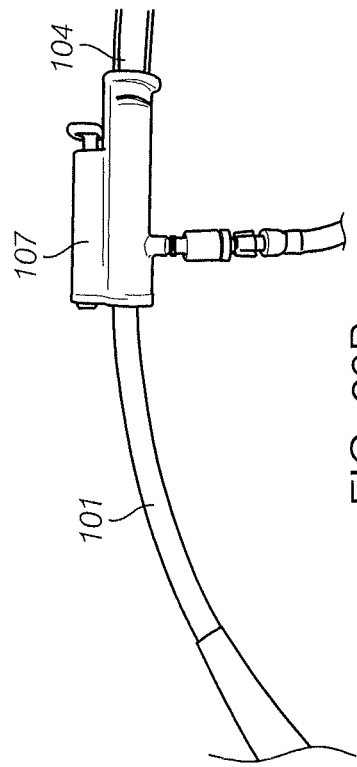
FIGS. 29A-E show attachment of a device for endoscopic advancement to an endoscope.
Figure 29B:
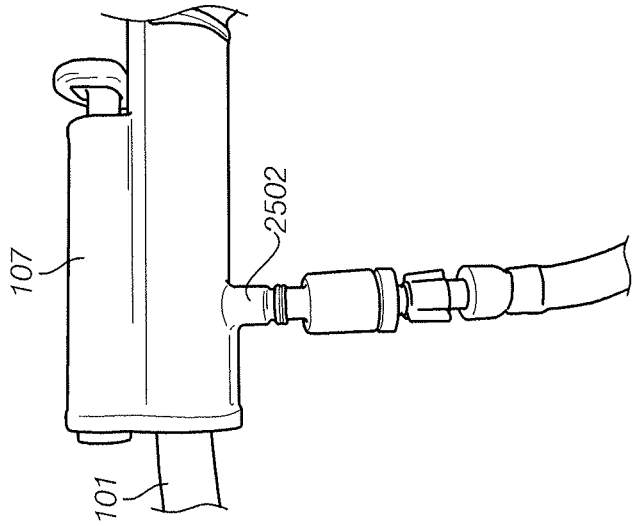
Figure 29E:
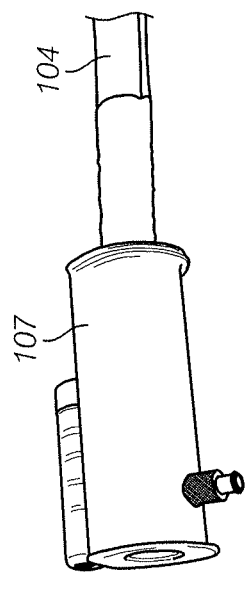
Figure 29C:
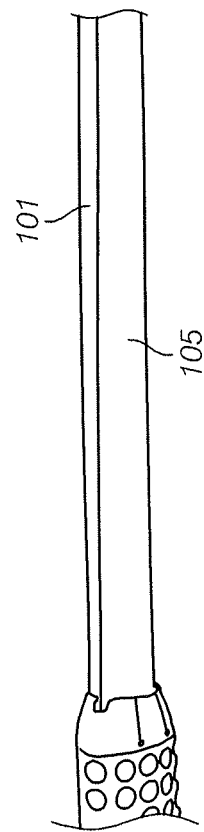
Figure 29D:
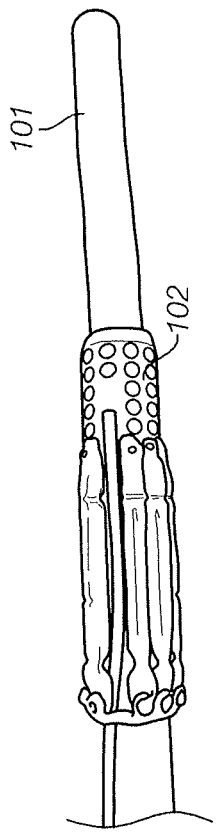

For example, referring to FIGS. 29A-E, the device 100 can first be connected to an inner element the use wishes to advance through the gastrointestinal tract (or other lumen), such as endoscope 101. To begin, referring to FIG. 29A, the endoscope 101 can be placed through the handle 107. As shown in FIG. 29B, the endoscope 101 can be advanced through the overtube 104 until the endoscope 101 exits the overtube 104, and the handle 107 is near the endoscope 101 proximal end. As shown in FIG. 29C, the telescoping line 105 can then be attached to the endoscope 101 (e.g., to avoid tangling during use). As shown in FIG. 29D, the distal tip 102 can then be attached to the endoscope 101. Finally, as shown in FIG. 29E, vacuum can be attached to the vacuum input 2502 on the handle 107.

Figure 30A:
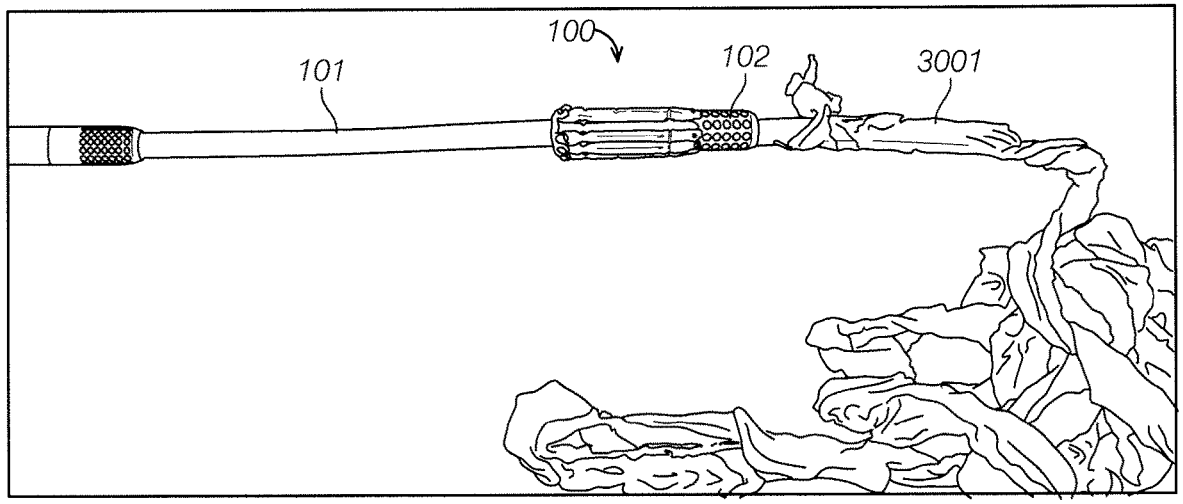
FIGS. 30A-30H show use of a device for endoscopic advancement in the small intestine.
Figure 30B:
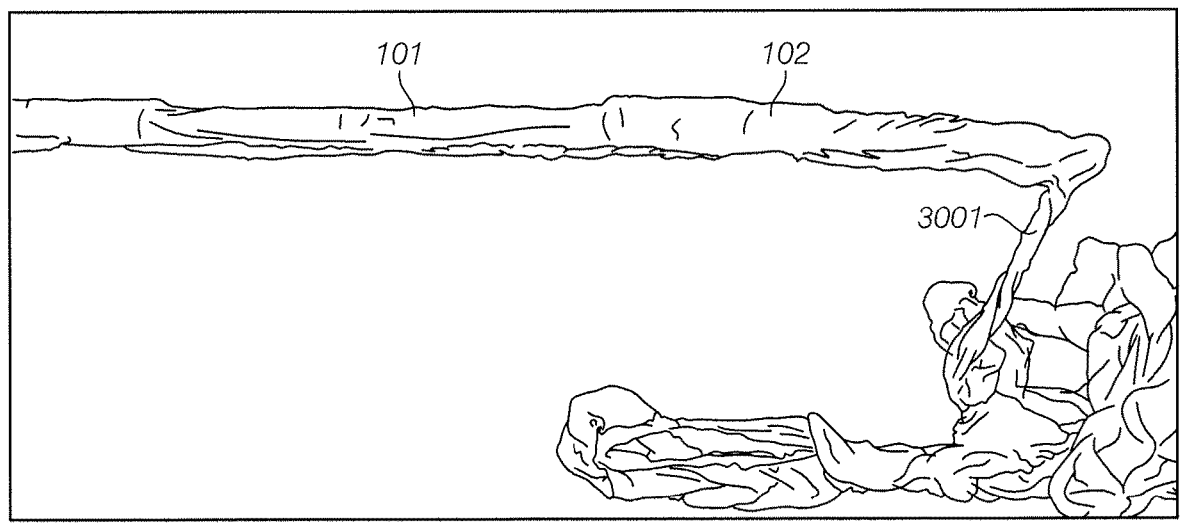
Figure 30C:
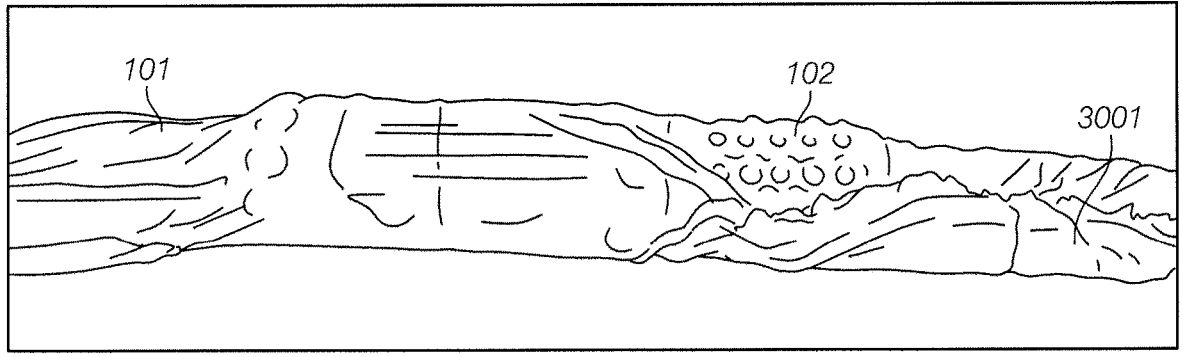
Figure 30D:
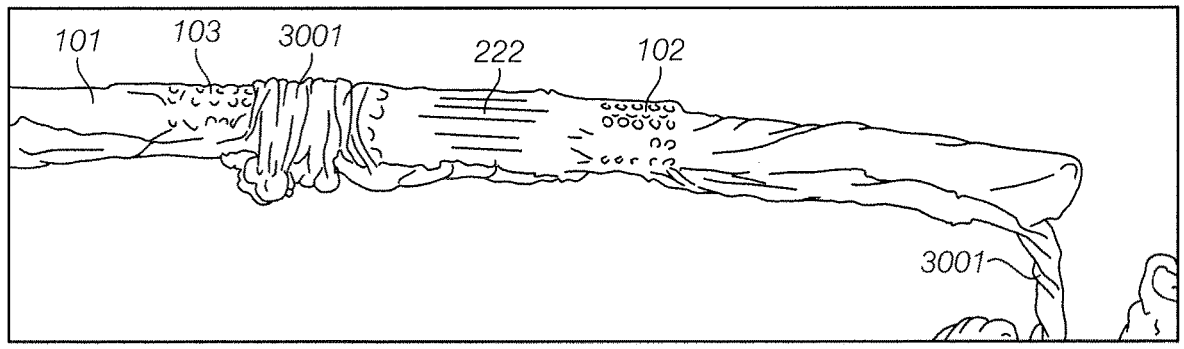
Figure 30E:
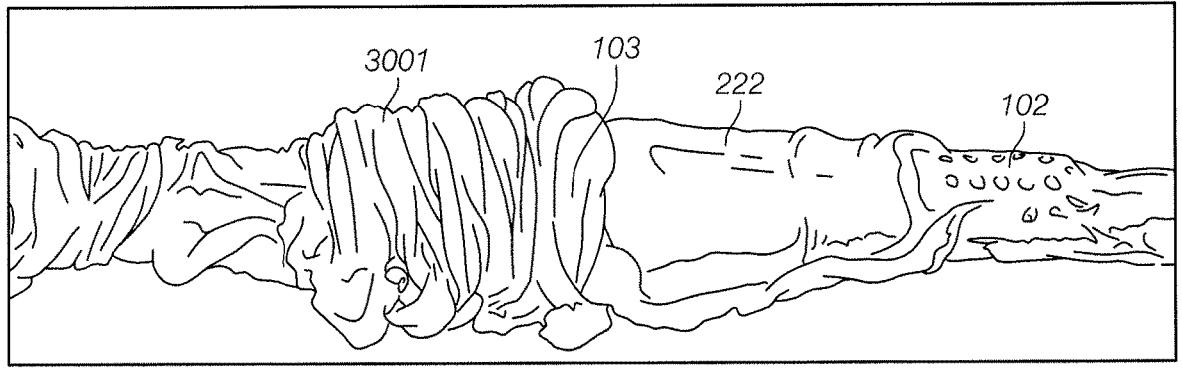
Figure 30F:
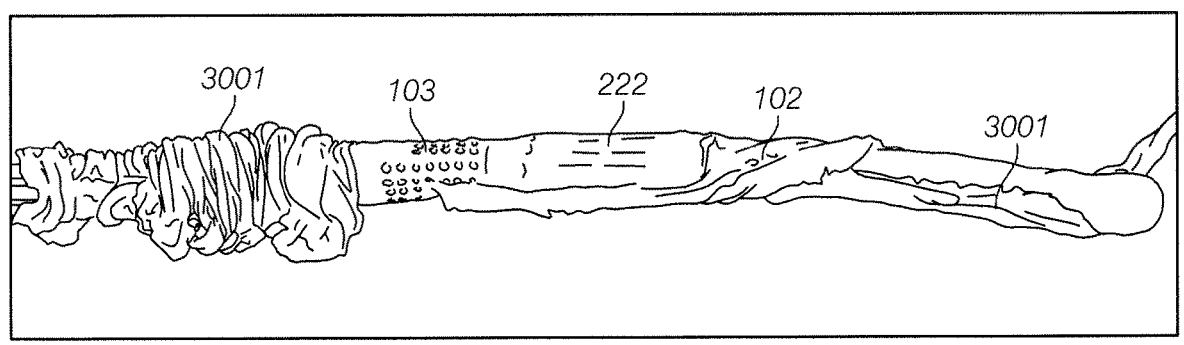
Figure 30G:
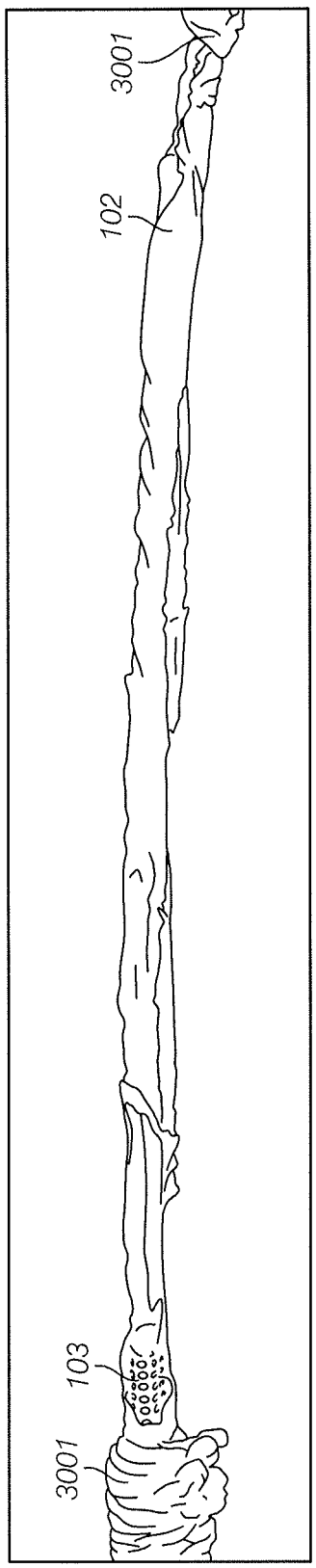
Figure 30H:

Once set up (as shown in FIGS. 29A-29E), the endoscope 101 and attached device 100 can be inserted into the small intestine, such as orally or anally (as shown in FIGS. 30A-30H). As shown in FIG. 30A, the endoscope 101 and device 100 can be advanced to the start of the small intestine 3001. As shown in FIG. 30B, the distal vacuum port 102 of the device 100 and endoscope 101 can then be advanced further into the small intestine 3001, such as about 18 to 24 inches, by pushing forward on the endoscope. The distal vacuum port 102 can then be activated to suction tissue of the small intestine 3001 thereto, as shown in FIG. 30C. As shown in FIG. 30D, the space between the distal vacuum port 102 and the proximal vacuum port 103 can be reduced until the the proximal vacuum port hits the blocking element 222 by pulling on the proximal end of the endoscope. As this relative motion between the vacuum portions 102, 103 occurs, tissue of the small intestine 3001 is pleated. Referring to FIG. 30E, the distal vacuum port 102 can continue to be pulled proximally over the proximal vacuum port 103, causing the blocking element 222 to radially expand. As the blocking element 222 expands, a wall is created that blocks the tissue pleats from moving distally over the distal vacuum port 102. Further, as the distal vacuum port 102 is pulled proximally, the proximal vacuum port 103 moves fully inside of the blocking element 222, causing the pleats to move proximal of the proximal vacuum port 103. Referring to FIG. 30F, the proximal vacuum port 103 can then be activated and the distal vacuum port 102 released. As shown in FIG. 30G, the distal vacuum port 102 can then be pushed distally through the tissue of the small intestine 3001 about 18 to 24 inches as the proximal vacuum port 103 holds the tissue. Referring to FIG. 30H, once the distal vacuum port 102 is in place, the distal vacuum 102 can be activated and the proximal vacuum 103 released, and the steps can be performed again until the endoscope 101 has reached the desired location, such as until the endoscope has traveled the entire length of the small intestine. It should be understood that although described herein as be performed by moving the distal vacuum port 102 distally or proximally, the proximal vacuum port 103 can also be moved proximally or distally to obtain the same relative motion between the two port 102, 103 and provide advancement of the scope through the small intestine.

Figure 31A:
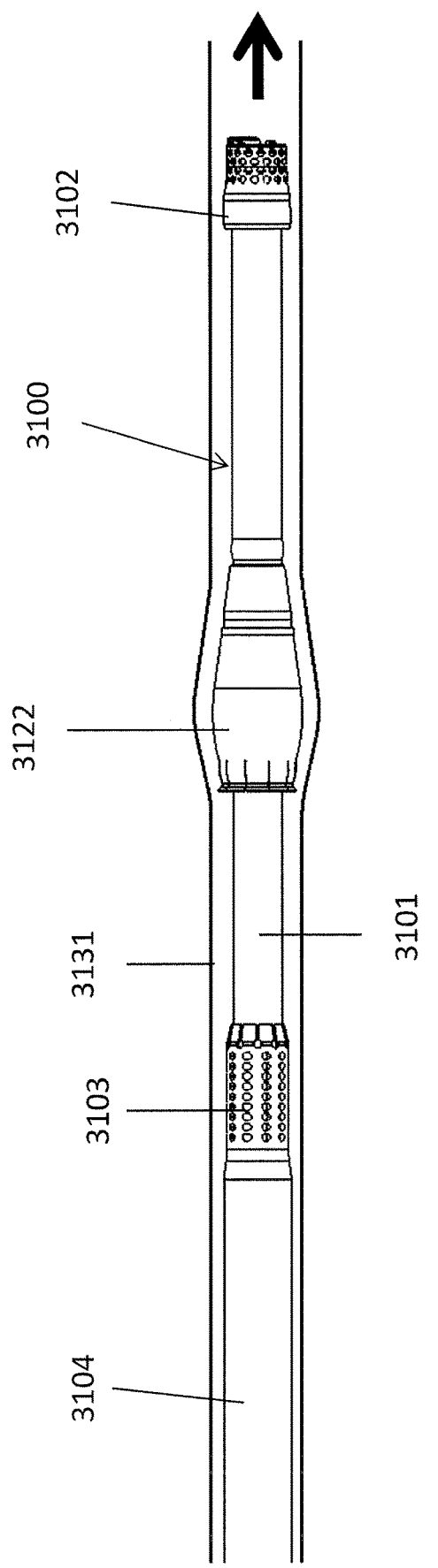
FIGS. 31A-F show use of a device for endoscopic advancement in the small intestine.
Figure 31B:
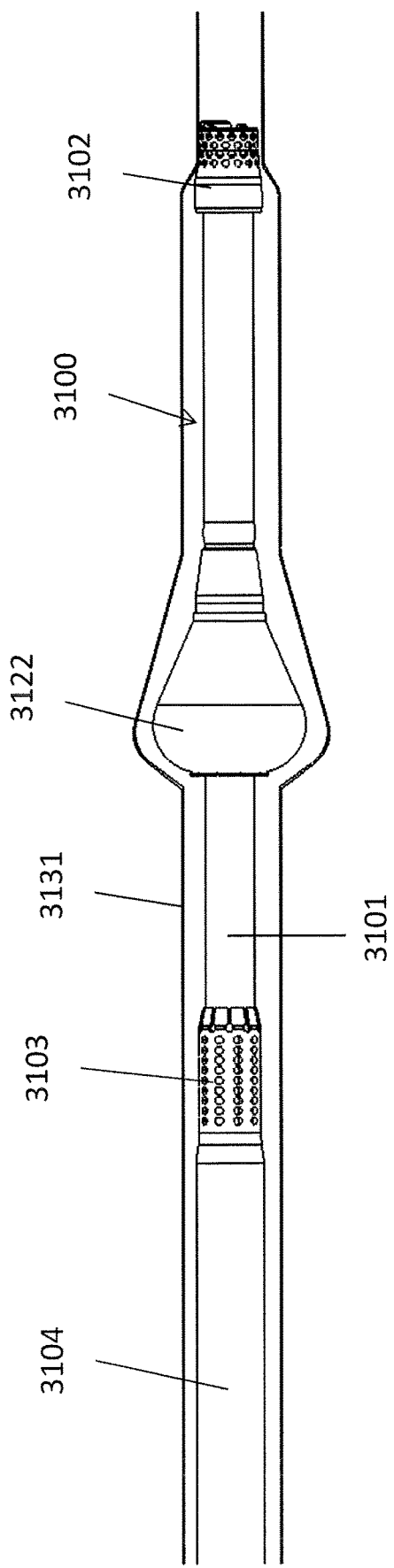
Figure 31C:
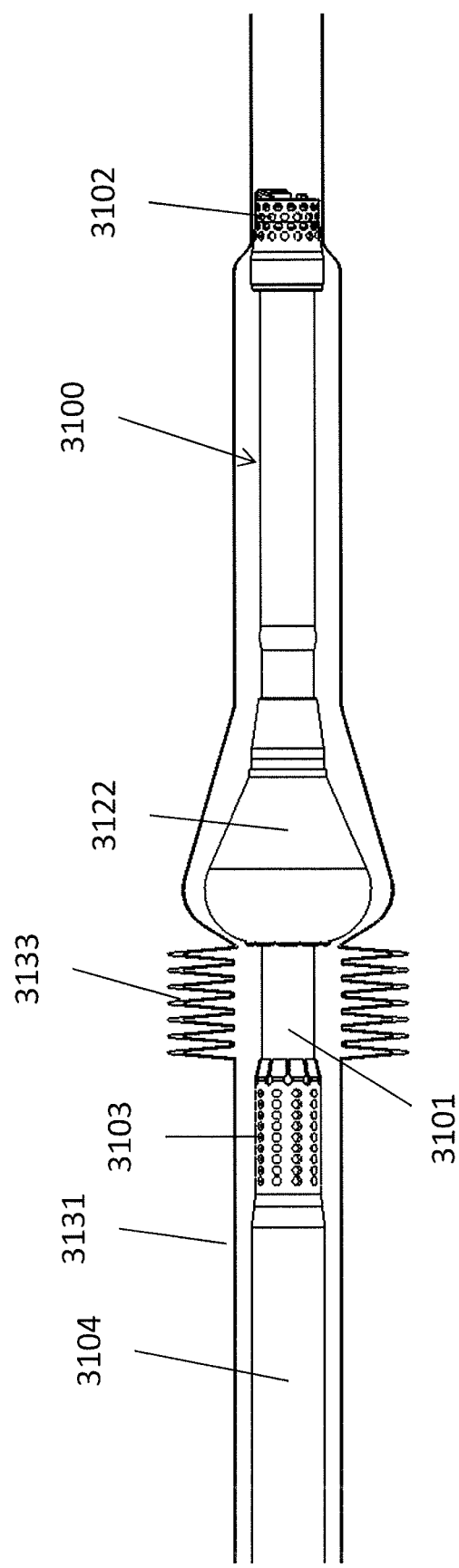
Figure 31D:
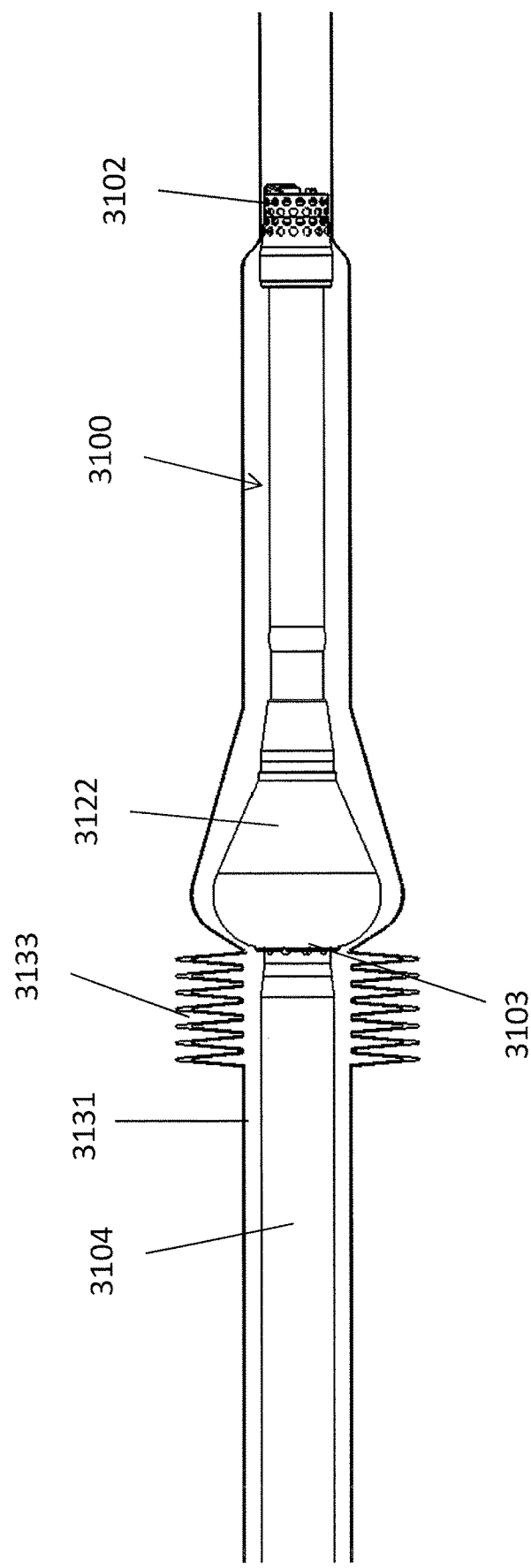
Figure 31E:
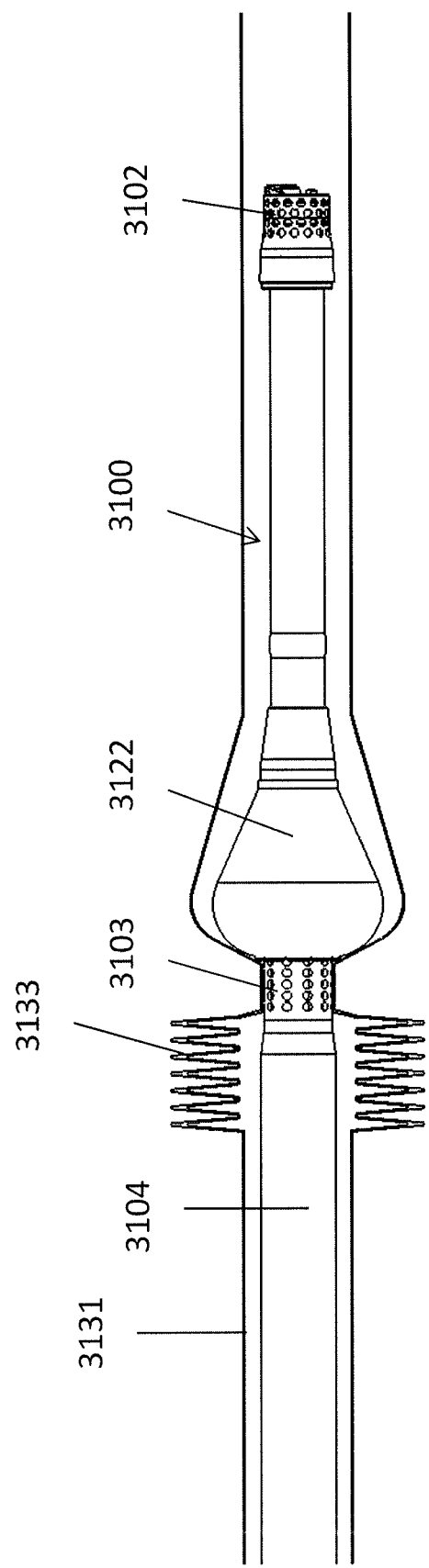
Figure 31F:
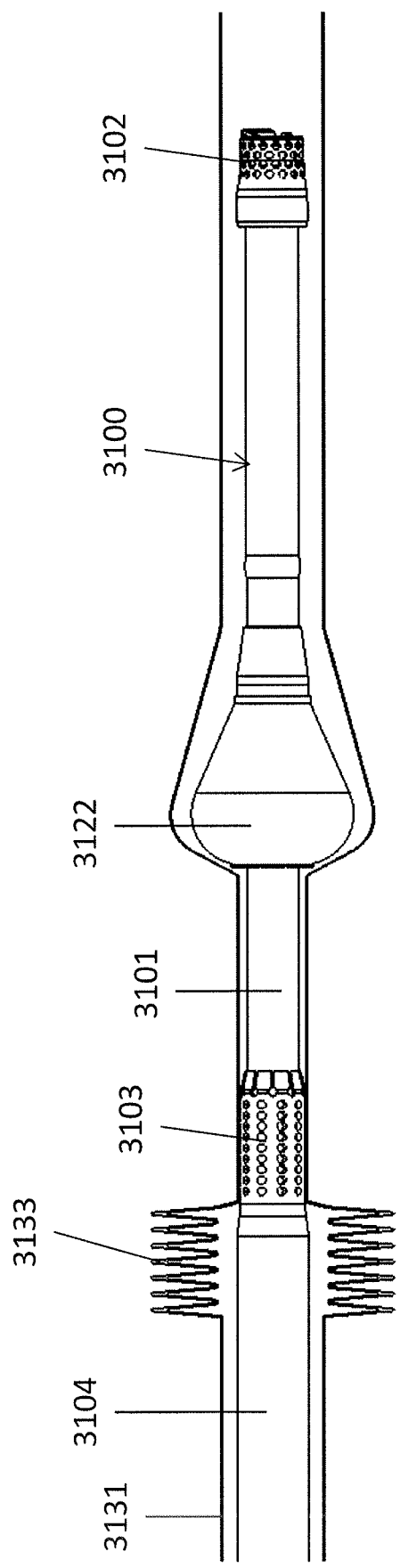

As another example, referring to FIGS. 31A-31F, the device 3100 works similarly to device 100 for advancement of the scope 3100 through the lumen 3131. Thus, at FIG. 31A, the device 3100 is inserted into the lumen 3131 in the distal direction (indicated by the arrow) while the balloon blocking element 3122 is deflated and the vacuum ports 3102, 3104 are deactivated. At FIG. 31B, the balloon blocking element 3122 is inflated (and can remain inflated throughout the entire procedure). The distal vacuum 3102 is then activated, thereby suctioning tissue of the lumen 3101 against the distal port 3102 (and pulling vacuum on the lumen 3131 distal to the distal port 3102). At FIG. 31C, the proximal vacuum port 3103 and distal vacuum port 3102 are moved towards one another while the distal vacuum port 3102 is activated. The expanded blocking element 3122 prevents the tissue of the lumen 3131 from traveling distally past the blocking element 3122 and/or the distal vacuum 3102, thereby creating pleats 3133 of tissue in the lumen. At FIG. 31D, the blocking element 3122 is slid over the proximal vacuum port 3103 so as to transfer the pleats 3133 proximal of the proximal vacuum port 3103. At FIG. 31E, the vacuum on the distal vacuum port 3102 is released, and the vacuum on the proximal vacuum port 3103 is activated, thereby suctioning tissue of the lumen 3131 thereto (distal to the pleats 3133). As shown at FIG. 31F, the distal vacuum port 3102 can then be moved further distally through the lumen 3131. The process can then be repeated so as to incrementally move the device scope 3101 and device 3101 distally through the lumen 3131.

Visual Indicator

Figure 49A:
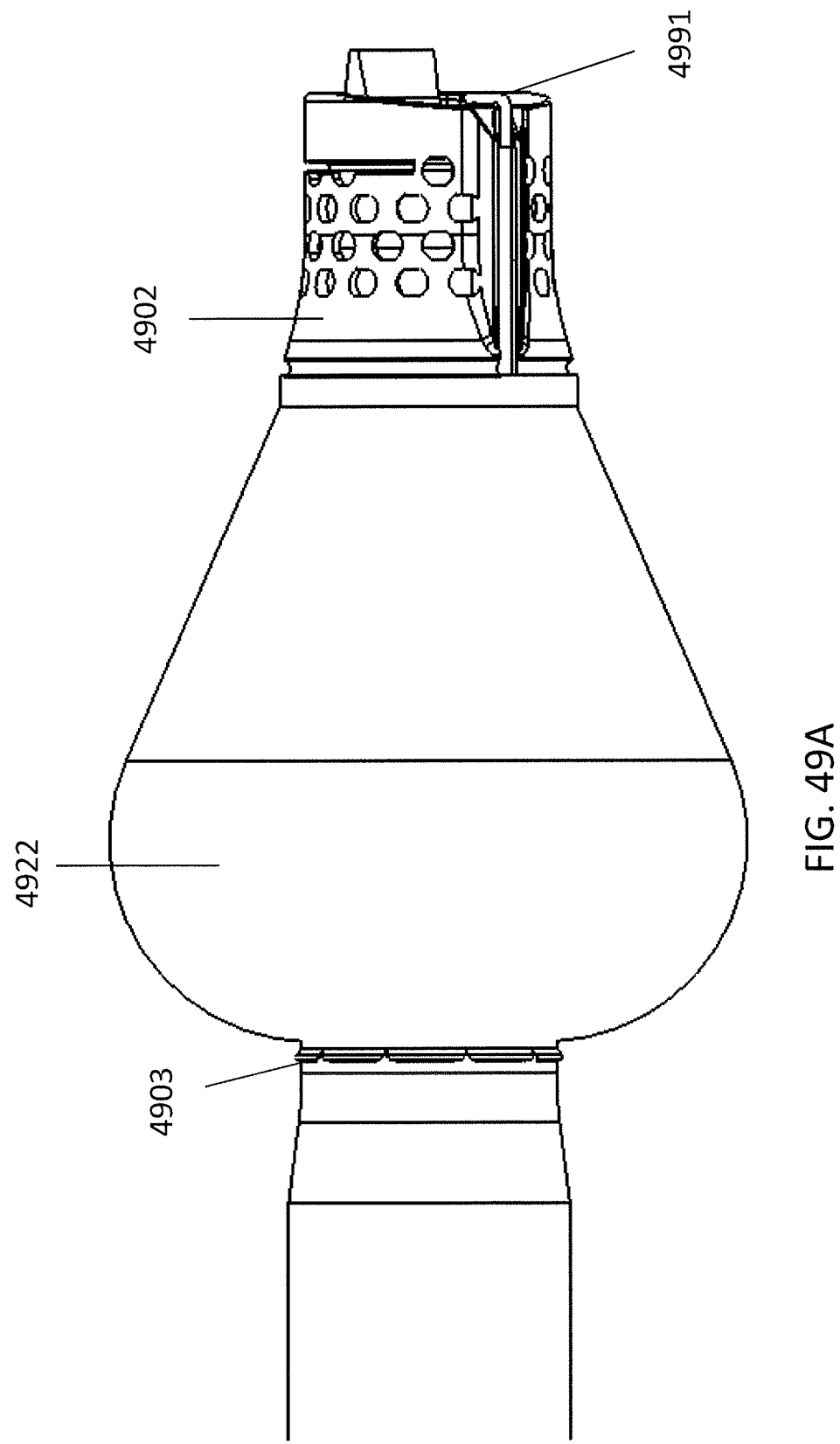
FIGS. 49A-B show a distal vacuum port including an indicator element for indicating proper docking of the proximal vacuum port within the blocking element.
Figure 49B:
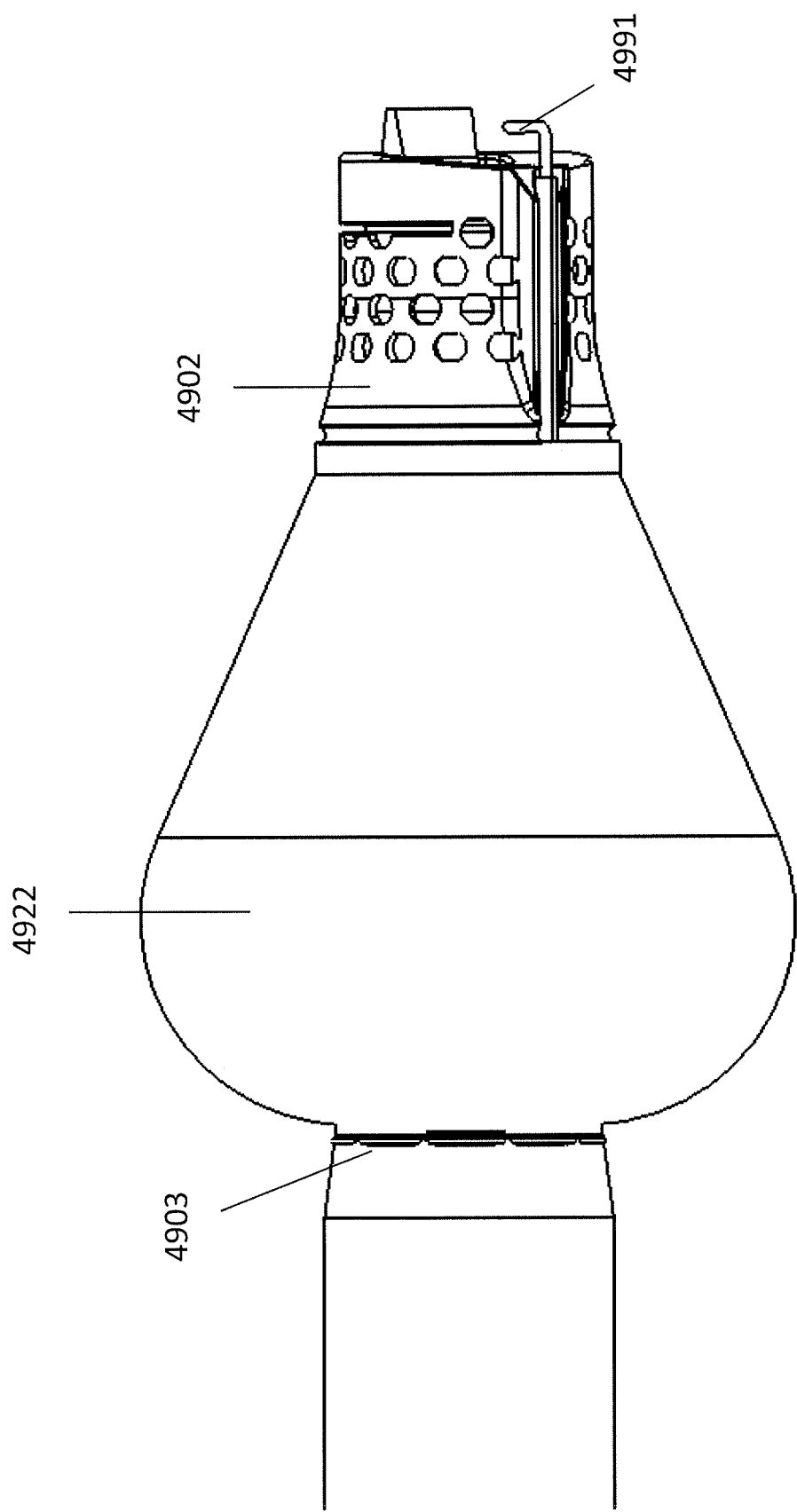
Figure 50E:
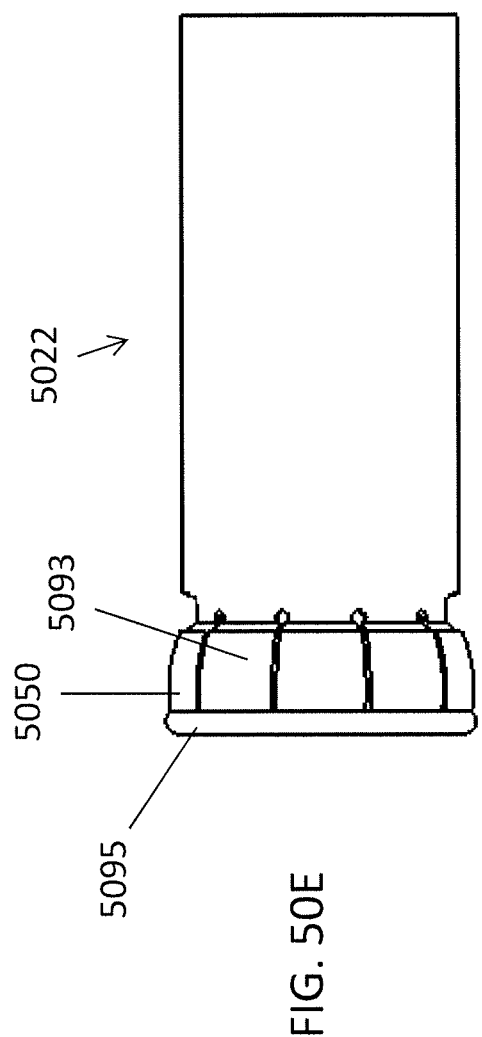
Figure 50F:
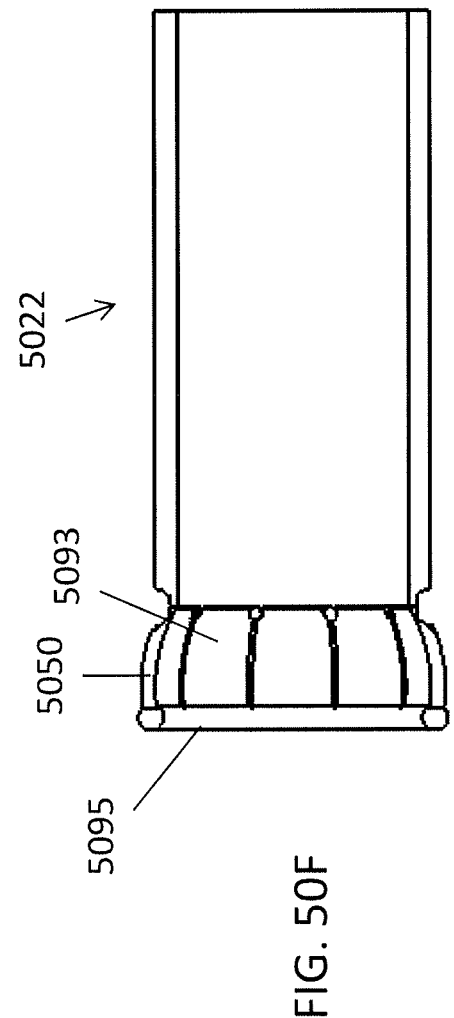

In some embodiments, the device can include a visual indicator thereon to indicate a state of the device (e.g., vacuums on/off, balloon inflated/deflated, proximal vacuum port fully docked inside of the balloon blocking element, etc.). For example, a "red out" in the scope viewer can indicate that the distal tip vacuum port is on (i.e., causing the tissue to suction to the scope lens). Further, referring to FIGS. 49A-B, in some embodiments, an indicator element 4991 on the distal vacuum port 4902 can be configured to be pushed distally when the proximal vacuum port 4903 is fully docked or positioned within the balloon blocking element 4922 (thus indicating that all of the pleated tissue had been pushed proximal to the proximal vacuum port 4903, similar to as shown in FIG. 31D). In some embodiments, a spring, such as a coil spring, wave spring, local compression spring, or "hit plate" can push the element 4991 distally when acted upon by the proximal vacuum port 4903. In some embodiments, the indicator element 4991 acts as a visual indicator that docking is complete by being positioned over the camera of the scope so as to be viable in the resulting image. In some embodiments, the indicator element 4991 acts as a visual indicator that docking is complete by moving the tissue off of the end of the scope, thereby locally lifting off red-out tissue. FIG. 49A thus shows that the proximal vacuum port 4903 is not fully docked while FIG. 49B shows that the proximal vacuum port 4903 is fully docked. Another example of an indicator includes an electronic indicator, such as an LED that light up when sensors (e.g., magnetic sensors or hall sensors) on the proximal vacuum port and the distal vacuum port are in proximity. Yet another example of an indicator includes a magnetic indicator arranged such that a magnet on the proximal vacuum port and a magnet on the distal vacuum port, when in proximity, repel or attract to create a change in the image seen distal to the camera. The visual indicator can be a reciprocating cable that is flexible, extending through a tube that is coiled around the scope's shaft and extending to its exit at the distal end of element 4902.

ADDITIONAL EMBODIMENTS

Figure 59:
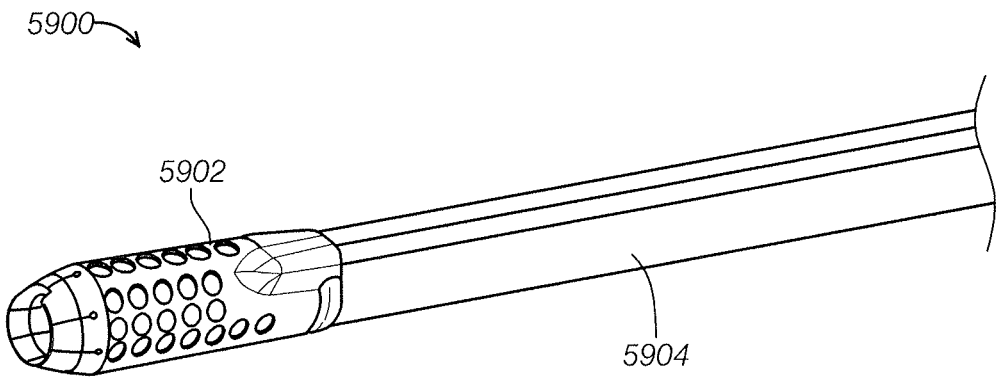
FIG. 59 shows another embodiment of a device for endoscopic advancement through the small intestine.
Figure 60:
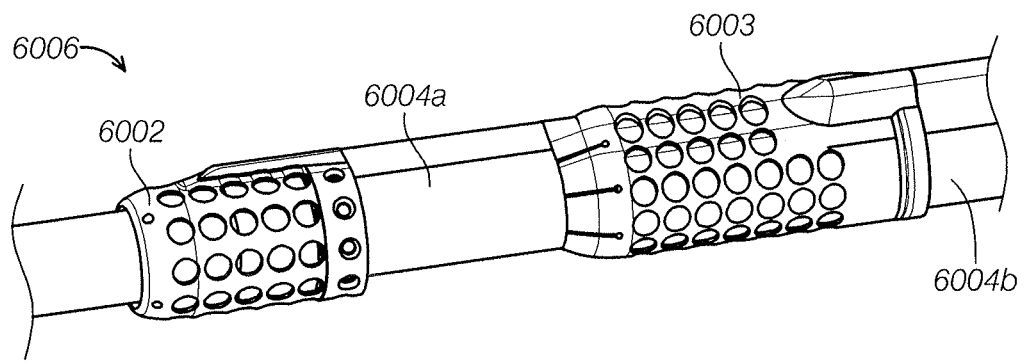
FIG. 60 shows another embodiment of a device for endoscopic advancement through the small intestine.

Although the devices described herein has been described as including a distal vacuum port that is attached to the endoscope, other set-ups are possible. For example, FIG. 59 shows a device 5900 that includes just a single vacuum port 5902 attached to an overtube 5904. FIG. 60 shows a device including two overtubes that slide relative to one another. The distal vacuum port 6002 is attached to an inner overtube 6004a while the proximal vacuum port 6003 is attached to an outer overtube 6004b.

Figure 61A:
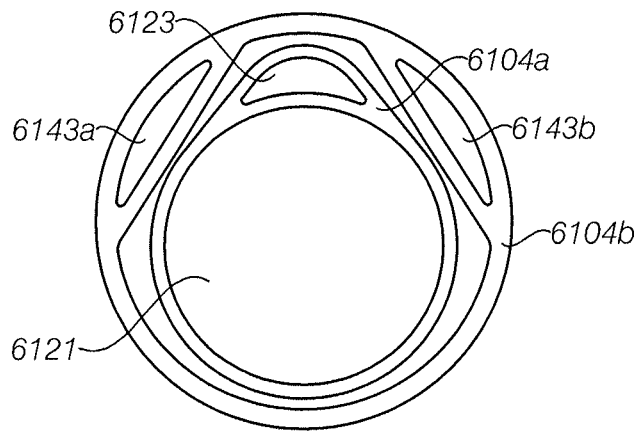
FIGS. 61A-61C show various designs for a dual overtube device for endoscopic advancement through the small intestine.
Figure 61B:
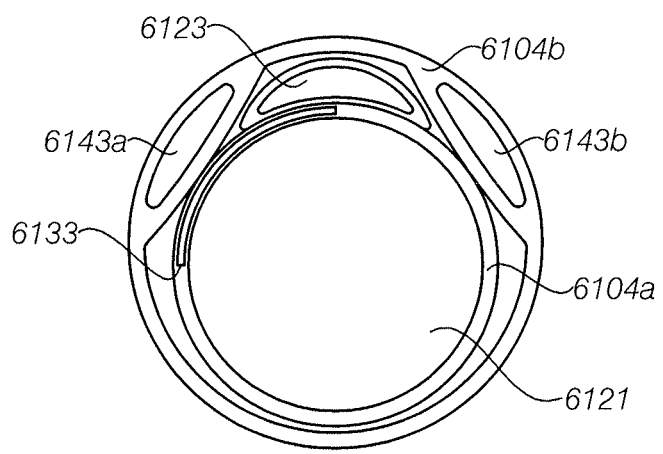
Figure 61C:
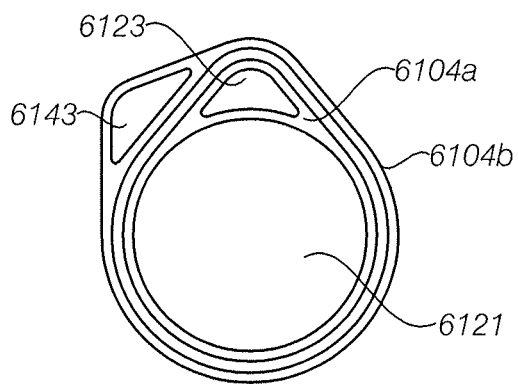

Various set-ups for a dual overtube system (as shown in FIG. 60) can be used, as shown in FIGS. 61A-C. Referring to FIG. 61A, the inner and outer overtubes 3204a,b can be multi-lumen extrusions. The inner overtube 6104a includes a central lumen 6121 for the endoscope and a side lumen 6123 for one of the vacuum lines 105, 106. The outer overtube 6104b can extend therearound and have lumens 3343a,b that extend on either side of the lumen 6123 for redundant vacuum lines. FIG. 61B is similar to the set-up of FIG. 61A, but includes an in-laid reinforcing coil 6133 in the inner tube 6104a. FIG. 61C is likewise similar, but includes only a single outer overtube lumen 6143.

Figures 62A, 62B:
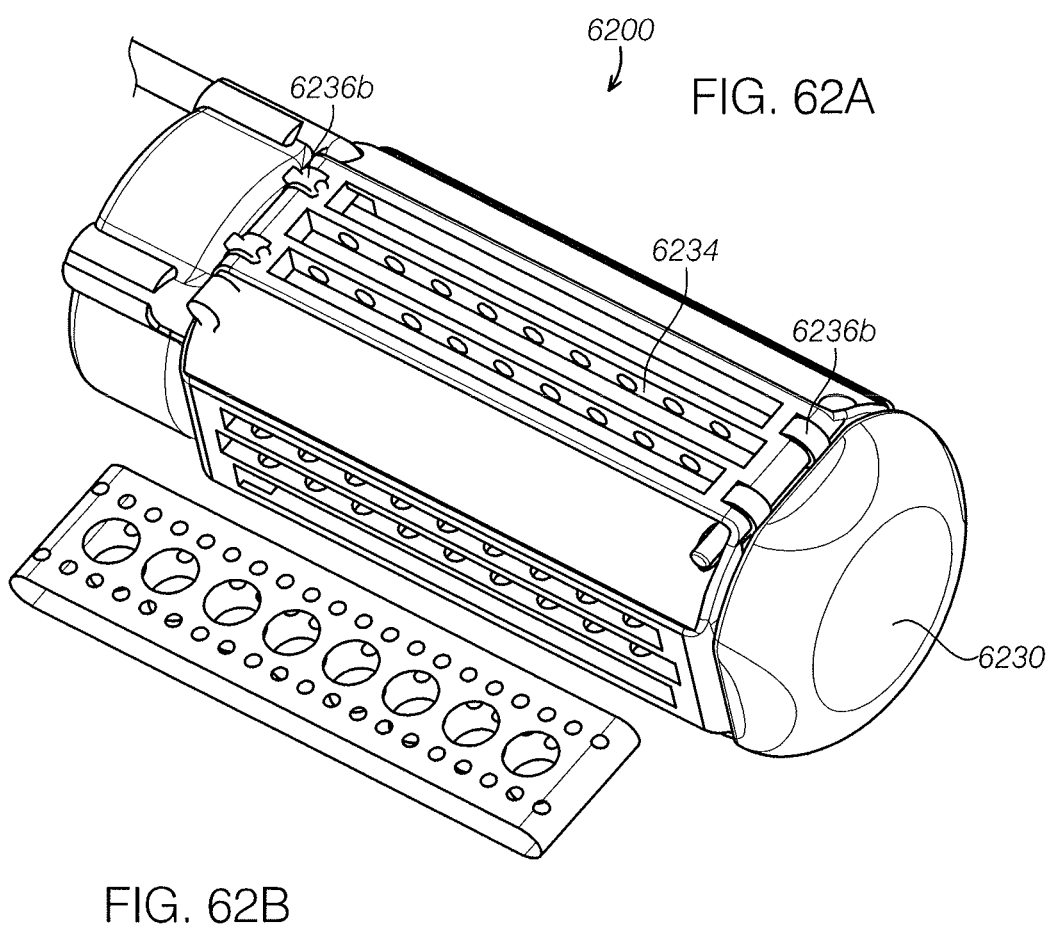
FIGS. 62A-B show various views of another embodiment of a device for endoscopic advancement through the small intestine.

Referring to FIGS. 62A-B, rather than having vacuum ports that are movable relative to one another, a device 6200 can include one or more movable planar vacuum belt 6234. The movable planar vacuum belt 6234 can roll over a cylindrical feature 6236a,b at either end, e.g., similar to a tank tread or conveyor belt, to create a perforated belt through which vacuum is drawn. As the belt 6234 is turned (for example, by turning a toothed cog into mating female features in the belt's surface), tissue that is suctioned to the belt can be moved along with the belt 6234, thereby moving tissue along the device (and/or the device through the tissue). The scope can be configured to go through a central lumen 6230. The device 6200 can include a plurality of vacuum belts arranged circumferentially therearound. For example, as shown in FIGS. 62A-B, there can be four different vacuum belts.

Figure 63A:
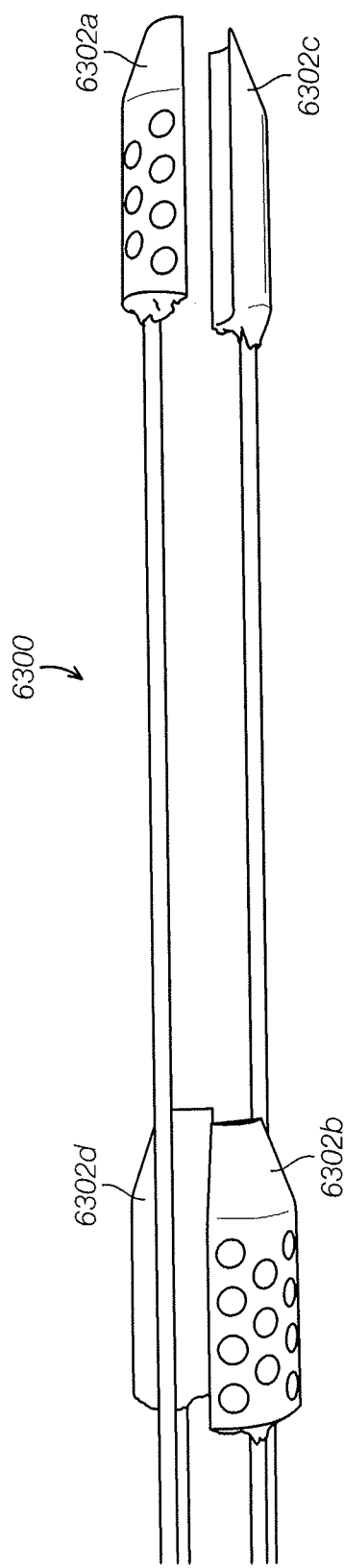
FIGS. 63A-B show various views of another embodiment of a device for endoscopic advancement through the small intestine.
Figure 63B:
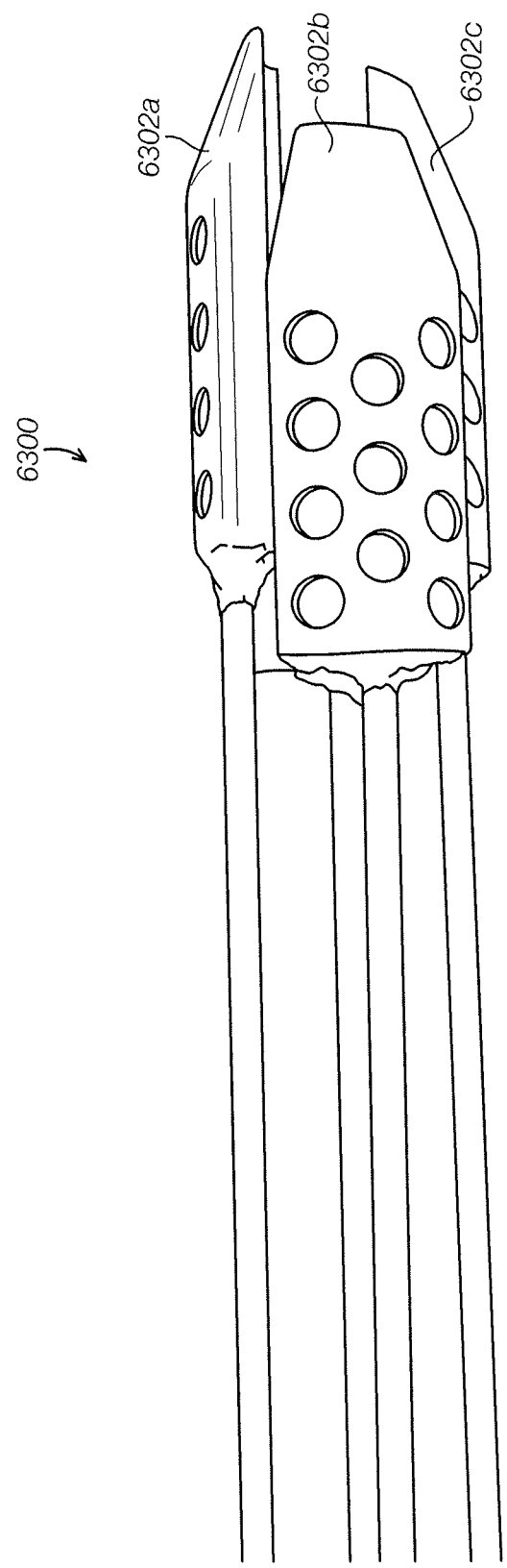

Referring to FIGS. 63A-63B, a device 6300 can include a distal vacuum port that has a plurality of sections 6302a, b,c,d that can move relative to one another. For example, a first set (sections 6302a,c) can move axially relative to a second set (sections 6302b,d). Likewise, vacuum can be applied to each set alternatively to move through the tissue.

Figure 64:
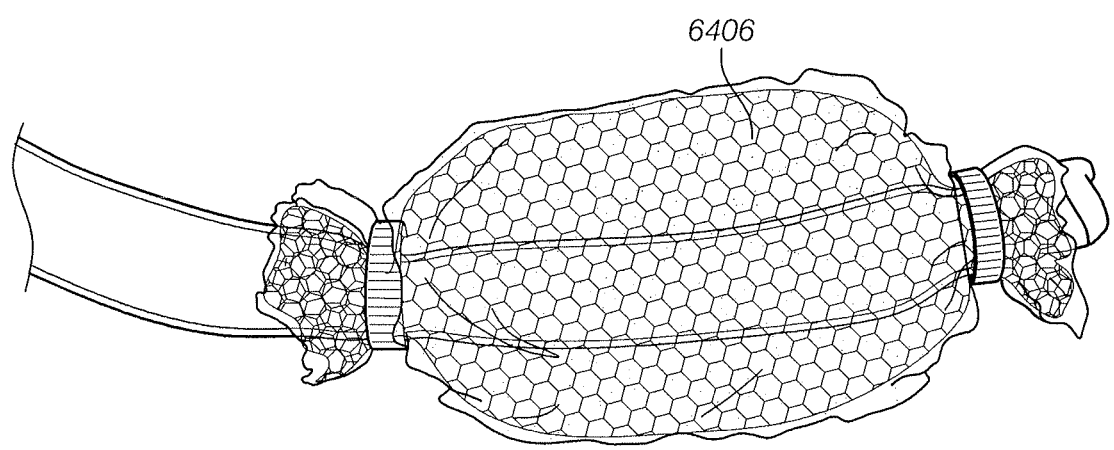
FIG. 64 shows another embodiment of a device for endoscopic advancement through the small intestine.
Figure 66C:
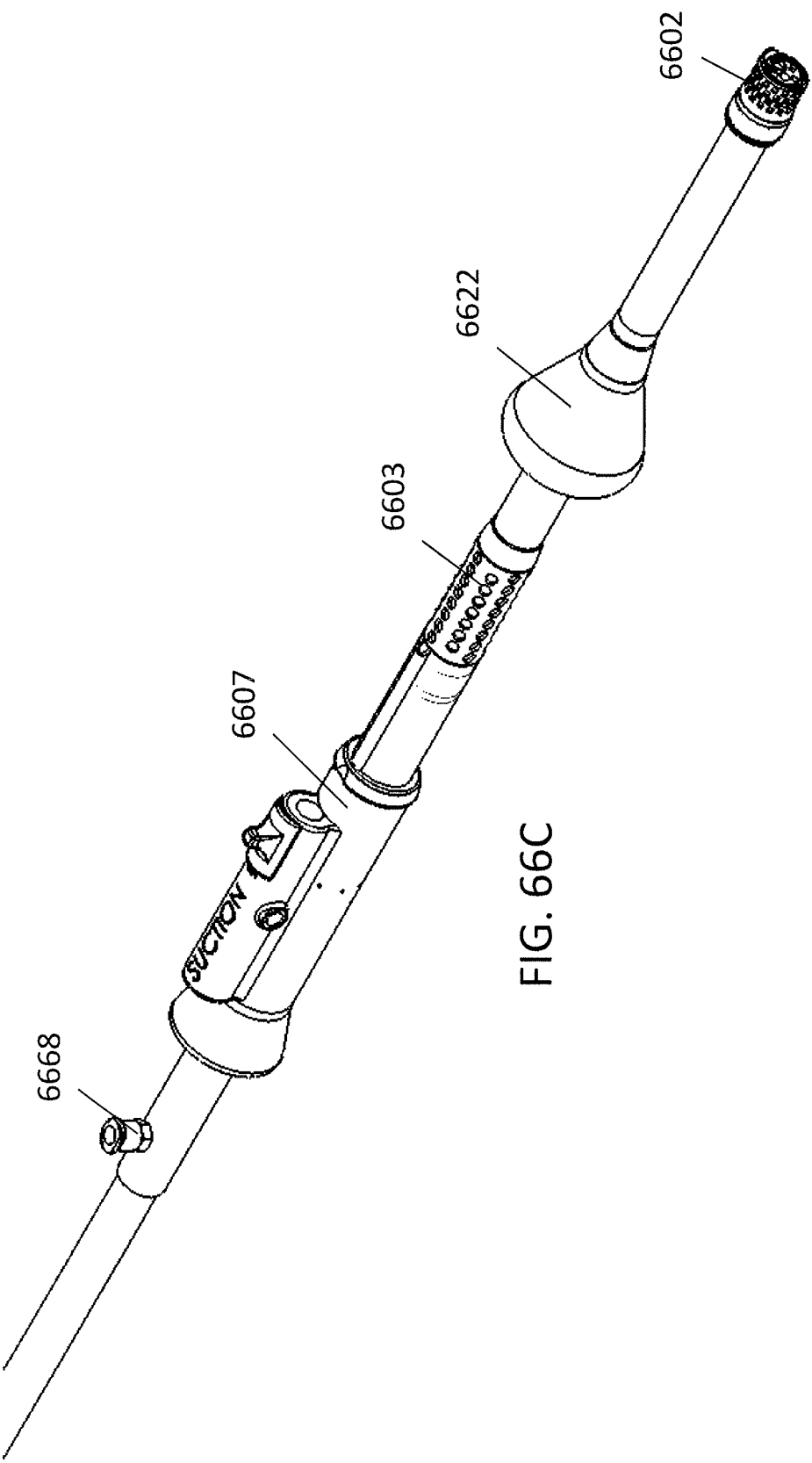
Figure 66D:
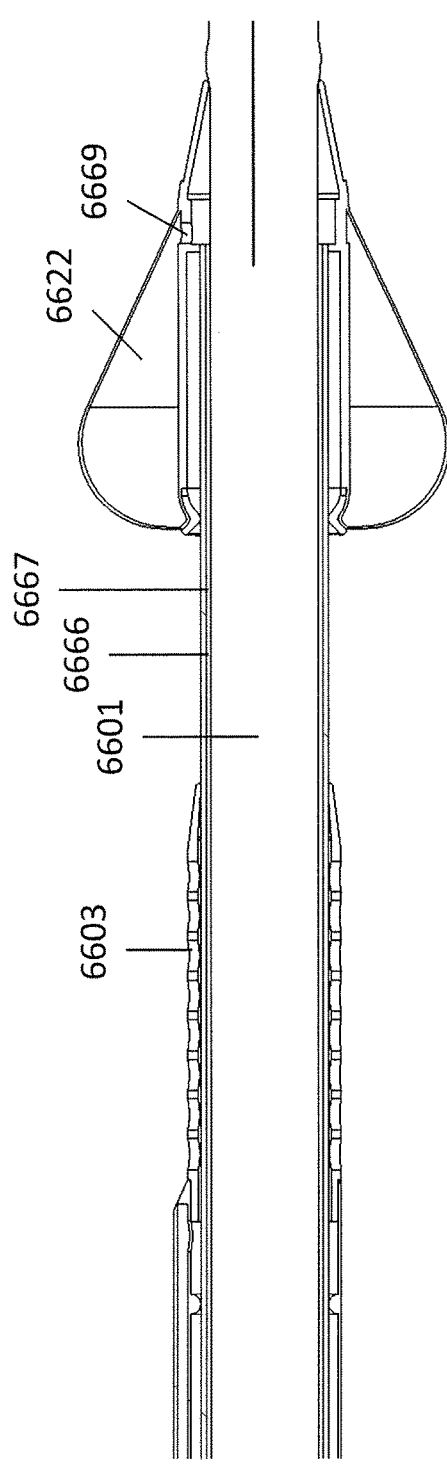
Figure 66E:
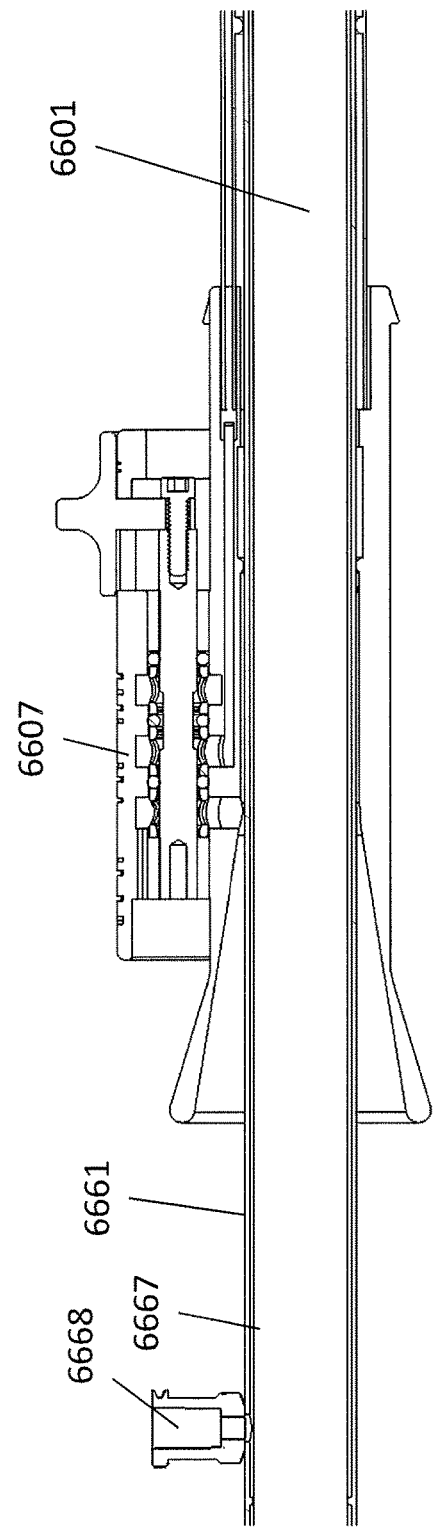
Figure 66F:
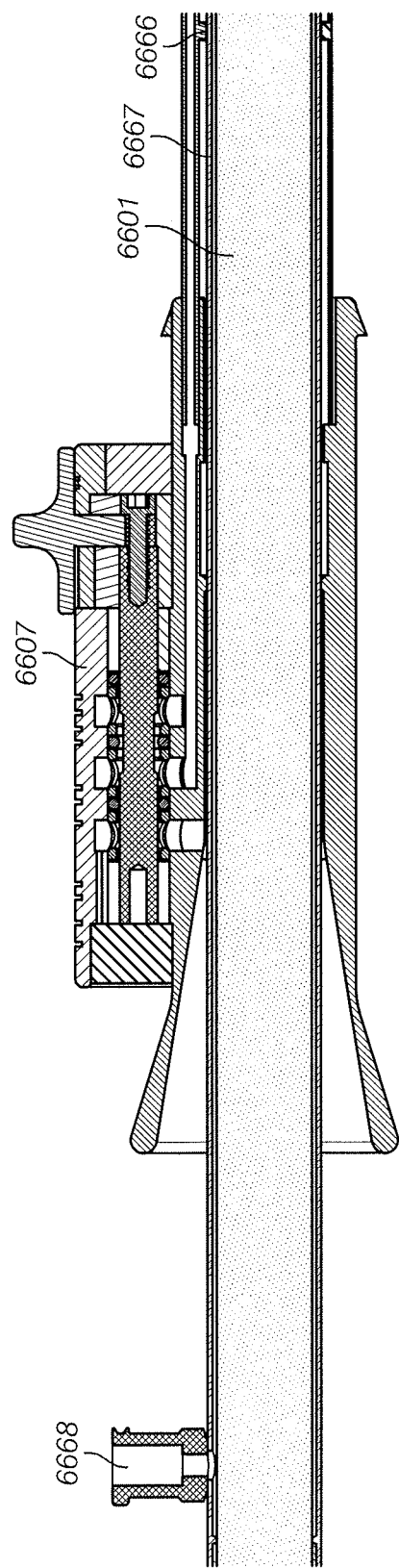
Figure 66G:
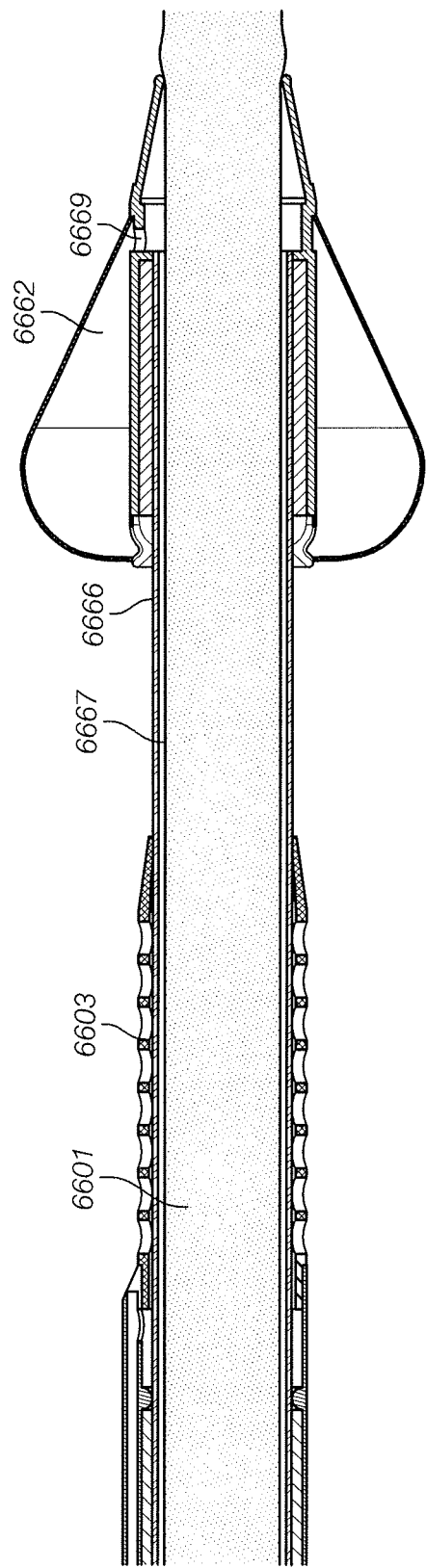
Figure 66H:
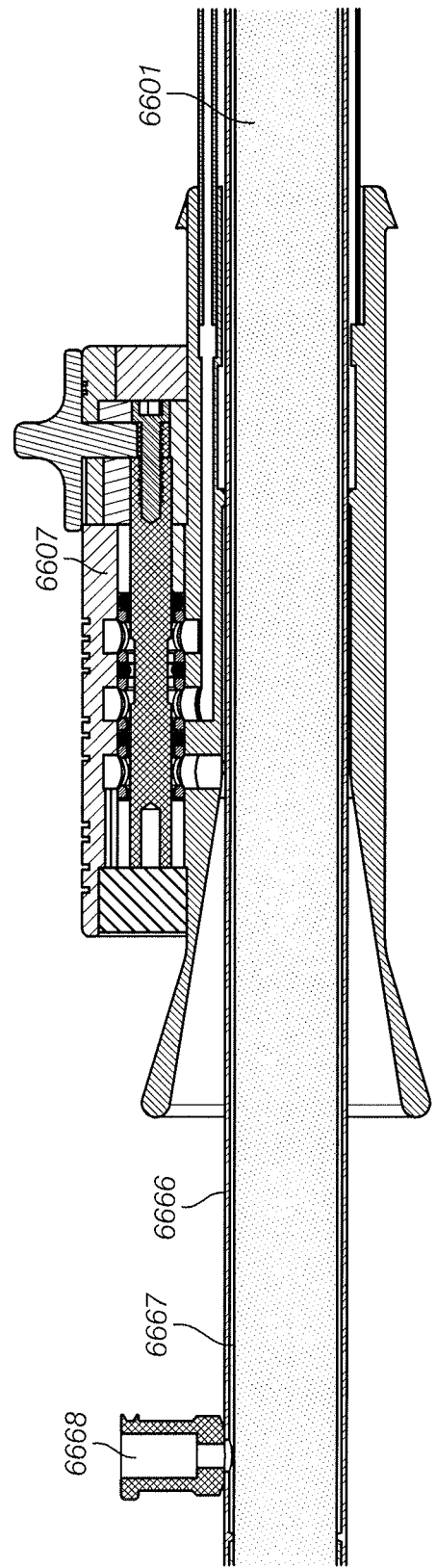
Figure 68:
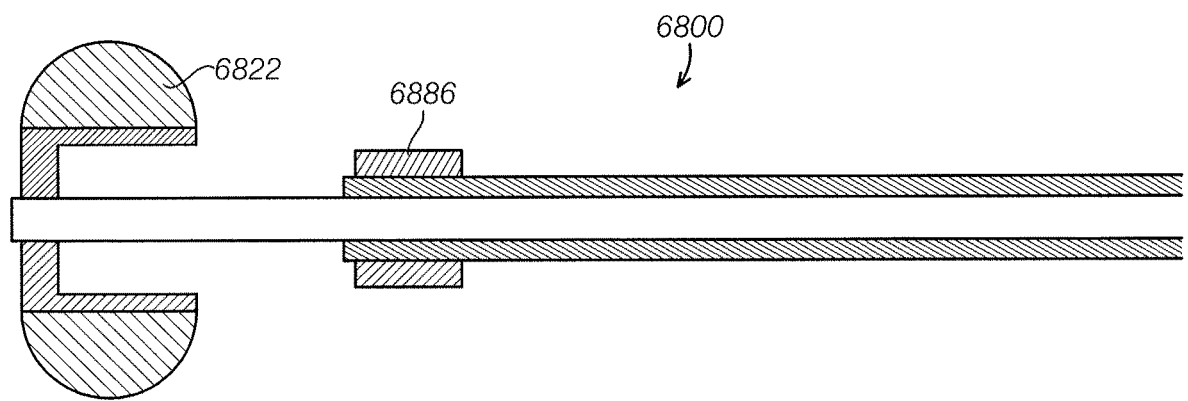
FIG. 68 shows a device for endoscopic advancement through the small intestine wherein the proximal vacuum port is replaced with an inflatable element.

Referring to FIG. 64, in some embodiments, one or more balloons 6406 can be used in place of the vacuum ports. In some embodiments, the balloons can act as gripping mechanisms on their own rather than using vacuum. In other embodiments, the balloons can include an inner wall to hold pressure, an outer wall that is perforated, and an intermediate space therebetween that can be maintained by spacers. As the balloon is inflated, it can expand to contact the tissue of the intestine. At that point, the vacuum can be turned on, pulling vacuum into the intermediate space and out the perforations. As a result, tissue can be suctioned to the outside of the balloon, enabling subsequent manipulation. In another embodiment, the inner wall of the balloon can include an outward force created by springs, including wire that is pre-set to an outward geometry. As the springs are released, the diameter increased, the surface is brought out to the tissue, and then the vacuum can be turned on to suction the tissue onto the outside surface. FIG. 68 shows another device 6800 wherein the proximal vacuum port has been replaced with a balloon 6886. The balloon 6886 is still configured to fit radially within the blocking element 6822.

Although the devices herein have been described as being used over an endoscope, the devices can also be configured as a discrete unit that functions independently without having to utilize a pre-existing endoscope. The discrete unit can function untethered (i.e., with on-board elements) or tethered (with an umbilical). In some embodiments, the umbilical can have a feature that allows it to unspool as it is advanced, such that the umbilical is not dragged nor subject to notable capstan drag forces relative to the small intestine that the unit weaves through as it advances through the small intestine.

Although the grabbing mechanisms of the devices described herein have been described as moving relative to one another by manual activation, other activation mechanisms are possible, such as with bellows, a motor, or a pneumatic/hydraulic actuator.

In embodiments where one or more of the grabbing mechanisms are vacuums, vacuum lines can extend from the port(s) back to a vacuum source. To modulate the attachment force and physiological tissue response, vacuum pressure and flow rate can be modulated. For example, the system can operate at or near full vacuum (760 mm Hg) or at partial vacuum (600, 500, 300, 250, 120, 50 mmHg). Vacuum can be applied continuously or intermittently. Flow rates can be varied, for example, from 10 to 40 to 100 liters per minute.

In embodiments where the blocking element is an inflatable element or balloon and one or more vacuum ports are used as the grabbing mechanisms, the balloon can be configured to stay inflated throughout the entire procedure. Doing so can advantageously create two zones—a proximal zone proximal to the inflated balloon and a distal balloon that is distal to the inflated balloon. The proximal zone can be under vacuum (by the vacuum ports) while the distal zone can be insufflated (such as with an insufflator). Having the proximal zone under vacuum can advantageously help with pleating of the tissue while having the distal zone insufflated can advantageously increase visibility through the lens of the scope within the lumen.

Figure 67:
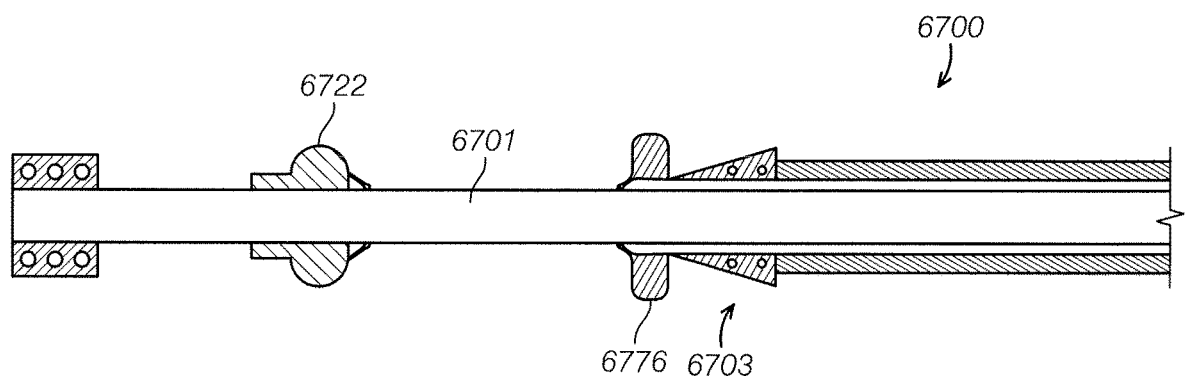
FIG. 67 shows a device for endoscopic advancement through the small intestine with an inflatable element on the proximal vacuum port.

In some embodiments, referring to FIG. 67, a device 6700 with a balloon blocking element 6722 (or other type of blocking element) can further include an inflatable element or balloon 6776 attached to the distal end of the proximal vacuum port 6703, thereby preventing vacuum from moving distal to the balloon 6776.

It should be understood that any feature described with respect to one embodiment herein can be replaced or supplemented with any feature described with respect to any other embodiment described herein.

System Layout

Referring to FIG. 65, the devices described herein can be connected to a variety of different control components. For example, the device 100 (or any other device described herein) can be positioned over the endoscope 101, which can be attached to a monitor 10, a video processor 6512, a tip wash 6516, instruments 6518 for use therewith, a pressurized air or insufflation source 6501, and a vacuum source 6505. The device 100 can likewise be connected to the vacuum source through a suction fluid collection canister and line 6503.

CONCLUSIONS

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An apparatus for advancing through a gastrointestinal tract, the apparatus comprising:
    first and second grabbing mechanisms adapted to grab and release tissue of the gastrointestinal tract, the first and second grabbing mechanisms being axially movable with respect to each other along the gastrointestinal tract; and
    a radially expandable blocking element disposed proximal to the first grabbing mechanism and movable with the first grabbing mechanism, wherein the blocking element is configured to slide over at least a portion of the second grabbing mechanism, the blocking element being adapted to enable tissue of the intestinal tract to move axially with respect to second grabbing mechanism.

2. The apparatus of claim 1, further comprising actuators adapted to actuate the first and second grabbing mechanisms to grab and release tissue.

3. The apparatus of claim 1, wherein the first grabbing mechanism is attachable to an inner element and the second grabbing mechanism is attached to an outer element configured to at least partially surround the inner element.

4. The apparatus of claim 3, further comprising a connecting mechanism configured to releasably attach the first grabbing mechanism to the inner element.

5. The apparatus of claim 3, wherein the inner element comprises an endoscope.

6. The apparatus of claim 3, wherein the outer element comprises an overtube.

7. The apparatus of claim 6, wherein the overtube supports actuator lines extending to the first and second grabbing mechanisms.

8. The apparatus of claim 1, wherein at least one of first grabbing mechanism and second grabbing mechanism comprises a vacuum port.

9. The apparatus of claim 1, wherein the second grabbing mechanism comprises a vacuum port and the first grabbing mechanism is attachable to an endoscope, the apparatus further comprising a distal cap adapted to cover a distal end of the endoscope and a seal adapted to seal against an outer surface of the endoscope proximal to the cap to form a vacuum chamber in fluid communication with a working channel of the endoscope and with the vacuum port.

10. The apparatus of claim 9, further comprising an opening in the cap adapted to align with the working channel of the endoscope and a valve disposed in the opening.

11. The apparatus of claim 1, wherein the blocking element comprises a balloon.

12. The apparatus of claim 11, further comprising an overtube attached to the balloon and defining a balloon inflation channel communicating with an interior of the balloon.

13. The apparatus of claim 1, wherein the blocking element comprises a plurality of radially movable elements.

14. The apparatus of claim 1, wherein the blocking mechanism comprises a wiping element.

15. The apparatus of claim 1, wherein the apparatus comprises a distal end and a proximal end, wherein the radially expandable blocking element is disposed closer to the proximal end than first grabbing mechanism.

* * * * *